United States Patent
Denning et al.

(10) Patent No.: US 8,672,883 B2
(45) Date of Patent: Mar. 18, 2014

(54) FLUID DELIVERY DEVICE AND METHODS

(76) Inventors: C. Garyen Denning, Lexington, KY (US); Theodore J. Mosler, Raleigh, NC (US); David L. Foshee, Apex, NC (US); Robert C. Hall, Apex, NC (US); Andrew J. Corson, Apex, NC (US)

( * ) Notice: Subject to any disclaimer, the term of this patent is extended or adjusted under 35 U.S.C. 154(b) by 47 days.

(21) Appl. No.: 13/546,454

(22) Filed: Jul. 11, 2012

(65) Prior Publication Data
US 2013/0018311 A1    Jan. 17, 2013

Related U.S. Application Data

(60) Provisional application No. 61/585,017, filed on Jan. 10, 2012, provisional application No. 61/552,241, filed on Oct. 27, 2011, provisional application No. 61/541,002, filed on Sep. 29, 2011, provisional application No. 61/540,517, filed on Sep. 28, 2011, provisional application No. 61/521,503, filed on Aug. 9, 2011, provisional application No. 61/506,498, filed on Jul. 11, 2011.

(51) Int. Cl.
*A61M 5/00* (2006.01)

(52) U.S. Cl.
USPC .......................................................... 604/110

(58) Field of Classification Search
USPC .......................................................... 604/110
See application file for complete search history.

(56) References Cited

U.S. PATENT DOCUMENTS

| | | |
|---|---|---|
| 2,864,366 A | 12/1958 | Miskel |
| 4,832,695 A | 5/1989 | Rosenberg et al. |
| 4,886,495 A | 12/1989 | Reynolds |
| 5,135,514 A | 8/1992 | Kimber |
| 5,137,511 A | 8/1992 | Reynolds |
| 5,322,515 A | 6/1994 | Karas et al. |
| 5,324,272 A | 6/1994 | Smedley et al. |
| 5,364,369 A | 11/1994 | Reynolds |
| 5,382,241 A | 1/1995 | Choudhury et al. |
| 5,468,232 A | 11/1995 | Nagunuma |

(Continued)

FOREIGN PATENT DOCUMENTS

| | | |
|---|---|---|
| DE | 2458004 A1 | 6/1976 |
| FR | 1117356 A | 5/1956 |

(Continued)

OTHER PUBLICATIONS

International Search Report; PCT/US2012/046288; Date of Mailing: Sep. 28, 2012; 2 pages.

(Continued)

*Primary Examiner* — Aarti B Berdichevsky
(74) *Attorney, Agent, or Firm* — Ulmer & Berne LLP

(57) ABSTRACT

A fluid delivery device includes a cartridge and a syringe. The cartridge includes a housing and a stopper positioned within a fluid chamber defined by the housing. The syringe includes a needle, and an outer body and an inner core which cooperate to receive at least a portion of the housing. When the fluid delivery device is in a first configuration, at least a portion of the cartridge is positioned within the syringe and the stopper is connected to the inner core. In a second configuration, a lumen defined by the needle is in fluid communication with the fluid chamber. The inner core and stopper are movable distally relative to the outer body and needle as the fluid delivery device is transitioned from the first to the second configuration. In a third configuration, the cartridge and syringe cooperate to disable the fluid delivery device.

20 Claims, 75 Drawing Sheets

(56) References Cited

U.S. PATENT DOCUMENTS

| | | | |
|---|---|---|---|
| 5,496,293 A | 3/1996 | Huggenberger |
| 5,520,649 A | 5/1996 | Novacek et al. |
| 5,554,125 A | 9/1996 | Reynolds |
| 5,569,193 A | 10/1996 | Hofstetter et al. |
| 5,573,513 A | 11/1996 | Wozencroft |
| 5,624,402 A | 4/1997 | Imbert |
| 5,637,087 A | 6/1997 | O'Neil et al. |
| 5,709,666 A | 1/1998 | Reynolds |
| 5,718,690 A | 2/1998 | Gettig |
| 5,743,879 A | 4/1998 | Kriesel |
| 5,785,682 A | 7/1998 | Grabenkort |
| 5,876,372 A | 3/1999 | Grabenkort et al. |
| 5,891,086 A | 4/1999 | Weston |
| 5,893,397 A | 4/1999 | Peterson et al. |
| 5,925,029 A | 7/1999 | Jansen et al. |
| 5,931,817 A | 8/1999 | Nguyen et al. |
| 5,938,637 A | 8/1999 | Austin et al. |
| 5,989,227 A | 11/1999 | Vetter et al. |
| 6,027,472 A | 2/2000 | Kriesel et al. |
| 6,027,482 A | 2/2000 | Imbert |
| 6,090,093 A | 7/2000 | Thibault et al. |
| 6,113,583 A | 9/2000 | Fowles et al. |
| 6,117,113 A | 9/2000 | Novacek et al. |
| 6,146,361 A | 11/2000 | DiBiasi et al. |
| 6,189,580 B1 | 2/2001 | Thibault et al. |
| 6,190,364 B1 | 2/2001 | Imbert |
| 6,193,688 B1 | 2/2001 | Balestracci et al. |
| 6,213,994 B1 | 4/2001 | Jansen et al. |
| 6,352,522 B1 | 3/2002 | Kim et al. |
| 6,378,714 B1 | 4/2002 | Jansen et al. |
| 6,485,460 B2 | 11/2002 | Eakins et al. |
| 6,524,295 B2 | 2/2003 | Daubert et al. |
| 6,562,011 B1 | 5/2003 | Buch-Rasmussen et al. |
| 6,569,115 B1 | 5/2003 | Barker et al. |
| 6,582,408 B1 | 6/2003 | Buch-Rasmussen et al. |
| 6,599,264 B1 | 7/2003 | Erni et al. |
| 6,607,508 B2 | 8/2003 | Knauer |
| 6,610,041 B2 | 8/2003 | Daubert et al. |
| 6,626,309 B1 | 9/2003 | Jansen et al. |
| 6,635,043 B2 | 10/2003 | Daubert et al. |
| 6,648,859 B2 | 11/2003 | Bitdinger et al. |
| 6,673,034 B2 | 1/2004 | Castellano |
| 6,706,031 B2 | 3/2004 | Manera |
| 6,726,652 B2 | 4/2004 | Eakins et al. |
| 6,752,180 B2 | 6/2004 | Delay |
| 6,821,268 B2 | 11/2004 | Balestracci |
| 6,846,303 B2 | 1/2005 | Eakins et al. |
| 6,902,543 B1 | 6/2005 | Cherif-Cheikh et al. |
| 6,942,643 B2 | 9/2005 | Eakins et al. |
| 6,945,963 B2 | 9/2005 | Langley et al. |
| 6,981,963 B2 | 1/2006 | Barker et al. |
| 7,004,929 B2 | 2/2006 | McWethy et al. |
| 7,044,125 B2 | 5/2006 | Vedrine et al. |
| 7,083,599 B2 | 8/2006 | Alchas et al. |
| 7,112,187 B2 | 9/2006 | Karlsson |
| 7,195,623 B2 | 3/2007 | Burroughs et al. |
| 7,331,941 B2 | 2/2008 | Vetter et al. |
| 7,338,469 B2 | 3/2008 | Barker et al. |
| 7,470,258 B2 | 12/2008 | Barker et al. |
| 7,503,907 B1 | 3/2009 | Lesch, Jr. |
| 7,569,036 B2 | 8/2009 | Domkowski et al. |
| 7,695,449 B2 | 4/2010 | Wang et al. |
| 7,862,543 B2 | 1/2011 | Potter et al. |
| 7,918,821 B2 | 4/2011 | Mahurkar |
| 7,927,314 B2 | 4/2011 | Kuracina et al. |
| 7,967,772 B2 | 6/2011 | McKenzie et al. |
| 7,981,081 B2 | 7/2011 | Marsh et al. |
| 2004/0225258 A1 | 11/2004 | Balestracci |
| 2004/0267194 A1 | 12/2004 | Sano et al. |
| 2006/0178644 A1 | 8/2006 | Reynolds |
| 2007/0100294 A1 | 5/2007 | Sugita et al. |
| 2007/0135767 A1 | 6/2007 | Gillespie, III et al. |
| 2008/0183140 A1 | 7/2008 | Paproski et al. |
| 2008/0188799 A1 | 8/2008 | Mueller-Beckhaus et al. |
| 2009/0124981 A1 | 5/2009 | Evans |
| 2009/0149816 A1 | 6/2009 | Hetzler et al. |
| 2010/0049144 A1 | 2/2010 | McConnell et al. |
| 2010/0262121 A1 | 10/2010 | Millerd |
| 2010/0298779 A1 | 11/2010 | Hetzler et al. |
| 2011/0015578 A1 | 1/2011 | Lowke |
| 2011/0046550 A1 | 2/2011 | Schiller et al. |

FOREIGN PATENT DOCUMENTS

| | | |
|---|---|---|
| GB | 2471524 A | 1/2011 |
| WO | 99/62577 | 12/1999 |
| WO | 2004050151 | 6/2004 |
| WO | 2010075920 | 7/2010 |
| WO | 2011029184 | 3/2011 |

OTHER PUBLICATIONS

Written Opinion of the International Searching Authority; PCT/US2012/046288; Date of Mailing: Sep. 28, 2012; 5 pages.

Syringe barrel end caps and tip caps; http://gluebond.com/syrcaps.htm; retrieved: Jul. 15, 2011; 3 pages.

Hospira iSecure Syringe; http://www.hospira.com/Products/isecuresyringes.aspx; link identified: Jul. 20, 2011; link printed: Sep. 9, 2013; 1 page.

Dispensing syringe; http://www.directindustry.com/prod/panacol-elosol/dispensing-syringes-38500-335030.html; retrieved: Jul. 15, 2011; 2 pages.

Pharmaceutical & Medical Packaging News—Prefilled Syringes; May 2003, vol. 11, Issue 5; http://safetysyringes.com/pdf/PMPNreprintCFO.pdf; retrieved: Jul. 18, 2011; 8 pages.

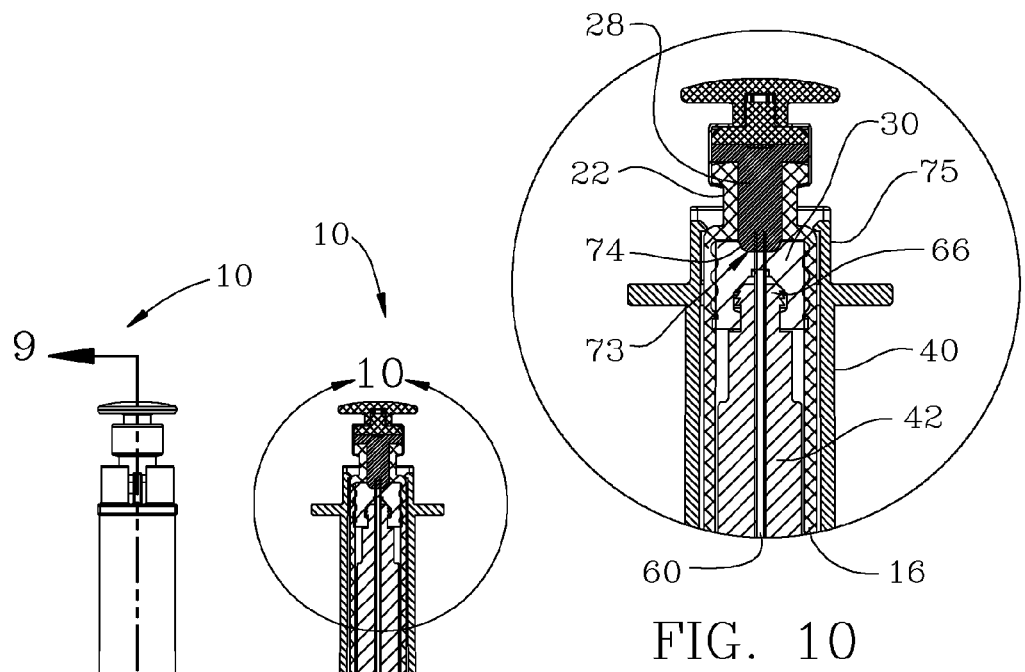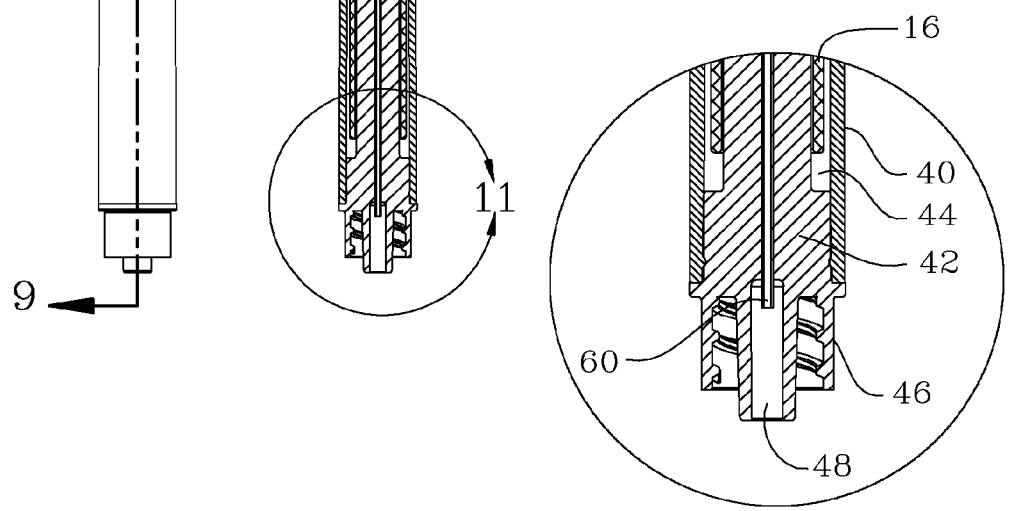
FIG. 8  FIG. 9  FIG. 11

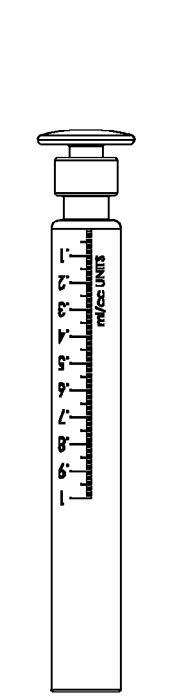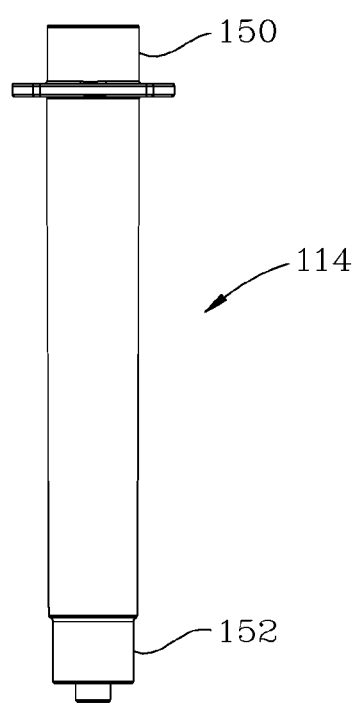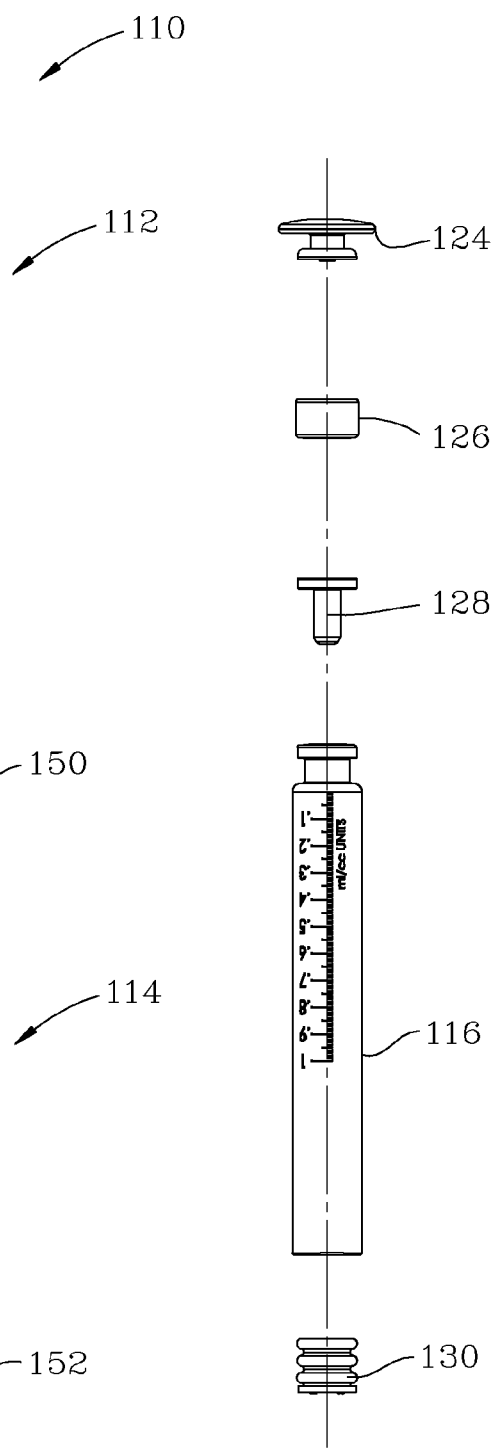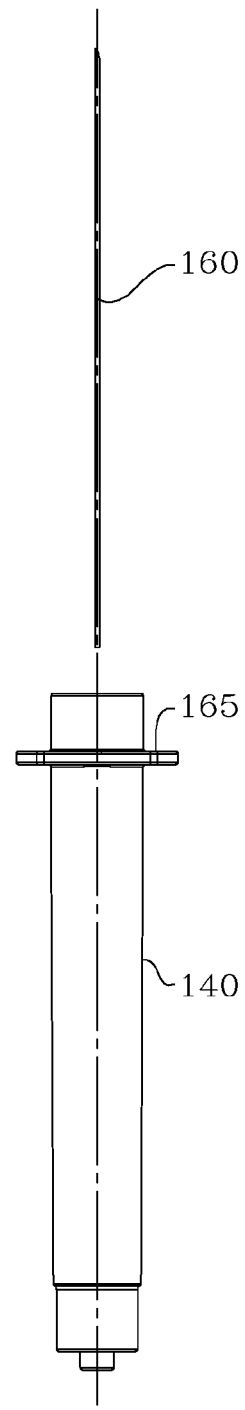
FIG. 12  FIG. 13  FIG. 14

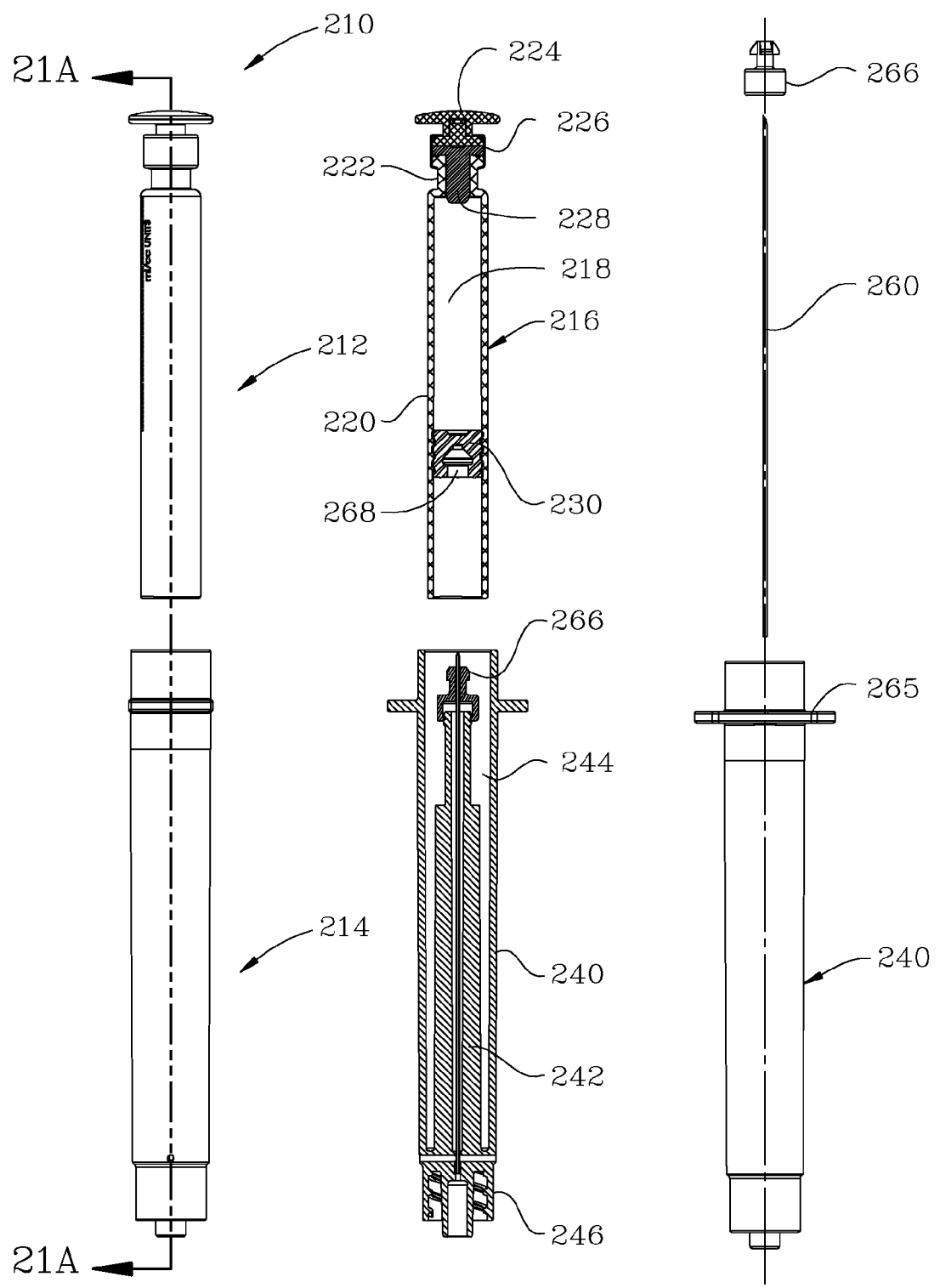

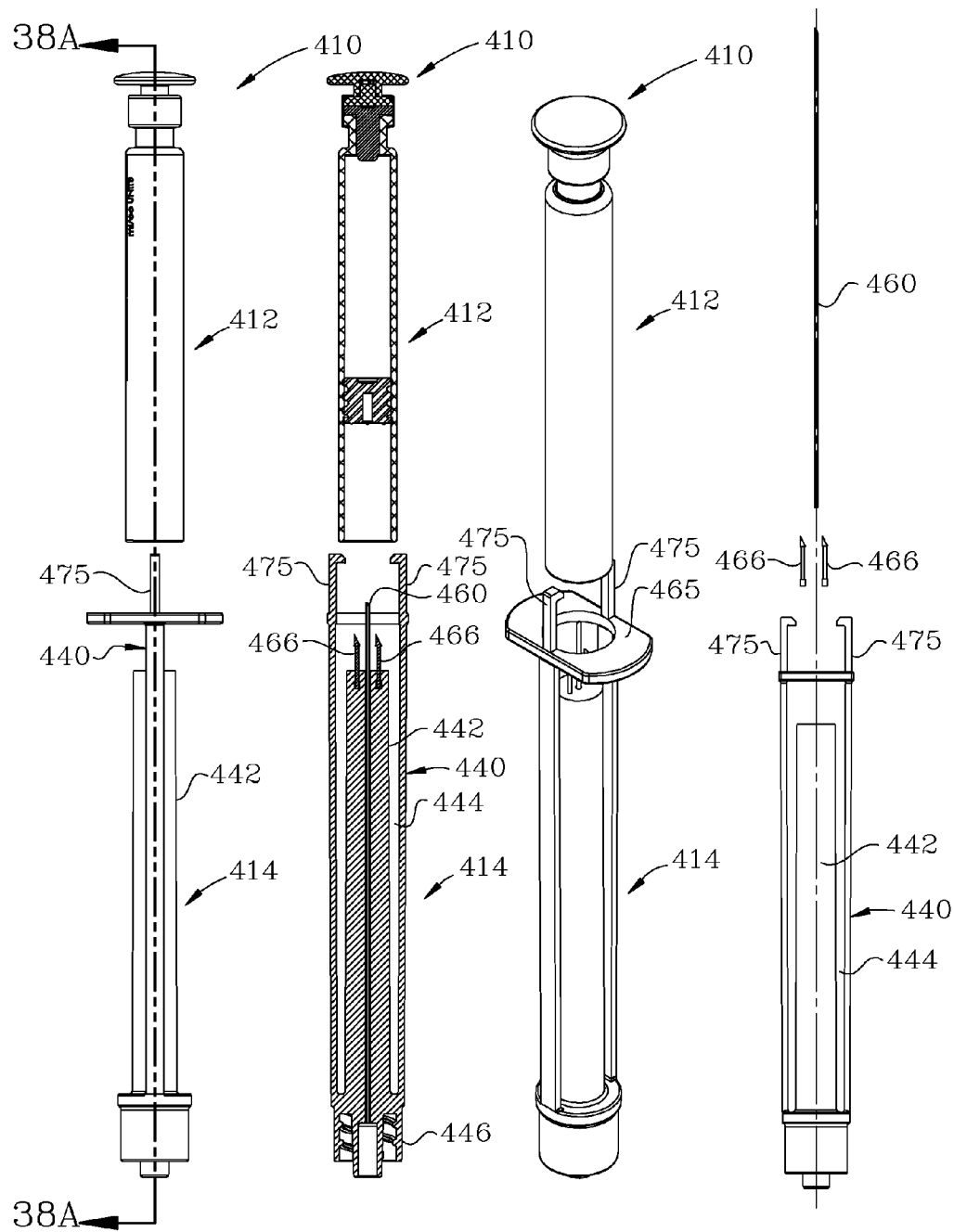

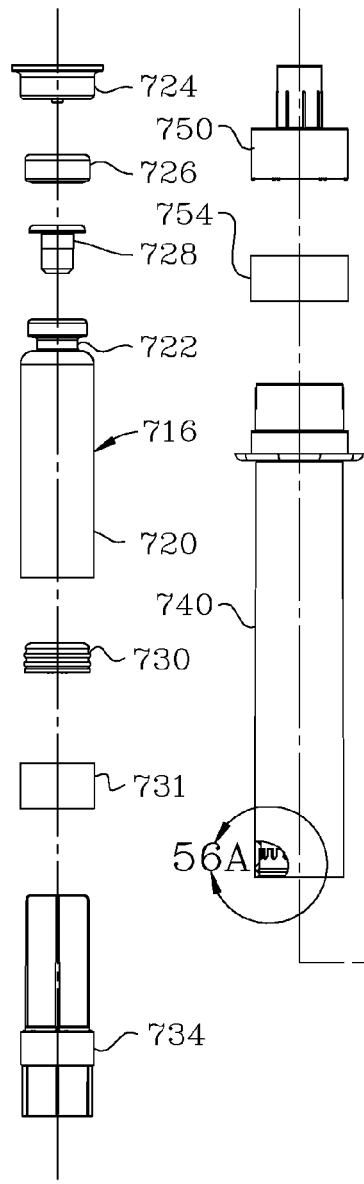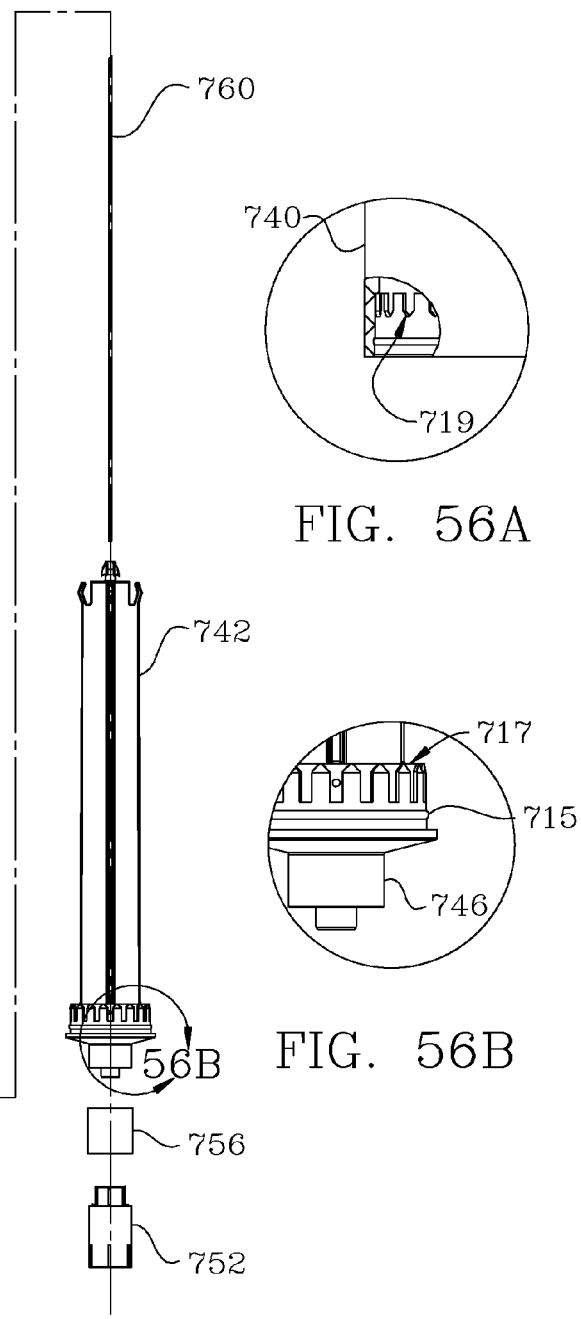
FIG. 55 FIG. 56 FIG. 56A FIG. 56B

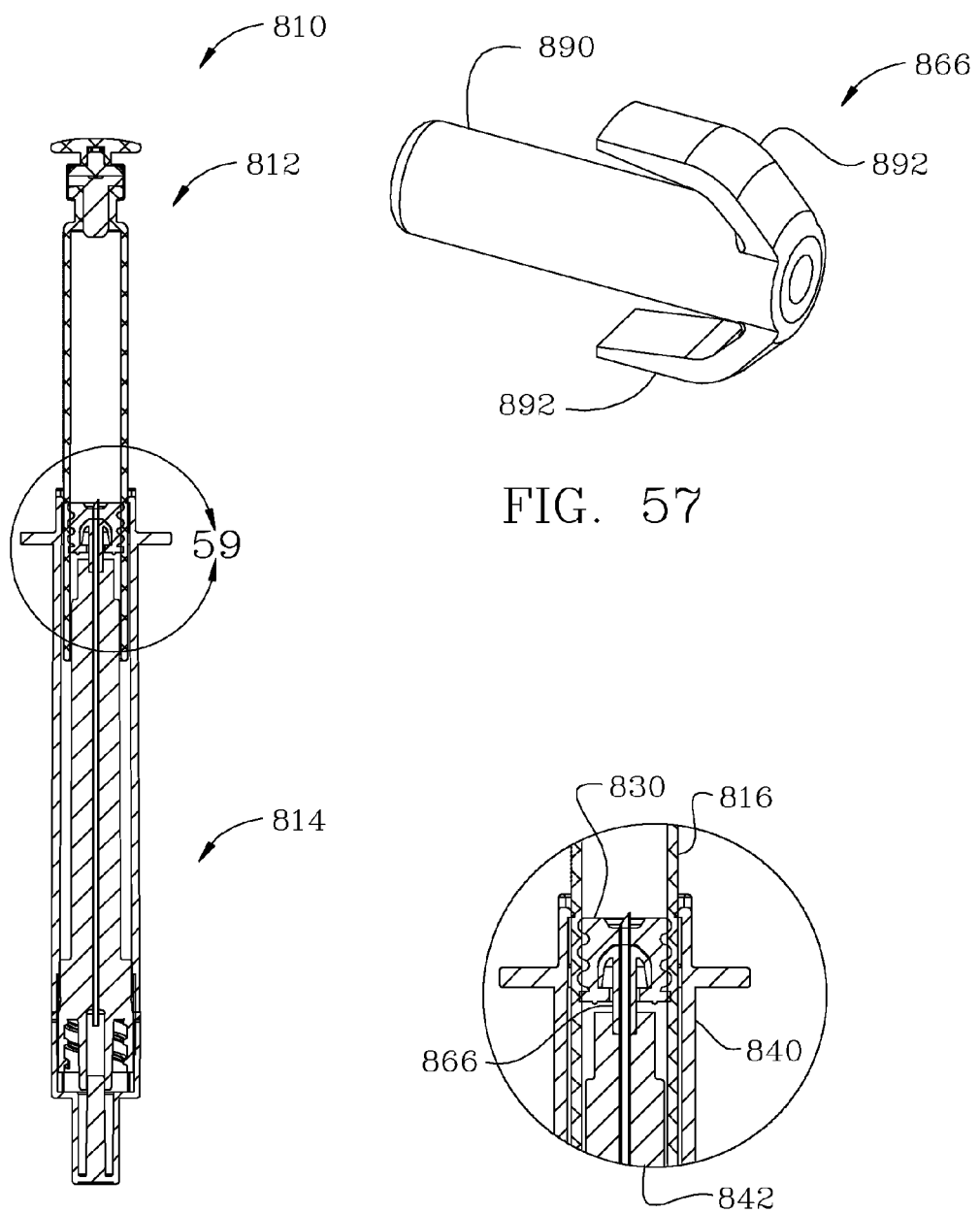

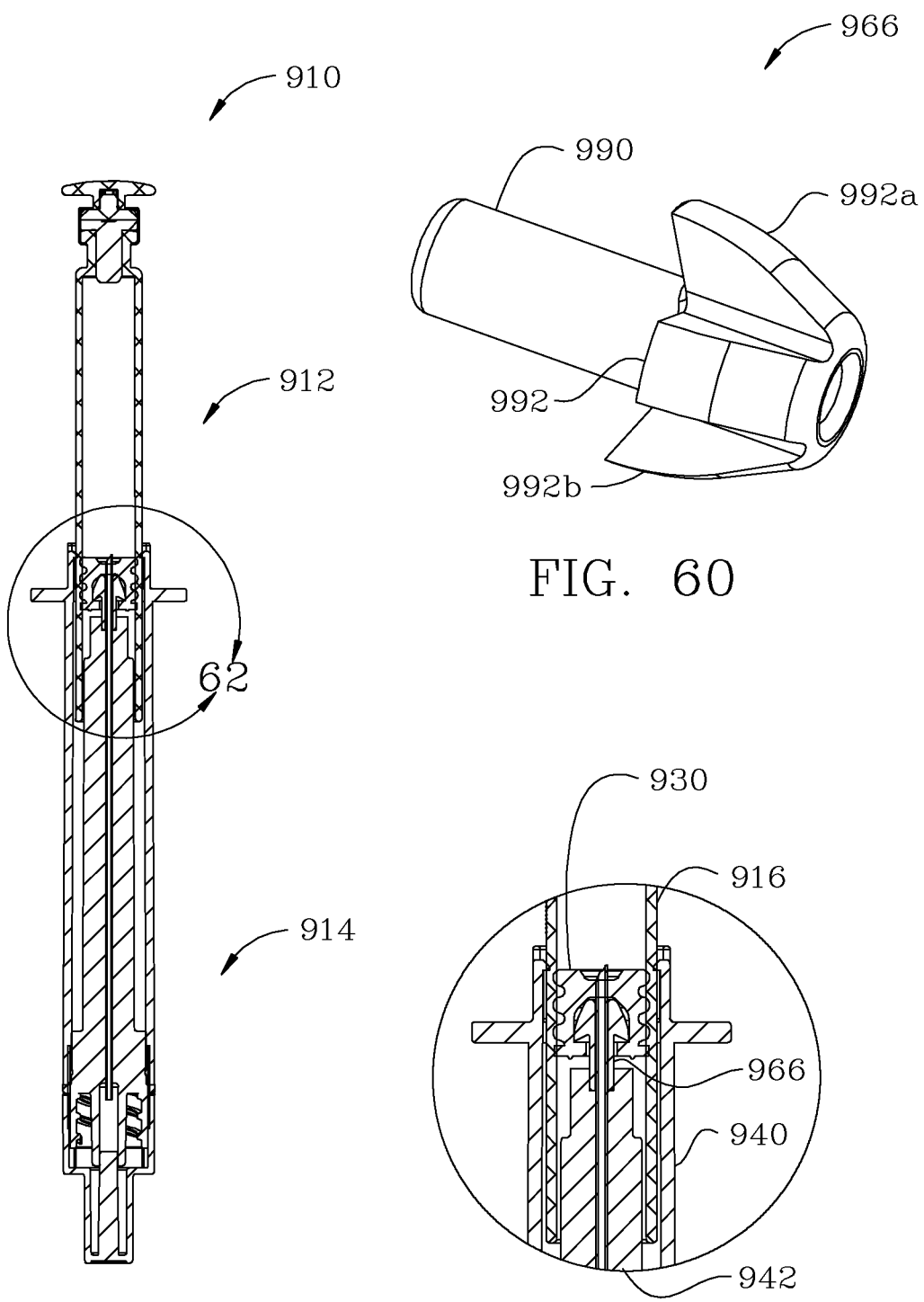

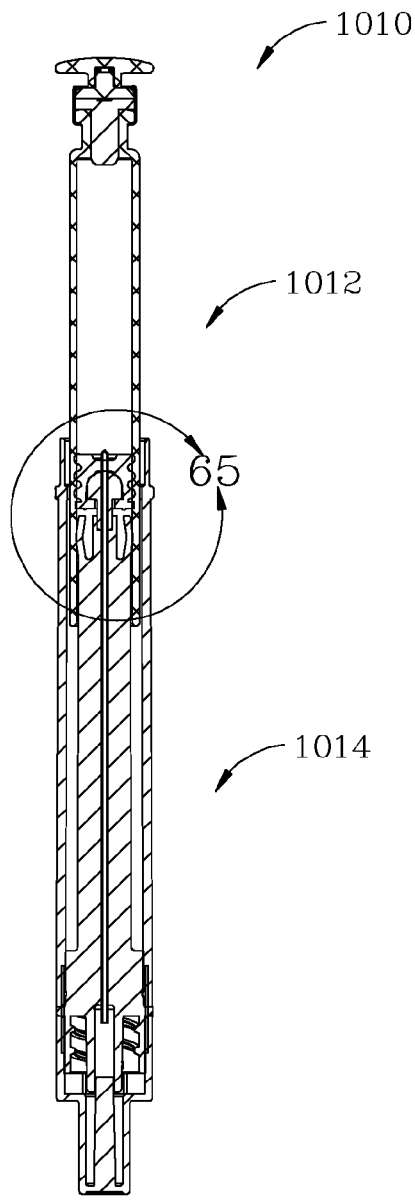
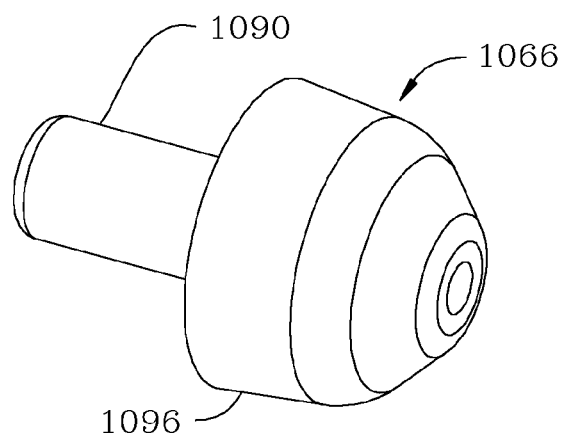
FIG. 63
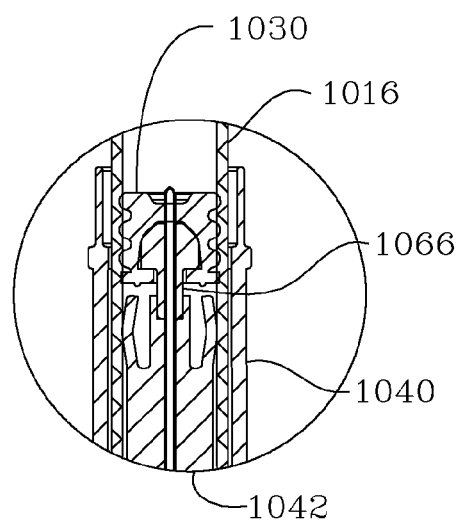
FIG. 64  FIG. 65

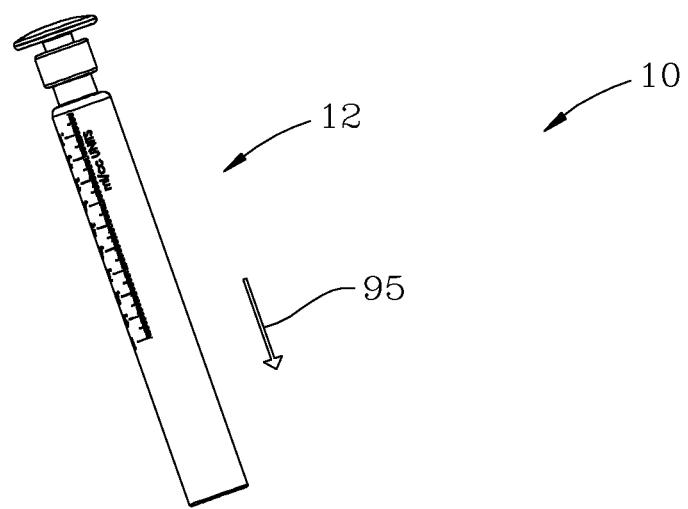
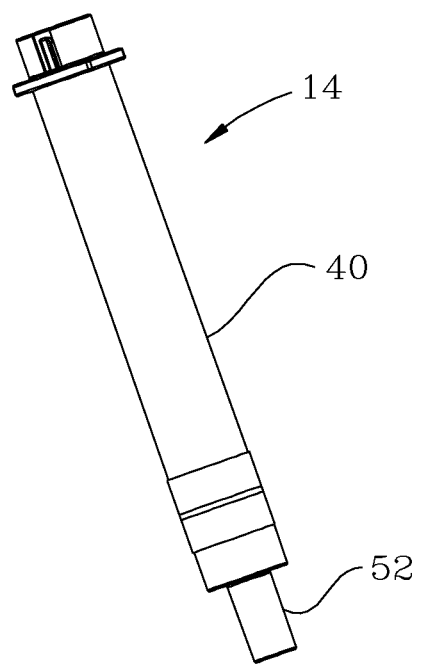
FIG. 66B

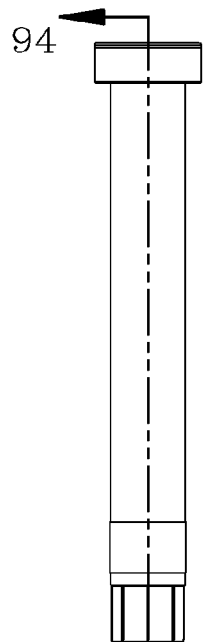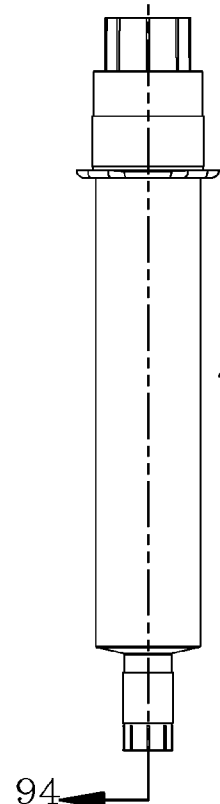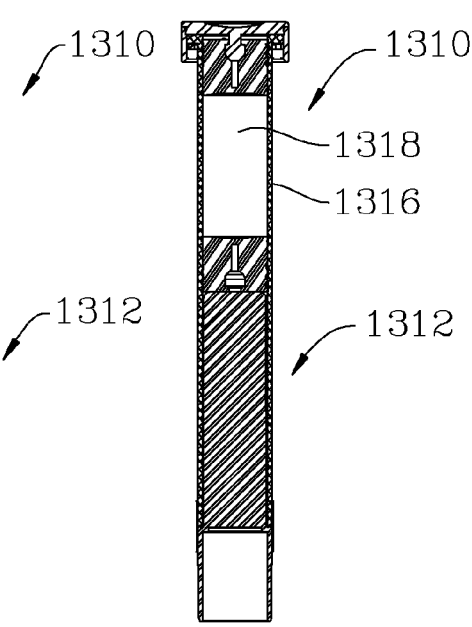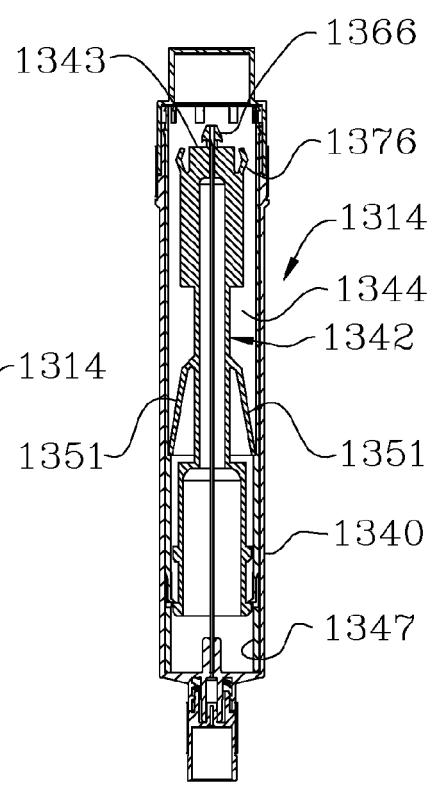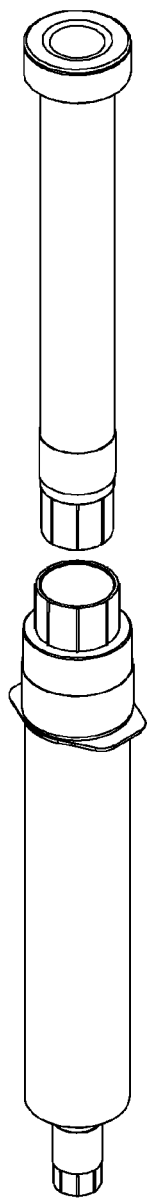
FIG. 93  FIG. 94  FIG. 95

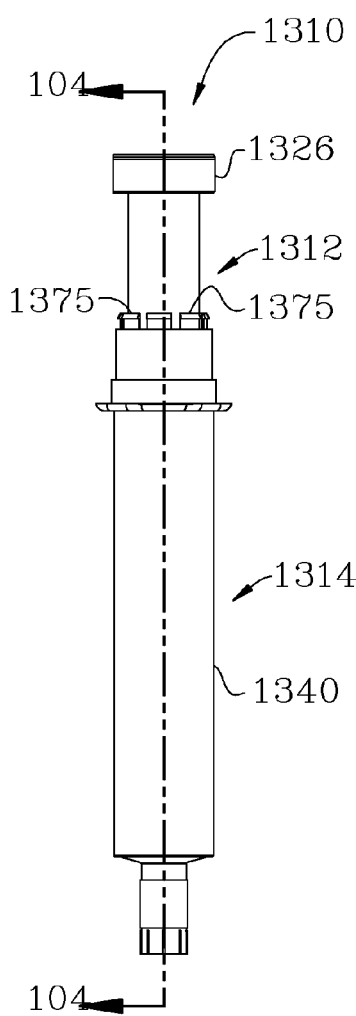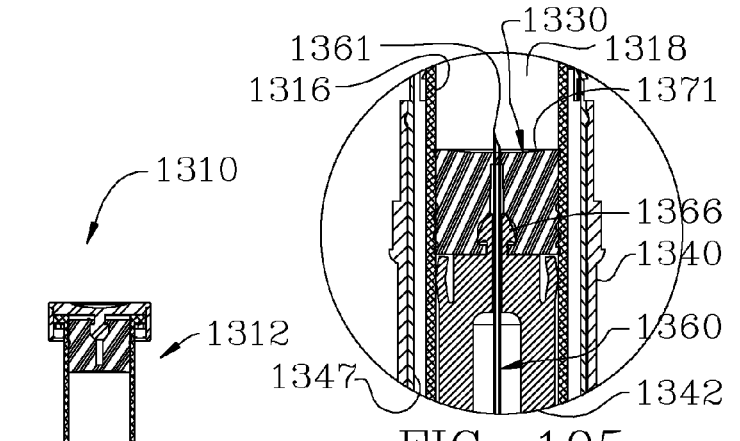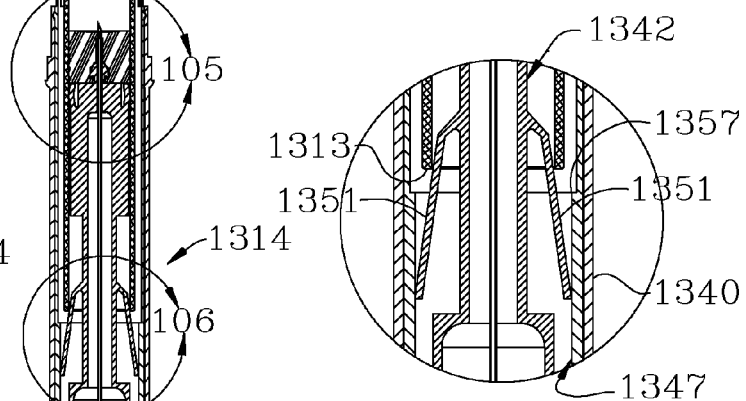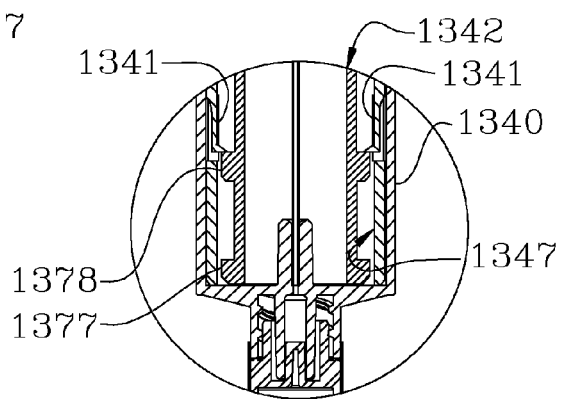
FIG. 103   FIG. 104   FIG. 105   FIG. 106   FIG. 107

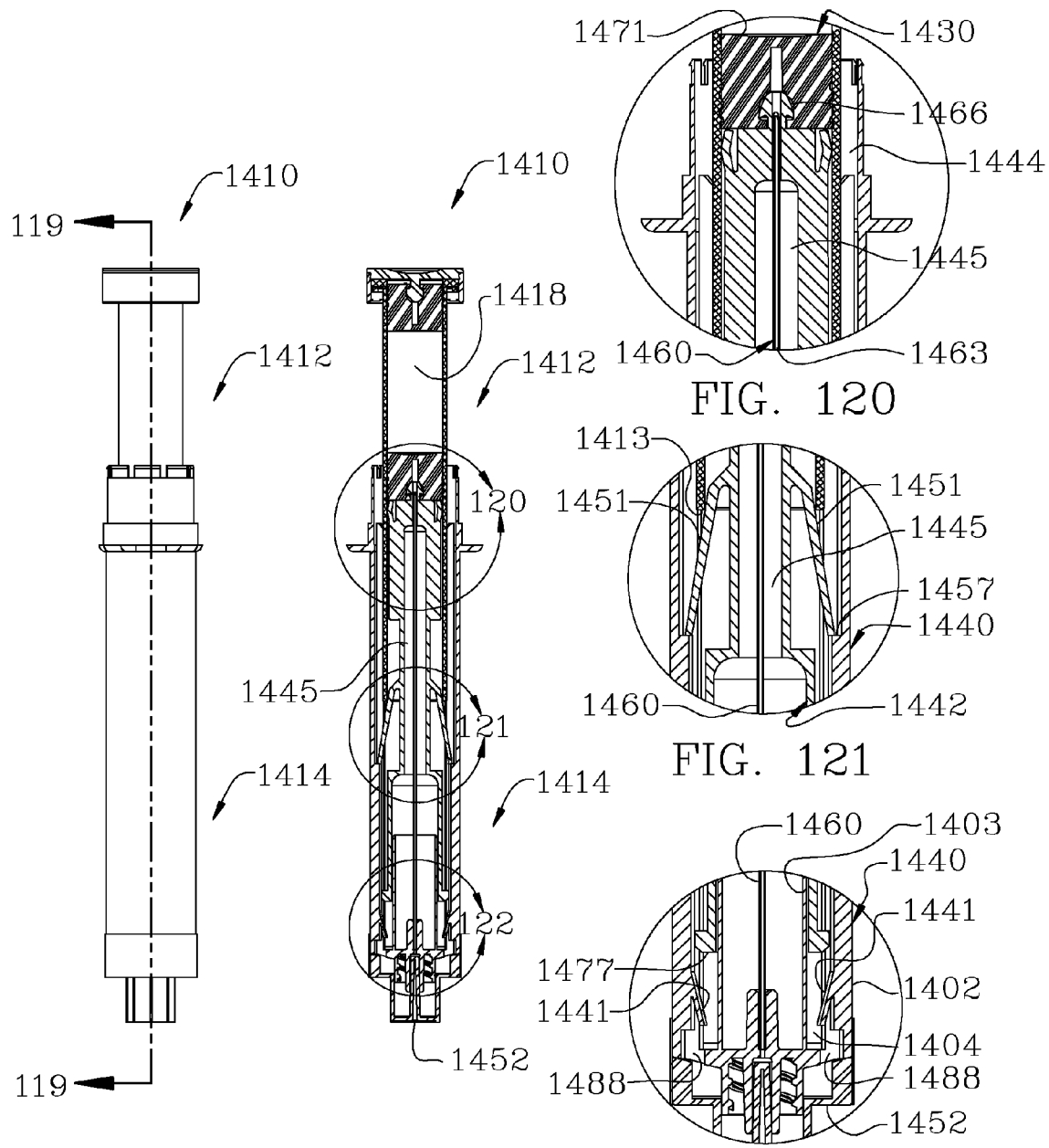

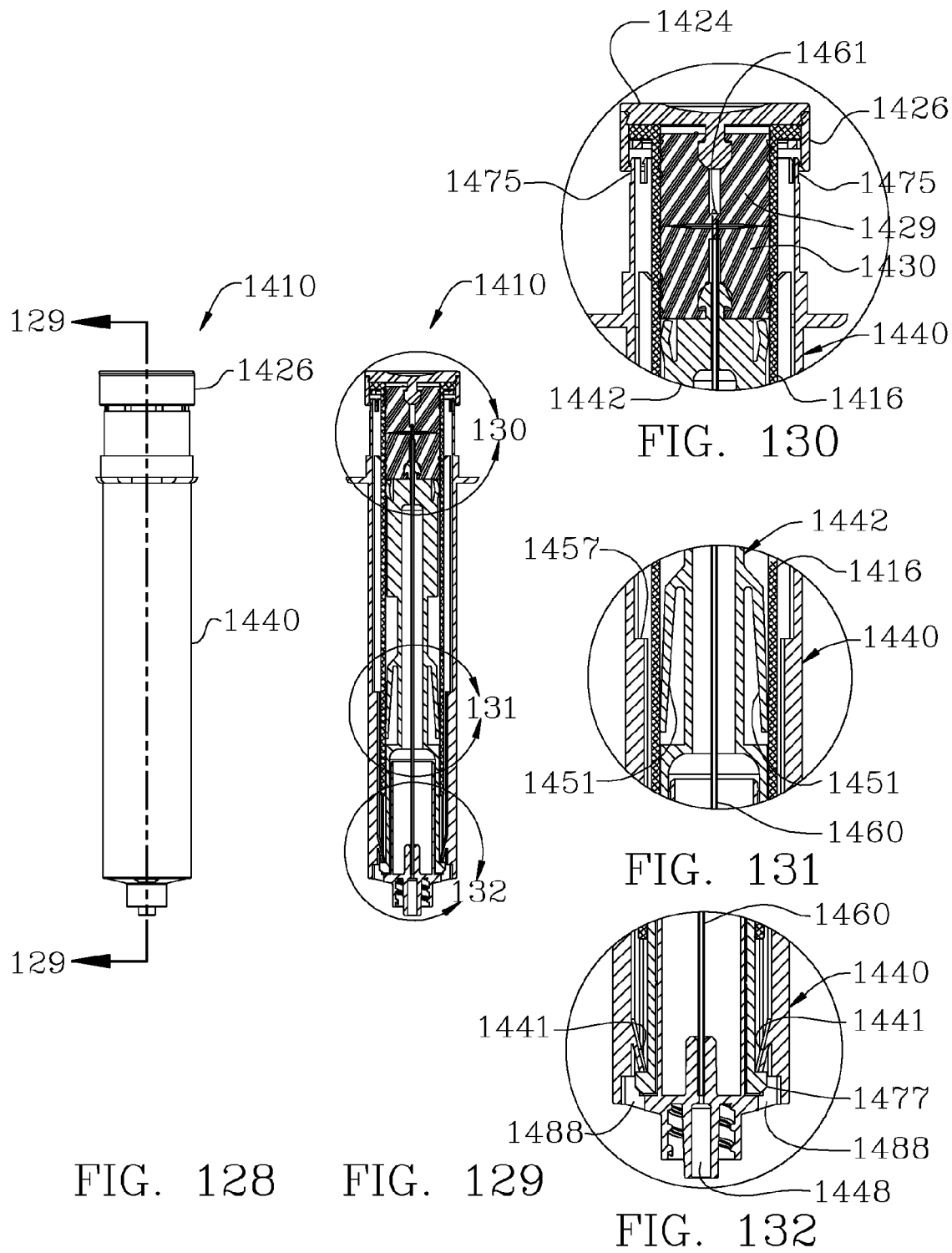

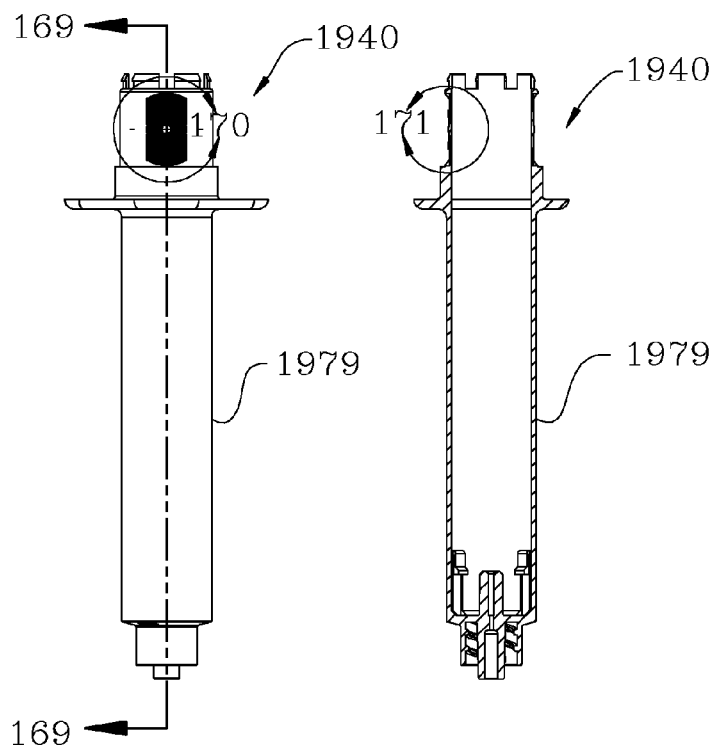
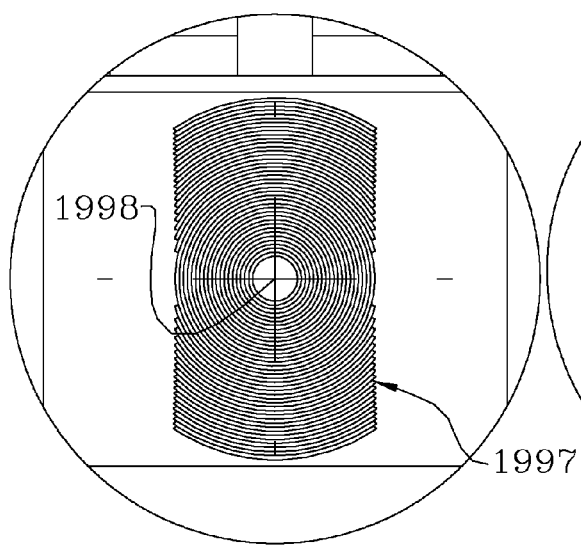
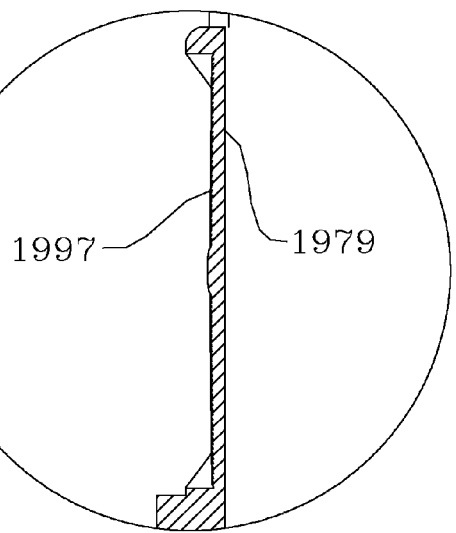
FIG. 168  FIG. 169  FIG. 170  FIG. 171

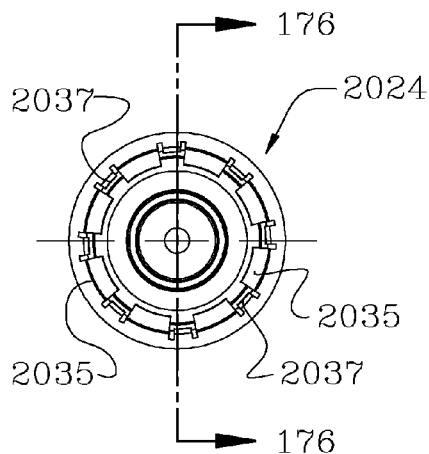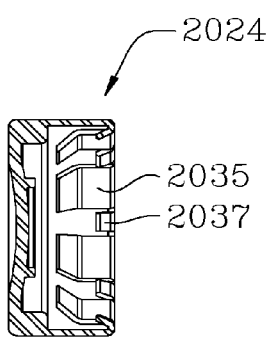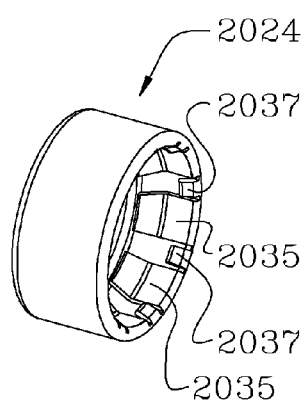
FIG. 175  FIG. 176  FIG. 177
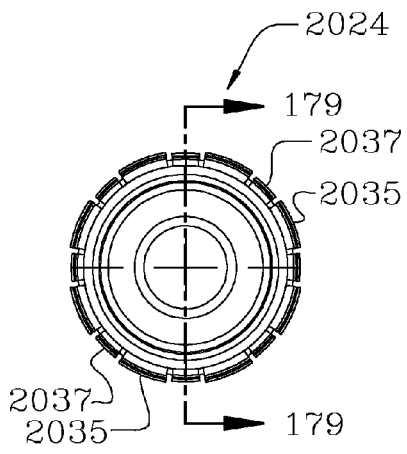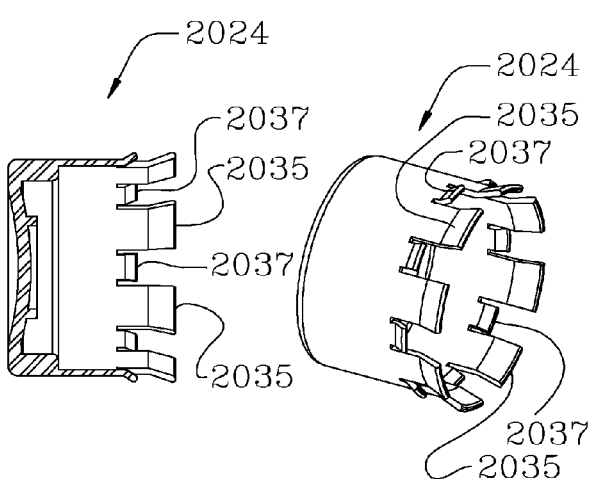
FIG. 178  FIG. 179  FIG. 180

FLUID DELIVERY DEVICE AND METHODS

REFERENCE TO RELATED APPLICATION

The present application claims priority of U.S. provisional application Ser. No. 61/585,017, filed Jan. 10, 2012, U.S. provisional application Ser. No. 61/552,241, filed Oct. 27, 2011, U.S. provisional application Ser. No. 61/541,002, filed Sep. 29, 2011, U.S. provisional application Ser. No. 61/540,517, filed Sep. 28, 2011, U.S. provisional application Ser. No. 61/521,503, filed Aug. 9, 2011, and U.S. provisional application Ser. No. 61/506,498, filed Jul. 11, 2011, and hereby incorporates these same applications herein by reference in their entirety.

TECHNICAL FIELD

This application relates generally to fluid delivery devices, and more particularly to fluid delivery devices that can be used to deliver medicinal fluids, and also relates to associated methods of manufacturing and using such fluid delivery devices.

BACKGROUND

Known devices used to administer medicinal fluids include syringes. Syringes typically include a cylindrical tube, or barrel, a plunger that is movable distally and proximally within a chamber defined by the cylindrical tube, and a needle coupled to one end of the cylindrical tube. Typically, medicinal fluid is aspirated into the chamber defined by the cylindrical tube by inserting the needle into a cartridge or vial containing medicinal fluid and then withdrawing the plunger proximally. Syringes are used to administer medicinal fluids to a patient directly, by injection, and indirectly, for example in conjunction with an intravenous set.

SUMMARY

According to one embodiment, a fluid delivery device includes a cartridge and a syringe. The cartridge includes a housing and a stopper. The housing defines a fluid chamber and the stopper is positioned within the fluid chamber and includes a proximal surface. The syringe includes an outer body, an inner core, and a needle. The outer body and the inner core cooperate to define a cavity configured to receive at least a portion of the housing of the cartridge. The needle defines a lumen and includes a proximal tip. When the fluid delivery device is in a first configuration, at least a portion of the cartridge is positioned within the syringe, the stopper of the cartridge is connected to the inner core, and the proximal tip of the needle is positioned distal of the proximal surface of the stopper. When the fluid delivery device is in a second configuration, the proximal tip of the needle extends through the proximal surface of the stopper such that the lumen defined by the needle is in fluid communication with the fluid chamber, wherein the inner core and the stopper are movable distally relative to the outer body and the needle as the fluid delivery device is transitioned from the first configuration to the second configuration. When the fluid delivery device is in a third configuration, the cartridge and the syringe cooperate to prevent relative axial movement between the cartridge and the syringe such that the fluid delivery device is disabled.

According to another embodiment, a fluid delivery device includes a cartridge and a syringe. The cartridge includes a housing and a stopper. The housing defines a fluid chamber and the stopper is positioned within the fluid chamber and includes a proximal surface. The syringe includes an outer body, an inner core, a barb, and a needle. The outer body and the inner core cooperate to define a cavity configured to receive at least a portion of the housing and the cartridge. The inner core is integrally formed with the barb as a unitary structure, and the inner core and the barb cooperate to define a first lumen. The needle defines a second lumen and includes a proximal tip. When the fluid delivery device is in a first configuration, at least a portion of the cartridge is positioned within the syringe, the barb of the syringe is connected to the stopper of the cartridge, and the proximal tip of the needle is positioned within the first lumen defined by the inner core and the barb. When the fluid delivery device is in a second configuration, the proximal tip of the needle extends beyond the barb and through the proximal surface of the stopper such that the second lumen defined by the needle is in fluid communication with the fluid chamber, wherein the inner core, the barb, and the stopper are movable distally relative to the outer body and the needle as the fluid delivery device is transitioned from the first configuration to the second configuration. When the fluid delivery device is in a third configuration, the cartridge and the syringe cooperate to prevent relative axial movement between the cartridge and the syringe such that the fluid delivery device is disabled.

According to another embodiment, a fluid delivery device includes a cartridge and a syringe. The cartridge includes a housing and a stopper. The housing defines a fluid chamber and the stopper is positioned within the fluid chamber and includes a proximal surface. The syringe includes an outer body, an inner core, a barb, a needle, and a male luer connection. The outer body and the inner core cooperate to define a cavity configured to receive at least a portion of the housing of the cartridge. The inner core is integrally formed with the barb as a unitary structure, and the inner core and the barb cooperate to define a first lumen. The needle defines a second lumen and includes a proximal tip. The male luer connection is integral with the outer body and defines a third lumen. The outer body of the syringe includes a plurality of circumferentially spaced retaining fingers and at least one flexible tab. The inner core of the syringe includes a distal end. The distal end of the inner core defines an annular notch and includes a proximal surface. When the fluid delivery device is in a first configuration, at least a portion of the cartridge is positioned within the syringe, the barb of the syringe is connected to the stopper of the cartridge, the at least one flexible tab of the outer body engages the annular notch defined by the inner core, and the proximal tip of the needle is positioned within the first lumen defined by the inner core and the barb and is distal of the proximal surface of the stopper. When the fluid delivery device is in a second configuration, the proximal tip of the needle extends beyond the barb and through the proximal surface of the stopper such that the second lumen defined by the needle is in fluid communication with the fluid chamber, wherein the inner core, the barb, and the stopper are movable distally relative to the outer body and the needle as the fluid delivery device is transitioned from the first configuration to the second configuration. When the fluid delivery device is in a third configuration, at least some of the retaining fingers of the outer body of the syringe engage the cartridge to prevent relative axial movement between the cartridge and the syringe such that the fluid delivery device is disabled. The at least one flexible tab of the outer body is disengaged from the annular notch defined by the inner core when the fluid delivery device is in each of the second and third configurations. The second lumen defined by the needle is in fluid communication with the third lumen defined by the male luer connection when the fluid delivery device is in each of the first, second and third configurations.

BRIEF DESCRIPTION OF THE DRAWINGS

It is believed that certain embodiments will be better understood from the following description taken in conjunction with the accompanying drawings in which:

FIG. 7 is an enlarged view of the encircled portion of FIG. 6, depicting a needle of the syringe extending through a stopper of the cartridge and into a fluid chamber defined by the cartridge;

FIG. 8 is a side elevational view of the fluid delivery device of FIG. 1, similar to FIG. 5, but depicting the cartridge translated distally within the syringe, relative to the position of the cartridge shown in FIG. 5, to achieve fluid delivery;

FIG. 9 is a cross-sectional view taking along line 9-9 in FIG. 8;

FIG. 10 is an enlarged view of a first encircled portion of FIG. 9, depicting the stopper of the cartridge positioned within the fluid chamber and in contacting engagement with a proximal neck of a housing of the cartridge, and depicting a plug extending through the neck, with the needle extending through the stopper and into the plug;

FIG. 11 is an enlarged view of a second encircled portion of FIG. 9;

FIG. 12 is a front elevational view of a fluid delivery device according to another embodiment, depicting a cartridge and a syringe of the fluid delivery device disconnected from one another;

FIG. 13 is an exploded view of the cartridge of the fluid delivery device of FIG. 12;

FIG. 14 is an exploded view of the syringe of the fluid delivery device of FIG. 12;

FIG. 21 is a side elevational view of a fluid delivery device according to another embodiment, depicting a cartridge and a syringe of the fluid delivery device disconnected from one another;

FIG. 21A is a cross-sectional view taken along line 21A-21A in FIG. 21;

FIG. 22 is an exploded view of the syringe of the fluid delivery device of FIG. 21;

FIG. 38 is a side elevational view of a fluid delivery device according to another embodiment, depicting a cartridge and a syringe of the fluid delivery device disconnected from one another;

FIG. 38A is a cross-sectional view taken along line 38A-38A in FIG. 38;

FIG. 38B is a perspective view of the fluid delivery device of FIG. 38, depicting the cartridge and the syringe disconnected from one another;

FIG. 39 is an exploded view of the syringe of the fluid delivery device of FIG. 38;

FIG. 54A is an enlarged view of the encircled portion of FIG. 54;

FIG. 55 is an exploded view of the cartridge of the fluid delivery device of FIG. 53;

FIG. 56 is an exploded view of the syringe of the fluid delivery device of FIG. 53 with a portion of the syringe shown in cutaway view;

FIG. 56A is an enlarged view of a first encircled portion of FIG. 56 with a portion of the syringe shown in cutaway view;

FIG. 56B is an enlarged view of a second encircled portion of FIG. 56;

FIG. 57 is a perspective view of a barb according to another embodiment, for use with a syringe of a fluid delivery device;

FIG. 58 is a cross-sectional view of a fluid delivery device according to another embodiment, including the barb of FIG. 57;

FIG. 59 is an enlarged view of the encircled portion of FIG. 58;

FIG. 60 is a perspective view of a barb according to another embodiment, for use with a syringe of a fluid delivery device;

FIG. 61 is a cross-sectional view of a fluid delivery device according to another embodiment, including the barb of FIG. 60;

FIG. 62 is an enlarged view of the encircled portion of FIG. 61;

FIG. 63 is a perspective view of a barb according to another embodiment, for use with a syringe of a fluid delivery device;

FIG. 64 is a cross-sectional view of a fluid delivery device according to another embodiment, including the barb of FIG. 63;

FIG. 65 is an enlarged view of the encircled portion of FIG. 64; and

FIGS. 66A-66D illustrate a method of use, according to one embodiment, of the fluid delivery device of FIG. 1;

FIG. 74 is an enlarged view of a first encircled portion of FIG. 73, depicting a movable stopper of the cartridge connected to an inner core of the syringe, and depicting a proximal tip of a needle of the syringe positioned distal of a proximal surface of the movable stopper;

FIG. 78 is an enlarged view of a first encircled portion of FIG. 77, depicting the proximal tip of the needle extending through the proximal surface of the movable stopper such that a lumen defined by the needle is in fluid communication with a fluid chamber defined by a housing of the cartridge;

FIG. 91 is an enlarged view of a first encircled portion of FIG. 90, depicting a movable stopper of the cartridge engaged with a fixed stopper of the cartridge, depicting a needle of the syringe extending through the movable stopper and into the fixed stopper, and depicting a proximal collar of an outer body of the syringe surrounding a proximal button and a collar of the cartridge to disable the fluid delivery device;

FIG. 93 is a side elevational view of a fluid delivery device according to another embodiment, depicting a cartridge and a syringe of the fluid delivery device disconnected from one another;

FIG. 94 is a cross-sectional view taken along line 94-94 in FIG. 93;

FIG. 95 is a perspective view of the fluid delivery device of FIG. 93, with the cartridge and the syringe disconnected from one another;

FIG. 100 is an enlarged view of a first encircled portion of FIG. 99, depicting a movable stopper of the cartridge connected to an inner core of the syringe, and depicting a proximal tip of a needle of the syringe positioned distal of a proximal surface of the movable stopper;

FIG. 101 is an enlarged view of a second encircled portion of FIG. 99, depicting a pair of flexible positioning members of the inner core engaged with an annular ledge of a sleeve of the syringe, and depicting a housing of the cartridge contacting, but not compressing, or flexing, the flexible positioning members;

FIG. 103 is a side elevational view of the fluid delivery device of FIG. 93, depicting the fluid delivery device in a second configuration, with the cartridge translated distally within the syringe, relative to the position of the cartridge shown in FIG. 98, by a relatively small amount such that a lumen defined by the needle of syringe is in fluid communication with a fluid chamber defined by the cartridge;

FIG. 104 is a cross-sectional view taken along line 104-104 in FIG. 103;

FIG. 105 is an enlarged view of a first encircled portion of FIG. 104 depicting the proximal tip of the needle extending through the proximal surface of the movable stopper such that the lumen defined by the needle is in fluid communication with the fluid chamber;

FIG. 106 is an enlarged view of a second encircled portion of FIG. 104, depicting the housing of the cartridge engaged with the flexible positioning members of the inner core such that the flexible positioning members are compressed, or flexed inwardly, positioning and disengaged from the annular ledge of the sleeve;

FIG. 107 is an enlarged view of a third encircled portion of FIG. 104, depicting the flexible tabs of the sleeve engaged with a second annular member of the inner core;

FIG. 111 is an enlarged view of a second encircled portion of FIG. 109, depicting the housing of the cartridge engaged with the flexible positioning members of the inner core such that the flexible positioning members are flexed farther inwardly relative to the position of the flexible positioning members shown in FIG. 106;

FIG. 112 is an enlarged view of a third encircled portion of FIG. 109, depicting the flexible tabs of the sleeve engaged with the second annular member of the inner core;

FIG. 113 is a side elevational view of a fluid delivery device according to another embodiment, depicting a cartridge and a syringe of the fluid delivery device disconnected from one another;

FIG. 114 is a cross-sectional view taken along line 114-114 in FIG. 113;

FIG. 115 is a perspective view of the fluid delivery device of FIG. 113, with the cartridge and the syringe disconnected from one another;

FIG. 116 is an exploded view of the cartridge of the fluid delivery device of FIG. 113;

FIG. 117 is an exploded view of the syringe of the fluid delivery device of FIG. 113;

FIG. 118 is a side elevational view of the fluid delivery device of FIG. 113, depicting the fluid delivery device in a first configuration, with the cartridge and the syringe connected to one another;

FIG. 119 is a cross-sectional view taken along line 119-119 in FIG. 118;

FIG. 120 is an enlarged view of a first encircled portion of FIG. 119, depicting a movable stopper of the cartridge connected to an inner core of the syringe, and depicting a proximal tip of a needle of the syringe positioned distal of a proximal surface of the movable stopper;

FIG. 121 is an enlarged view of a second encircled portion of FIG. 119, depicting a pair of flexible positioning members of the inner core engaged with an annular ledge of an outer body of the syringe, and depicting a housing of the cartridge contacting, but not compressing, or flexing, the flexible positioning members:

FIG. 122 is an enlarged view of a third encircled portion of FIG. 119, depicting an annular member of the inner core positioned proximally of a pair of flexible tabs of an outer body of the syringe;

Figure 67:
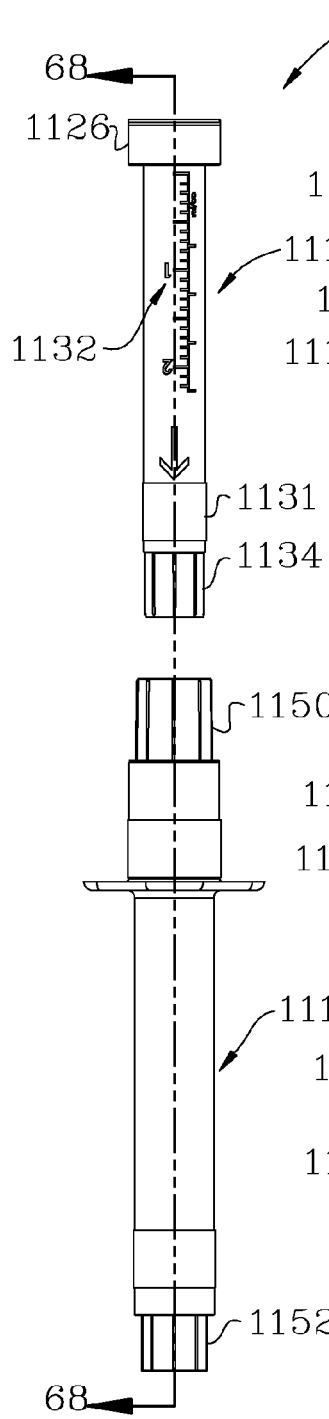
FIG. 67 is a front elevational view of a fluid delivery device according to another embodiment, depicting a cartridge and a syringe of the fluid delivery device disconnected from one another.
Figures 113, 114, 115:
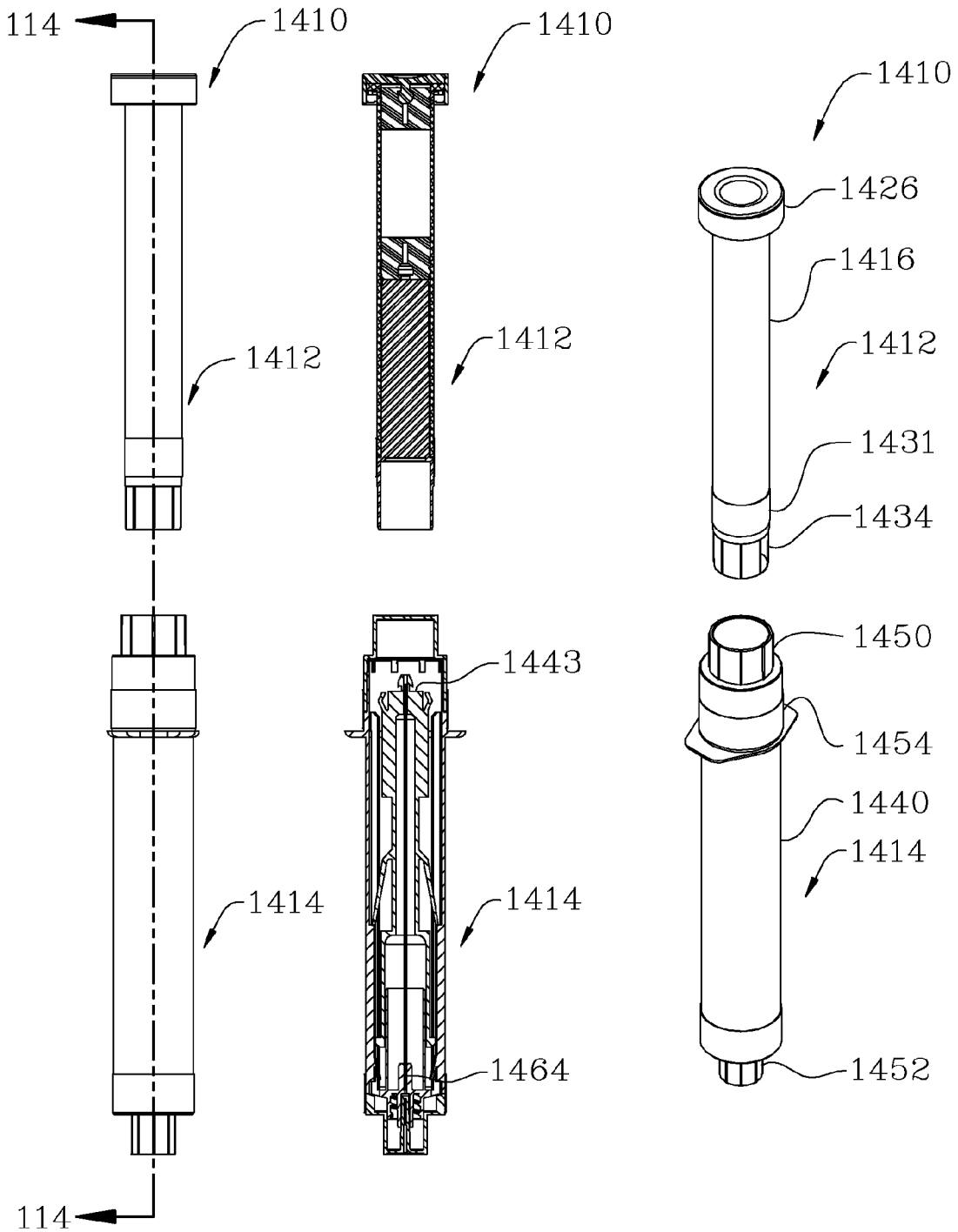
Figure 116:
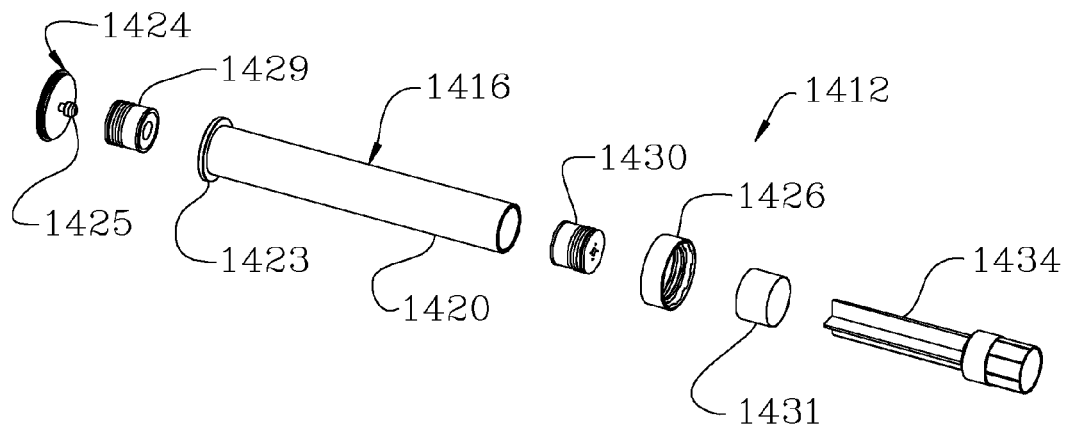
Figure 117:
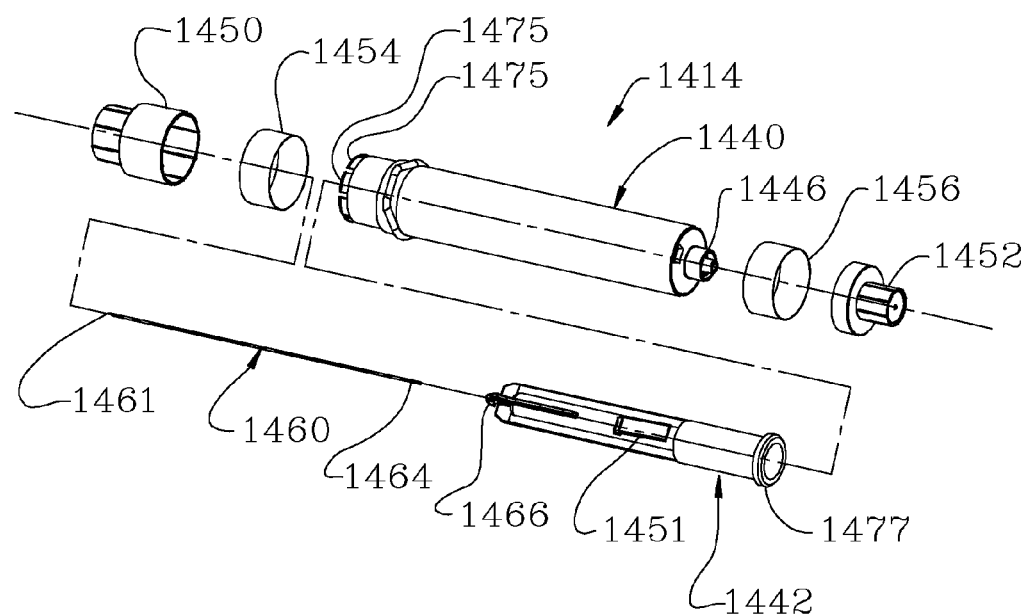
Figures 123, 124, 127:
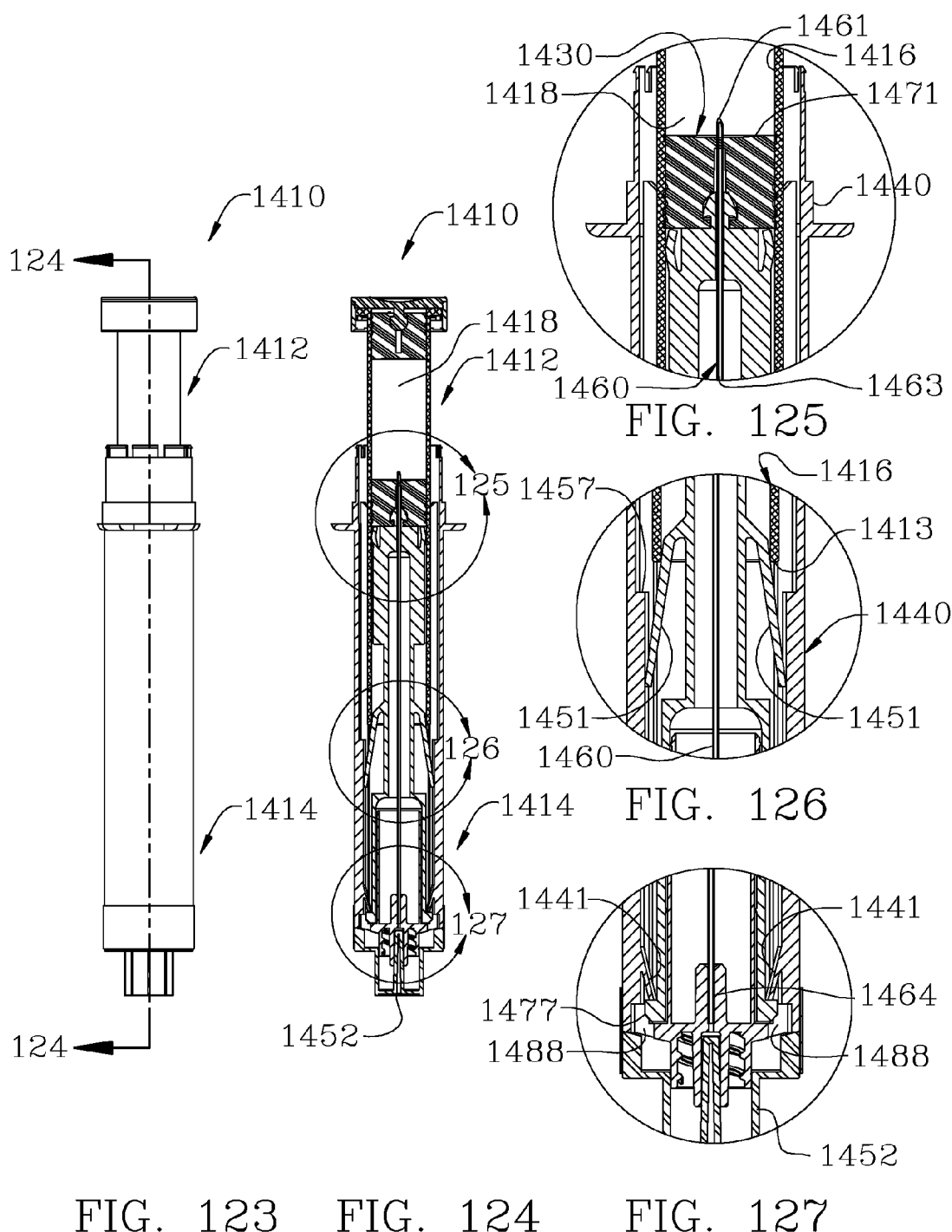
Figures 133, 134, 135:
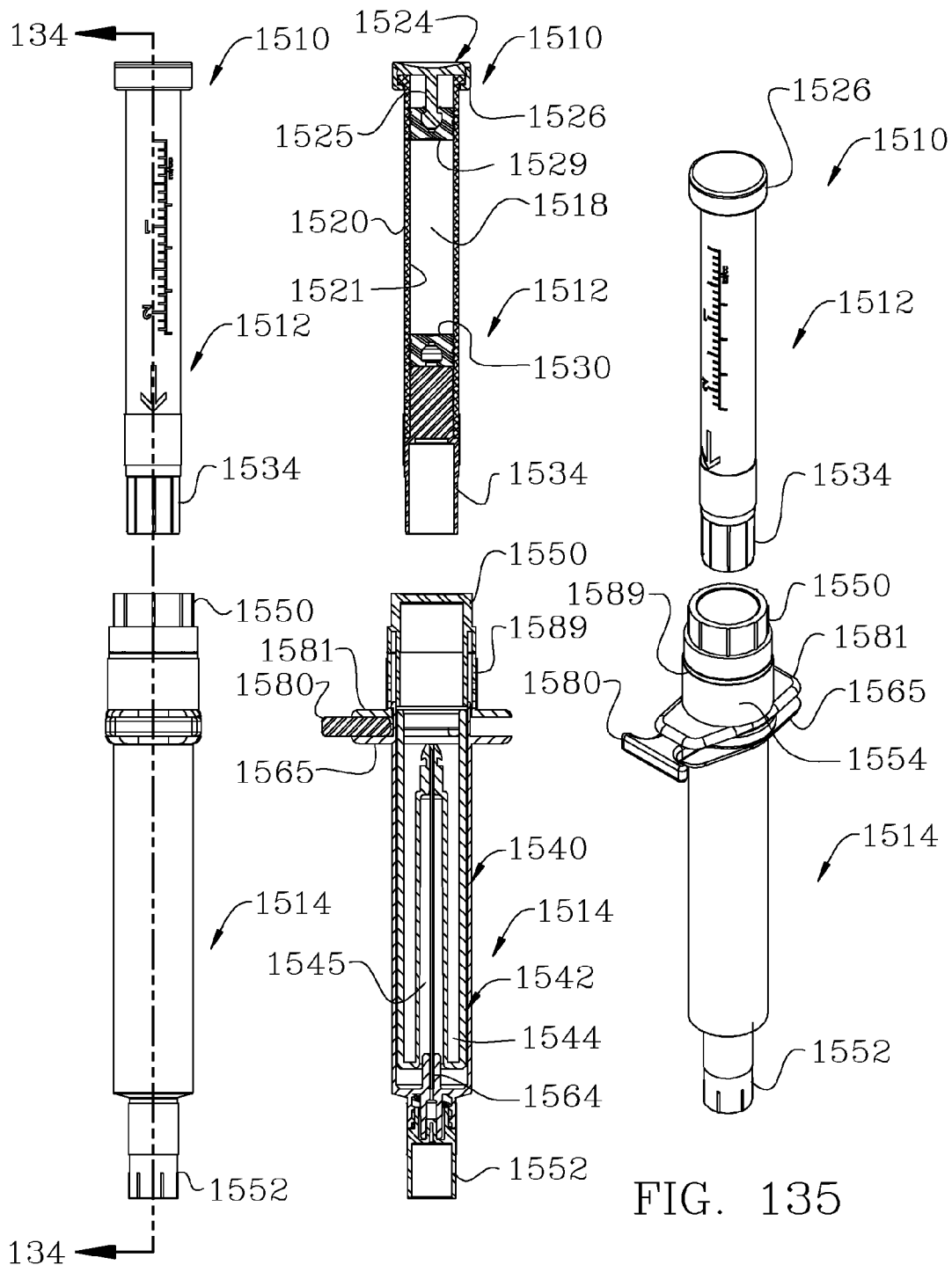
Figure 136:
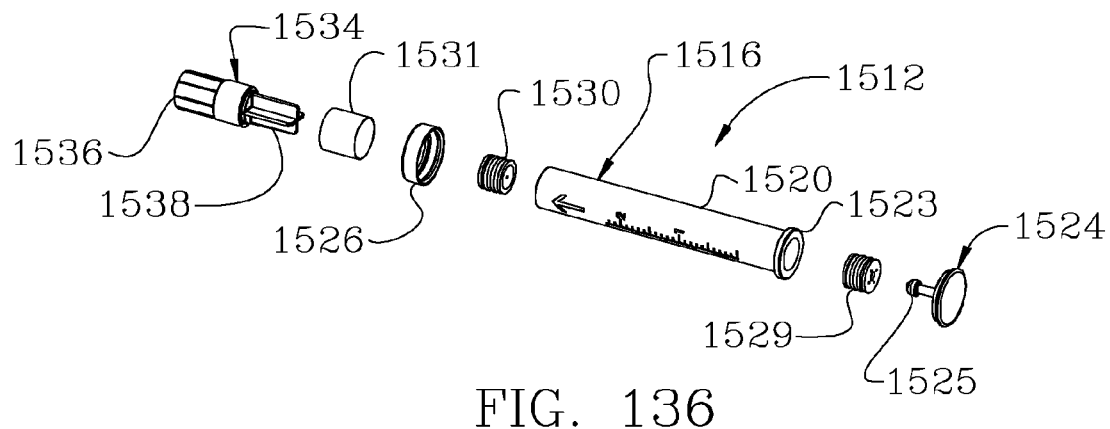
Figure 137:
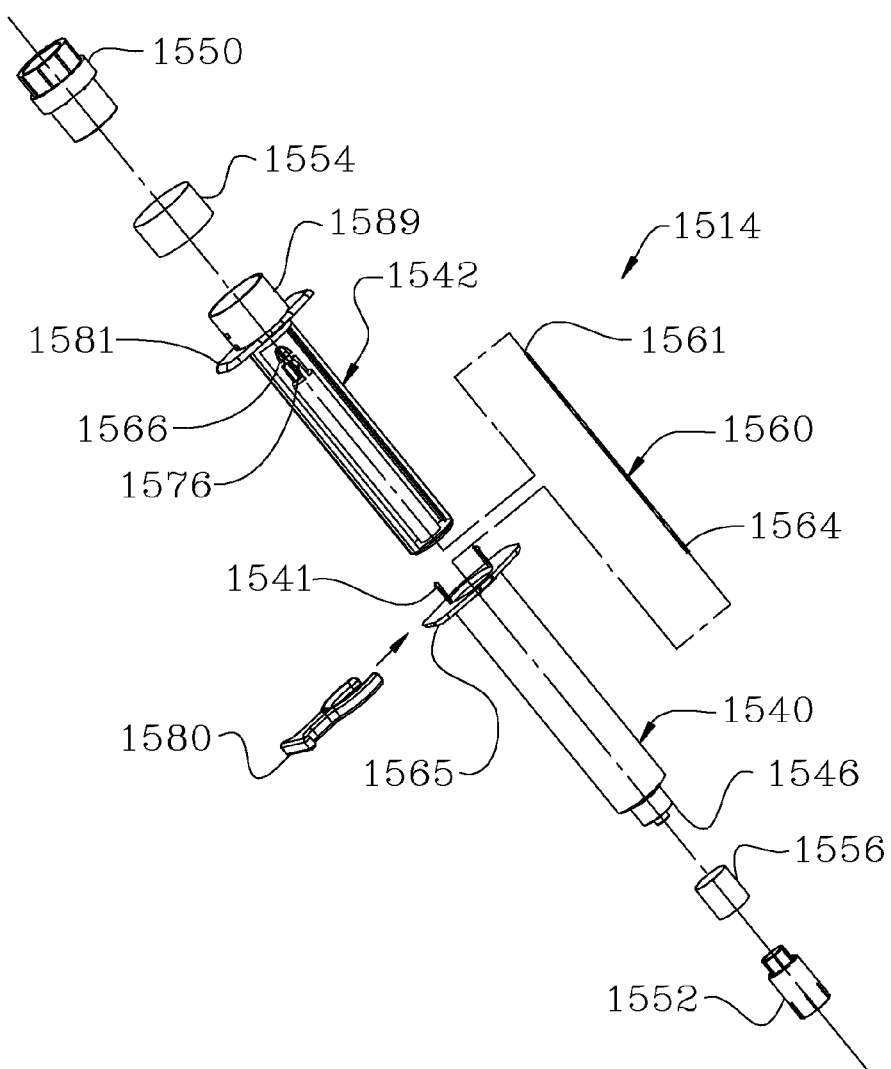
Figures 138, 139, 141:
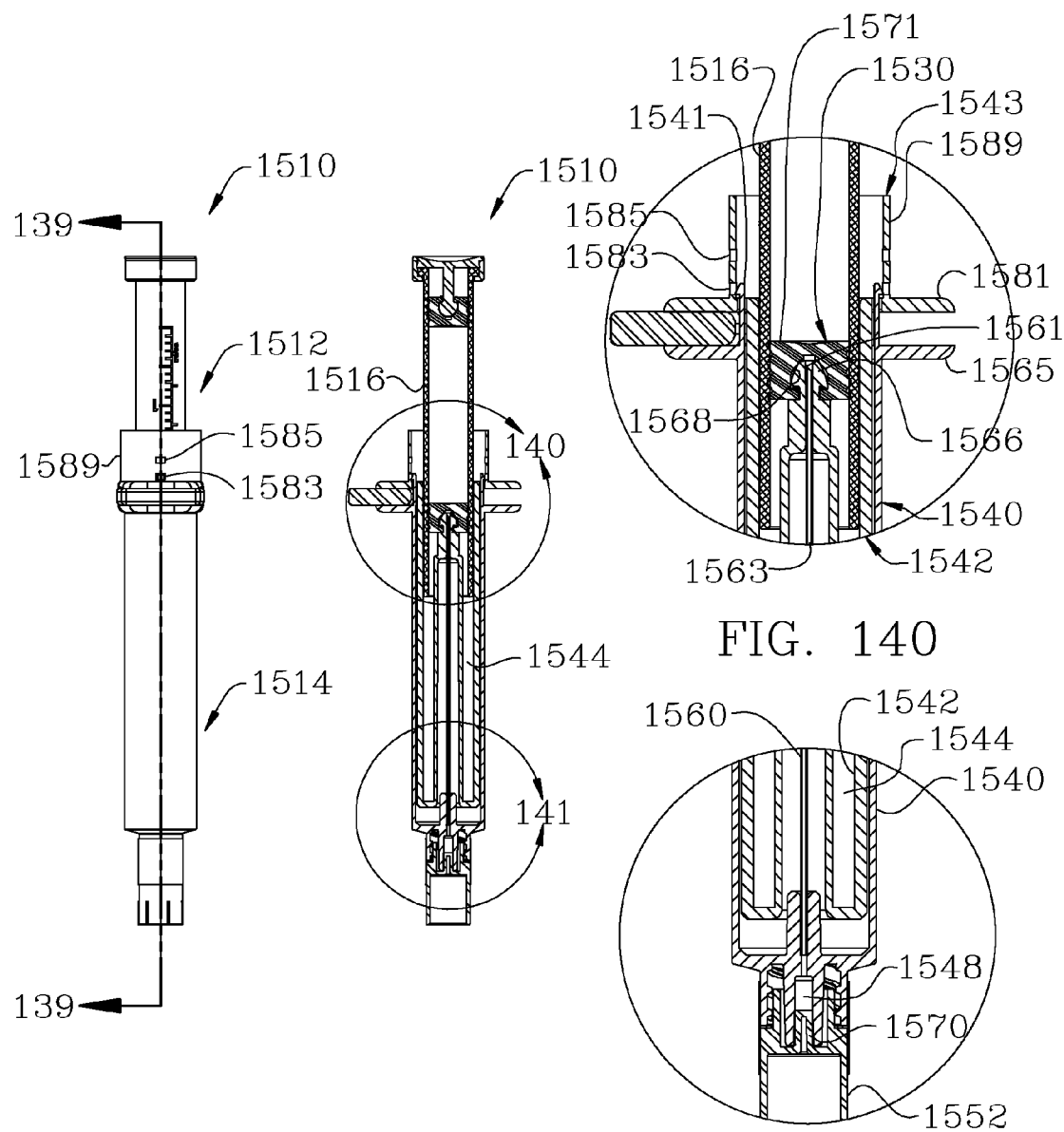
Figures 142, 143, 144, 145:
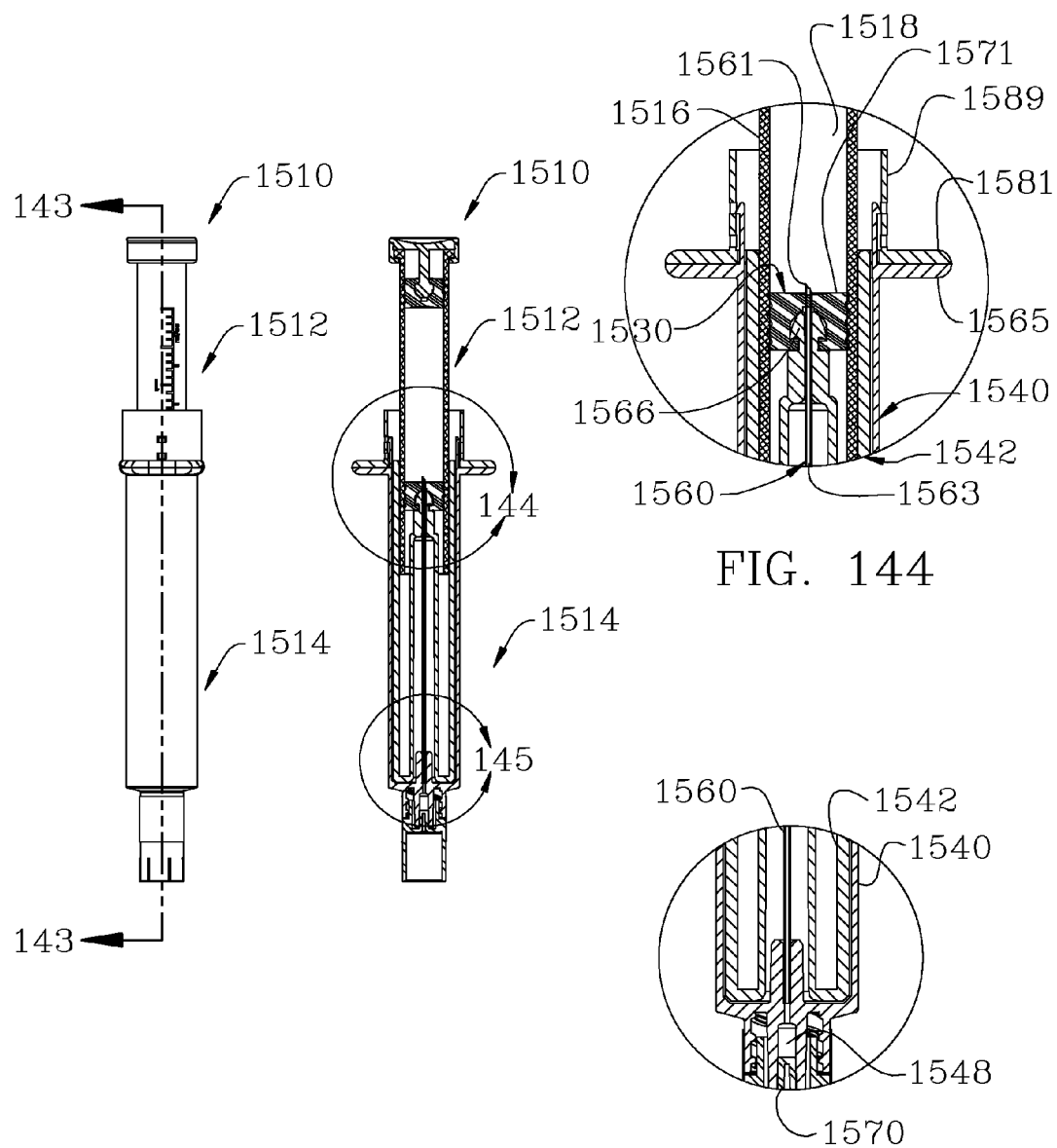
Figures 146, 147, 148, 149:
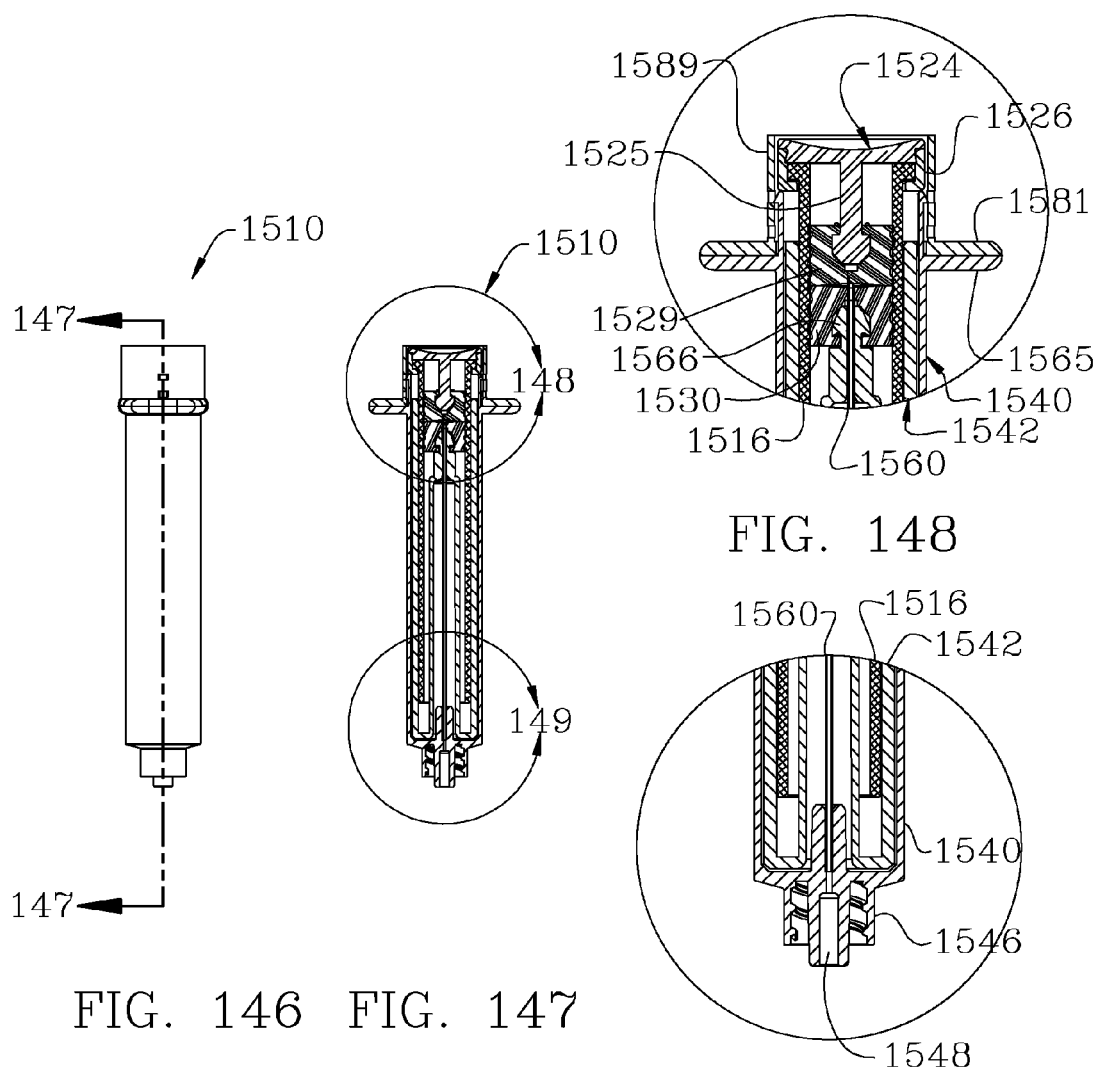
Figures 150, 151, 152:
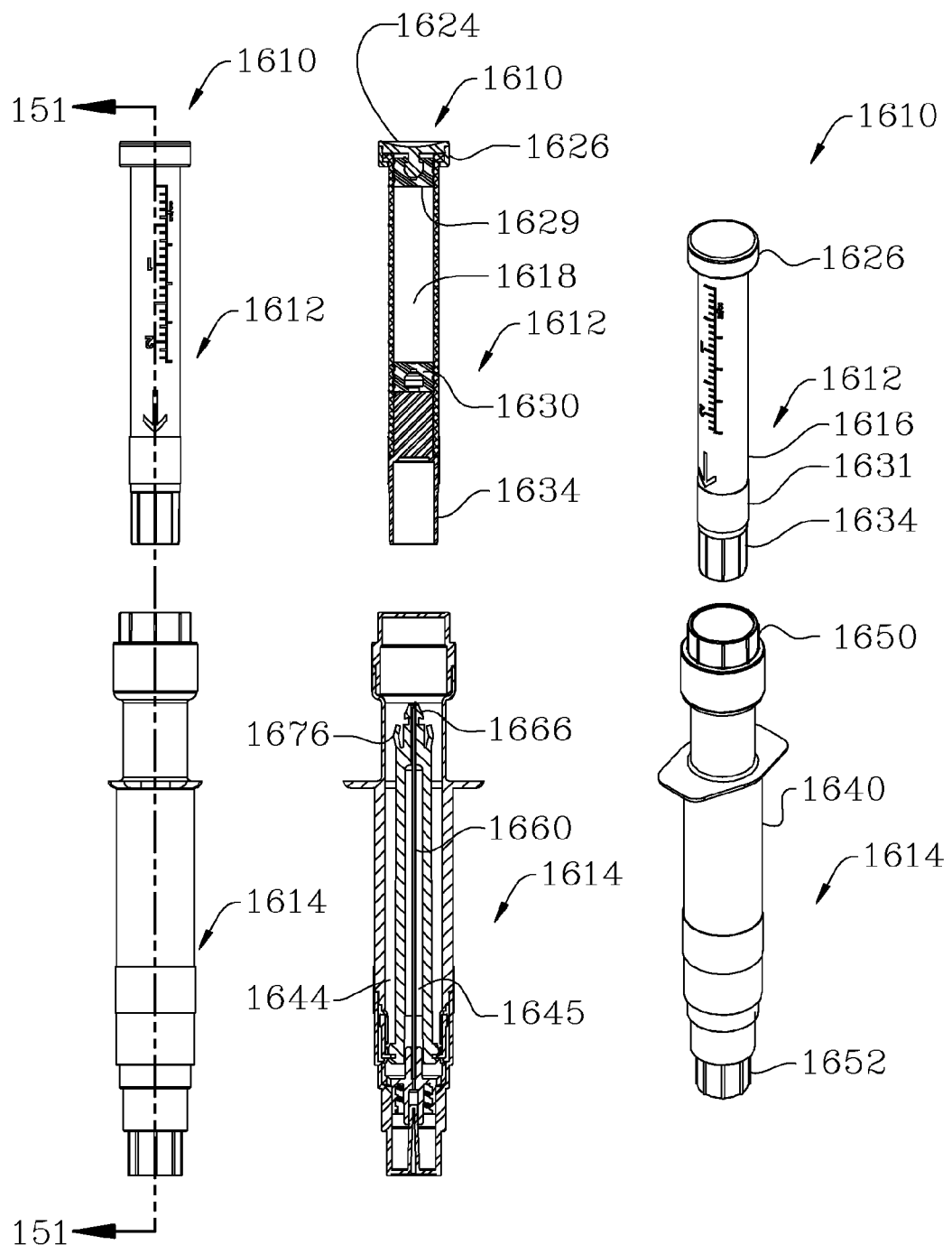
Figure 153:
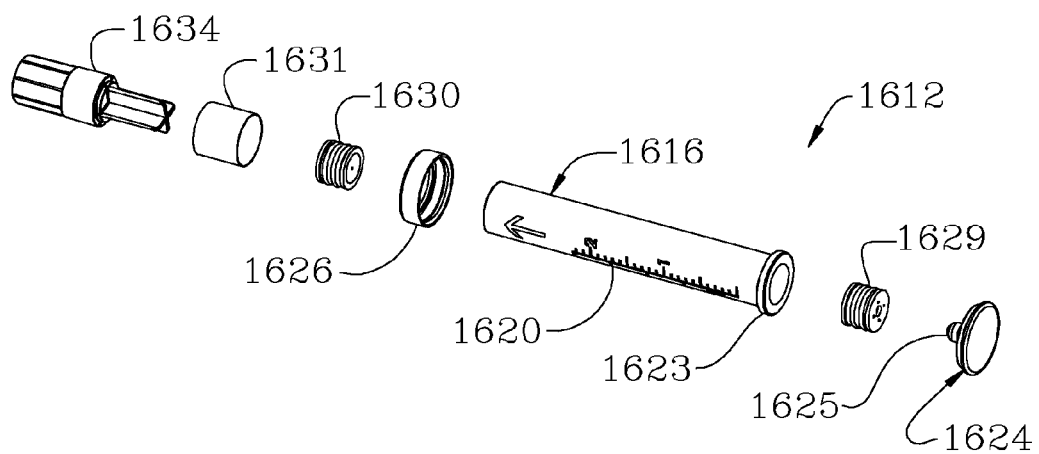
Figure 154:
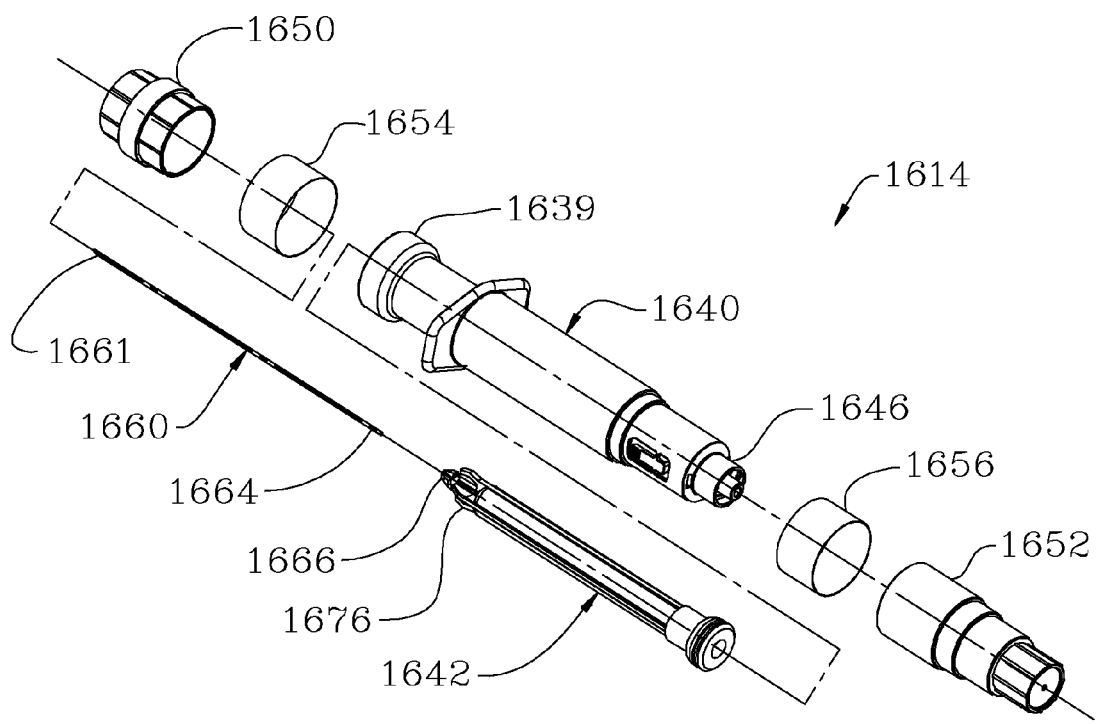
Figures 155, 156, 157, 158:
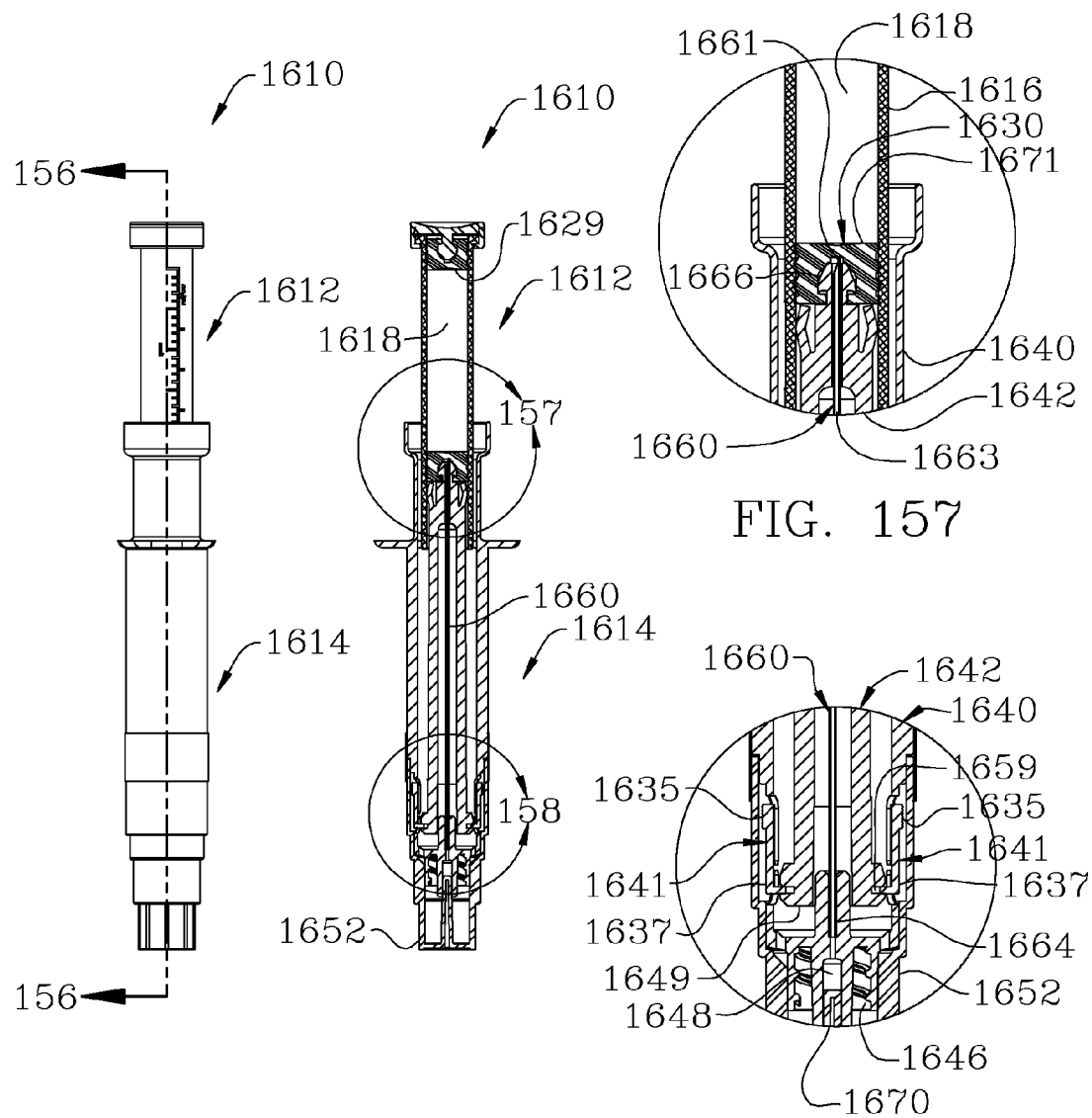
Figures 159, 160:
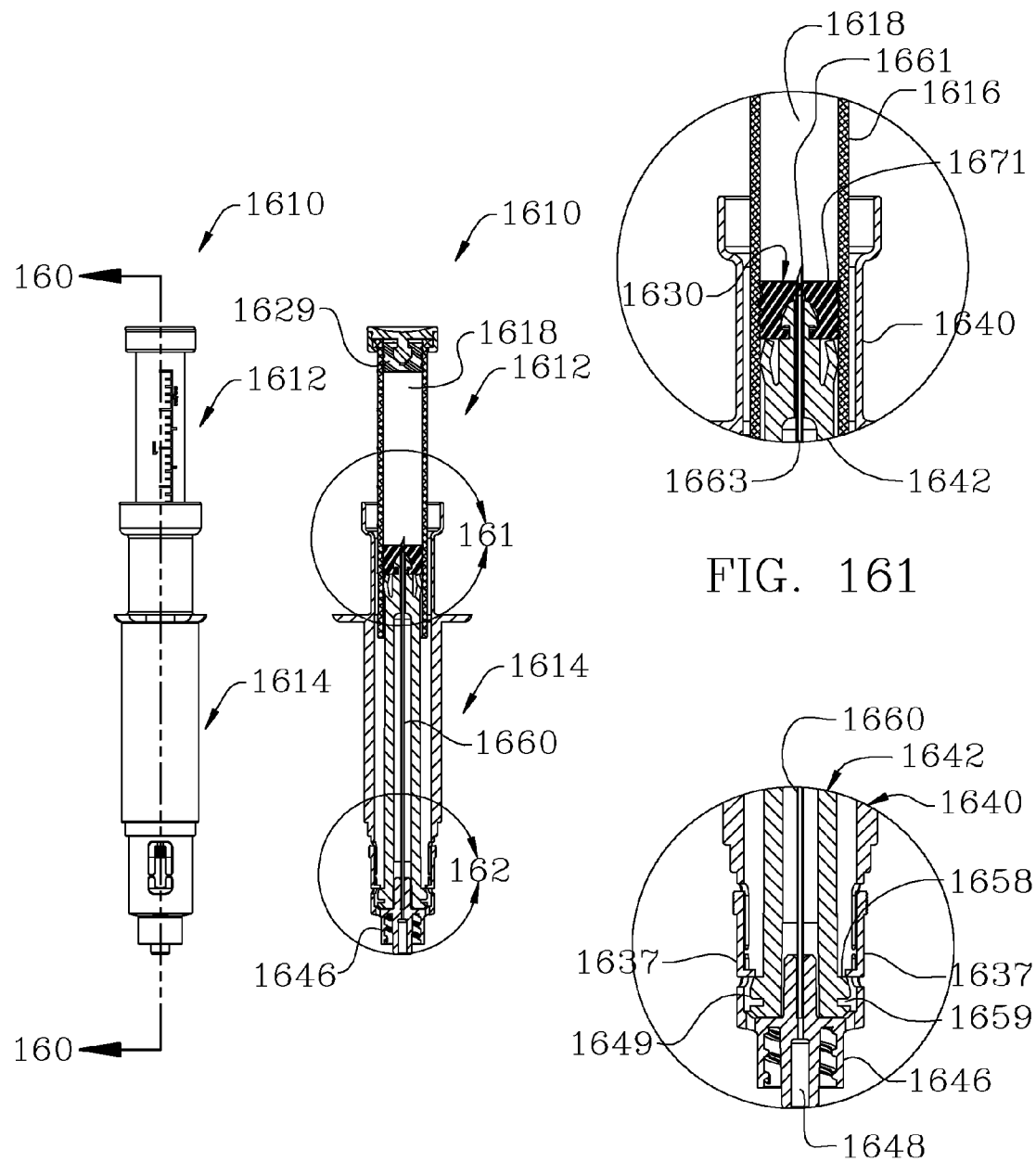
Figures 163, 164, 165:
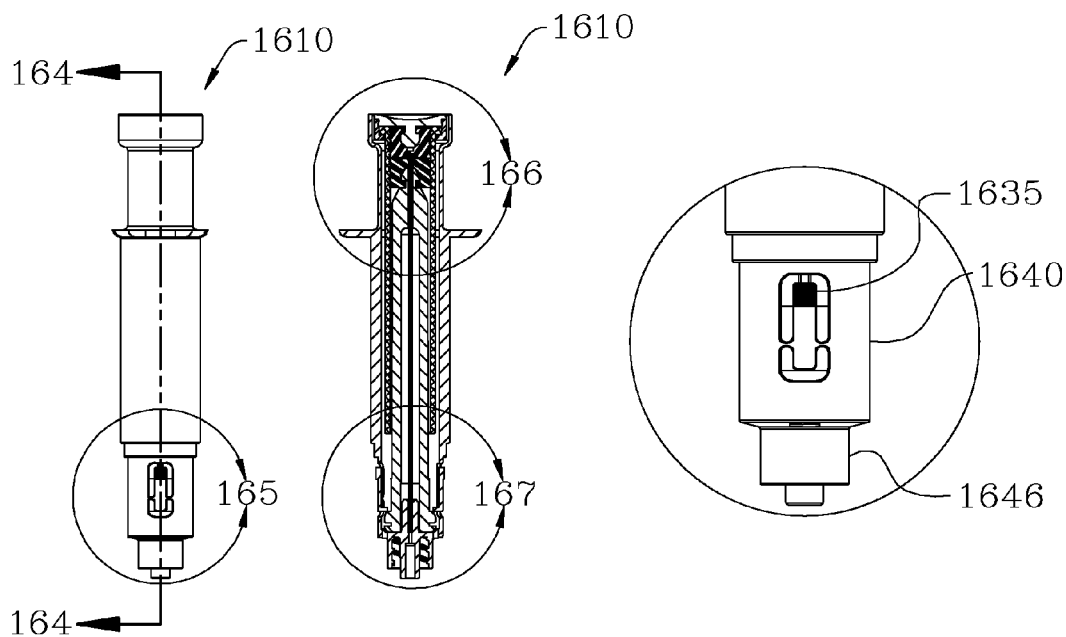
Figure 166:
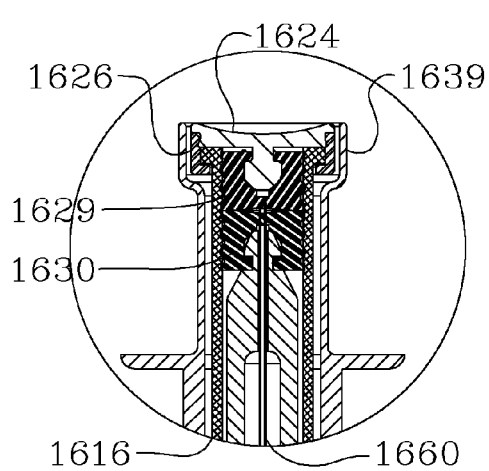
Figure 167:
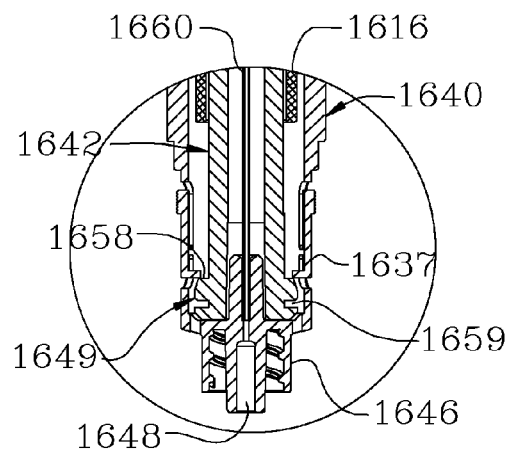
Figures 172, 173, 174:
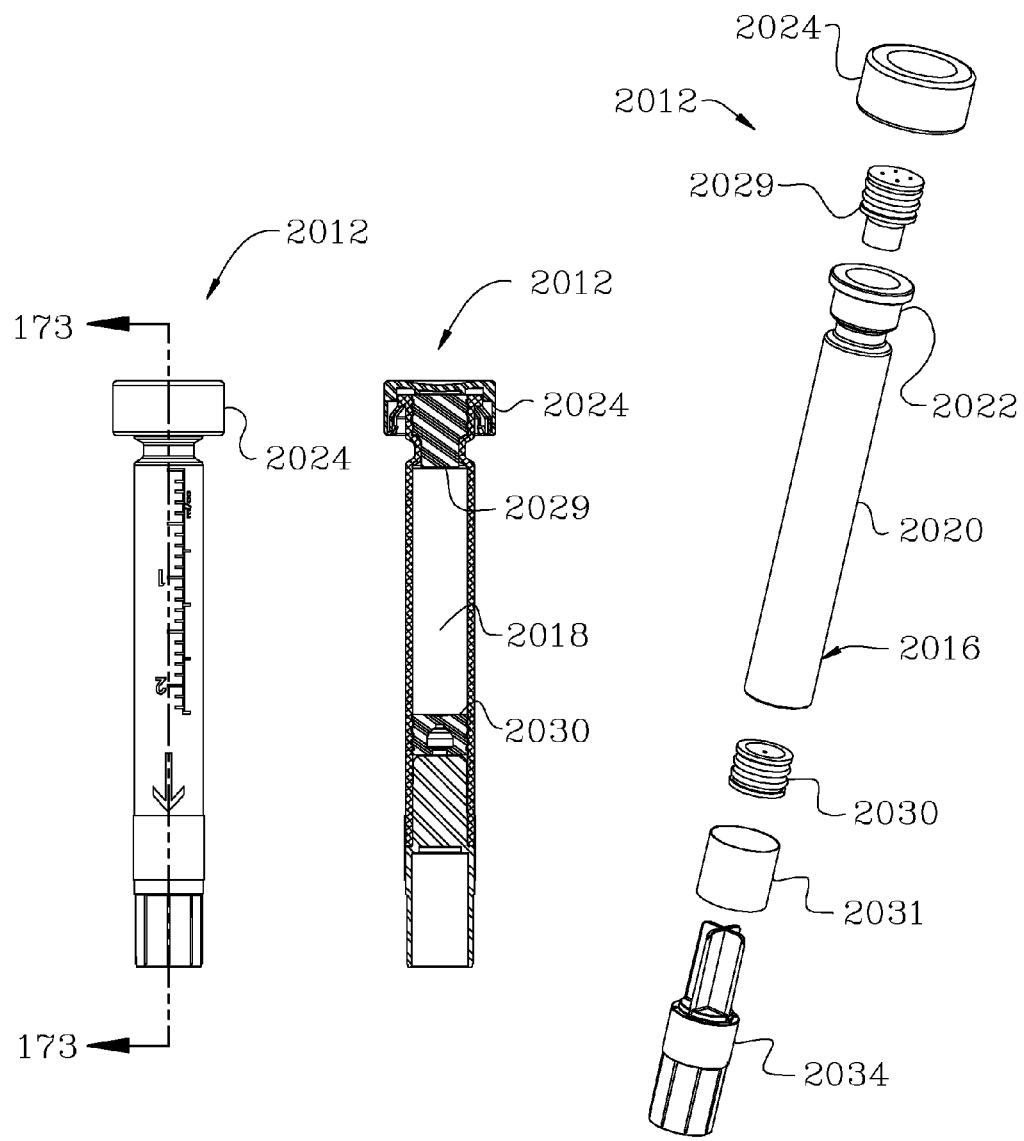
Figures 181, 182, 183:
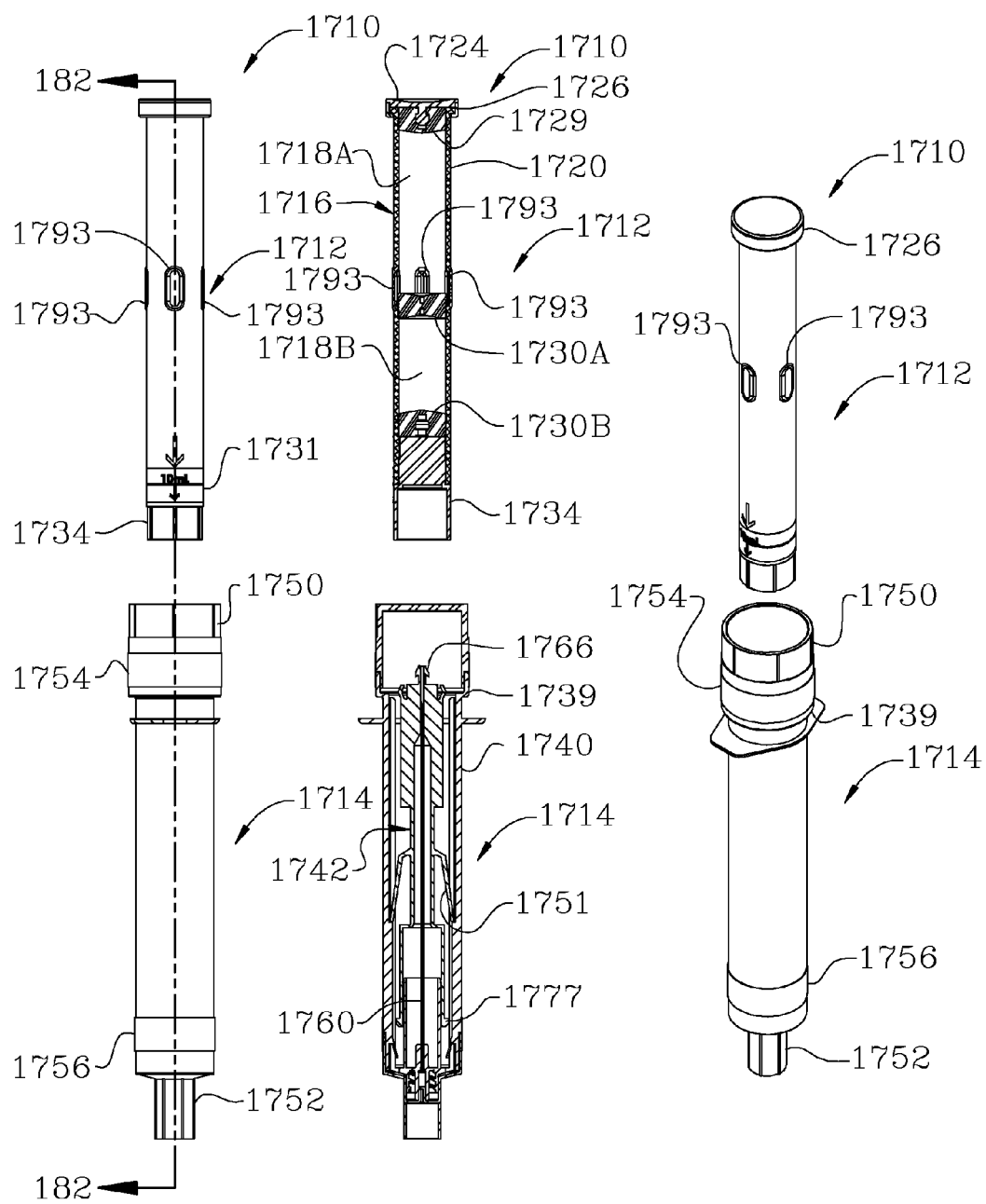
Figures 184, 185, 186, 187:
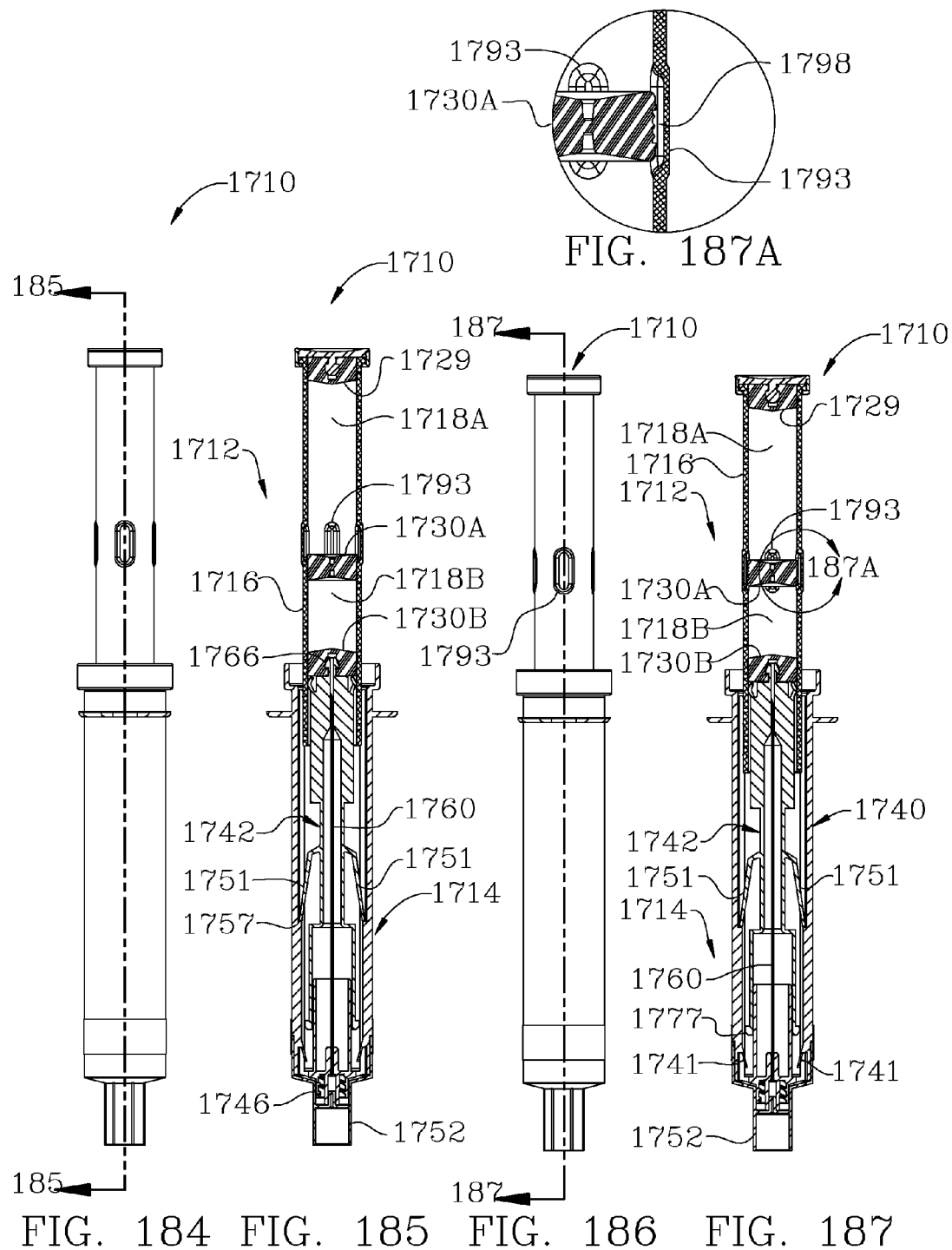
Figures 188, 189, 190, 191:
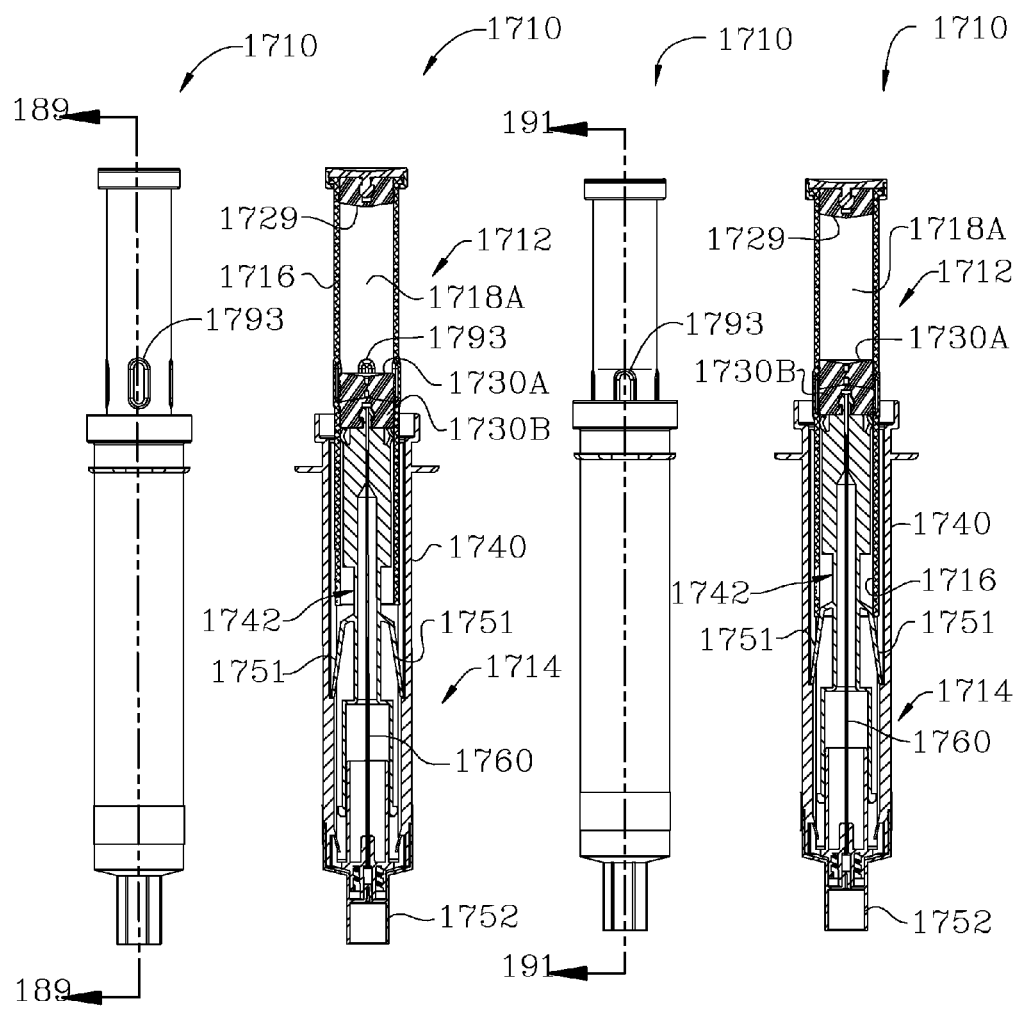
Figures 192, 193, 194, 195:
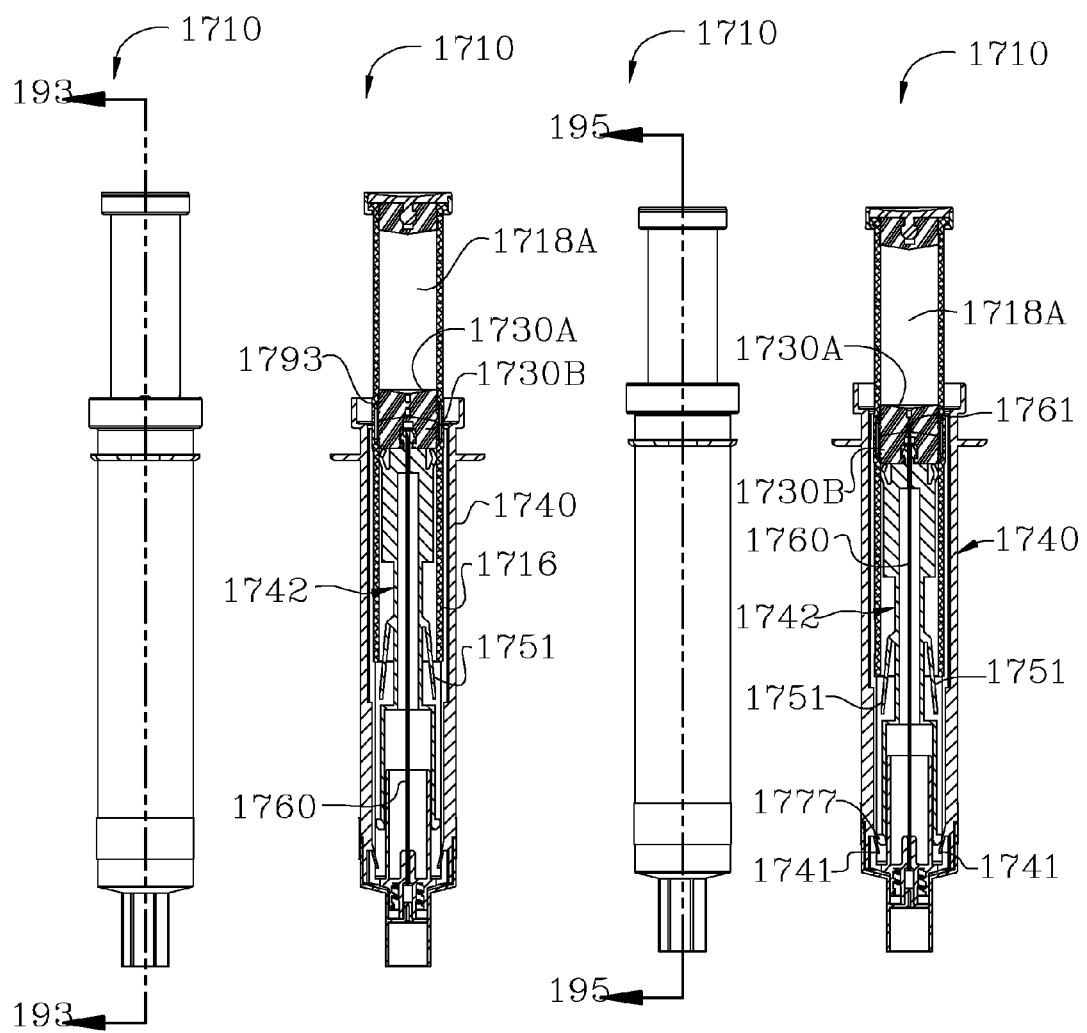
Figures 196, 197, 198, 199:
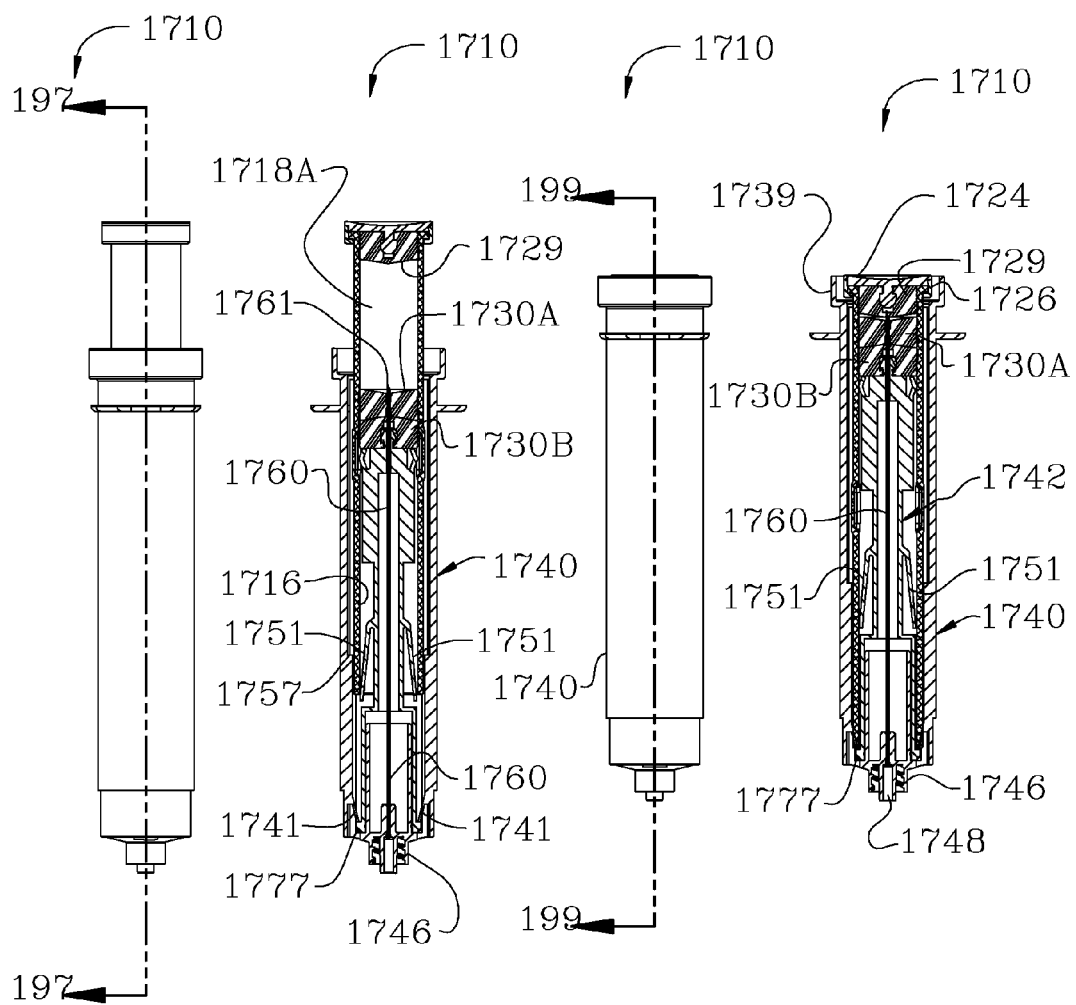
Figures 200, 201, 202:
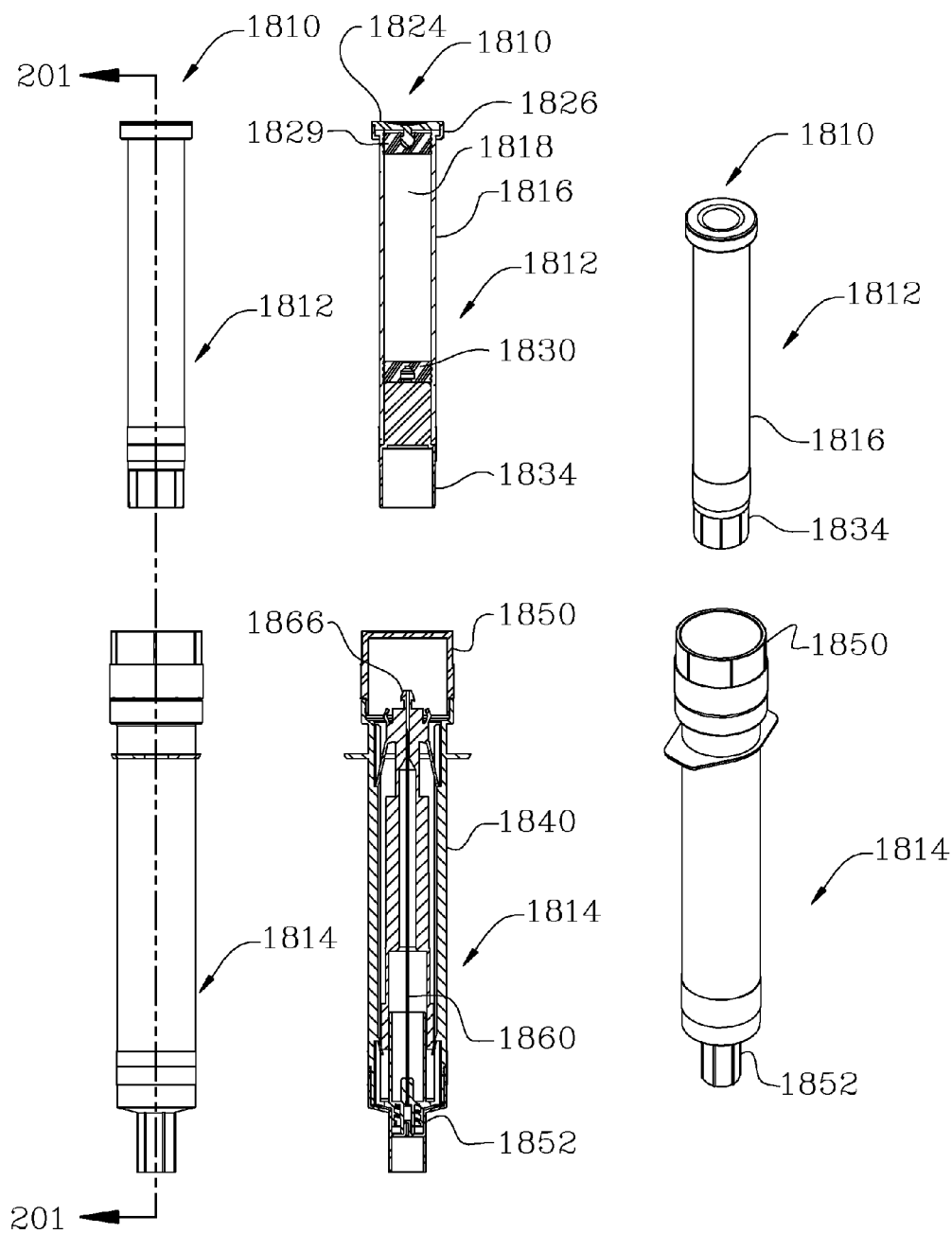
Figure 203:
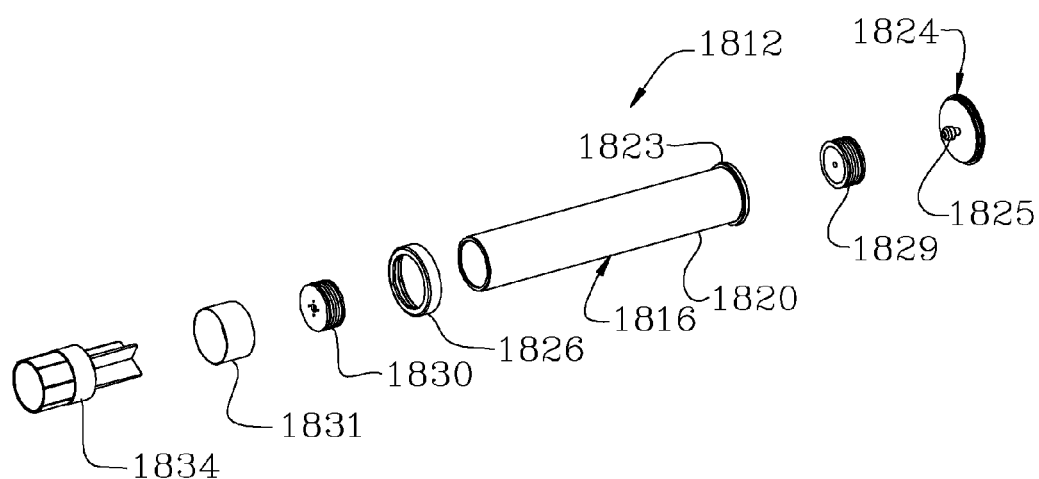
Figure 204:
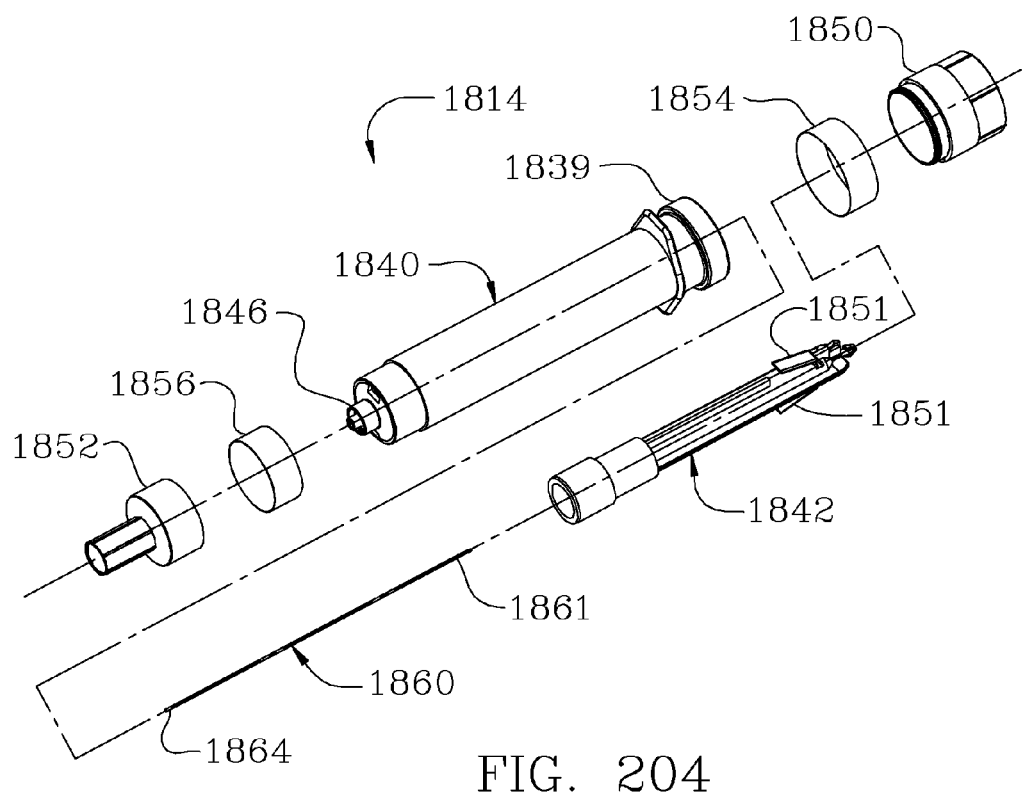
Figures 205, 206:
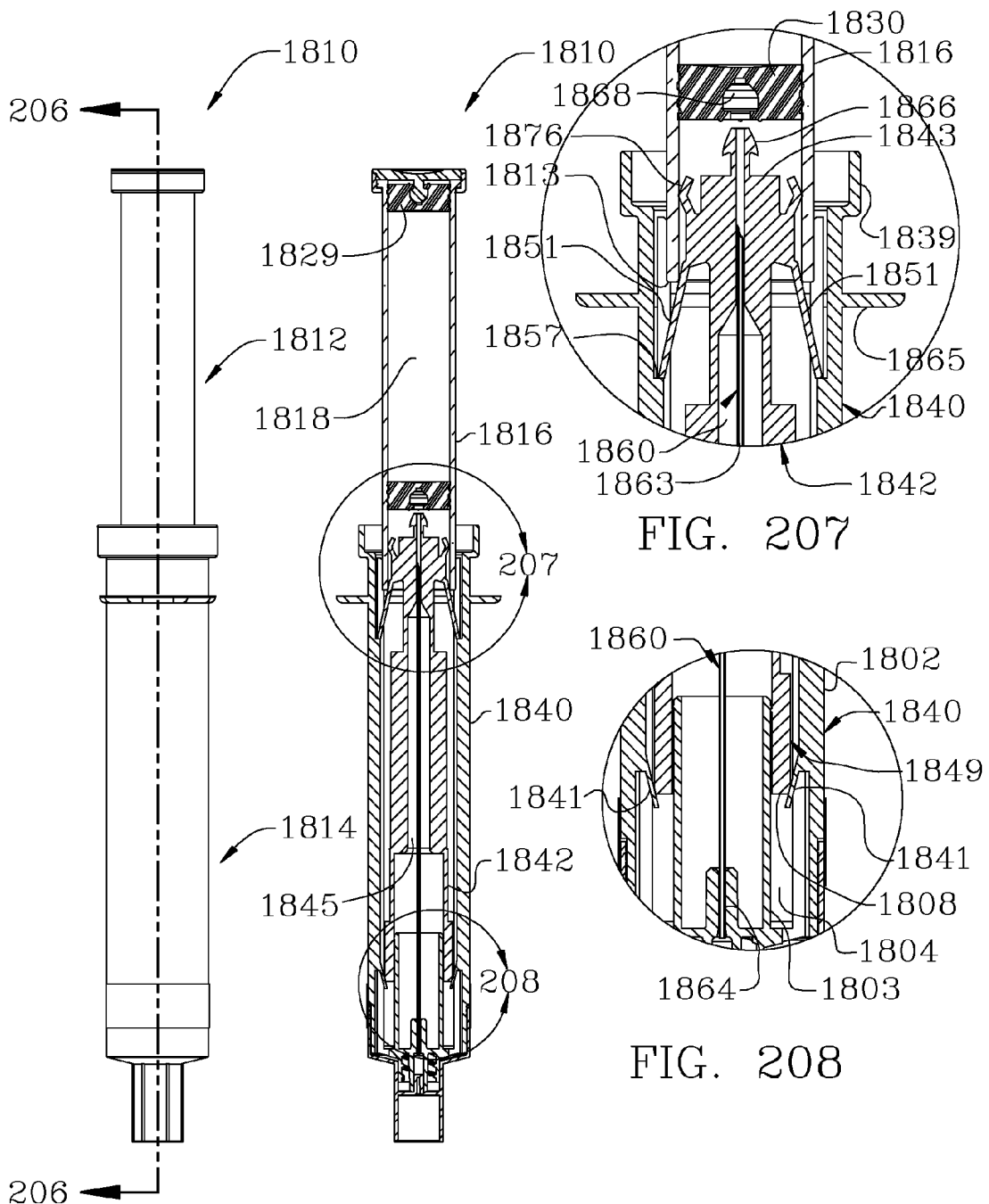
Figures 209, 210:
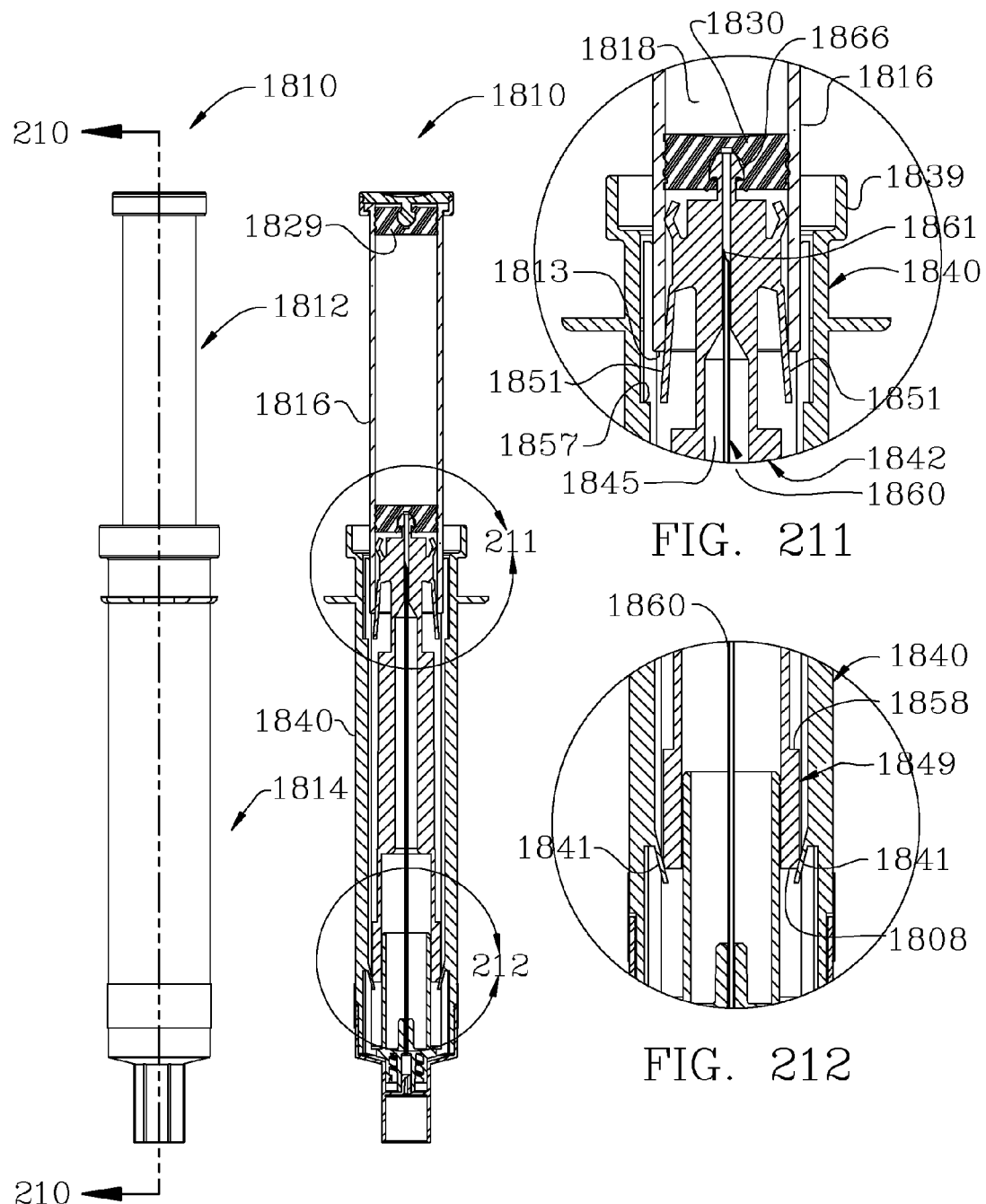
Figures 213, 214, 216:
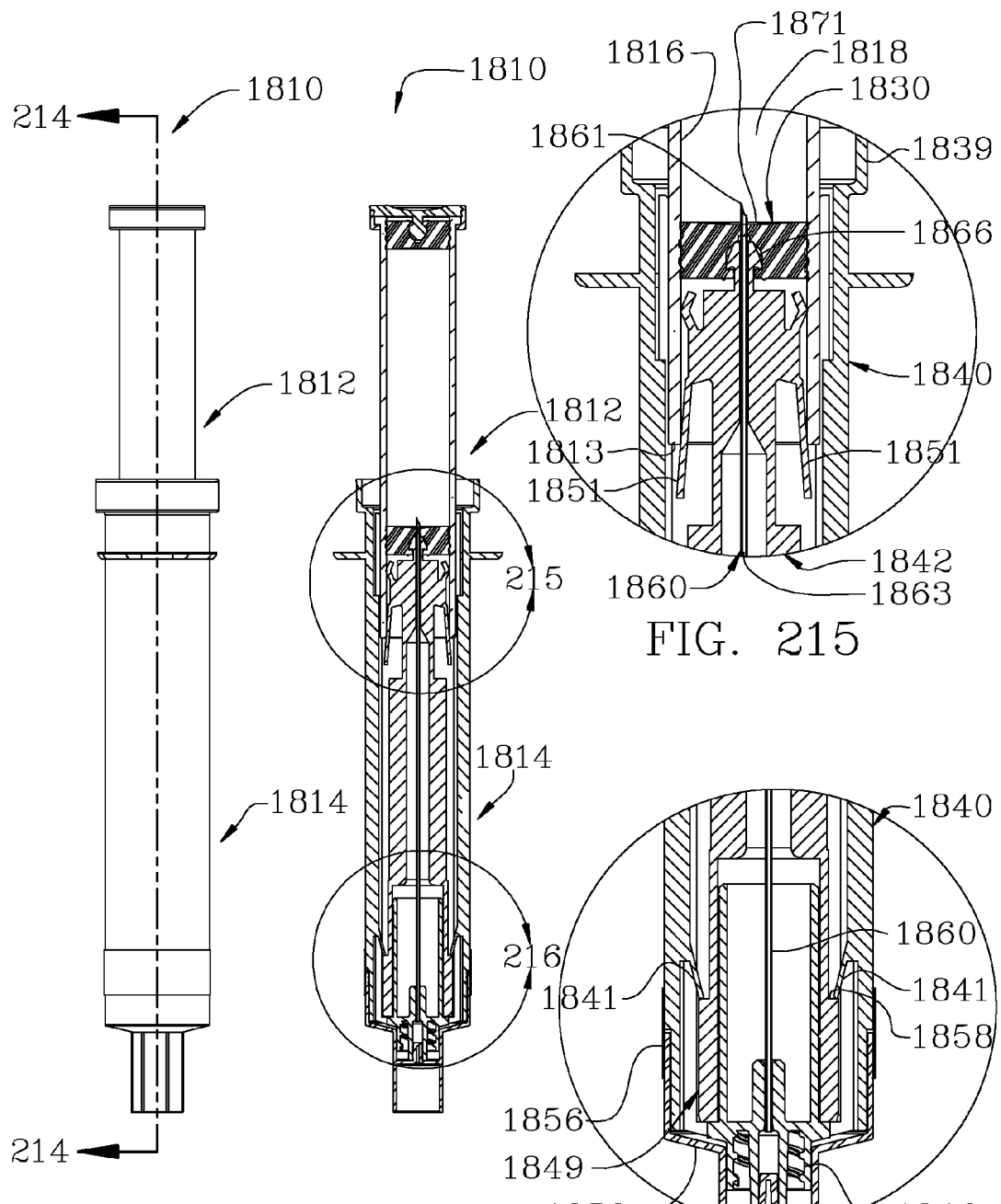
Figures 217, 218, 219, 220:
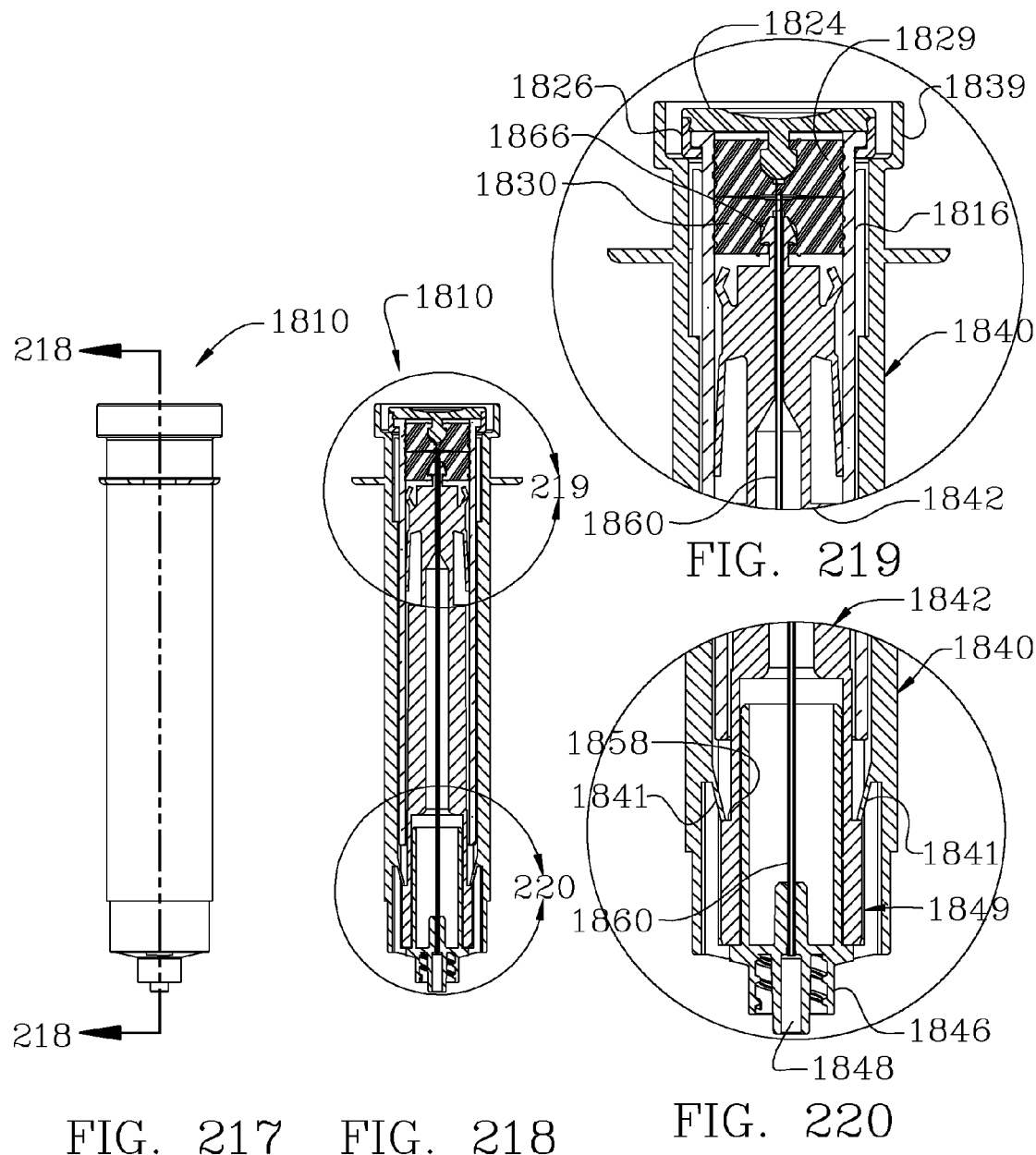

FIG. 123 is a side elevational view of the fluid delivery device of FIG. 113, depicting the fluid delivery device in a second configuration, with the cartridge translated distally within the syringe, relative to the position of the cartridge shown in FIG. 118, by a relatively small amount such that a lumen defined by the needle of the syringe is in fluid communication with a fluid chamber defined by the cartridge;

FIG. 124 is a cross-sectional view taken along line 124-124 in FIG. 123;

FIG. 125 is an enlarged view of a first encircled portion of FIG. 124, depicting the proximal tip of the needle extending through the proximal surface of the movable stopper such that the lumen defined by the needle is in fluid communication with the fluid chamber;

FIG. 126 is an enlarged view of a second encircled portion of FIG. 124, depicting the housing of the cartridge engaged with the flexible members of the inner core such that the flexible members are flexed inwardly and disengaged from the annular ledge of the outer body;

FIG. 127 is an enlarged view of a third encircled portion of FIG. 124, depicting the flexible tabs of the outer body engaged with the annular member of the inner core;

FIG. 128 is a side elevational view of the fluid delivery device of FIG. 113, depicting the fluid delivery device in a third configuration, with the cartridge translated distally within the syringe relative to the position of the cartridge shown in FIG. 123, to achieve fluid delivery;

FIG. 129 is a cross-sectional view taken along line 129-129 in FIG. 128;

FIG. 130 is an enlarged view of a first encircled portion of FIG. 129, depicting the movable stopper of the cartridge engaged with a fixed stopper of the cartridge and depicting the proximal tip of the needle extending into the fixed stopper;

FIG. 131 is an enlarged view of a second encircled portion of FIG. 129, depicting the housing of the cartridge engaged with the flexible positioning members of the inner core such that the flexible positioning members are flexed farther inwardly relative to the position of the flexible positioning members shown in FIG. 126;

FIG. 132 is an enlarged view of a third encircled portion of FIG. 129, depicting the flexible tabs of the outer body of the syringe engaged with the annular member of the inner core of the syringe;

FIG. 133 is a front elevational view of a fluid delivery device according to another embodiment, with a cartridge and a syringe of the fluid delivery device disconnected from one another;

FIG. 134 is a cross-sectional view taken along line 134-134 in FIG. 133;

FIG. 135 is a perspective view of the fluid delivery device in FIG. 133, depicting the cartridge and the syringe disconnected from one another;

FIG. 136 is an exploded view of the cartridge of the fluid delivery device of FIG. 133;

FIG. 137 is an exploded view of the syringe of the fluid delivery device of FIG. 133;

FIG. 138 is an front elevational view of the fluid delivery device of FIG. 133, depicting the fluid delivery device in a first configuration, with the cartridge and syringe connected to one another;

FIG. 139 is a cross-sectional view taken along line 139-139 in FIG. 138;

FIG. 140 is an enlarged view of a first encircled portion of FIG. 139, depicting a movable stopper of the cartridge connected to an inner core of the syringe, and depicting a proximal tip of a needle of the syringe positioned distal of a proximal surface of the movable stopper;

FIG. 141 is an enlarged view of a second encircled portion of FIG. 139, depicting a relationship between a distal end of the inner core and a distal end of the outer body of the syringe;

FIG. 142 is a front elevational view of the fluid delivery device of FIG. 133, depicting the fluid delivery device in a second configuration, with the cartridge translated distally within the syringe, relative to the position of the cartridge shown in FIG. 138, by a relatively small amount;

FIG. 143 is a cross-sectional view taken along line 143-143 in FIG. 142;

FIG. 144 is an enlarged view of a first encircled portion of FIG. 143, depicting the proximal tip of the needle of the syringe extending through the proximal surface of the movable stopper of the cartridge such that a lumen defined by the needle is in fluid communication with a fluid chamber defined by the cartridge;

FIG. 145 is an enlarged view of a second encircled portion of FIG. 143, depicting the distal end of the inner core in contacting engagement with the outer body;

FIG. 146 is a side elevational view of the fluid delivery device of FIG. 133, depicting the fluid delivery device in a third configuration, with the cartridge translated distally within the syringe, relative to the position of the cartridge shown in FIG. 142, such that the cartridge is inserted completely within the syringe, to achieve fluid delivery;

FIG. 147 is a cross-sectional view taken along line 147-147 in FIG. 146;

FIG. 148 is an enlarged view of a first encircled portion of FIG. 147, depicting the movable stopper of the cartridge engaged with a fixed stopper of the cartridge and depicting a proximal flange of the outer body of the syringe surrounding a proximal button and a collar of the cartridge to disable the fluid delivery device;

FIG. 149 is an enlarged view of a second encircled portion of FIG. 147, depicting the axial relationship among the respective distal ends of a housing of the cartridge and the inner core and outer body of the syringe;

FIG. 150 is a front elevational view of a fluid delivery device according to another embodiment, depicting a cartridge and a syringe of the fluid delivery device disconnected from one another;

FIG. 151 is a cross-sectional view taken along line 151-151 in FIG. 150;

FIG. 152 is a perspective view of the fluid delivery device of FIG. 150, with the cartridge and the syringe disconnected from one another;

FIG. 153 is an exploded view of the cartridge of the fluid delivery device of FIG. 150;

FIG. 154 is an exploded view of the syringe of the fluid delivery device of FIG. 150;

FIG. 155 is a front elevational view of the fluid delivery device of FIG. 150, depicting the fluid delivery device in a first configuration, with the cartridge and the syringe connected to one another;

FIG. 156 is a cross-sectional view taken along line 156-156 in FIG. 155;

FIG. 157 is an enlarged view of a first encircled portion of FIG. 156, depicting a movable stopper of the cartridge connected to an inner core of the syringe, and depicting a proximal tip of a needle of the syringe positioned distal of a proximal surface of the movable stopper;

FIG. 158 is an enlarged view of a second encircled portion of FIG. 156, depicting a pair of flexible tabs of the outer body of the syringe engaged with an annular notch defined by a distal end of the inner core of the syringe;

FIG. 159 is a front elevational view of the fluid delivery device of FIG. 150, depicting the fluid delivery device in a second configuration, with the cartridge translated distally within the syringe relative to the position of the cartridge shown in FIG. 155;

FIG. 160 is a cross-sectional view taken along line 160-160 in FIG. 159;

FIG. 161 is an enlarged view of a first encircled portion of FIG. 160, depicting the proximal tip of the needle extending through the proximal surface of the movable stopper such that a lumen defined by the needle is in fluid communication with the fluid chamber;

FIG. 162 is an enlarged view of a second encircled portion of FIG. 160, depicting the flexible tabs of the outer body disengaged from the annular notch of the distal end of the inner core and resting on top of a proximal surface of the distal end of the inner core;

FIG. 163 is a side elevational view of the fluid delivery device of FIG. 150, depicting the fluid delivery device in a third configuration, with the cartridge translated distally within the syringe, relative to the position of the cartridge shown in FIG. 159, such that the cartridge is inserted completely within the syringe to achieve fluid delivery;

FIG. 164 is a cross-sectional view taken along line 164-164 in FIG. 163;

FIG. 165 is an enlarged view of an encircled portion of FIG. 163, depicting a distal end of the outer body and a male luer connection of the syringe;

FIG. 166 is an enlarged view of a first encircled portion of FIG. 164, depicting the movable stopper of the cartridge engaged with a fixed stopper of the cartridge and depicting a proximal flange of the outer body of the syringe surrounding a proximal button and a collar of the cartridge to disable the fluid delivery device;

FIG. 167 is an enlarged view of a second encircled portions of FIG. 164, depicting the inner core and outer body of the syringe in the same relative positions as shown in FIG. 162 and depicting a position of a distal end of a housing of the cartridge with respect to the inner core and outer body of the syringe;

FIG. 168 is a front elevational view of an outer body of a syringe according to another embodiment, with the outer body including a Fresnel lens;

FIG. 169 is a cross-sectional view taken along line 169-169 in FIG. 168;

FIG. 170 is an enlarged view of an encircled portion of FIG. 168, depicting the Fresnel lens;

FIG. 171 is an enlarged view of an encircled portion of FIG. 169, depicting a thickness of the Fresnel lens and a thickness of an adjacent wall of the outer body;

FIG. 172 is a front elevational view of a cartridge of a fluid delivery device according to another embodiment, with the cartridge including a unitary cap;

FIG. 173 is a cross-sectional view taken along line 173-173 in FIG. 172;

FIG. 174 is an exploded view of the cartridge of FIG. 172;

FIG. 175 is a bottom view of the unitary cap of the cartridge of FIG. 172, depicting first and second pluralities of foldable tabs of the unitary cap in a folded configuration;

FIG. 176 is a cross-sectional view taken along line 176-176 in FIG. 175;

FIG. 177 is a perspective view of the unitary cap of FIG. 175, with the first and second pluralities of foldable tabs in a folded configuration;

FIG. 178 is a bottom view of the unitary cap of the cartridge of FIG. 172, depicting the first and second pluralities of the tabs in an extended configuration;

FIG. 179 is a cross-sectional view taken along line 179-179 in FIG. 178;

FIG. 180 is a perspective view of the unitary cap of the cartridge of FIG. 172, depicting the unitary cap in an as-molded configuration, with the first and second pluralities of foldable tabs in an extended configuration;

FIG. 181 is a side elevational view of a fluid delivery device according to another embodiment, depicting a cartridge and a syringe of the fluid delivery device disconnected from one another;

FIG. 182 is a cross-sectional view taken along line 182-182 in FIG. 181;

FIG. 183 is a perspective view of the fluid delivery device of FIG. 181, with the cartridge and the syringe disconnected from one another;

FIG. 184 is a side elevational view of the fluid delivery device of FIG. 181, depicting the cartridge and the syringe connected to one another;

FIG. 185 is a cross-sectional view taken along line 185-185 in FIG. 184, depicting a distal movable stopper of the cartridge connected to an inner core of the syringe, and depicting an axial relationship among bypass channels of the cartridge and a proximal chamber and a distal chamber defined by the cartridge, with the bypass channels being in fluid communication with the proximal chamber;

FIG. 186 is a side elevational view of the fluid delivery device of FIG. 181, depicting the cartridge translated distally within the syringe relative to the position of the cartridge shown in FIG. 184;

FIG. 187 is a cross-sectional view taken along line 187-187 in FIG. 186, depicting an intermediate movable stopper of the cartridge positioned such that the bypass channels are in fluid communication with each of the proximal chamber and the distal chamber;

FIG. 187A is an enlarged view of an encircled portion of FIG. 187, depicting an axial relationship between the intermediate movable stopper and one of the bypass channels;

FIG. 188 is a side elevational view of the fluid delivery device of FIG. 181, depicting the cartridge translated distally within the syringe relative to the position of the cartridge shown in FIG. 186;

FIG. 189 is a cross-sectional view taken along line 189-189 in FIG. 188, depicting the intermediate movable stopper engaged with the distal movable stopper and depicting the bypass channels in fluid communication with the proximal chamber only;

FIG. 190 is a side elevation view of the fluid device of FIG. 181, with the cartridge translated distally within the syringe relative to the position of the cartridge shown in FIG. 188;

FIG. 191 is a cross-sectional view taken along line 191-191 in FIG. 190, depicting the intermediate movable stopper and the distal movable stopper positioned such that the bypass channels are sealed and depicting a pair of flexible positioning members of the inner core engaged with a ledge of the outer body of the syringe;

FIG. 192 is a side elevational view of the fluid delivery device of FIG. 181, with the cartridge translated distally within the syringe relative to the position of the cartridge shown in FIG. 190;

FIG. 193 is a cross-sectional view taken along line 193-193 in FIG. 192, depicting the flexible positioning members of the inner core deflected inwardly due to contacting engagement with a housing of the cartridge such that the flexible positioning members are disengaged from the ledge of the outer body;

FIG. 194 is a side elevational view of the fluid delivery device of FIG. 181, depicting the cartridge translated distally within the syringe relative to the position of the cartridge shown in FIG. 192;

FIG. 195 is a cross-sectional view taken along line 195-195 in FIG. 194, depicting the inner core of the syringe translated distally relative to the outer body, with respect to the relative positions of the inner core and outer body shown in FIG. 193;

FIG. 196 is a side elevational view of the fluid delivery device of FIG. 181, with the cartridge translated distally within the syringe relative to the position of the cartridge shown in FIG. 194;

FIG. 197 is a cross-sectional view taken along line 197-197 in FIG. 196, depicting a distal end of the inner core in contacting engagement with the outer body and depicting a proximal tip of a needle of the syringe extending into the proximal chamber;

FIG. 198 is a side elevational view of the fluid delivery device of FIG. 181, depicting the cartridge translated distally within the syringe relative to the position of the cartridge shown in FIG. 196, such that the cartridge is inserted completely within the syringe;

FIG. 199 is a cross-sectional view taken along line 199-199 in FIG. 198, depicting the intermediate movable stopper in contacting engagement with the distal movable stopper and the fixed movable stopper, and depicting a proximal collar of the outer body surrounding a button and collar of the cartridge to disable the fluid delivery device;

FIG. 200 is a side elevational view of a fluid delivery device according to another embodiment, depicting a cartridge and a syringe of the fluid delivery device disconnected from one another;

FIG. 201 is a cross-sectional view taken along 201-201 in FIG. 200;

FIG. 202 is a perspective view of the fluid delivery device of FIG. 200, depicting the cartridge and the syringe disconnected from one another;

FIG. 203 is an exploded view of the cartridge of the fluid delivery device of FIG. 200;

FIG. 204 is an exploded view of the syringe of the fluid delivery device of FIG. 200;

FIG. 205 is a side elevational view of the fluid delivery device of FIG. 200, depicting the fluid delivery device in a first configuration, with the cartridge and the syringe connected to one another;

FIG. 206 is a cross-sectional view taken along line 206-206 in FIG. 205;

FIG. 207 is an enlarged view of a first encircled portion of FIG. 206, depicting a pair of flexible positioning members of an inner core of the syringe engaged with an annular ledge of an outer body of the syringe, and depicting a housing of the cartridge contacting, but not compressing, or flexing, the flexible position members, and further depicting a movable stopper of the cartridge disconnected from the inner core of the syringe;

FIG. 208 is an enlarged view of a second encircled portion of FIG. 206, depicting a pair of flexible tabs of the outer body of the syringe in contacting engagement with a distal end of the inner core of the syringe;

FIG. 209 is a side elevational view of the fluid delivery device of FIG. 200, depicting the fluid delivery device in a second configuration, with the cartridge translated distally within the syringe, relative to the position of the cartridge shown in FIG. 205;

FIG. 210 is a cross-sectional view taken along line 210-210 in FIG. 209;

FIG. 211 is an enlarged view of a first encircled portion of FIG. 210, depicting the housing of the cartridge engaged with the flexible positioning members such that they are deflected inwardly and are disengaged from the annular ledge of the outer body, and depicting the movable stopper of the cartridge connected with the inner core of the syringe, and further depicting a proximal tip of the needle spaced distally from the movable stopper;

FIG. 212 is an enlarged view of a second encircled portion of FIG. 210, depicting the flexible tabs of the outer body of the syringe engaged with the distal end of the inner core of the syringe;

FIG. 213 is a side elevational view of the fluid delivery device of FIG. 200, depicting the fluid deliver device in a third configuration, with the cartridge translated distally within the syringe relative to the position of the cartridge shown in FIG. 209;

FIG. 214 is a cross-sectional view taken along line 214-214 in FIG. 213;

FIG. 215 is an enlarged view of a first encircled portion of FIG. 214, depicting the proximal tip of the needle of the syringe extending through a proximal surface of the movable stopper such that a lumen defined by the needle is in fluid communication with a fluid chamber defined by the housing of the cartridge;

FIG. 216 is an enlarged view of a second encircled portion of FIG. 214, depicting the flexible tabs of the outer body engaged with a proximal surface of the distal end of the inner core;

FIG. 217 is a side elevational view of the fluid delivery device of FIG. 200, depicting the fluid delivery device in a fourth configuration, with the cartridge translated distally within the syringe relative to the position of the cartridge shown in FIG. 213, such that the cartridge is inserted completely within the syringe to achieve fluid delivery;

FIG. 218 is a cross-sectional view taken along line 218-218 in FIG. 217;

FIG. 219 is an enlarged view of a first encircled portion of FIG. 218, depicting the movable stopper of the cartridge engaged with a fixed stopper of the cartridge, and depicting a proximal collar of the outer body of the syringe surrounding a proximal button and a collar of the cartridge to disable the fluid delivery device;

FIG. 220 is an enlarged view of a second encircled portion of FIG. 218, depicting the inner core and the outer body of the syringe in the same relative positions as shown in FIG. 216, and depicting a position of the distal end of the housing of the cartridge relative to the inner core and outer body of the syringe; and FIGS. 221A-221E illustrate a method of use, according to one embodiment, of the fluid delivery device of FIG. 67.

DETAILED DESCRIPTION

Figure 1:
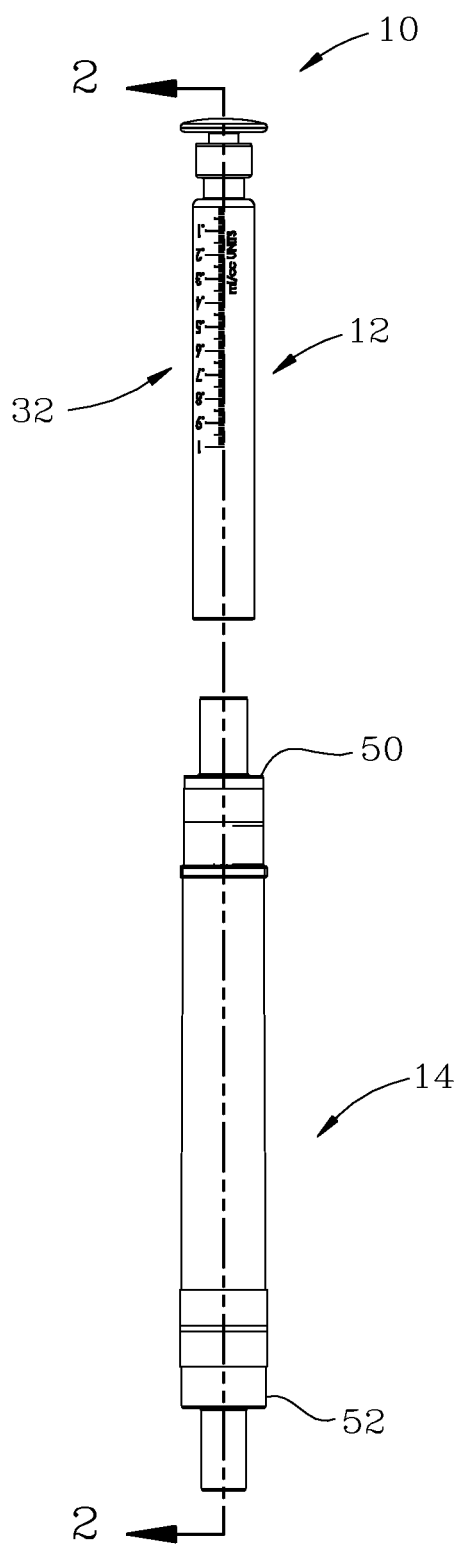
FIG. 1 is a side elevational view of a fluid delivery device according to one embodiment, depicting a cartridge and a syringe of the fluid delivery device disconnected from one another.
Figure 2:
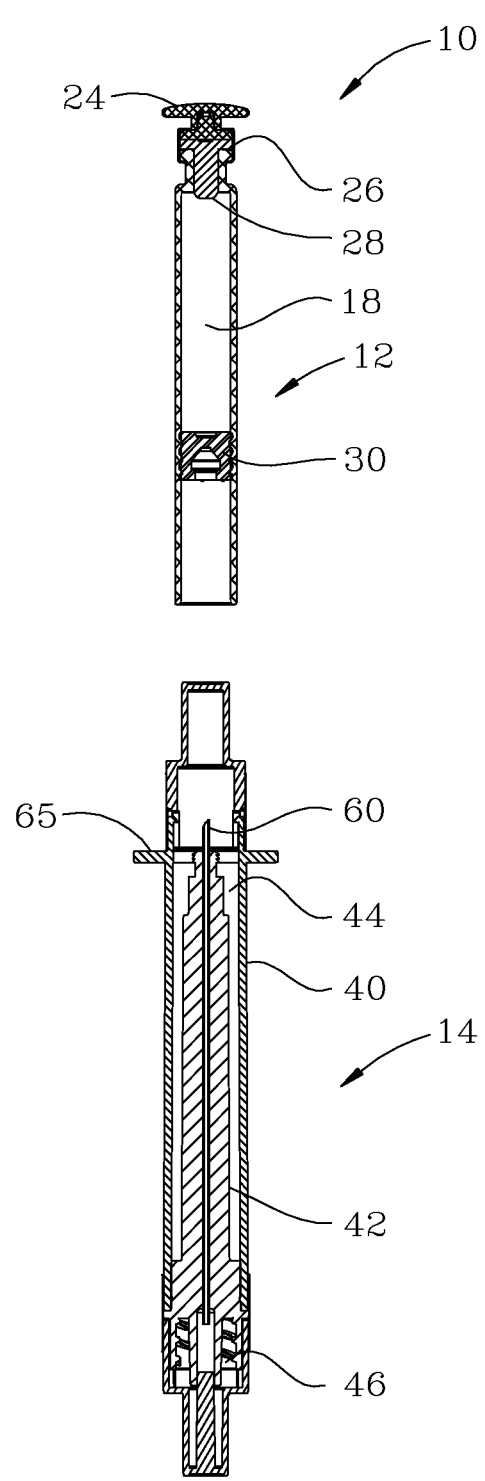
FIG. 2 is a cross-sectional view taken along line 2-2 in FIG. 1.
Figure 3:
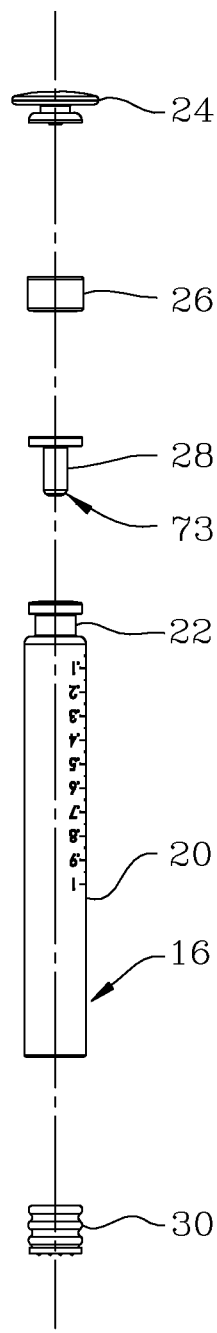
FIG. 3 is an exploded view of the cartridge of the fluid delivery device of FIG. 1.
Figure 4:
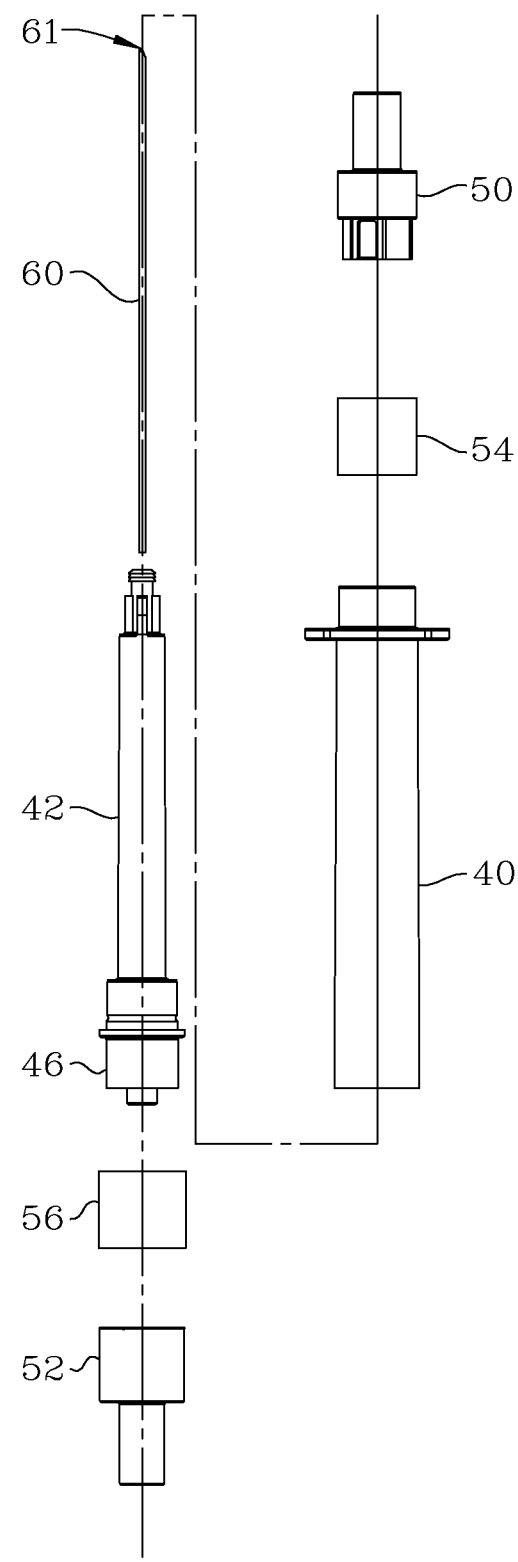
FIG. 4 is an exploded view of the syringe of the fluid delivery device of FIG. 1.

Referring to the drawings, wherein like numbers indicate the same or corresponding elements throughout the views, FIGS. 1-11 illustrate a fluid delivery device 10 according to one embodiment. The fluid delivery device 10 can be used to deliver fluids, e.g., medicinal fluids, as subsequently discussed in further detail. The fluid delivery device 10 can include a cartridge 12 and a syringe 14, which can be connected to one another, e.g., as depicted in FIGS. 5-11. The cartridge 12 can include a housing 16, which can be hollow and can define a fluid chamber 18, as shown in FIG. 2. The housing 16 of cartridge 12 can include a generally cylindrical portion 20 and a proximal neck 22, which can be integral with a proximal end of the generally cylindrical portion 20 of housing 16, as shown in FIG. 3. The cartridge 12 can also include a proximal button 24, a crimp 26, a plug 28 and a stopper 30.

The plug 28 can be inserted into the neck 22 of the housing 16 of cartridge 12, and a distal end of the plug 28 can protrude into the fluid chamber 18 defined by the housing 16 (refer to FIGS. 2, 6, 9 and 10). The plug 28 can include a distal surface 73 that can define a lead-in chamfer 74 (FIG. 10), which can facilitate the insertion of plug 28 into neck 22. The proximal button 24 can abut the plug 28, and the crimp 26 can secure both the plug 28 and the proximal button 24 to the neck 22 of housing 16, as shown in FIG. 10.

The housing 16 of cartridge 12 can be made of glass or plastic, or any other suitable material which can, for example, exhibit a high moisture barrier property. The housing 16 can be clear or colored, e.g., the housing 16 can have an amber color, for use with light-sensitive liquids. The proximal button 24 can be made of plastic, crimp 26 can be made of metal, e.g., aluminum, or a metal alloy, and the stopper 30 can be made of a resilient material, e.g., silicone rubber. The foregoing materials of construction of housing 16, proximal button 24, and crimp 26 are provided by way of illustration, and not of limitation, as any other suitable material can be used to manufacture any of these components of cartridge 12.

The stopper 30 can be positioned within the fluid chamber 18, for example as shown in FIG. 2. The material of stopper 30, e.g., silicone rubber, can facilitate sealing the stopper 30 against an inside surface of the generally cylindrical portion 20 of housing 16, for purposes of preventing fluid within the fluid chamber 18 from leaking past the stopper 30. The stopper 30 can be coated with a lubricant, such as silicone, that can facilitate movement of the stopper 30 within the housing 16 of the cartridge 12. The cartridge 12 can include graduations or indicia, indicated generally at 32 in FIG. 1, that can be applied to or integrally formed with, the generally cylindrical portion 20 of housing 16 of cartridge 12. Indicia 32 can provide an indication of the volume of fluid within the fluid chamber 18. The housing 16 of cartridge 12 can be sized and configured, in cooperation with the location of stopper 30 within housing 16, to contain various volumes of fluids such as, for example, from about 0.5 ml to about 20 ml of fluid, from about 1 ml to about 5 ml of fluid, about 2 ml of fluid, or about 3 ml of fluid. The cartridge 12 can be a pre-filled cartridge, such as when fluid is injected into the fluid chamber 18, prior to inserting the neck 22 of housing 16, and prior to the connection of the cartridge 12 and syringe 14. The stopper 30 can be positioned axially at any suitable location within the fluid chamber 18 where, for example, the stopper can have an initial position that defines a desired fluid volume.

Figures 5, 6:
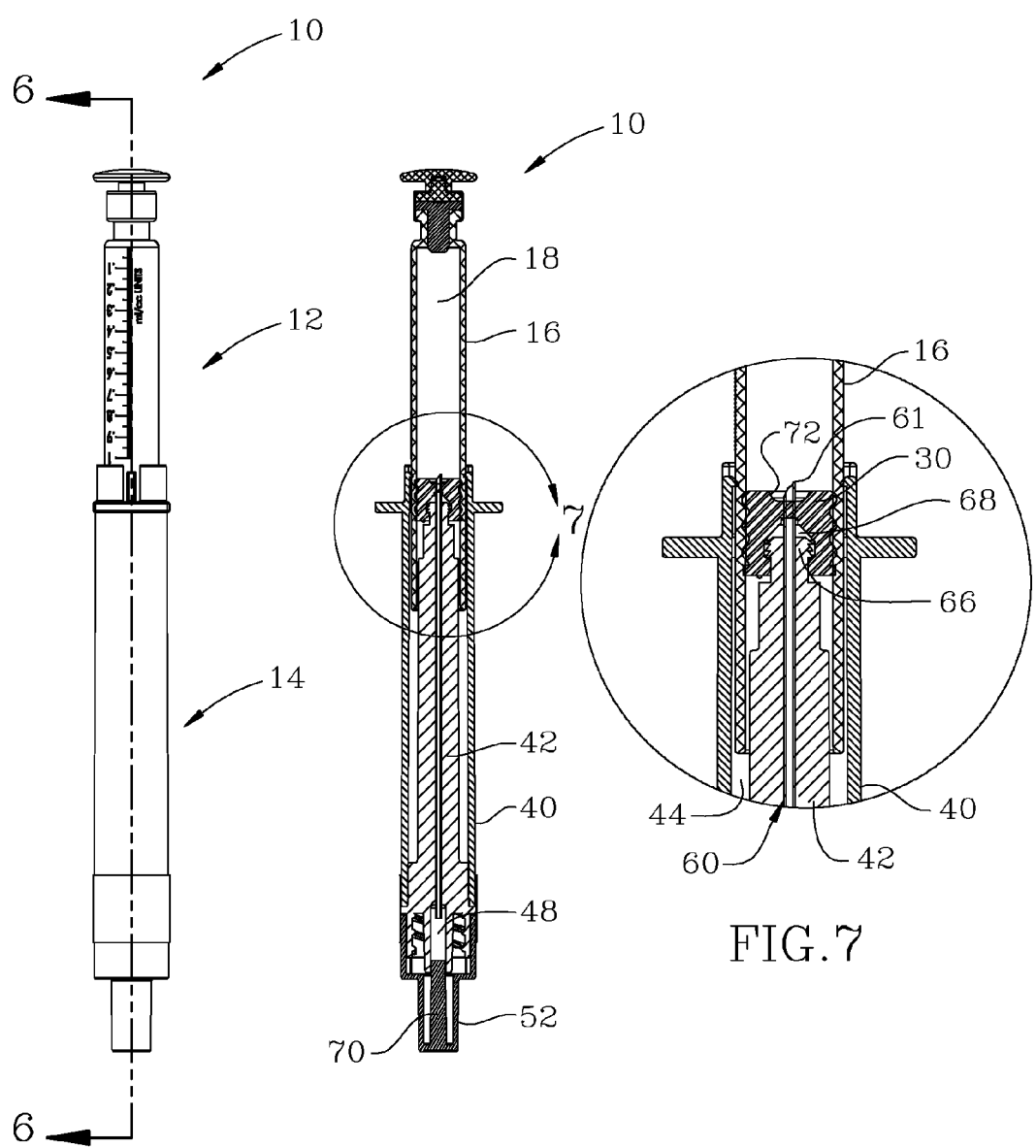
FIG. 5 is a side elevational view of the fluid delivery device of FIG. 1, depicting the cartridge and the syringe connected to one another.
FIG. 6 is a cross-sectional view taken along line 6-6 in FIG. 5.

The syringe 14 can include an outer body 40, which can be generally cylindrical, and an inner core 42. As shown in FIGS. 2, 6 and 9, a substantial portion of the inner core 42 can be positioned within, and surrounded by, the outer body 40 of syringe 14. The outer body 40 and inner core 42 of the syringe 14 can be made separately from one another, and then secured to one another, for example using adhesives, or any suitable structure or arrangement. Each of the outer body 40 and inner core 42 can be made of any suitable material such as, for example, plastic. In one embodiment, each of the outer body 40 and inner core 42 can be molded, e.g., injection molded, from clear or opaque resins such as polypropylene (PP), polycarbonate (PC), or any other suitable method. In other embodiments, as discussed subsequently herein, fluid delivery devices can be provided that include syringes having an outer body and an inner core that can be integrally formed with one another as a unitary structure. The outer body 40 and the inner core 42 of syringe 14 can cooperate to define a cavity 44 that can receive at least a portion of the housing 16 of cartridge 12 where, for example, the housing 16 can be retained within the cartridge 12 with a friction fit.

The syringe 14 can also include a male luer connection 46 which can be formed integrally with the inner core 42 and positioned at a distal end of the inner core 42. The male luer connection 46 can define a lumen 48 (FIGS. 6 and 11) extending therethrough in a longitudinal direction. The male luer connection 46 can permit the fluid delivery device 10 to be connected with standard devices normally connected to a male luer connection, for example, intravenous sets or female luer attachment needles. A configuration of lumen 48, extending in a longitudinal direction, can permit the male luer connection 46 to be connected to a wide variety of commonly available female needle-free valves, or any other suitable valve.

The syringe 14 can also include a proximal end cap 50, which can be removably secured to a proximal end of the outer body 40, and a distal end cap 52, which can be removably secured to the inner core 42 or outer body 40 of syringe 14 (FIGS. 1 and 2) and can surround the male luer connection 46. Syringe 14 can also include a tamper evident label 54, which can be secured to both the proximal end cap 50 and the outer body 40, and a tamper evident label 56, which can be secured to the distal end cap 52, outer body 40 and the inner core 42. The combination of the proximal end cap 50, the distal end cap 52, and the tamper evident labels 54, 56 can provide an indication to an end user of the fluid delivery device 10 that a fluid flow path through the fluid delivery device 10 is sterile prior to initial use.

The syringe 14 can also include a needle 60, which can be positioned within a bore defined by the inner core 42 of syringe 14. As shown in FIG. 2, a distal tip of the needle 60 can protrude beyond the inner core 42 of syringe 14, which can permit the needle 60 to be overmolded with the inner core 42. The syringe 14 can also include a flange 65 that can be integral with the outer body 40 of syringe 14, and can be adjacent a proximal end of the outer body 40. Flange 65 can facilitate the operation of the fluid delivery device 10. For example, the flange 65 can be sized and configured to receive one or more fingers of a health care provider using the fluid delivery device 10.

After removing the proximal end cap 50, and inserting the cartridge 12 into the syringe 14 a sufficient distance axially, along a longitudinal axis (not shown) of the fluid delivery device 10, a barb 66 formed on a proximal end of the inner core 42 of syringe 14 can be received within a recess 68 defined by the stopper 30, to connect the stopper 30 to the inner core 42, as shown in FIG. 7. The barb 66 and recess 68 can have mating portions with complementary shapes that can facilitate the connection of barb 66 to stopper 30. When the cartridge 12 and syringe 14 are positioned as shown in FIGS. 5-7, a proximal tip 61 of the needle 60 can extend through the stopper 30, such that a lumen defined by the needle 60 is in fluid communication with the fluid chamber 18 defined by cartridge 12 and with the lumen 48 defined by the male luer connection 46. During the initial insertion of cartridge 12 into syringe 14, the distal end cap 52 can be retained, which can prevent fluid from inadvertently spraying out from the lumen 48. In this regard, the distal end cap 52 can include a plug 70 that can extend into the lumen 48 defined by the male luer connection 46 as shown in FIG. 6. Hydrostatic forces can assist in connecting stopper 30 to the barb 66 of inner core 42 during the insertion of cartridge 12 into syringe 14 until the proximal tip of 61 the needle 60 extends through the stopper 30 and the lumen defined by needle 60 is in fluid communication with the fluid chamber 18.

Fluid can be expelled from the fluid chamber 18, such that the fluid is delivered from the fluid delivery device 10 through lumen 48, by removing the distal end cap 52 and pushing the cartridge 12 in a distal direction within or along syringe 14, until such time that the cartridge 12 and syringe 14 are positioned as shown in FIGS. 8-11. As shown in FIG. 10, after fluid delivery, the stopper 30 can be positioned in contacting engagement with the neck 22 of the container 16 of cartridge 12 and with the plug 28 that extends through neck 22. The proximal tip 61 of needle 60 can extend into the plug 28. The resilient material of plug 28 can generally minimize the force transferred through the fluid delivery device 10 when the cartridge is substantially fully inserted into the syringe 14 by accepting the proximal tip 61 of needle 60. The syringe 14 can include a plurality of circumferentially spaced fingers 75, which can engage the neck 22 of cartridge 12 to secure cartridge 12 and syringe 14 in the relative positions shown in FIG. 10. In one embodiment, at the end of the stroke of the cartridge 12 within the syringe 14, the fingers 75 can engage neck 22 in a snap fit.

The lead-in chamfer 74 of the distal surface 73 of plug 28 can protrude distally beyond neck 22, which can avoid creation of an annular void, or space, between the lead-in chamfer 74 and an inner surface of neck 22, which could result in an undesirable retention of fluid within such a space, at the end of the stroke cartridge 12 within syringe 14. The distal surface 73 of plug 28, which defines the lead-in chamfer 74, can have a shape that can be complementary to a shape of a recessed portion 72 (FIG. 7) of a proximal surface of stopper 30, which mates with the distal surface 73 of plug 28. As shown in FIG. 10, after the full stroke, or travel, of cartridge 12 within syringe 14, the proximal tip 61 of needle 60 can extend into plug 28 by a relatively small distance, for example, with a distal-most point of the proximal tip 61 of needle 60, which can be angled as shown in FIG. 7, being in close proximity to the distal surface 73 of plug 28. This can result from the proximal tip 61 of needle 60 extending proximally beyond stopper 30 by a relatively small distance as shown in FIG. 7. The complementary shapes of the distal surface 73 of plug 28 and the recessed portion 72 of stopper 30, and the spatial relationship between the needle 60 and stopper 30, can at least minimize any residual fluid within the fluid chamber 18 at the end of the travel of cartridge 12 within syringe 14.

Figures 15, 16, 17:
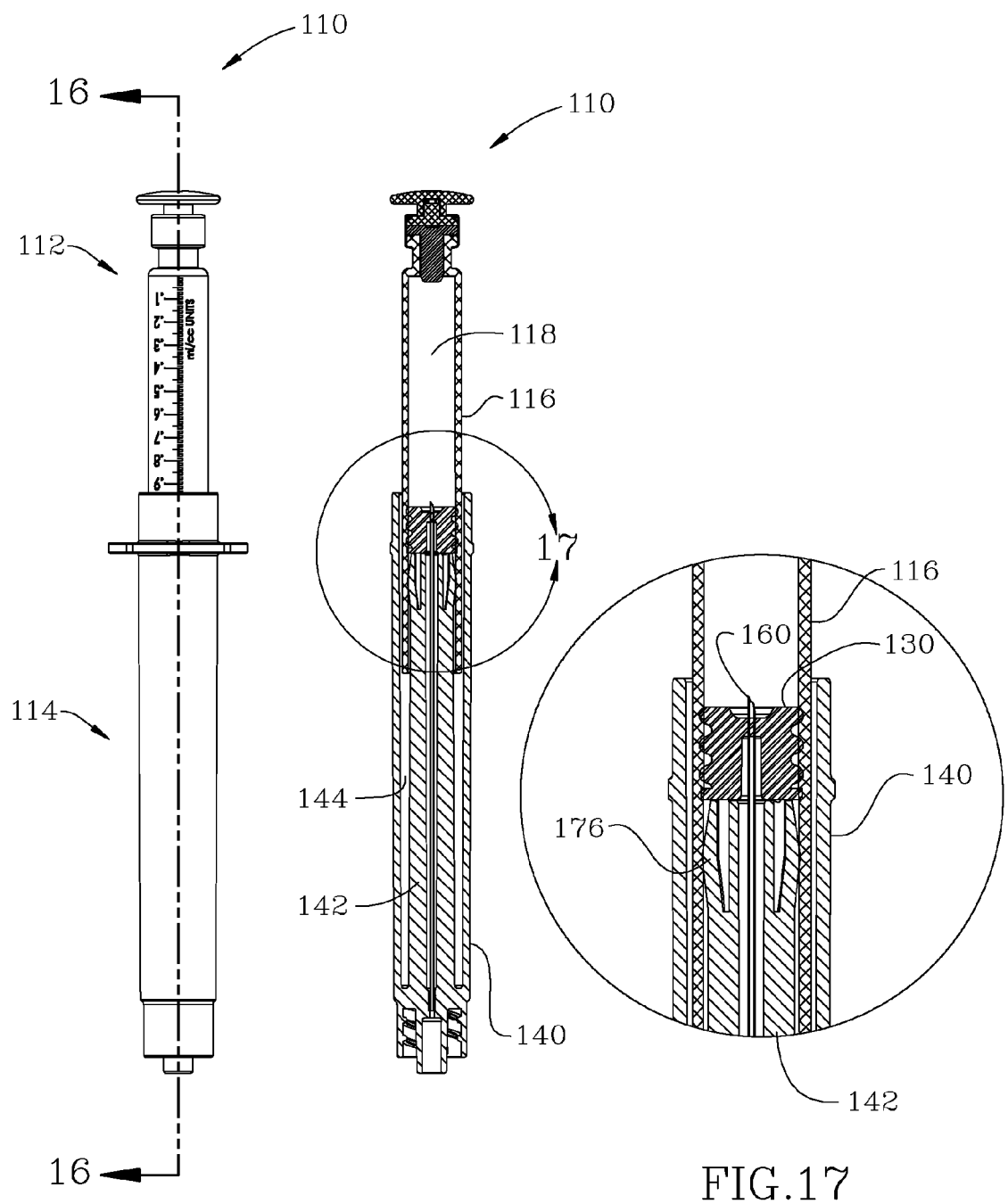
FIG. 15 is a front elevational view of the fluid delivery device of FIG. 12, depicting the cartridge and the syringe connected to one another.
FIG. 16 is a cross-sectional view taken along line 16-16 in FIG. 15.
FIG. 17 is an enlarged view of the encircled portion of FIG. 16, depicting a needle of the syringe extending through a stopper of the cartridge and into a fluid chamber defined by the cartridge.

FIGS. 12-20 illustrate a fluid delivery device 110 according to another embodiment. The fluid delivery device 110 can include a cartridge 112 and a syringe 114. The cartridge 112 can include a housing 116 that can define a fluid chamber 118 as shown in FIG. 16. The cartridge 112 can further include a proximal button 124, a crimp 126 and a plug 128 which can be secured to one another and to a neck of the housing 116 as described previously with regard to the corresponding parts of the fluid delivery device 10. Cartridge 112 can further include a stopper 130 positioned within the fluid chamber 118. The syringe 114 can include an outer body 140 and an inner core 142. The outer body 140 and the inner core 142 can be integrally molded as a unitary structure, and can cooperate to define a cavity 144 that can receive at least a portion of the housing 116 of cartridge 112. The syringe 114 can also include a needle 160 positioned within a bore formed by the inner core 142.

FIGS. 15-17 depict the cartridge 112 inserted into the syringe 114 and, more particularly, depict a distal portion of the housing 116 of cartridge 112 inserted within the cavity 144. The relative positions of cartridge 112 and syringe 114 shown in FIGS. 15-17, can result in the needle 160 extending through the stopper 130 of cartridge 112 and into the fluid chamber 118, as shown in FIGS. 16 and 17. Unlike the fluid delivery device 10, the stopper 130 of cartridge 112 is not fixed to the inner core 142 of syringe 114. For example, the inner core 142 does not include a barb on a proximal end thereof, for purposes of engaging the stopper 130. Consequently, the fluid delivery device 110 is not capable of bi-directional fluid flow, but can only achieve uni-directional fluid flow, i.e., by expelling fluid from the fluid chamber 118.

The syringe 114 can further include a plurality of flexible guides 176, or friction fingers, which can be formed at a proximal end of the inner core 142 of syringe 114. The flexible guides 176 can project radially outwardly such that they press against an inner surface of the housing 116 of cartridge 112, to retain housing 116 in position relative to syringe 114 until such time that a health care provider exerts sufficient force upon the cartridge 112 to move it relative to the syringe 114. The flexible guides 176 can be generally "bow-shaped" as shown in FIG. 17, to facilitate sliding engagement with housing 116 during insertion of cartridge 112. The syringe 114 can also include a proximal end cap 150, a distal end cap 152, and a flange 165 that can be integral with the body 140.

Figure 18:
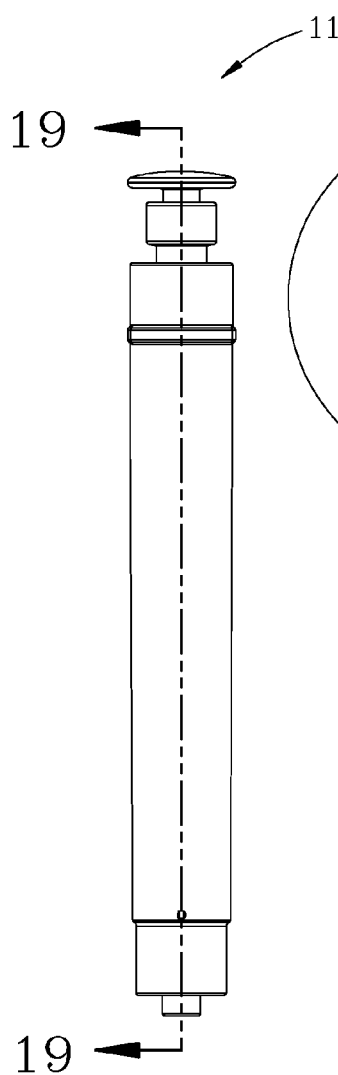
FIG. 18 is a side elevational view of the fluid delivery device of FIG. 12 similar to FIG. 15, but depicting the cartridge translated distally within the syringe, relative to the position of the cartridge shown in FIG. 15, to achieve fluid delivery.
Figure 19:
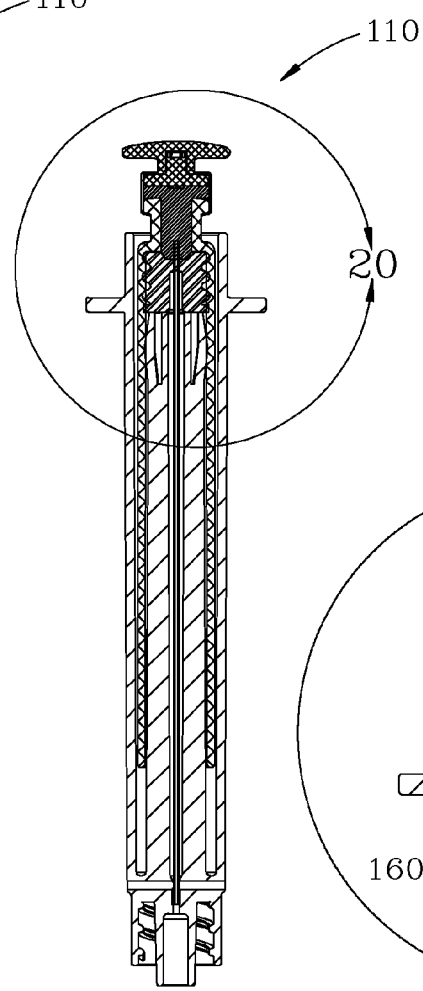
FIG. 19 is a cross-sectional view taken along line 19-19 in FIG. 18.
Figure 20:
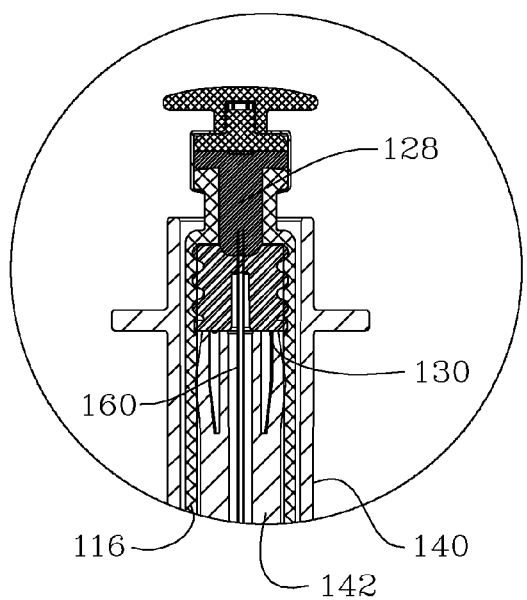
FIG. 20 is an enlarged view of the encircled portion of FIG. 19, depicting the stopper of the cartridge positioned within the fluid chamber and in contacting engagement with a proximal neck of a housing of the cartridge, and depicting a plug extending through the neck, with the needle extending through the stopper and into the plug.
Figure 23:
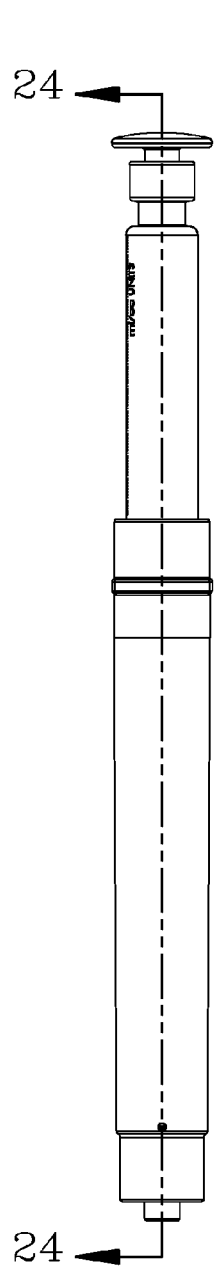
FIG. 23 is a side elevational view of the fluid delivery device of FIG. 21, depicting the cartridge and the syringe connected to one another and in relative axial positions that do not facilitate fluid delivery.
Figure 24:
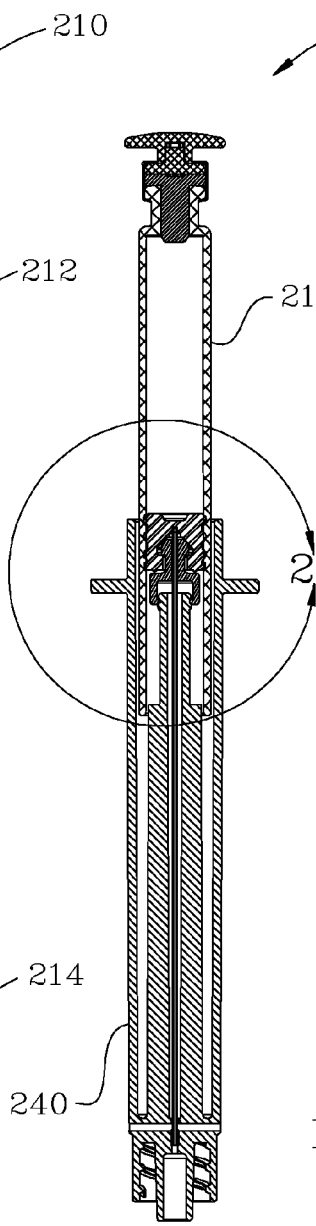
FIG. 24 is a cross-sectional view taken along line 24-24 in FIG. 23.

FIGS. 18-20 depict the fluid delivery device 110 after fluid delivery, with the housing 116 of the cartridge 112 substantially completely inserted into the cavity 144 defined by the outer body 140 and the inner core 142 of syringe 114. As shown in FIG. 20, the stopper 130 is positioned within a proximal end of the housing 116 and is in contacting engagement with a neck of the housing 116 and with the plug 128.

Similar to the fluid delivery device 10, a distal surface of plug 128 and a recess defined by stopper 130 can have complementary shapes to minimize residual fluid within the fluid chamber 118.

FIGS. 21-28 illustrate fluid delivery device 210 according to another embodiment. The fluid delivery device 210 can include a cartridge 212 and a syringe 214. As in previous embodiments, the cartridge 212 can be inserted into the syringe 214 to discharge fluid from the fluid delivery device 210. As shown in FIG. 21A, the cartridge 212 can include a housing 216 that can define a fluid chamber 218, and can include a generally cylindrical portion 220 and a neck 222. The cartridge 212 can also include a proximal button 224 and plug 228, which can be secured to the neck 222 of housing 216 using a crimp 226. The cartridge 212 can include a stopper 230 positioned within the fluid chamber 218. The stopper 230 can define a recess 268, which can be configured to receive a barb 266 (FIG. 21A) of syringe 214. The stopper 230 can include a proximal surface having a recessed portion 272 that has a shape which can be complementary to a shape of a distal surface of the plug 228 for purposes of at least minimizing any residual fluid within the fluid chamber 218 after delivery of fluid from the fluid delivery device 210.

The syringe 214 can have an outer body 240, an inner core 242 and a male luer connection 246, which can be integrally molded with one another as a unitary structure. The male luer connection 246 can define a lumen 248. This unitary structure can define a bore 211 (FIG. 27), or aperture, that can facilitate fixing a distal end of a needle 260 of the syringe 214 to the unitary structure, for example with any suitable adhesive. The syringe 214 can also include a flange 265, which can be integrally formed with the outer body 240, inner core 242 and male luer connection 246. The flange 265 can be configured to facilitate operation of the fluid delivery device 210. The outer body 240 and inner core 242 can cooperate to define a cavity 244 that can be configured and sized to receive at least a portion of housing 216.

Figure 25:
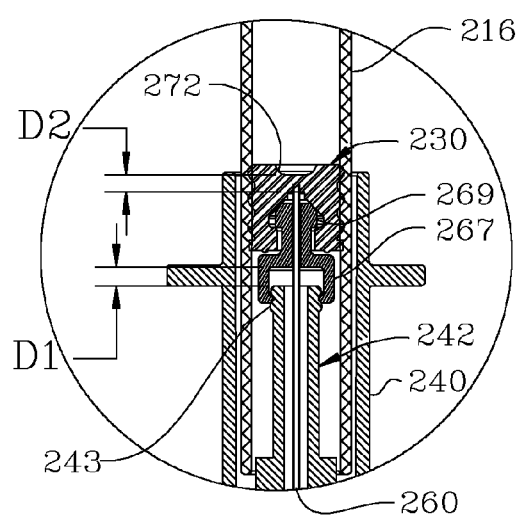
FIG. 25 is an enlarged view of the encircled portion of FIG. 24, depicting a barb of the syringe engaged with a stopper of the cartridge, with the stopper and the barb in a first position relative to an inner core of the syringe, and depicting a needle of the syringe spaced apart from a fluid chamber defined by the cartridge.

As shown in FIG. 25, the barb 266 of syringe 214 can include an annular portion 267 and a head 269 integral with the annular portion 267. The head 269 can have a shape that can be complementary to at least a portion of the recess 268 defined by stopper 230, and the annular portion 267 can be configured to engage a proximal end 243 of the inner core 242 of syringe 214. The barb 266 can be secured to the proximal end 243 of inner core 242 such that an axial gap, designated D1 in FIG. 25, can initially exist between a proximal end surface of the proximal end portion 243 of the inner core 242, and an opposing surface of the annular portion 267 of barb 266. The annular portion 267 of barb 266 can have one or more distal protrusions that can extend inwardly and can engage a groove extending at least partially around the proximal end portion 243 of the inner core 242.

As a health care provider pushes the proximal button 224 of cartridge 212 to insert the cartridge 212 into syringe 214, the resulting hydrostatic force can assist in attaching the stopper 230 to the barb 266. During initial travel of the cartridge 212 within syringe 214, the resistance to movement of the cartridge 212 can be relatively low, until such time that the head 269 of barb 266 engages stopper 230. The recess 268 defined by stopper 230 and the head 269 of barb 266 can be shaped and sized such that the head 269 of barb 266 snaps into the recess 268.

Figures 26, 27, 28:
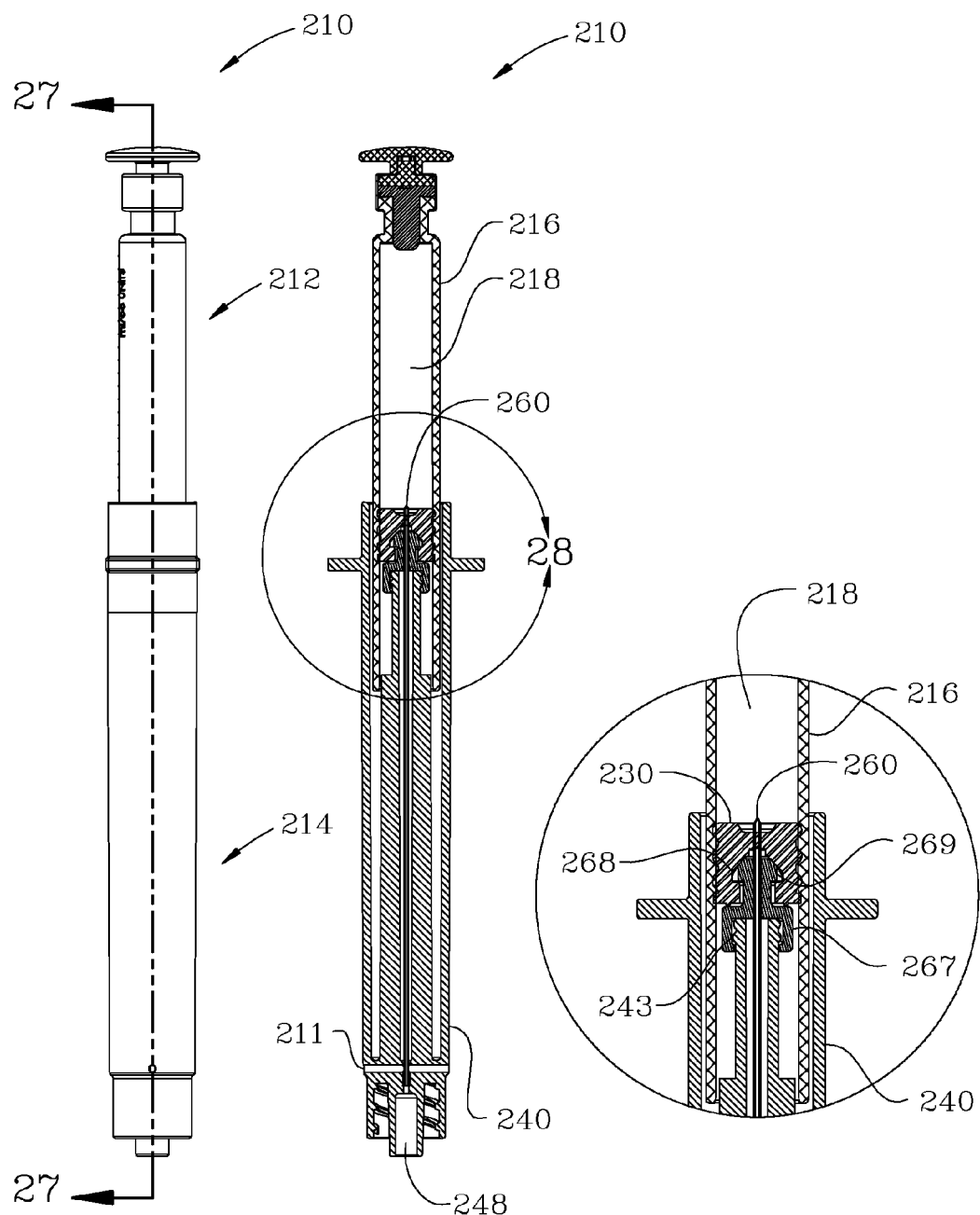
FIG. 26 is a side elevational view depicting the fluid delivery device of FIG. 23, where the cartridge is translated farther distally, relative to the syringe, by a relatively small distance sufficient to seat the barb upon the inner core of the syringe.
FIG. 27 is a cross-sectional view taken along line 27-27 in FIG. 26.
FIG. 28 is an enlarged view of the encircled portion of FIG. 27, depicting the barb of the syringe in a second position, translated distally relative to the position of the barb shown in FIG. 25, such that the barb is seated upon the inner core of the syringe, and depicting the needle of the syringe extending through the stopper of the cartridge and into the fluid chamber.
Figures 29, 30, 30A, 31:
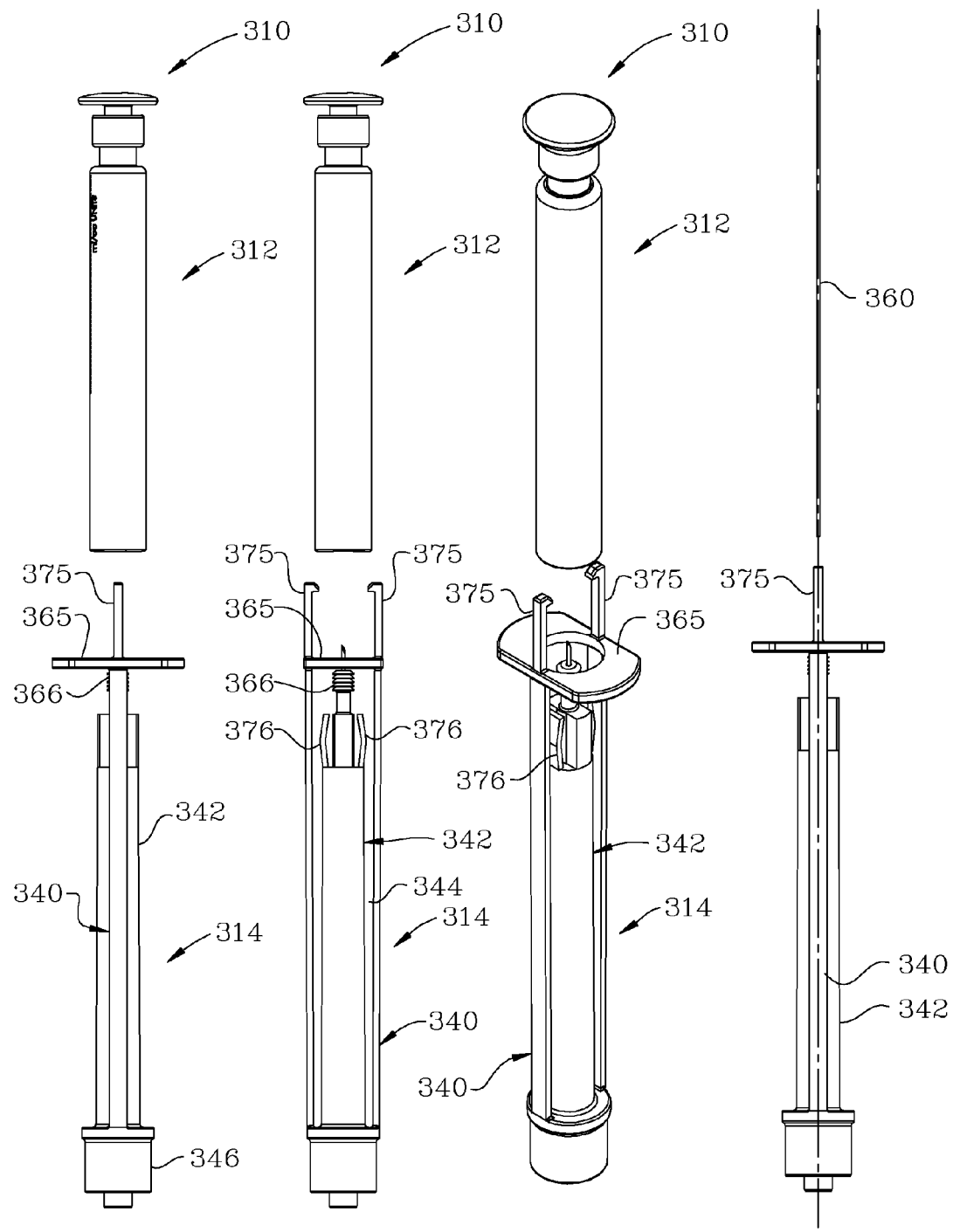
FIG. 29 is a side view of a fluid delivery device according to another embodiment, depicting a cartridge and a syringe of the fluid delivery device disconnected from one another.
FIG. 30 is a front view of the fluid delivery device of FIG. 29, depicting the cartridge and the syringe disconnected from one another.
FIG. 30A is a perspective view of the fluid delivery device of FIG. 29, depicting the cartridge and the syringe disconnected from one another.
FIG. 31 is an exploded view of the syringe of the fluid delivery device of FIG. 29.
Figure 32:
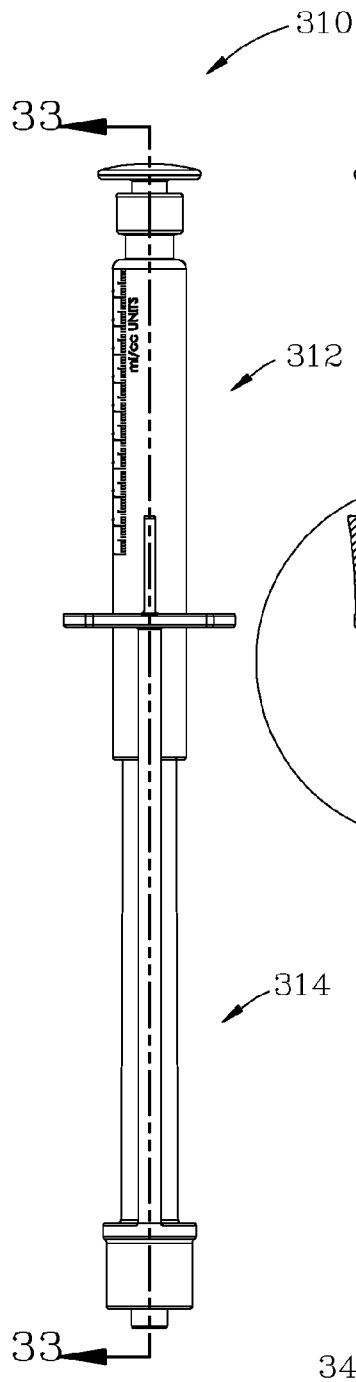
FIG. 32 is a side view of the fluid delivery device of FIG. 29, depicting the cartridge and the syringe connected to one another.

The stopper 230 can be configured to have a membrane thickness, indicated at D2 in FIG. 25, which can be a minimum distance between the recess 268 defined by stopper 230 and the recessed portion 272 of the proximal surface of stopper 230. The proximal end portion 243 of the inner core 242 and the barb 266 of syringe 214, and the stopper 230 of cartridge 212, can be sized and configured such that the distance D1 can be greater than or equal to the distance D2. This relationship can prevent the needle 260 from being inserted through stopper 230 until such time that the barb 266 is substantially completely seated upon the proximal end portion 243 of the inner core 242, as shown in FIG. 28, which depicts a proximal tip of the needle 260 extending just slightly beyond the stopper 230 into the fluid chamber 218. Minimizing the distance that the needle 260 extends beyond stopper 230 can facilitate minimizing an amount of any residual fluid within the fluid chamber 218, as described previously. The two axial positions of the barb 266 relative to the proximal end portion 243 of the inner core 242 shown in FIGS. 25 and 28, can allow increased manufacturing variance without loss of functionality, as compared to other barb and stopper configurations. For example, the configuration of the barb 266 and the proximal end portion 243 of the inner core 242 can facilitate the accommodation of manufacturing tolerances associated with the length of needle 260 while maintaining a minimum protrusion of the needle 260 beyond stopper 230, when the barb 266 is completely seated upon the proximal end portion 243 of the inner core 242. The connection of stopper 230 with barb 266 can permit the fluid delivery device 210 to achieve bi-directional fluid flow, i.e., flow out of and into the flow chamber 218, via a lumen defined by the needle 260 and lumen 248. Use of barb 266 can facilitate the prevention of inadvertent premature spraying of fluid from the fluid delivery device 210, by alerting a health care provider of the initial engagement of the barb 266 with stopper 230, when the needle 260 has not pierced the stopper 230, so that the health care provider can avoid the application of excessive force to cartridge 212 in order to pierce stopper 230 with needle 260.

Figure 33:
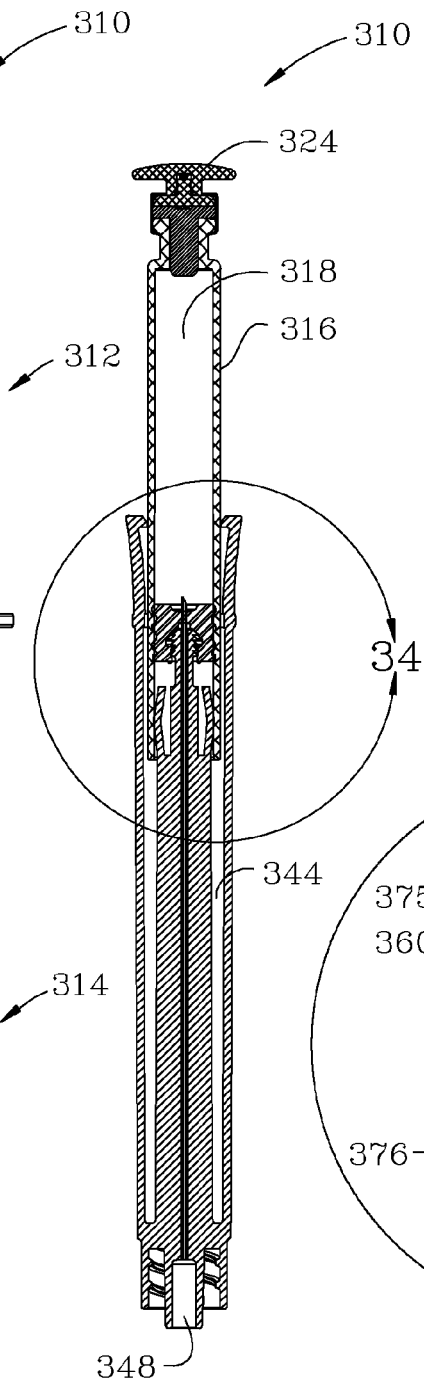
FIG. 33 is a cross-sectional view taken along line 33-33 in FIG. 32.

FIGS. 29-37 illustrate a fluid delivery device 310 according to another embodiment. Fluid delivery device 310 can include a cartridge 312 and a syringe 314. The cartridge 312 can be inserted into the syringe 314, as with previous embodiments of the fluid delivery device. As shown in FIG. 33, the cartridge 312 can include a housing 316 that can define a fluid chamber 318, and can also include a proximal button 324 that can facilitate inserting the cartridge 312 into the syringe 314. Cartridge 312 can also include a stopper 330 (FIG. 34) that can be positioned within the fluid chamber 318.

The syringe 314 can include an outer body 340, an inner core 342, and a male luer connection 346 which can be integrally formed with one another, e.g. by molding, as a unitary structure. All exterior surfaces of the outer body 340, inner core 342 and male luer connection 346 can be molded with a pair of opposing cores, thus alleviating possible manufacturing challenges associated with drafted surfaces over long distances and/or thin steel conditions. The outer body 340 and inner core 342 can cooperate to define a cavity 344 that can be configured to receive at least a portion of housing 316. The male luer connection 346 can define a lumen 348.

Figure 34:
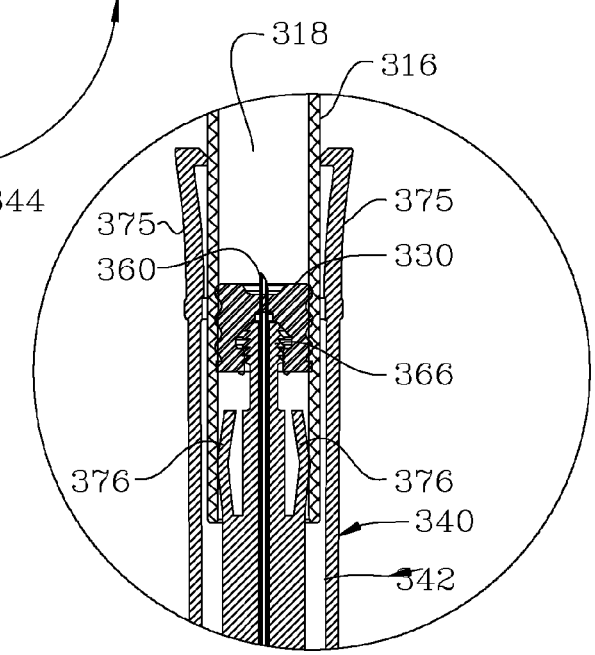
FIG. 34 is an enlarged view of the encircled portion of FIG. 33, depicting a needle of the syringe extending through a stopper of the cartridge and into a fluid chamber defined by the cartridge.

The syringe 314 can also include a needle 360, a flange 365, a plurality of flexible guides 376 or friction fingers, and a plurality of retaining fingers 375. The flexible guides 376 can assert an outward force against the housing 316 to facilitate holding the cartridge 312 in position with respect to the syringe 314. The syringe 314 can also include a barb 366 integral with the inner core 342. The barb 366 can engage a recess defined by the stopper 330 of cartridge 312, to connect the stopper 330 to the barb 366, as shown in FIGS. 34 and 37.

Figure 35:
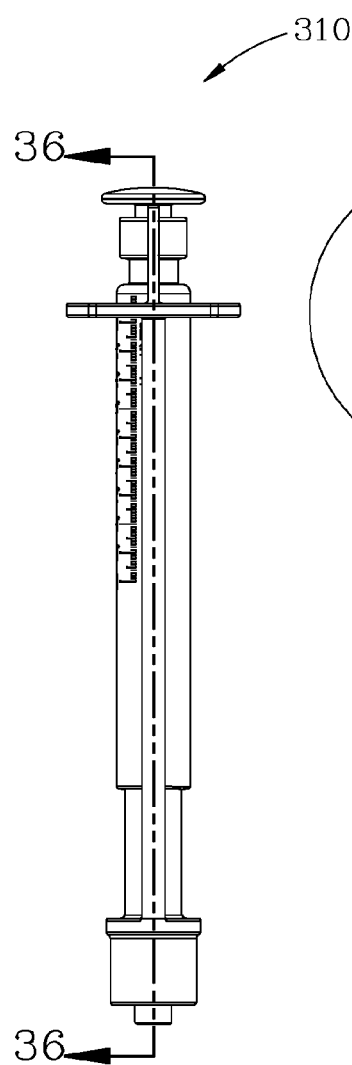
FIG. 35 is a side view of the fluid delivery device of FIG. 29, similar to FIG. 32, but depicting the cartridge translated distally within the syringe, relative to the position of the cartridge shown in FIG. 32, to achieve fluid delivery.
Figure 36:
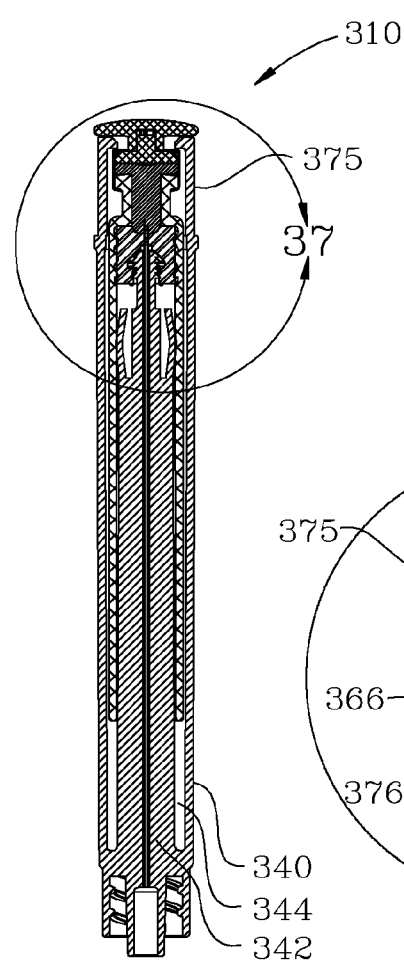
FIG. 36 is a cross-sectional view taken along line 36-36 in FIG. 35.
Figure 37:
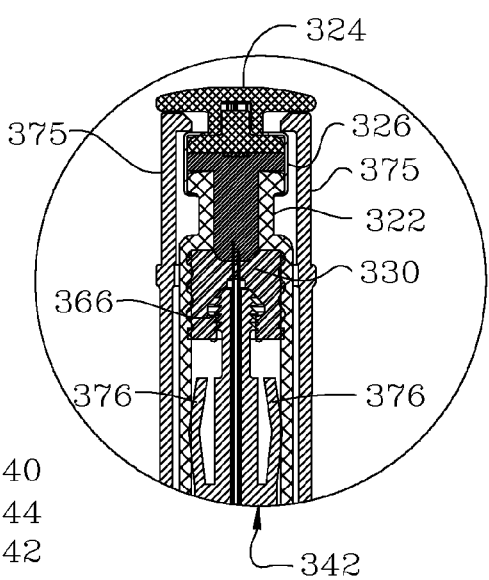
FIG. 37 is an enlarged view of the encircled portion of FIG. 36, depicting the stopper of the cartridge positioned within the fluid chamber and in contacting engagement with a proximal neck of a housing of the cartridge, and depicting a plug extending through the neck, with the needle extending through the stopper and into the plug.

When the cartridge 312 has been substantially fully inserted into the syringe 314 as shown in FIGS. 35-37, to achieve fluid delivery, a proximal end of each of the retaining fingers 375 can be positioned axially between the proximal button 324 of cartridge 312 and a crimp 326 of cartridge 312, as shown in FIG. 37. The crimp 326 can be used to secure the proximal button 324 to a neck 322 of the housing 316 of cartridge 312. As a result, the retaining fingers 375 can retain the cartridge 312 and syringe 314 in the relative positions depicted in FIGS. 35-37, which can prevent removal of the cartridge 312.

Figures 40, 41, 42:
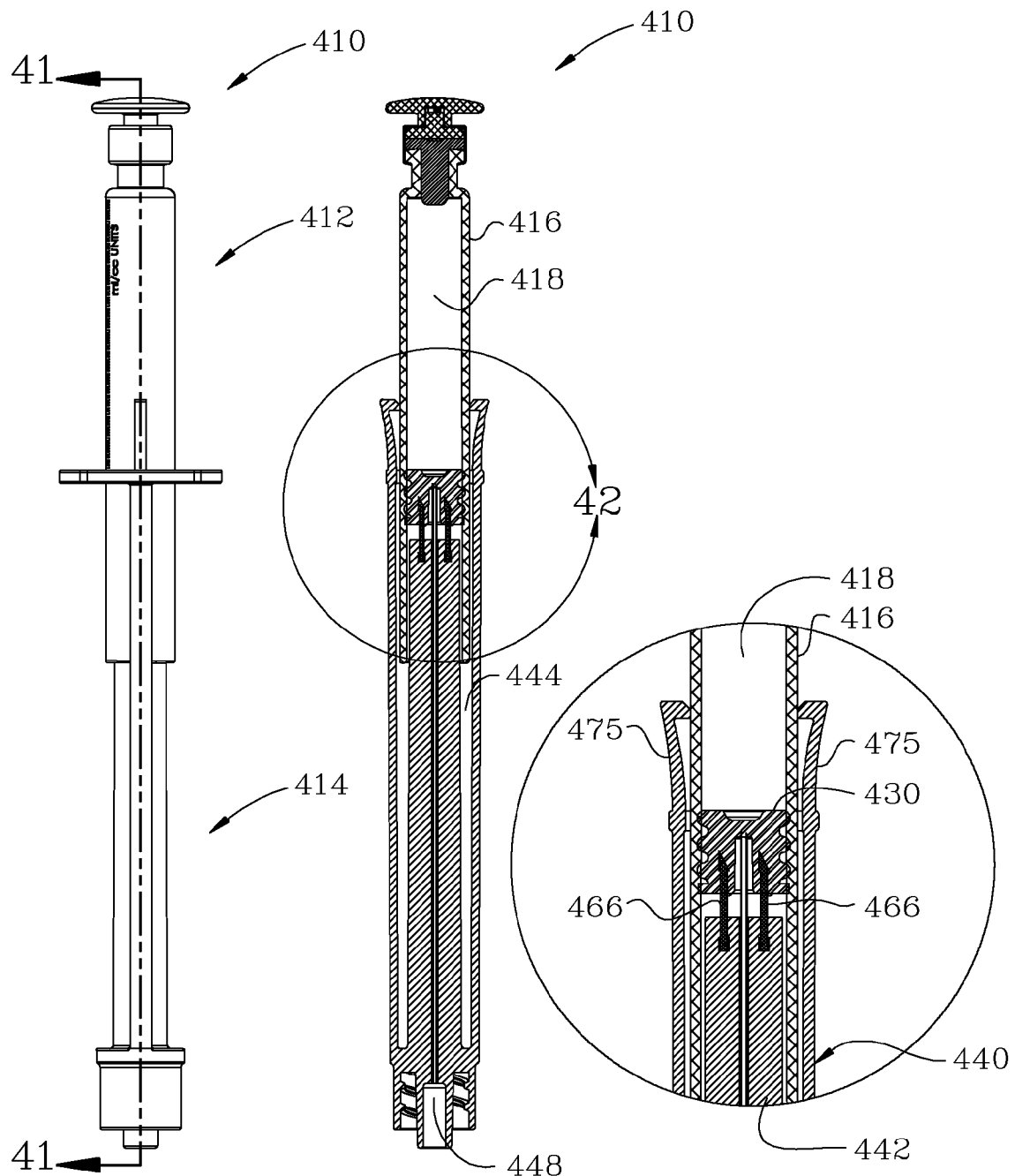
FIG. 40 is a side elevational view of the fluid delivery device of FIG. 38, depicting the cartridge and the syringe connected to one another.
FIG. 41 is a cross-sectional view taken along line 41-41 in FIG. 40.
FIG. 42 is an enlarged view of the encircled portion of FIG. 41, depicting barbs of the syringe engaged with a stopper of the cartridge, and depicting a needle of the syringe extending partially into the stopper such that the needle is not in fluid communication with a fluid chamber defined by the cartridge.
Figures 43, 44, 45:
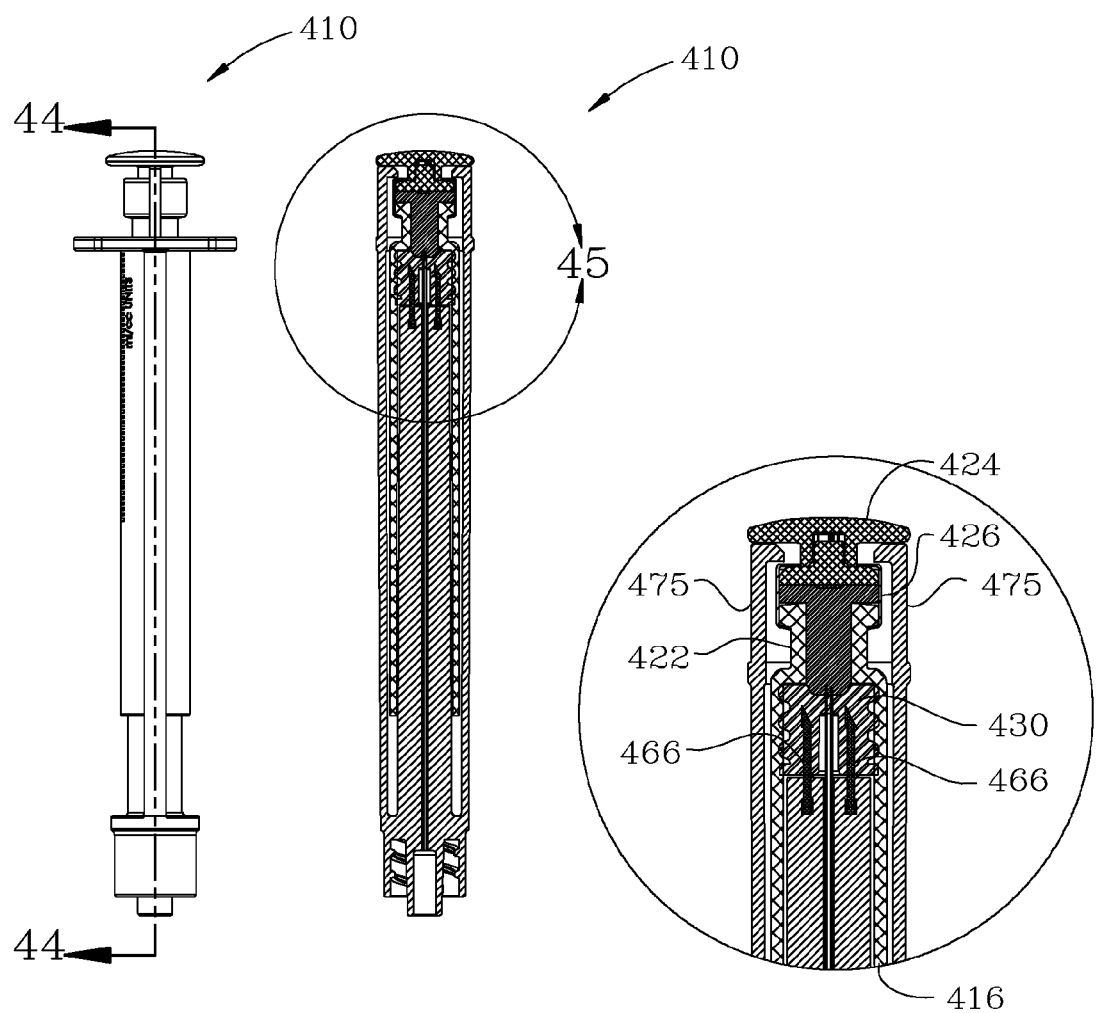
FIG. 43 is a side view of the fluid delivery device of FIG. 38, similar to FIG. 40, but depicting the cartridge translated distally within the syringe, relative to the position of the cartridge shown in FIG. 40, to achieve fluid delivery.
FIG. 44 is a cross-sectional view taken along line 44-44 in FIG. 43.
FIG. 45 is an enlarged view of the encircled portion of FIG. 44, depicting the stopper of the cartridge positioned within the fluid chamber and in contacting engagement with a proximal neck of a housing of the cartridge, and depicting a plug extending through the neck, with the needle extending through the stopper and into the plug.

FIGS. 38-45 illustrate a fluid delivery device 410 according to another embodiment. The fluid delivery device 410 can include a cartridge 412 and a syringe 414. As shown in FIGS. 41 and 42, the cartridge 412 can include a housing 416 that can define a fluid chamber 418 and can further include a stopper 430 positioned within the fluid chamber 418. As shown in FIG. 45, the housing 416 can include a neck 422 and the cartridge 412 can further include a proximal button 424 and a crimp 426 that can be used to secure the proximal button 424 and a plug of cartridge 412 to the neck 422.

The syringe 414 can include an outer body 440 and an inner core 442 that can cooperate to define a cavity 444 (FIG. 38A) that can be sized and configured to receive at least a portion of the housing 416 of cartridge 412. The syringe 414 can also include a needle 460, with a substantial portion of needle 460 positioned within the inner core 442, as shown in FIG. 38A. The syringe 414 can also include a male luer connection 446 at a distal end of syringe 414. The male luer connection 446 can define a lumen 448 (FIG. 41). The syringe 414 can also include a flange 465 to facilitate operation of the fluid delivery device 410 by a healthcare provider, and a plurality of retaining fingers 475, which can function as described previously with respect to the fingers 375 of the fluid delivery device 310.

The syringe 414 can include one or more barbs 466, which can be pin barbs, and can be secured to a proximal end of the inner core 442 of syringe 414. During insertion of the cartridge 412 into the syringe 414, the barbs 466 of syringe 414 can engage, and can extend into, the stopper 430 of cartridge 412. The engagement of stopper 430 with barbs 466 can prevent the stopper 430 from moving proximally away from syringe 412, which can permit bi-directional fluid flow when a lumen defined by the needle 460 is in fluid communication with the fluid chamber 418. More particularly, the engagement of barbs 466 with stopper 430 can permit fluid to be expelled from the fluid chamber 418 such that it discharges through lumen 448, and can also permit aspiration of fluid into the fluid chamber 418 from lumen 448.

Figure 46:
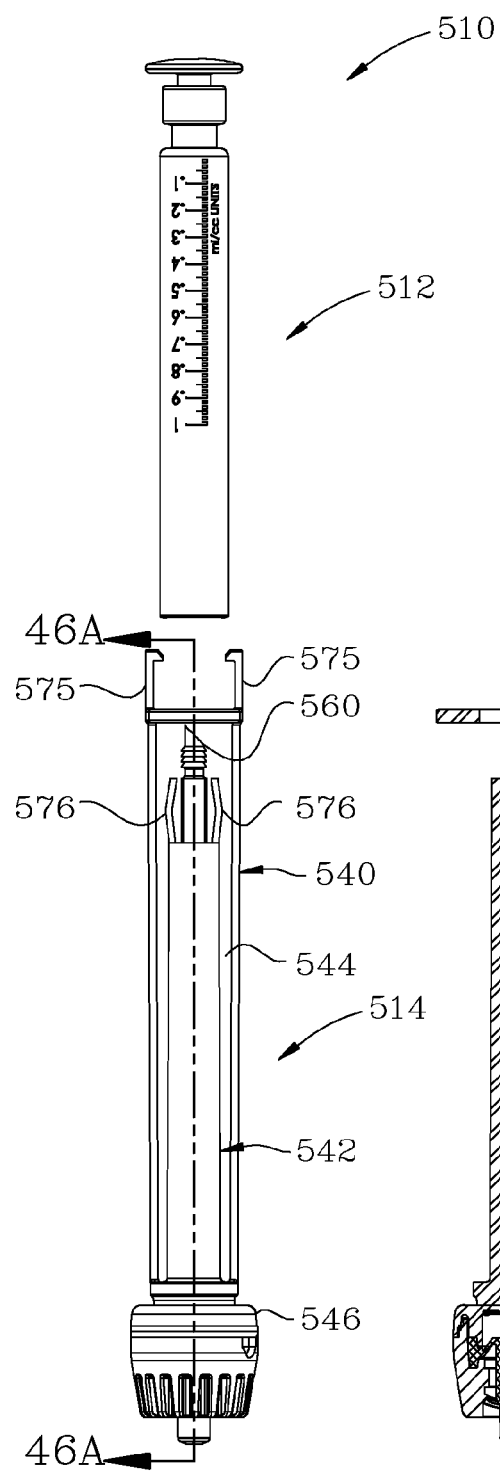
FIG. 46 is a front elevational view of a fluid delivery device according to another embodiment, depicting a cartridge and a syringe of the fluid delivery device disconnected from one another.
Figure 46A:
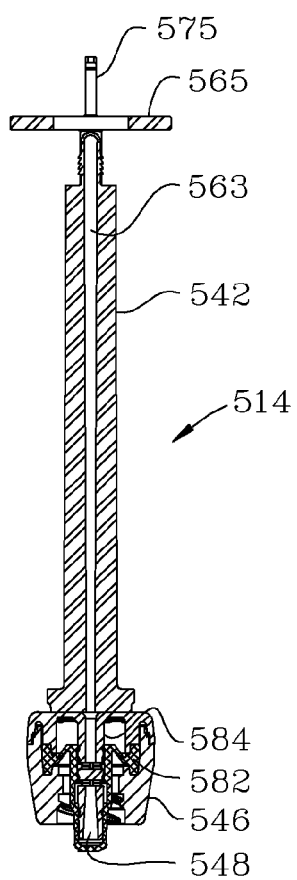
FIG. 46A is a cross-sectional view taken along line 46A-46A in FIG. 46.
Figure 47:
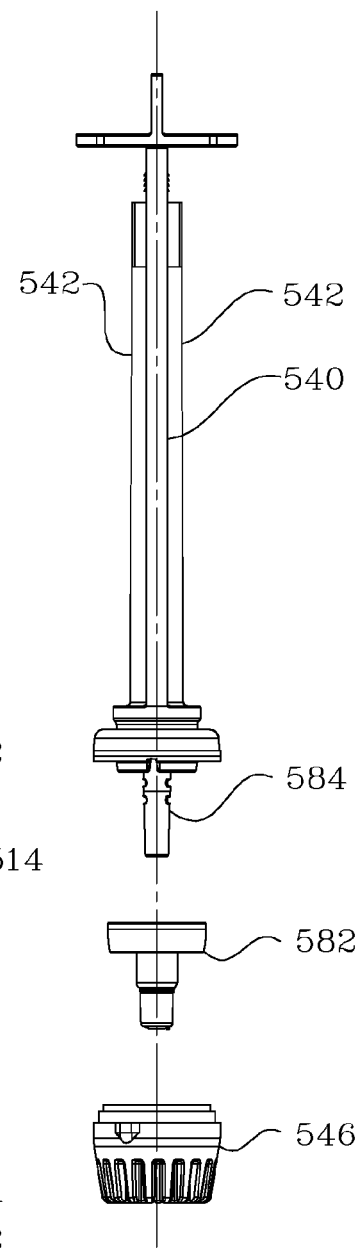
FIG. 47 is an exploded view of the syringe of the fluid delivery device of FIG. 46.
Figure 48:
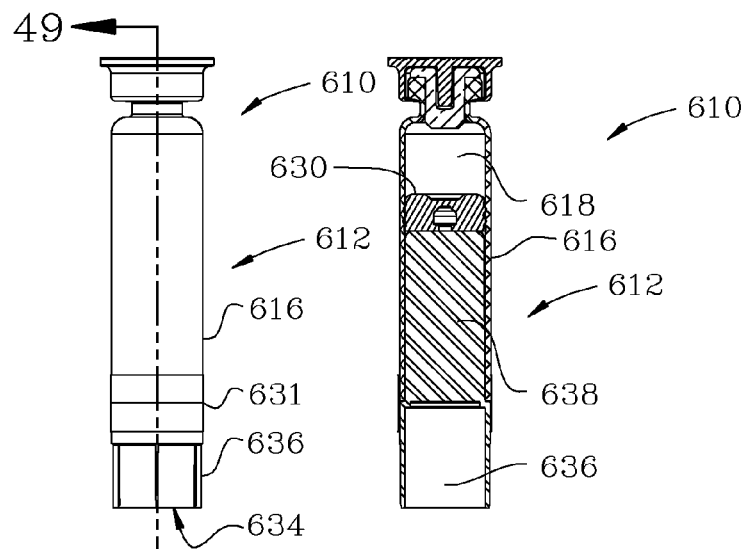
FIG. 48 is a side elevational view of a fluid delivery device according to another embodiment, depicting a cartridge and a syringe of the fluid delivery device disconnected from one another.

FIGS. 46-47 illustrate a fluid delivery device 510 according to another embodiment. The fluid delivery device 510 can include a cartridge 512 and a syringe 514. The syringe 514 can include an outer body 540 and an inner core 542, which can cooperate to define a cavity 544 that can be sized and configured to receive at least a portion of a housing of the cartridge 512. The fluid delivery device 510 does not include a metal needle, but instead includes a proximal tip of a needle 560, which can be integrally formed with the inner core 542 from any suitable plastic material. Additionally, the inner core 542 can define a lumen 563 that can be in fluid communication with the proximal tip of needle 560. The syringe 514 can also include a flange 565 to facilitate use of the fluid delivery device 510 by the hand of a healthcare provider, and can further include a plurality of retaining fingers 575 and a plurality of flexible guides 576 or friction fingers. The retaining fingers 575 and flexible guides 576 can function in a manner as described previously with respect to the corresponding components of previous embodiments, for example the retaining fingers 375 and flexible guides 376 of the fluid delivery device 310.

The fluid delivery device 510 can further include a needle-free valve that can include a male luer connection 546, which can define a lumen 548, a seal 582, which can be made of a resilient material, e.g., silicone rubber, and a valve stem 584, which can be an extension of the inner core 542. The seal 582 can prevent fluid from discharging from the fluid delivery device 510, through lumen 548, until such time that a female luer connection is connected to the male luer connection 546 of the needle free valve. The needle free valve can be particularly useful in applications where hazardous fluids are provided by the fluid delivery device 510.

FIGS. 48-52 illustrate a fluid delivery device 610 according to another embodiment. The fluid delivery device 610 can include a cartridge 612 and a syringe 614. Similar to previous embodiments, the cartridge 612 can include a housing 616 that can define a fluid chamber 618 (FIG. 49), and housing 616 can include a generally cylindrical portion 620 and a neck 622. The cartridge can further include a proximal button 624, a crimp 626 and a plug 628, and the crimp 626 can secure the plug 628 to the neck 622 of housing 616. The cartridge 612 can further include a stopper 630 which can be positioned within the fluid chamber 618.

Figure 49:
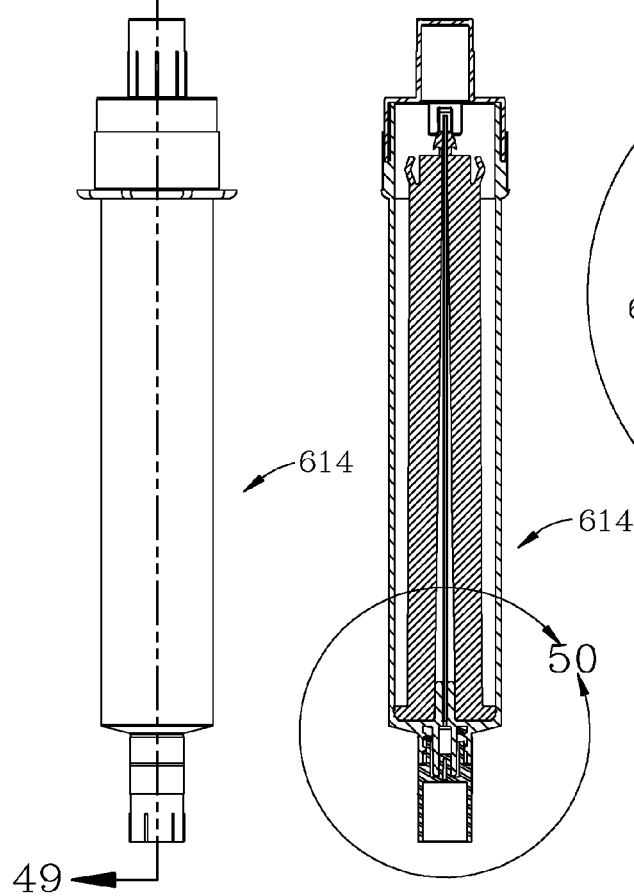
FIG. 49 is a cross-sectional view taken along line 49-49 in FIG. 48.

Unlike previous embodiments, the cartridge 612 can also include a cap 634, which can include an annular distal portion 636 and a proximal portion 638 integral with the annular distal portion 636. The proximal portion 638 can include a plurality of circumferentially spaced fins. Cap 634 can be inserted into fluid chamber 618, as shown in FIG. 49, to position the stopper 630 at a desired position within the fluid chamber 618 to achieve a desired volume of fluid within the fluid chamber 618. For example, the cap 634 can be positioned so that about 3 ml of fluid can be contained within the fluid chamber 618. However, the size of housing 616 and the position of cap 634 can be selected such that more than 3 ml of fluid or less than 3 ml of fluid can be contained within the fluid chamber 618. A tamper evident label 631 can be secured to both the cap 634 and the housing 616. The cap 634 can be removed from the housing 616 at any suitable time prior to the insertion of the cartridge 612 into the syringe 614.

An inside diameter of the generally cylindrical portion 620 of housing 616 can be larger than an inside diameter of the generally cylindrical portion of the housing of some other fluid delivery devices. For example, for certain applications, the inside diameter of the generally cylindrical portion 620 of housing 616 can be about ½ in. and an inside diameter of the generally cylindrical portion 20 of housing 16 of cartridge 12 of the fluid delivery device 10 can be about ⅓ in. Accordingly, the magnitude of hydrostatic pressure within the generally cylindrical portion 620 of housing 616 can be less than the magnitude of the hydrostatic pressure within the generally cylindrical portion 20 of housing 16, with the same magnitude of force applied to cartridge 612 and cartridge 12 during insertion of cartridges 612 and cartridge 12 into syringes 614 and 14, respectively. The inside diameter of the generally cylindrical portion 620 of housing 616 and the inside diameter of the generally cylindrical portion 20 of housing 16 can be greater than, or less than, the respective magnitudes described above.

The cap 634 can also be utilized to permit the cartridge 612 to be pre-filled using a process that is commonly referred to as a "vial-filling" process. Vial-filling processes can require a distal end of the vial or cartridge to be filled to be positioned on, and extend upwardly from, a support surface. A fluid discharge device, e.g., a nozzle, of the vial-filling equipment can then be inserted through the neck 622 of housing 616 of cartridge 612 to inject fluid into the fluid chamber 618.

Figure 50:
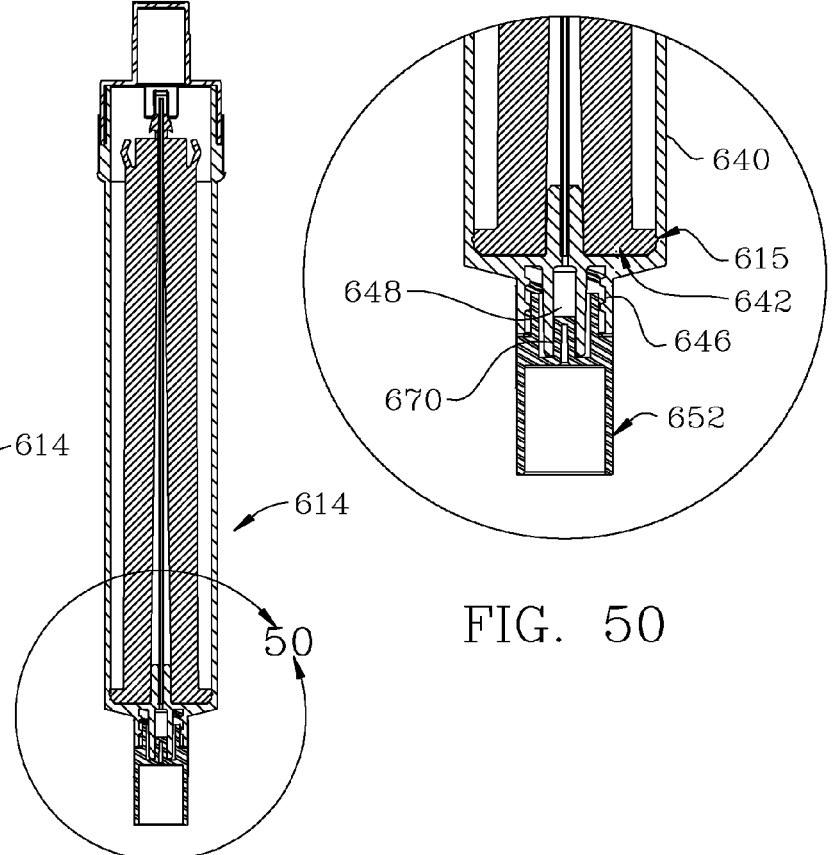
FIG. 50 is an enlarged view of the encircled portion of FIG. 49.
Figures 51, 52:
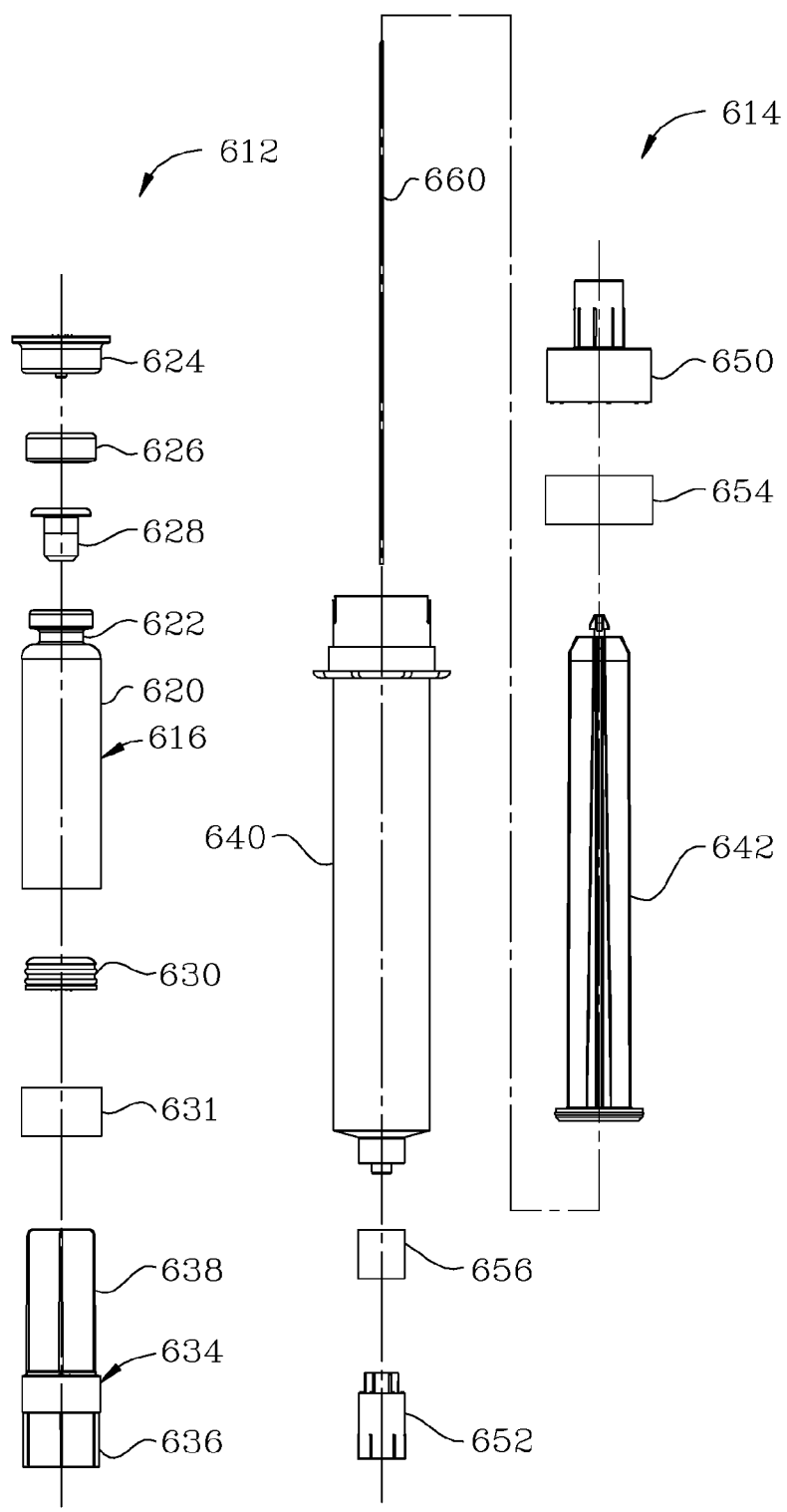
FIG. 51 is an exploded view of the cartridge of the fluid delivery device of FIG. 48.
FIG. 52 is an exploded view of the syringe of the fluid delivery device of FIG. 48.
Figures 53, 54:
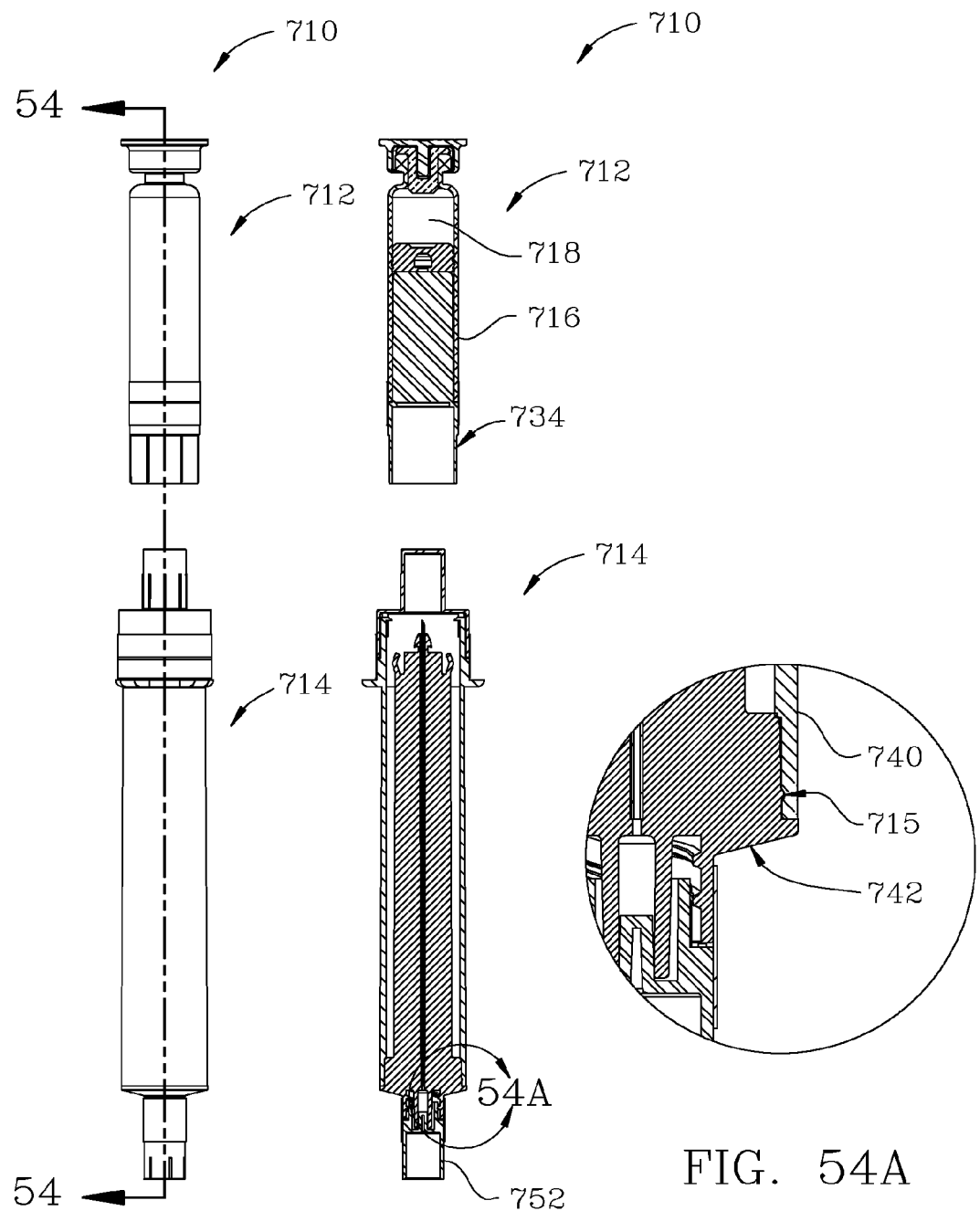
FIG. 53 is a side elevational view of a fluid delivery device according to another embodiment, depicting a cartridge and a syringe of the fluid delivery device disconnected from one another.
FIG. 54 is a cross-sectional view taken along line 54-54 in FIG. 53.

The syringe 614 can include an outer body 640, an inner core 642, and a needle 660. The outer body 640 and inner core 642 can be formed separately from one another, e.g. by injection molding. A distal end of the inner core 642 can include an annular snap ring 615 (FIG. 50) that can engage a mating recess formed on an inner surface of the outer body 640 to prevent axial movement of the inner core 642 relative to the outer body 640. The needle 660 can be positioned within a bore defined by the inner core 642, and the needle 660 can extend beyond a proximal end of the inner core 642. As shown in FIG. 52, the syringe 614 can further include a proximal end cap 650, a distal end cap 652 and tamper evident labels 654 and 656. Tamper evident label 654 can be secured to both the proximal end cap 650 and the outer body 640. The cap 634 can be removed from cartridge 612 and the proximal end cap 650 can be removed from syringe 614 to permit insertion of the cartridge 612 into the syringe 614. As shown in FIG. 50, the syringe can include a male luer connection 646, which can define a lumen 648. The male luer connection 646 can be integrally molded with the outer body 640. Distal end cap 652 can include a plug 670 that can protrude into the lumen 648, which can prevent undesired spraying of fluid out of lumen 648 during initial insertion of the cartridge 612 into the syringe 614 to connect the stopper 630 to syringe 614, prior to the desired delivery of fluid from the fluid delivery device 610 through lumen 648. The tamper evident label 656 can be initially secured to both the distal end cap 652 and the male luer connection 646.

FIGS. 53-56B illustrate a fluid delivery device 710 according to another embodiment. The fluid delivery device 710 can include a cartridge 712 and a syringe 714. The cartridge 712 can include a housing 716, which can define a fluid chamber 718 (FIG. 54), and which can include a generally cylindrical portion 720 and a neck 722 as shown in FIG. 55. The cartridge 712 can further include a proximal button 724, a crimp 726 and a plug 728. The crimp 726 can secure the proximal button 724 and the plug 728 to the neck 722 of the housing 716. The cartridge 712 can also include a stopper 730, which can be positioned within the fluid chamber 718. Similar to the fluid delivery device 610, the cartridge 712 of the fluid deliver device 710 can include a cap 734, which can be configured similar to or the same as cap 634 of fluid delivery device 610, and can be inserted into the fluid chamber 718 to establish the desired volume of pre-filled fluid within the fluid chamber 718.

The syringe 714 of the fluid delivery device 710 can include an outer body 740, an inner core 742, a male luer connection 746, a proximal end cap 750, a distal end cap 752, tamper evident labels 754 and 756, and a needle 760. The outer body 740 and inner core 742 can be separately formed, e.g., using a molding process such as injection molding. The inner core 742 can include an annular snap ring 715 (FIG. 54A) extending around an outer surface of the inner core 742 that can engage a mating recess, or groove, defined by an inner surface of the outer body 740. The snap ring 715 can prevent relative axial movement between the inner core 742 and the outer body 740. Alternatively, a separate retention device such as an O-ring can be used in lieu of the integrally formed snap ring 715. In this instance, the O-ring could engage mating grooves defined by the outer surface of the inner core 742 and the inner surface of the outer body 740. A tamper evident label 731 can be secured to both the cap 734 and the housing 716 until removal of cap 734 is desired.

The male luer connection 746 can be integrally formed with the inner core 742 of syringe 714, unlike the fluid delivery device 610 where the male luer connection 646 is shown to be integral with the outer body 640. The syringe 714 can include anti-rotation features to prevent the inner core 742 from rotating relative to the outer body 740 as a result of connecting the male luer connection 746 to a female luer connection. For example, the inner core 742 can include a plurality of circumferentially alternating ridges and slots, indicated generally at 717 in FIG. 56B, which can extend around an exterior of the inner core 742, and which can be located proximate the male luer connection 746. The outer body 740 can include a plurality of circumferentially alternating ridges and slots, indicated generally at 719 in FIG. 56A that can extend around an interior of the outer body 740. The plurality of alternating ridges and slots 717 of the inner core 742 can be interconnected with the plurality of alternating ridges and slots 719 of the outer body 740 to prevent relative rotation between the inner core 742 and the outer body 740, for example during connection of a female luer connection to the male luer connection 746.

FIG. 57 illustrates a barb 866, which can be used with a variety of fluid delivery devices, such as a fluid delivery device 810 that is shown in FIGS. 58 and 59. The barb 866 can include a stem 890 and a plurality of spaced fingers 892 that can be integral with the stem 890. The fluid delivery device 810 can include a cartridge 812 and a syringe 814. The cartridge 812 can include a housing 816 and a stopper 830. The stopper 830 can be positioned in a fluid chamber defined by the housing 816. The syringe 814 can include an outer body 840 and an inner core 842. The barb 866 can be connected to the inner core 842. When the cartridge 812 is inserted into the syringe 814, as shown in FIGS. 58 and 59, the barb 866 can engage the stopper 830. More particularly, the fingers 892 of the barb 866 can be positioned in a recess defined by the stopper 830 to connect the stopper 830 to the barb 866, such that the fluid delivery device 810 is capable of bi-directional fluid flow.

FIG. 60 illustrates a barb 966 according to another embodiment. The barb 966 can be used with a variety of fluid delivery devices, such as a fluid delivery device 910 which is shown in FIGS. 61 and 62. The barb 966 can include a stem 990 and a plurality of fingers 992 that can be integral with the stem 990. One or more of the fingers 992, e.g., fingers 992a and 992b, can include an extended point, i.e., can extend outwardly farther from the stem 990 than other ones of the fingers 992. The fluid delivery device 910 can include a cartridge 912 and a syringe 914. The cartridge 912 can include a housing 916 that can define a fluid chamber, and can also include a stopper 930 that can be positioned within the fluid chamber. The syringe 914 can include an outer body 940 and an inner core 942. The barb 966 can be secured to a proximal end of the inner core 942, and can engage the stopper 930. As shown in FIGS. 61 and 62, when the cartridge 912 is inserted into the syringe 914, the fingers 992 of barb 966 can be positioned within a recess defined by the stopper 930 to connect the stopper 930 to barb 966, such that the fluid delivery device 910 is capable of bi-directional fluid flow.

FIG. 63 illustrates a barb 1066 according to another embodiment, which can be used with a variety of fluid delivery devices, such as a fluid delivery device 1010 that is shown in FIGS. 64 and 65. The barb 1066 can include a stem 1090 and a dome head 1096. The dome head 1096 can be solid. The fluid delivery device 1010 can include a cartridge 1012 and a syringe 1014. The cartridge 1012 can include a housing 1016 that can define a fluid chamber, and can also include a stopper 1030 that can be positioned within the fluid chamber. The syringe 1014 can include an outer body 1040 and an inner core 1042. The stem 1090 of the barb 1066 can be secured to a proximal end of the inner core 1042, and the dome head 1096 of the barb 1066 can be positioned within a recess defined by the stopper 1030 to connect the stopper 1030 to the barb 1066, such that the fluid delivery device 1010 is capable of bi-directional fluid flow.

Figure 66A:
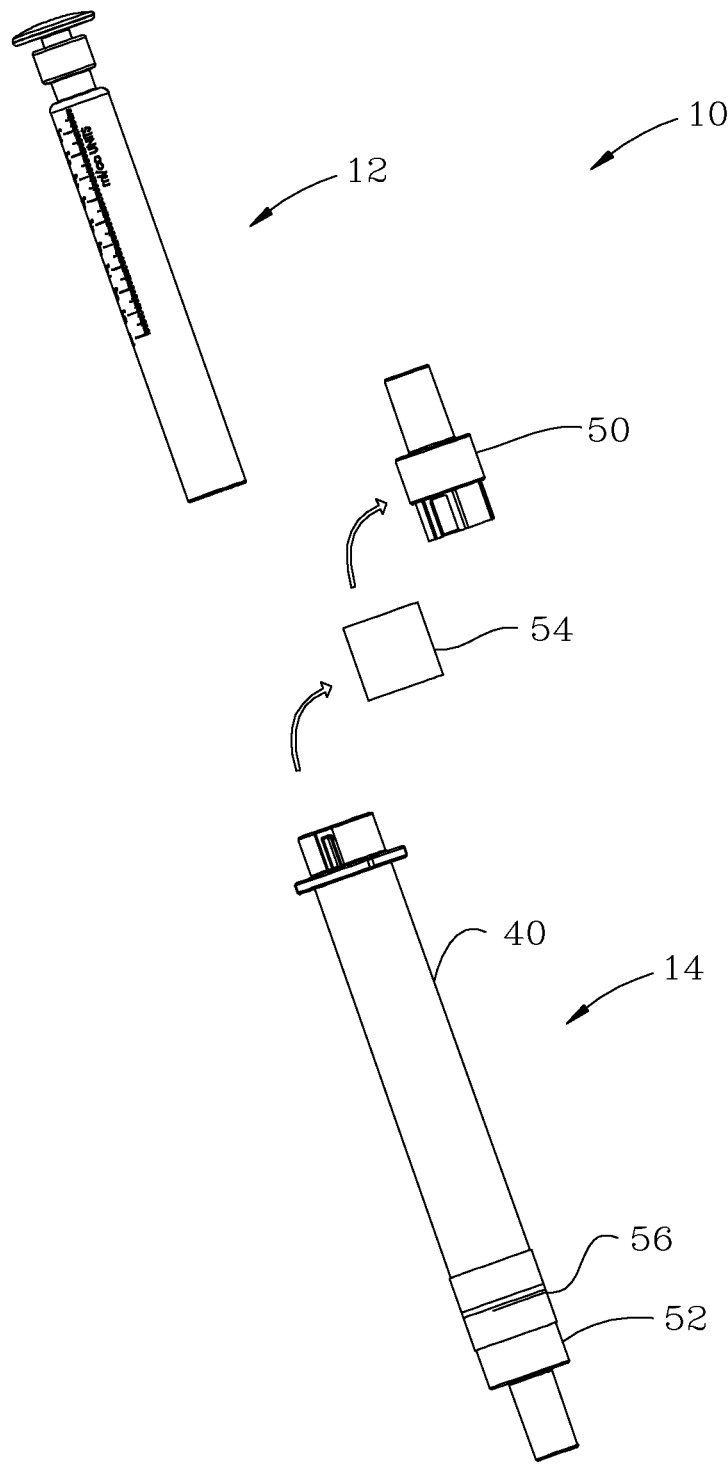
Figure 66C:
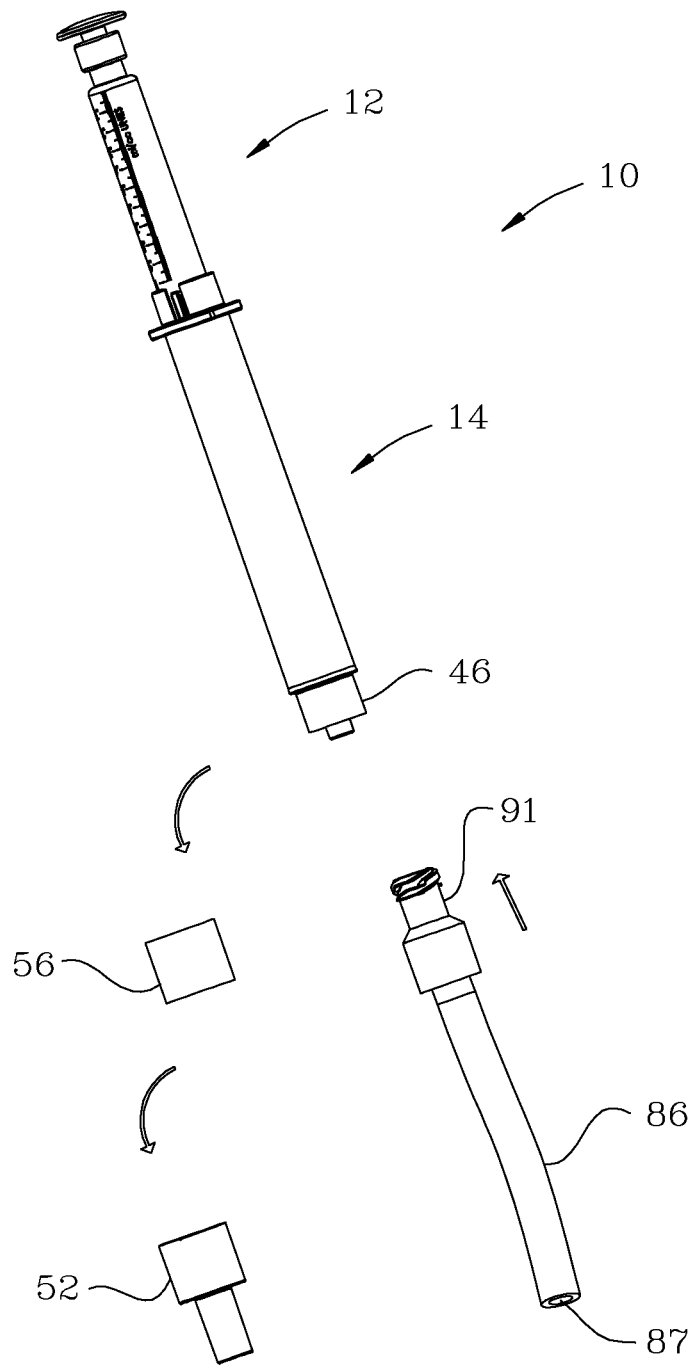

FIGS. 66A-66D illustrate a method, according to one embodiment, of using the fluid delivery device 10 of FIG. 1. The cartridge 12 can be pre-filled with medicinal fluid prior to inserting the cartridge 12 into the syringe 14. As shown in FIG. 66A, and as preparation for inserting the cartridge 12 into the syringe 14, the tamper evident label 54 can be removed from the outer body 40 and the proximal end cap 50 of syringe 14. The proximal end cap 50 can then be removed, with the distal end cap 52 remaining installed. The cartridge 12 can then be inserted into the syringe 14 as indicated generally by the arrow 95 in FIG. 66B. The distal end cap 52 can remain installed during the initial insertion of the cartridge 12 into the syringe 14 until such time that the needle 60 (not shown in FIGS. 66A-66D) penetrates the stopper 30 and a lumen defined by the needle 60 is in fluid communication with the fluid chamber 18 (stopper 30 and fluid chamber 18 not shown in FIGS. 66A-66D). The relative positions of cartridge 12 and syringe 14 when the needle 60 is initially in fluid communication with the fluid chamber 18 is depicted generally in FIG. 66C. During this process, the distal end cap 52 can prevent fluid from spraying out of the lumen 48 (not shown in FIGS. 66A-66D) of the male luer connection 46, which is undesirable. In this regard, the distal end cap 52 can include a plug 70 (not shown in FIGS. 66A-66D) that can be inserted into the lumen 48 (not shown in FIGS. 66A-66D). The tamper evident label 56 and the distal end cap 52 can then be removed from the syringe 14, as shown in FIG. 66C. The above method of using the fluid delivery device 10 is provided by way of illustration, not limitation. For example, the method can be completed in a different order, and may include other actions or sequences in certain applications, for example the use of aspiration after the distal end cap 52 has been removed and the lumen defined by needle 60 is in fluid communication with both the fluid chamber 18 and lumen 48. Furthermore, the methods of using other embodiments of the fluid delivery device can be different than the method described above.

Figure 66D:
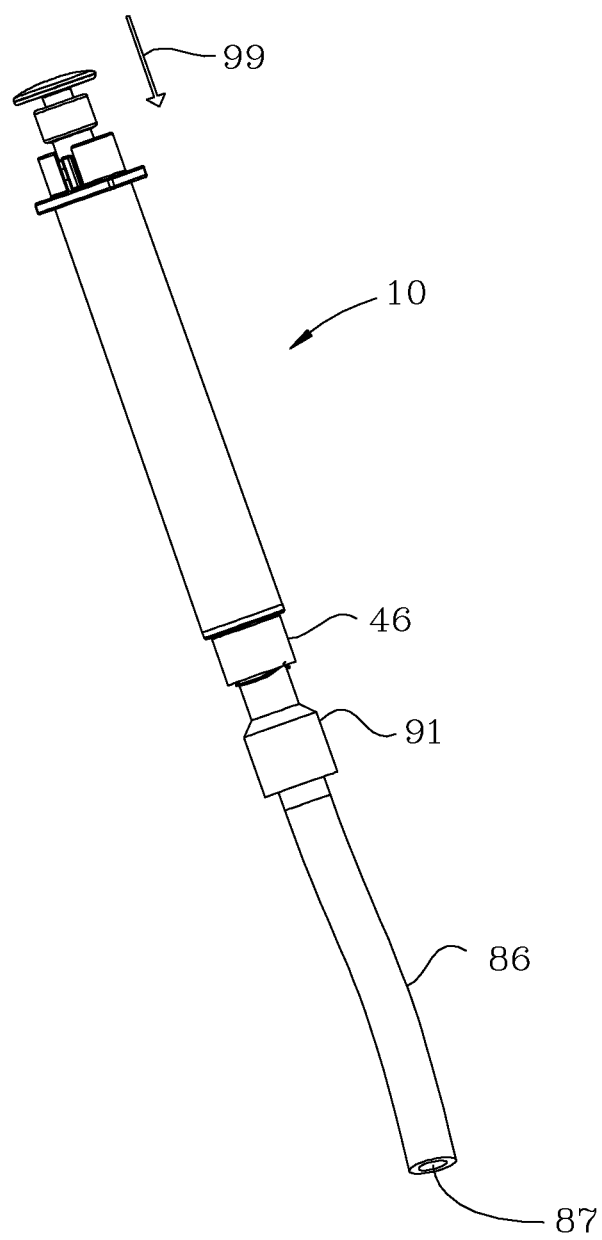

The fluid delivery device 10 can then be connected to any of a variety of devices that can be utilized to administer the medicinal fluid within the fluid delivery device 10 to a patient. For example, in one application, the male luer connection 46 of the fluid delivery device 10 can be connected to a female luer connection 91 that can be secured to a tube 86 of an intravenous set, as illustrated in FIGS. 66C and 66D. The medicinal fluid within the fluid chamber 18 can be discharged, or delivered, through the lumen 48 into a lumen 87 defined by the tube 86, by inserting the cartridge 12 farther into the syringe 14 in a distal direction, as indicated generally by arrow 99 in FIG. 66D. The medicinal fluid can then be selectively administered to a patient as desired.

Figure 68:
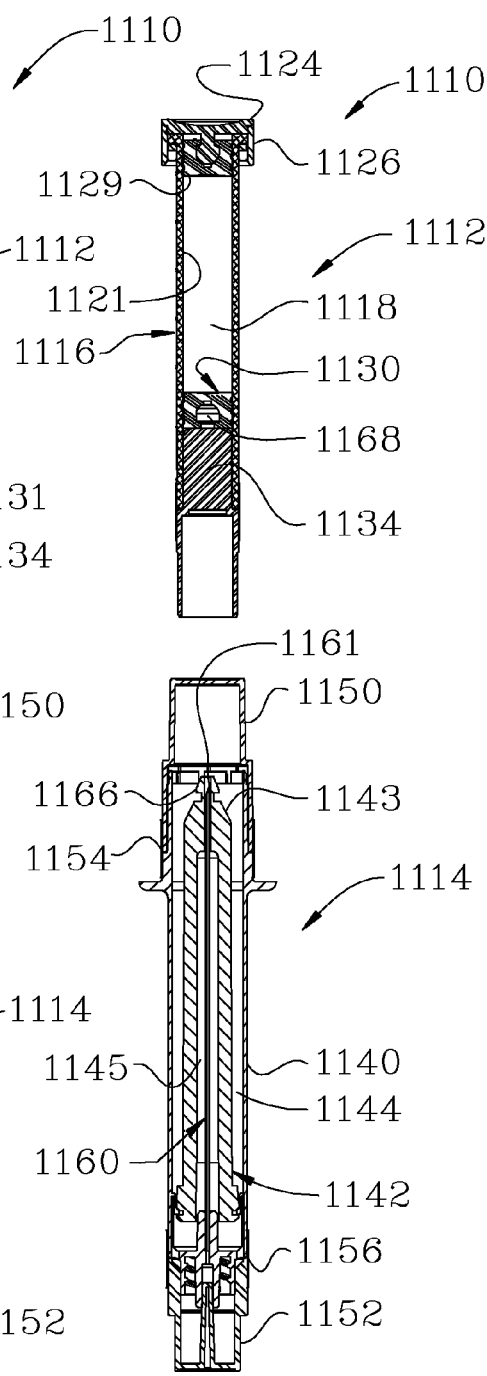
FIG. 68 is a cross-sectional view taken along line 68-68 in FIG. 67.

FIGS. 67-83 illustrate a fluid delivery device 1110 according to another embodiment. The fluid delivery device 1110 can include a cartridge 1112 and a syringe 1114. The cartridge 1112 can include a housing 1116 that can define a fluid chamber 1118. The housing 1116 of cartridge 1112 can include a generally cylindrical portion 1120 and a proximal flange 1123, which can be integral with a proximal end of the generally cylindrical portion 1120 of housing 1116 as shown in FIG. 70. The cartridge 1112 can be supported by flange 1123 during a process used to fill the fluid chamber 1118 with a desired volume of medicinal fluid. The cartridge 1112 can also include a proximal button 1124, a collar 1126 or crimp, a stopper 1129 and a stopper 1130. In one embodiment, stoppers 1129 and 1130 can have the same configuration, and in other embodiments, stoppers 1129 and 1130 can have different configurations. The proximal button 1124 can include a distal protrusion 1125 that can engage a recess 1127 (FIG. 82) defined by the stopper 1129 to retain, or fix, the stopper 1129 in position within the fluid chamber 1118. The distal protrusion 1125 can engage recess 1127 in a snap fit. As shown in FIG. 68, the collar 1126 can secure the proximal button 1124 to the housing 1116 of cartridge 1112. The stopper 1130 can be movable relative to the housing 1116.

The cartridge 1112 can also include a cap 1134, which can include an annular distal portion 1136 and a proximal portion 1138 integral with the annular distal portion 1136. The proximal portion 1138 can be formed as a plurality of circumferentially spaced fins. Cap 1134 can be inserted into the fluid chamber 1118, as shown in FIG. 68, to position the stopper 1130 at a desired position within the fluid chamber 1118 to achieve a desired volume within the fluid chamber 1118 for receiving medicinal fluid. For example, the stopper 1130 and the stopper 1129, which can be initially spaced apart from one another as shown in FIG. 68, can cooperate with the housing 1116 to define a sealed portion of the fluid chamber 1118 that is suitable for receiving medicinal fluid. The stopper 1129 can be initially spaced proximally from the stopper 1130 as shown in FIG. 68. An initial axial distance between the stopper 1129 and the stopper 1130 can cooperate with an inside diameter of the generally cylindrical portion 1120 of the housing 1116 to establish the desired, sealed volume for receiving medicinal fluid within the fluid chamber 1118. The stopper 1130 can be made of a resilient material, for example silicone rubber, which can facilitate sealing of the stopper 1130 against an inner surface 1121 of the generally cylindrical portion 1120 of housing 1116, for purposes of preventing fluid within the fluid chamber 1118 from leaking past the stopper 1130. The stopper 1130 can be coated with a lubricant, such as silicone, which can facilitate relative movement between the stopper 1130 and the housing 1116. The cartridge 1112 can include graduations or indicia, indicated generally at 1132 in FIG. 67, which can be applied to, or integrally formed with, the generally cylindrical portion 1120 of housing 1116 of cartridge 1112. Graduations 1132 can provide an indication of the volume of fluid of within the fluid chamber 1118.

Figure 69:
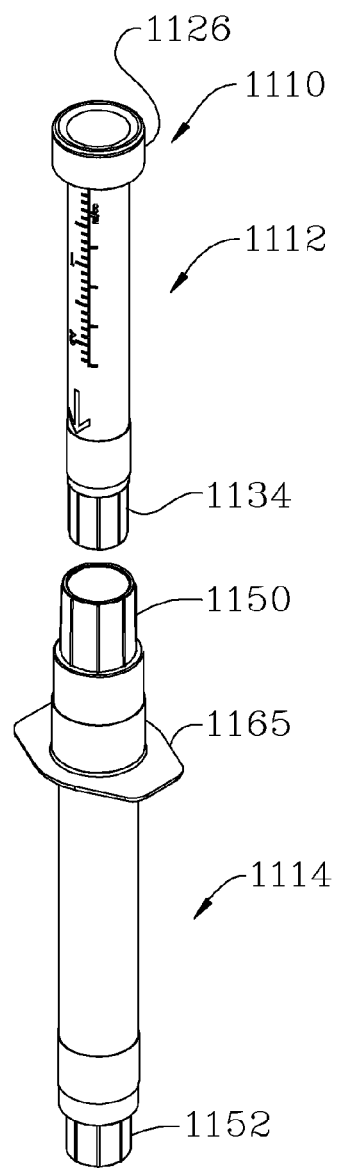
FIG. 69 is a perspective view of the fluid delivery device of FIG. 67, depicting the cartridge and the syringe disconnected from one another.
Figure 70:
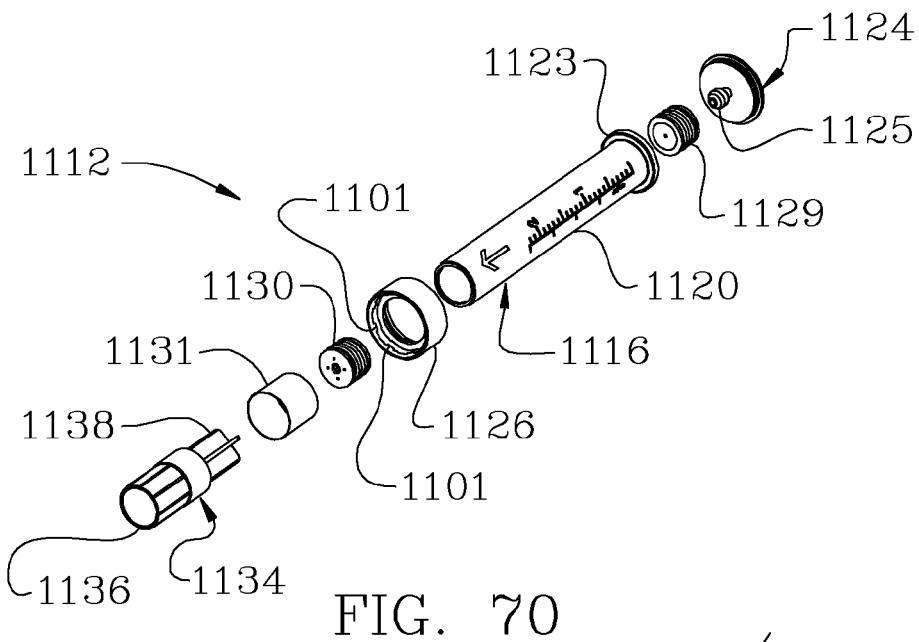
FIG. 70 is an exploded view of the cartridge of the fluid delivery device of FIG. 67.

The cap 1134 can remain engaged with the housing 1118 of cartridge 1112, as shown in FIGS. 67-69, until cartridge 1112 is connected to the syringe 1114. A tamper evident label 1131 can be secured to the cap 1134 and the housing 1116, and can provide an indication to an end user that the cartridge 1112 is sterile prior to the initial connection to syringe 1114. The syringe 1114 can include an outer body 1140 and an inner core 1142. The inner core 1142 can be positioned within, and surrounded by, the outer body 1140 of syringe 1114, as shown in FIGS. 68, 73, 77, and 81. The outer body 1140 and inner core 1142 of the syringe 1114 can be made separately from one another, and inner core 1142 can be movable within the outer body 1140 to achieve a "staged" insertion of cartridge 1112 within syringe 1114. The outer body 1140 and inner core 1142 can cooperate to define a cavity 1144 (FIGS. 68 and 73) that can be configured to receive at least a portion of the housing 1116 of cartridge of 1112 where, for example, the housing 1116 can be retained within the syringe 1114 with a friction fit, for example as subsequently described.

Figure 71:
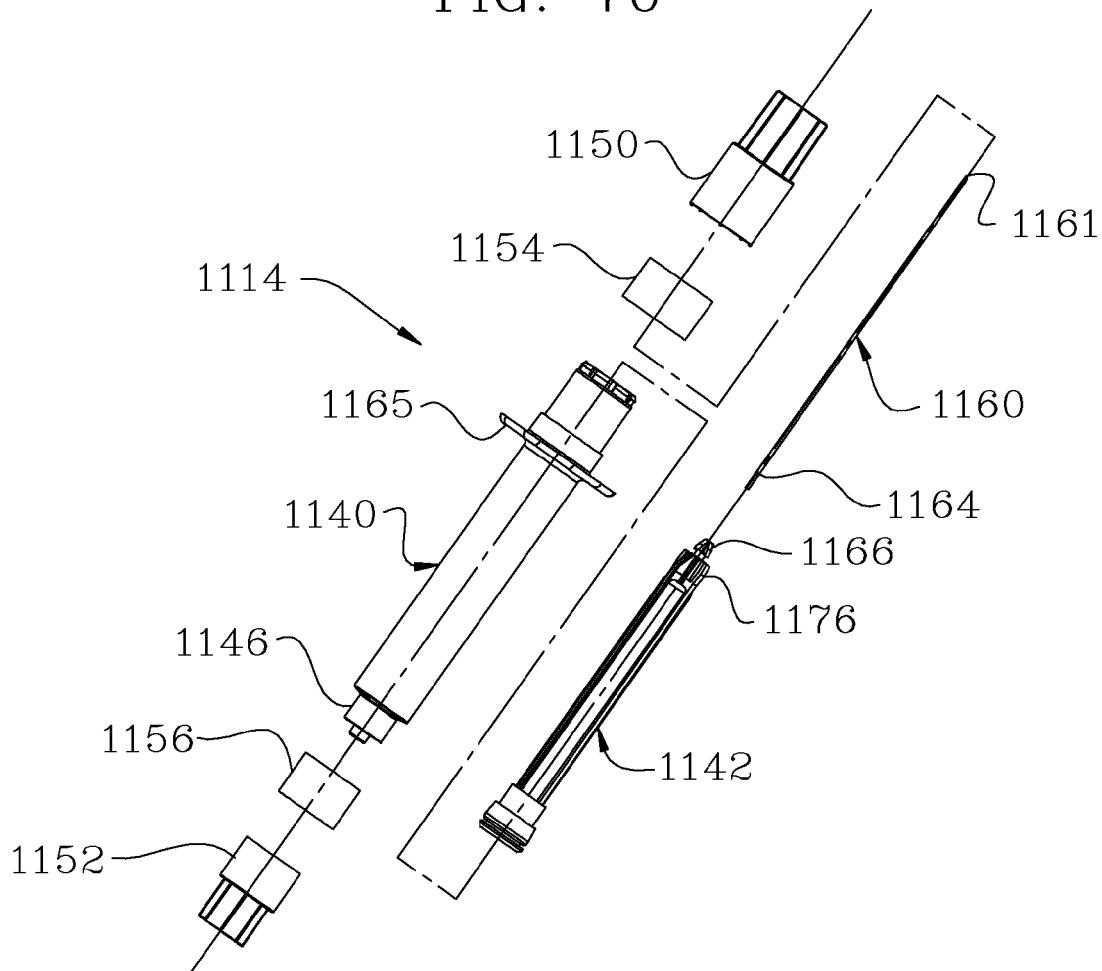
FIG. 71 is an exploded view of the syringe of the fluid delivery device of FIG. 67.
Figures 72, 73, 75:
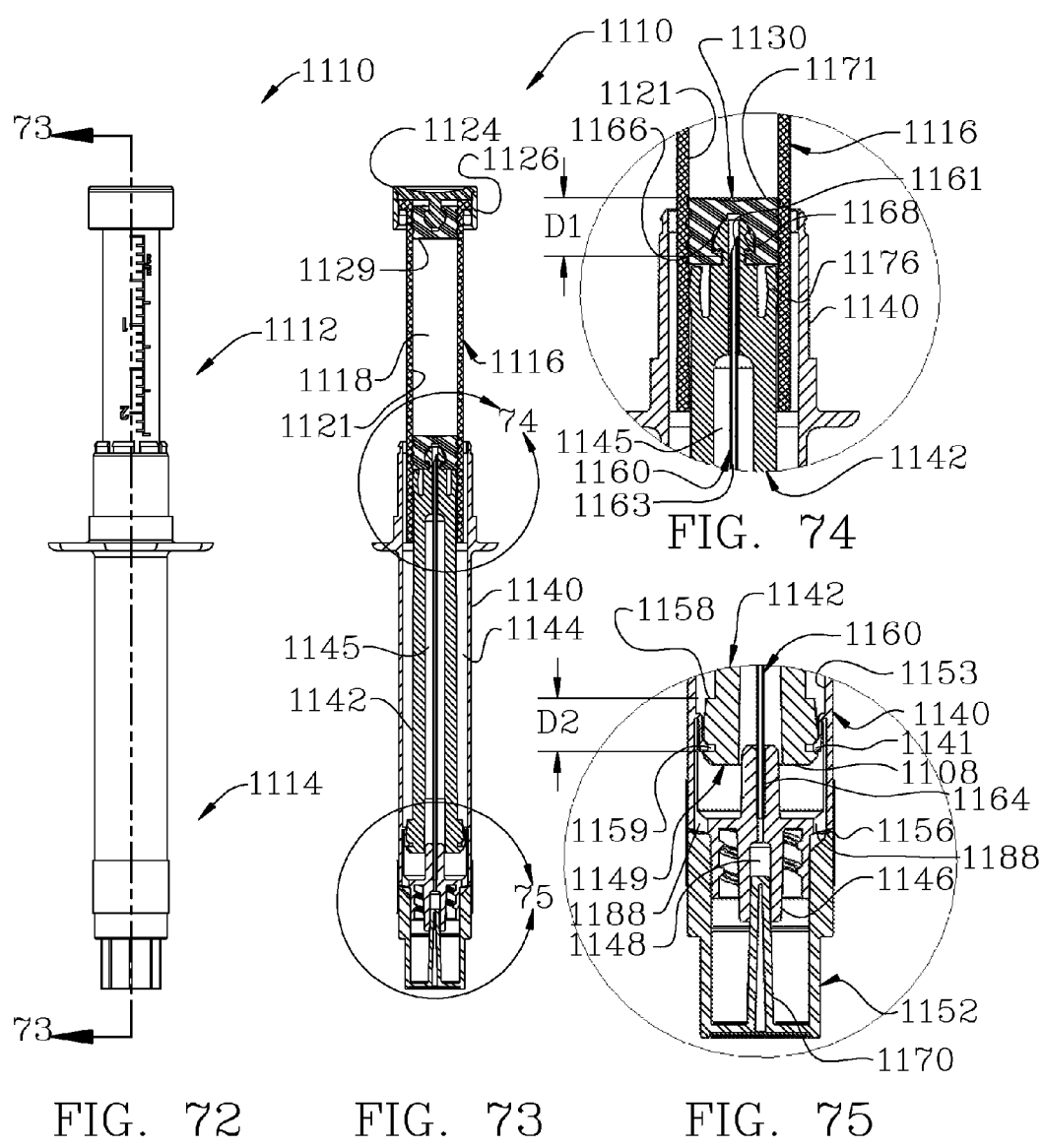
FIG. 72 is a front elevational view of the fluid delivery device of FIG. 67, depicting the fluid delivery device in a first configuration, with the cartridge and the syringe connected to one another.
FIG. 73 is a cross-sectional view taken along lines 73-73 in FIG. 72.
FIG. 75 is an enlarged view of a second encircled portion of FIG. 73, depicting a distal end of the inner core of the syringe engaged with flexible fingers of an outer body of the syringe.

The syringe 1114 can also include a male luer connection 1146, which can be integrally formed with the outer body 1140 and can be positioned at a distal end of the outer body 1140. The male luer connection 1146 can define a lumen 1148 (FIG. 75) extending therethrough in an axial, or longitudinal, direction. The male luer connection 1146 can permit fluid delivery device 1110 to be connected with standard devices normally connected to a male luer connection, for example, intravenous sets or female luer attachment needles. The configuration of lumen 1148 in an axial, or longitudinal, direction, can permit the male luer connection 1146 to be connected to a wide variety of commonly available female needle-free valves, or any other suitable valve. As shown in FIG. 71, the syringe 1114 can also include a proximal end cap 1150, which can be removably secured to a proximal end of the outer body 1140 as shown in FIG. 68, and a distal end cap 1152, which can be removably secured to at least one of the male luer connection 1146 and the outer body 1140 as shown in FIGS. 68 and 75. Syringe 1114 can also include a tamper evident label 1154, which can be secured to both the proximal end cap 1150 and the outer body 1140 (FIG. 68), and a tamper evident label 1156, which can be secured to the distal end cap 1152 and the outer body 1140 (FIG. 68). The combination of the proximal end cap 1150, the distal end cap 1152, and the tamper evident labels 1154, 1156 can provide an indication to an end user of the fluid delivery device 1110 that a fluid flow path through the syringe 1114 is sterile prior to initial use.

The syringe 1114 can also include a needle 1160 (FIG. 71), which can include a proximal tip 1161 and a distal end 1164, and can define a lumen 1163 (FIG. 74). As shown in FIGS. 68 and 71, the syringe 1114 can also include a barb 1166. The barb 1166 can be integral with a proximal end 1143 of the inner core 1142 as shown in FIG. 68. In one embodiment, barb 1166 can be integrally formed with the inner core 1142 as a unitary structure. The inner core 1142 and barb 1166 can cooperate to define a cavity 1145, or lumen, and, as shown in FIG. 68, prior to connection of cartridge 1112 and syringe 1114, a substantial portion of needle 1160 can be positioned within lumen 1145. The distal end 1164 of needle 1160 can be secured, or fixed, to the outer body 1140 as shown in FIG. 75, for example using adhesives, such that the lumen 1163 defined by needle 1160 is in fluid communication with the lumen 1148 defined by the male luer connection 1146. Suitable adhesives can include cyanoacrylate or a UV adhesive, for example if the outer body 1140 is made from a clear resin. In other embodiments, a needle and an outer body of a syringe can be configured such that the needle can be overmolded with the outer body.

Similar to other embodiments of the fluid delivery device, the components of the fluid delivery device 1110 can be packaged and/or shipped separately. For example, the cartridge 1112 and syringe 1114 can be packaged and/or shipped separately. As shown in FIG. 68, prior to connection of cartridge 1112 and syringe 1114, or the insertion of cartridge 1112 into syringe 1114, the proximal tip 1161 of the needle 1160 can be positioned within the lumen 1145 defined by the inner core 1142 and barb 1166 such that the proximal tip 1161 does not extend beyond the barb 1166. This can provide an additional safety feature to avoid inadvertent "needle sticks". For example, the presence of the proximal end cap 1150 can prevent a user from being inadvertently stuck by the proximal tip 1161 of needle 1160 as long as the proximal end cap 1150 is secured to the outer body 1140 of syringe 1114. However, when the proximal cap 1150 is removed, i.e., prior to insertion of the cartridge 1112 into syringe 1114, the positioning of the proximal tip 1161 within barb 1166 can provide this safety feature, i.e., to avoid inadvertent "needle sticks". This safety feature can also be provided in other embodiments of the fluid delivery device. The syringe 1114 can also include a flange 1165 (FIG. 71) that can be integral with the outer body 1140. The flange 1165 can facilitate operation of the fluid delivery device 1110. For example, the flange 1165 can be sized and configured to receive one or more fingers of a health care provider using the fluid delivery device 1110.

After removing the cap 1134 of cartridge 1112 and the proximal end cap 1150 of the syringe 1114, the cartridge 1112 can be inserted, at least partially, into the syringe 1114. During the insertion of the cartridge 1112 into the syringe 1114, the housing 1116 of cartridge 1112 can move, or translate, distally within the cavity 1144. FIGS. 72-75 depict the fluid delivery device in a first configuration, with the cartridge 1112 inserted into the syringe 1114 by a distance axially, along a longitudinal axis (not shown) of the fluid delivery device 1110, which results in the barb 1166 of syringe 1114 engaging a recess 1168 defined by the stopper 1130 of cartridge 1112, such that at least a portion of the barb 1166 is positioned within the recess 1168. In one embodiment, the barb 1166 can be positioned substantially entirely within the recess 1168, as shown in FIG. 74. The barb 1166 and the recess 1168 can have mating portions with complementary shapes that can facilitate the connection of barb 1166 to stopper 1130, which can also secure, or connect, the inner core 1142 of syringe 1114 to stopper 1130 of cartridge 1112. When the cartridge 1112 and syringe 1114 are positioned as shown in FIGS. 72-75, the proximal tip 1161 of the needle 1160 can remain within the lumen 1145 defined by the inner core 1142 and barb 1166, such that the proximal tip 1161 does not extend beyond barb 1166 and does not extend through the stopper 1130, and the lumen 1163 defined by needle 1160 is not in fluid communication with the fluid chamber 1118.

The syringe 1114 can also include a plurality of flexible guides 1176, or friction fingers, which can be circumferentially spaced and can be formed at the proximal end 1143 of the inner core 1142 of syringe 1114. As shown in FIG. 74, the flexible guides 1176 can project radially outwardly such that they press against the inner surface 1121 of the generally cylindrical portion 1120 of the housing 1116 of cartridge 1112. The flexible guides 1176 can be generally "bow-shaped" as shown in FIG. 74, to facilitate sliding engagement with housing 1116 during insertion of cartridge 1112. The contacting engagement of the flexible guides 1176 with the inner surface 1121 can prevent the cartridge 1112 from falling out of, or disengaging, the syringe 1114, if the fluid delivery device 1110 is temporarily turned upside down and the barb 1166 has not yet been connected to the stopper 1130. The positioning of the proximal tip 1161 of needle 1160 within barb 1166, as shown in FIG. 74, can also provide a redundant safety feature, i.e., in addition to the flexible guides 1176, to prevent inadvertent needle sticks in the event the cartridge 1112 and syringe 1114 become disconnected. During the initial insertion of the cartridge 1112 within the syringe 1114, the distal end cap 1152 of syringe 1114 can remain installed as shown in FIG. 75, to prevent fluid from inadvertently spraying out of, or discharging from, the fluid delivery device 1110.

Figures 76, 77, 79:
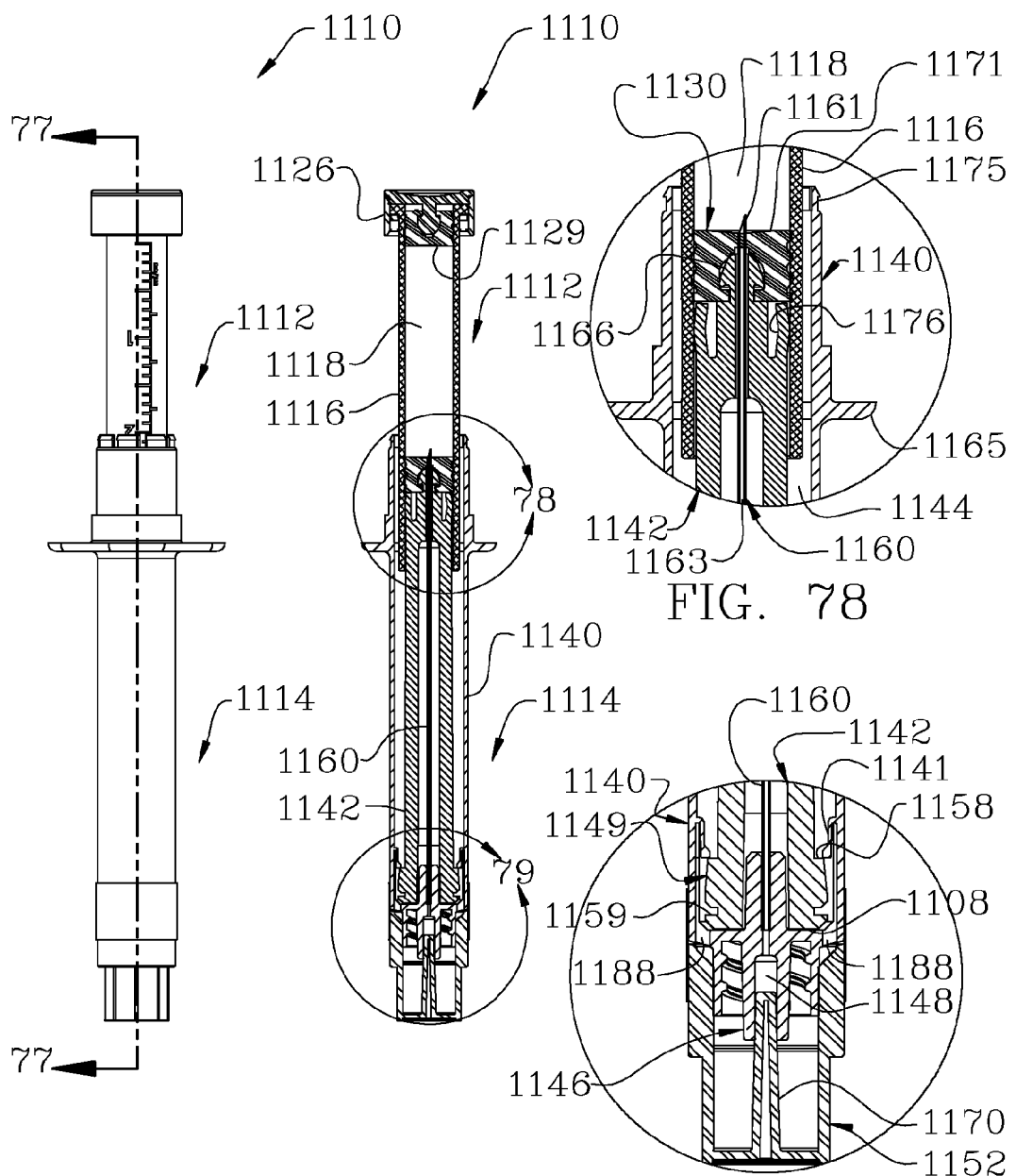
FIG. 76 is a front elevational view of the fluid delivery device of FIG. 67, depicting the fluid delivery device in a second configuration, with the cartridge translated distally within the syringe, relative to the position of the cartridge in FIG. 72, by a relatively small amount such that the needle of the syringe is in fluid communication with a fluid chamber defined by the cartridge.
FIG. 77 is a cross-sectional view taken along the line 77-77 in FIG. 76.
FIG. 79 is an enlarged view of a second encircled portion of FIG. 77, depicting the inner core of the syringe in a locked position relative to the outer body of the syringe, to prevent relative axial movement between the inner core and the body, and depicting a distal cap of the syringe installed.

A distal end 1149 (FIG. 75) of the inner core 1142 can include an annular proximal surface 1158 and can define an annular notch 1159, or groove. The distal end 1149 can also include a distal surface 1108. The outer body 1140 of syringe 1114 can include a plurality of circumferentially spaced, flexible tabs 1141, or fingers, that can extend inwardly from an inner surface 1153 of the outer body 1140, as shown in FIG. 75. A distal end of the outer body 1140 can include a plurality of process holes 1188 (FIGS. 75, 79 and 83), or apertures, which can facilitate forming the flexible tabs 1141. When installed, the distal end cap 1152 can cover the process holes 1188, as shown in FIGS. 75 and 79, which can facilitate maintaining a sterile environment within syringe 1114. When the cartridge 1112 and syringe 1114 are positioned axially relative to one another as shown in FIGS. 72-75, such that the proximal tip 1161 of the needle 1160 does not penetrate through the stopper 1130, the flexible tabs 1141 of the outer body 1140 of syringe 1114 can engage the annular notch 1159 defined by the inner core 1142. The engagement of tabs 1141 in the annular notch 1159 can facilitate retaining the outer body 1140 and inner core 1142 in the relative positions shown in FIGS. 72-75, until such time that sufficient force is exerted on the inner core 1140 to disengage the flexible tabs 1141 from the annular notch 1159, which permits the inner core 1142 to be moved, or translated, farther distally within the outer body 1140.

As the fluid delivery device 1110 transitions from the first configuration shown in FIGS. 72-75 to a second configuration shown in FIGS. 76-79, the inner core 1142, the barb 1166 and the stopper 1130 can move distally relative to the outer body 1140 and needle 1160 such that the proximal tip 1161 of the needle 1160 extends beyond the barb 1166 and through the stopper 1130, with the lumen 1163 defined by needle 1160 being in fluid communication with the fluid chamber 1118. In this configuration, the inner core 1142 can bottom out on the outer body 1140, with the distal surface 1108 of the distal end 1149 of the inner core 1142 in contacting engagement with the outer body 1140, as shown in FIG. 79. As the cartridge 1112 is pushed, or inserted, farther into the syringe 1114, relative to the position of the cartridge shown in FIG. 73, hydrostatic force can push the inner core 1142 distally relative to the outer body 1140, due to the connection of the stopper 1130 to the inner core 1142, at least until such time that the proximal tip 1161 of needle 1160 extends through a proximal surface 1171 of the stopper 1130 and the lumen 1163 defined by the needle 1160 is in fluid communication with the fluid chamber 1118, for example as shown in FIG. 78. When the stopper 1130, inner core 1142 and outer body 1140 are in the relative axial positions shown in FIGS. 72-75, the proximal tip 1161 of needle 1160 can be distal of the proximal surface 1171 of the stopper 1130, and can be spaced from the proximal surface 1171 by a distance D1 as shown in FIG. 74. The annular notch 1159 defined by the inner core 1142 can be spaced from the proximal surface 1158 of the distal end 1149 of the inner core 1142 by a distance D2 as shown in FIG. 75. The distances D1 and D2 can be selected such that D2 is greater than or equal to D1, such that the proximal tip 1161 of needle 1160 can extend through the stopper 1130, with the lumen 1163 defined by needle 1160 in fluid communication with the fluid chamber 1118, at substantially the same time, or prior to the time, that the distal end 1149 of the inner core 1142 of syringe 1114 bottoms out against, or engages, the outer body 1140 of syringe 1114 as shown in FIG. 79. With the inner core 1142 and outer body 1140 of syringe 1114 positioned as shown in FIG. 79, the flexible tabs 1141 of the outer body 1140 can engage, or rest on top of, the proximal surface 1158 of the distal end 1149 of the inner core 1142 and the distal surface 1108 of the inner core 1142 can be in contacting engagement with the outer body 1140, which can retain the inner core 1142 in a "locked-out" position relative to the outer body 1140 of syringe 1114, i.e., to prevent the inner core 1142 from moving axially relative to the outer body 1140. The contacting engagement of the flexible tabs 1141 of outer body 1140 with the proximal surface 1158 of the distal end 1149 of the inner core 1142 can prevent the inner core 1142 from moving proximally relative to the outer body 1140, and the contacting engagement of the distal surface 1108 of the inner core 1142 with the outer body 1140 can prevent the inner core 1142 from moving distally relative to the outer body 1140. The distal end cap 1152 can remain secured to the male luer connection 1146, during further insertion of the cartridge 1112 into syringe 1114, for example, from the position shown in FIGS. 72-75 to the position shown in FIGS. 76-79, which can prevent fluid from inadvertently spraying out of, or discharging from, the lumen 1148 defined by the male luer connection 1146. In this regard, the distal end cap 1152 can include a plug 1170 that can extend into the lumen 1148, as shown in FIGS. 75 and 79.

The previously described movements, or positioning, of cartridge 1112 relative to syringe 1114, and the movements of the inner core 1142 of syringe 1114 relative to the outer body 1140 of syringe 1114, prior to fluid delivery, can be considered to be a two-stage sequence, or operation, with the initial stage being the insertion of cartridge 1112 into syringe 1114 until the fluid delivery device 1110 is in the first configuration shown in FIGS. 72-75. In the first configuration, the stopper 1130 of cartridge 1112 engages the barb 1166 of syringe 1114, without the needle 1160 extending through the stopper 1130. The second stage can be considered to be the further insertion of cartridge 1112 into syringe 1114 until the fluid delivery device 1110 is in a second configuration, for example as shown in FIGS. 76-79, with the lumen 1163 defined by the needle 1160 in fluid communication within the fluid chamber 1118.

Figures 80, 81, 82, 83:
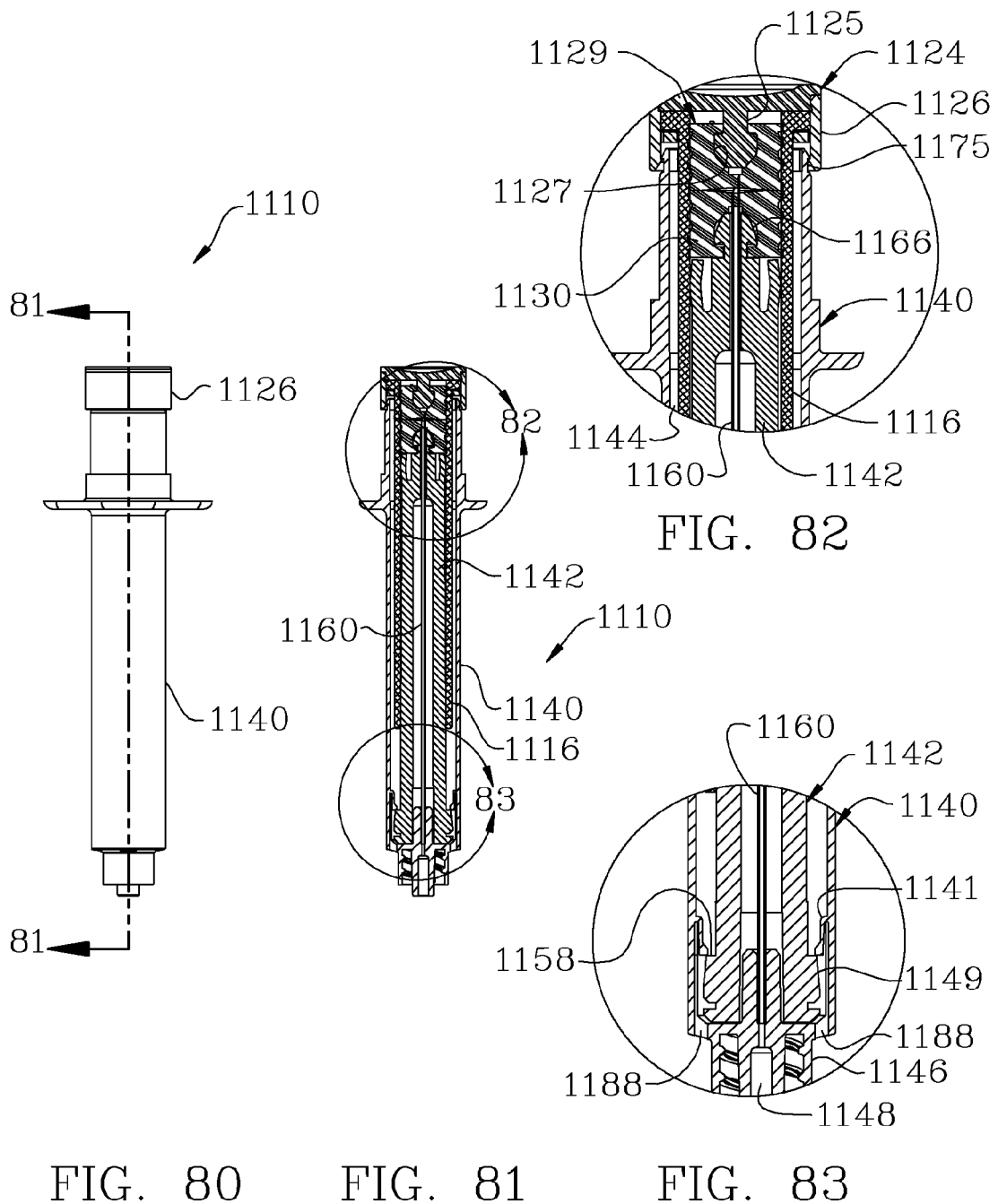
FIG. 80 is a front elevational view of the fluid delivery device of FIG. 67, depicting the fluid delivery device in a third configuration, with the cartridge translated distally within the syringe relative to the position of the cartridge shown in FIG. 76, to achieve fluid delivery.
FIG. 81 is a cross-sectional view taken along line 81-81 in FIG. 80.
FIG. 82 is an enlarged view of a first encircled portion of FIG. 81, depicting the movable stopper of the cartridge in contacting engagement with a fixed stopper of the cartridge and depicting the proximal tip of the needle extending into the fixed stopper of the cartridge, and also depicting retaining fingers of the outer body of the syringe engaged with a collar of the cartridge to prevent relative axial movement between the cartridge and the syringe such that the fluid delivery device is disabled.
FIG. 83 is an enlarged view of a second encircled portion of FIG. 81, depicting the inner core of the syringe in the locked position relative to the outer body of the syringe, with the distal cap of the syringe removed.

A third stage of operation of the fluid delivery device 1110 can be considered to be the expulsion of fluid from the fluid chamber 1118 and the disablement of the fluid delivery device 1110. Fluid can be expelled from the fluid chamber 1118, through the lumen 1163 defined by needle 1160 and then through the lumen 1148 defined by the male luer connection 1146, by removing the distal end cap 1152 and pushing the cartridge 1112 in a distal direction within or along syringe 1114, until such time that the cartridge 1112 and the syringe 1114 are positioned as shown in FIGS. 80-83. At the end of the stroke of cartridge 1112, the stopper 1130 can be positioned in contacting engagement with the stopper 1129, as shown in FIGS. 81 and 82. Mating faces of the stoppers 1129 and 1130 can have complementary shapes, which can at least minimize any residual fluid within the fluid chamber 1118 at the end of the travel, insertion, or stroke, of cartridge 1112 within syringe 1114. In this position, the proximal tip 1161 of needle 1160 can extend into the stopper 1129. The outer body 1140 of syringe 1114 can include a plurality of circumferentially spaced retaining fingers 1175, or arms, which can engage the collar 1126 of cartridge 1112 as shown in FIG. 82, to disable the fluid delivery device 1110 after fluid delivery, at the end-of-stroke position of cartridge 1112 within syringe 1114. For example, when the fluid delivery device 1110 is in a third configuration, such as that shown in FIGS. 80-83, at least some of the retaining fingers 1175 can engage respective ones of a plurality of circumferentially spaced tabs 1101 (FIG. 70), or lips, of the collar 1126 of cartridge 1112. The tabs 1101 can be formed at a distal end of the collar 1126. In one embodiment, the retaining fingers 1175 can be equally spaced circumferentially and the tabs 1101 can be equally spaced circumferentially. The tabs 1101 can be sized such that a width of each tab 1101, in a circumferential direction, can be greater than each of the circumferential gaps between adjacent pairs of the retaining fingers 1175 to ensure contacting engagement between at least some of the tabs 1101 and at least some of the retaining fingers 1175. The engagement of the retaining fingers 1175 with the tabs 1101 can prevent relative axial movement between the cartridge 1112 and the syringe 1114. In one embodiment, the retaining fingers 1175 can be flexible. In other embodiments, a collar of a cartridge can be provided with an annular ring, in lieu of circumferentially spaced tabs, which can engage retaining fingers of a syringe, such as the retaining fingers 1175.

Figures 84, 85, 86:
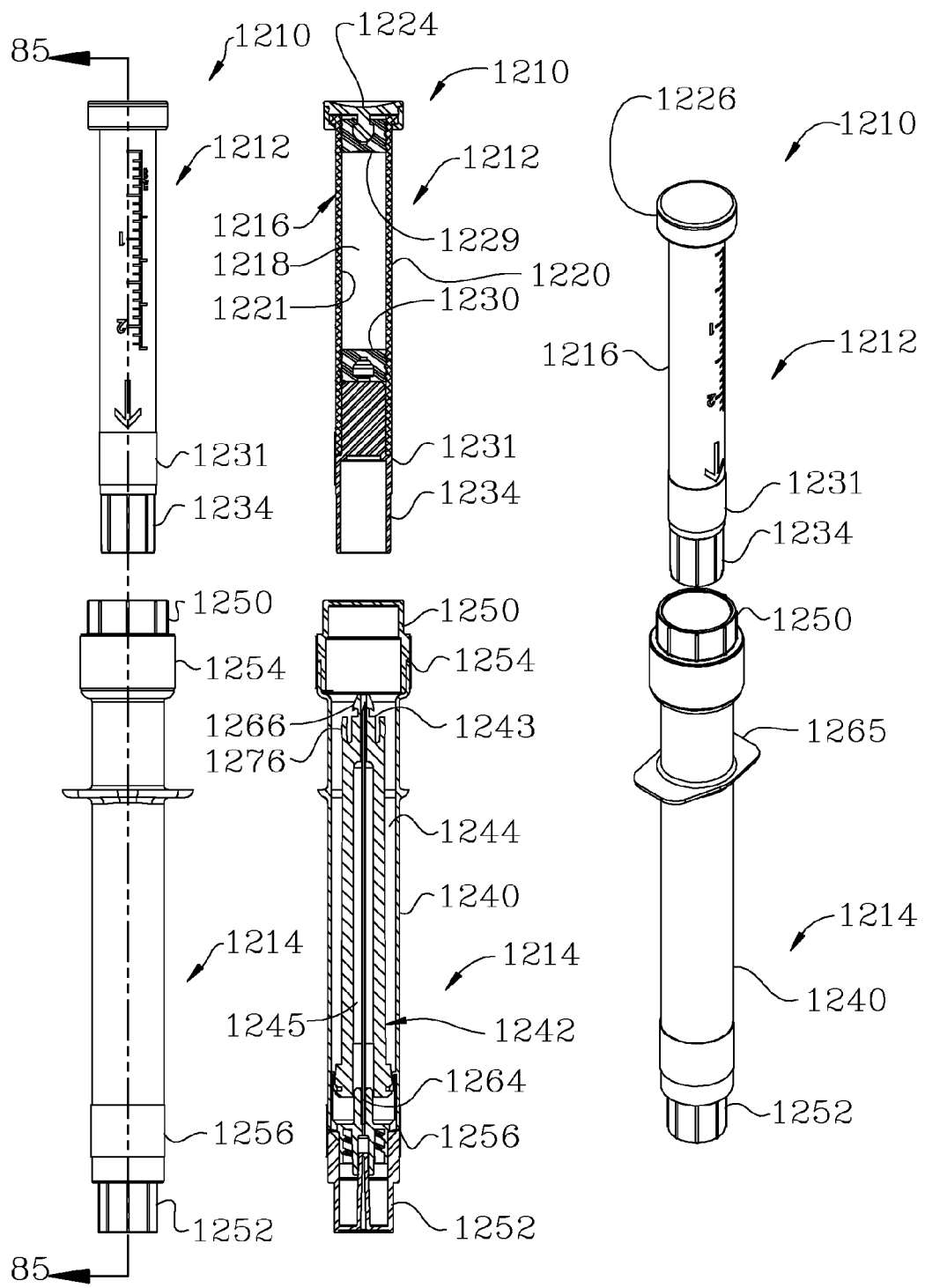
FIG. 84 is a front elevational view of a fluid delivery device according to another embodiment, depicting a cartridge and a syringe of the fluid delivery device disconnected from one another.
FIG. 85 is a cross-sectional view taken along line 85-85 in FIG. 84.
FIG. 86 is a perspective view of the fluid delivery device of FIG. 84, depicting the cartridge and the syringe disconnected from one another.
Figure 87:
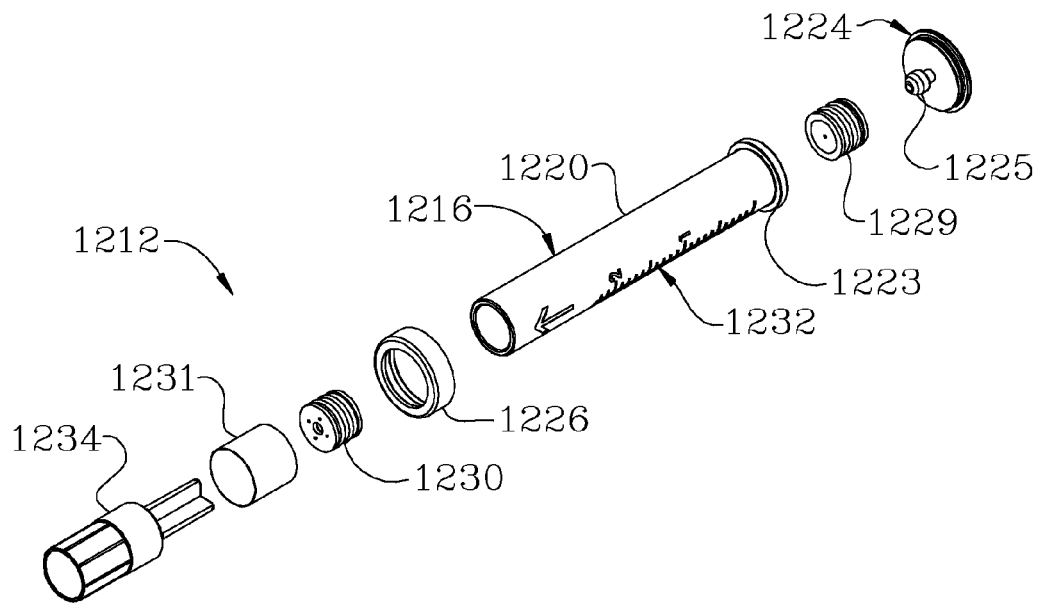
FIG. 87 is an exploded view of the cartridge of the fluid delivery device of FIG. 84.

FIGS. 84-92 illustrate a fluid delivery device 1210 according to another embodiment. The fluid delivery device 1210 can include a cartridge 1212 and a syringe 1214. The fluid delivery device 1210 can be the same as, or substantially the same as, the fluid delivery device 1110 with the exception of the manner in which the fluid delivery device 1210 is disabled at the end of the stroke of the cartridge 1212. At the end of the stroke of the cartridge 1212, the cartridge 1212 and syringe 1214 can cooperate to prevent, or at least substantially prevent, user access to the cartridge 1212, as shown in FIGS. 89-92. The cartridge 1212 can include a housing 1216 that can define a fluid chamber 1218 (FIG. 85). The housing 1216 can include a generally cylindrical portion 1220 and a proximal flange 1223, which can be integral with a proximal end of the generally cylindrical portion 1220 of housing 1216 as shown in FIG. 87. The cartridge 1212 can also include a proximal button 1224, a collar 1226 or crimp, and stoppers 1229 and 1230. The collar 1226 can secure the proximal button 1224 to the housing 1216. The proximal button 1224 can include a distal protrusion 1225 that can engage a recess 1227 (FIG. 91) defined by the stopper 1229 to retain the stopper 1229 in position within the fluid chamber 1218. The cartridge 1212 can include graduations, or indicia, indicated generally at 1232 in FIG. 87, which can be applied to, or integrally formed with, the generally cylindrical portion 1220 of housing 1216, and can provide an indication of the volume of fluid within the fluid chamber 1218. The cartridge 1212 can also include a cap 1234 that can be inserted into the fluid chamber 1218 to position the stopper 1230 at a desired location within the fluid chamber 1218, as shown in FIG. 85, and can also include a tamper evident label 1231 (FIG. 87) that can be secured to the cap 1234 and the housing 1216, as shown in FIGS. 84-85.

Figure 88:
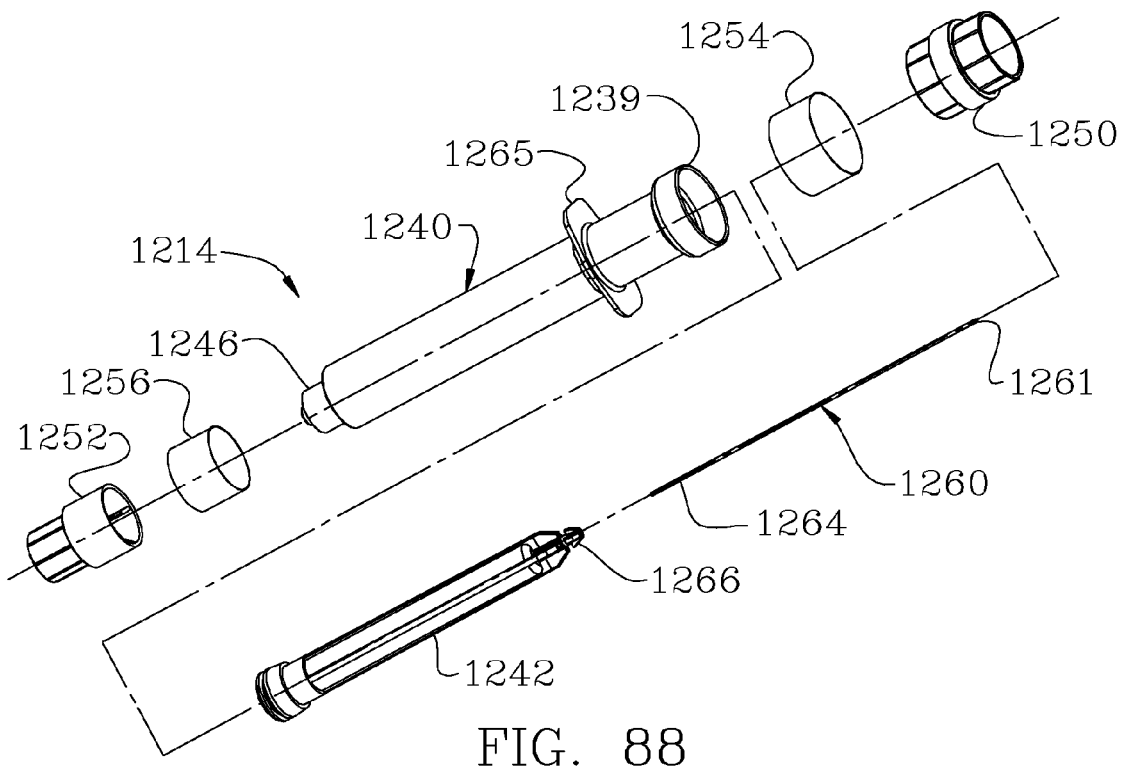
FIG. 88 is an exploded view of the syringe of the fluid delivery device of FIG. 84.
Figures 89, 90, 92:
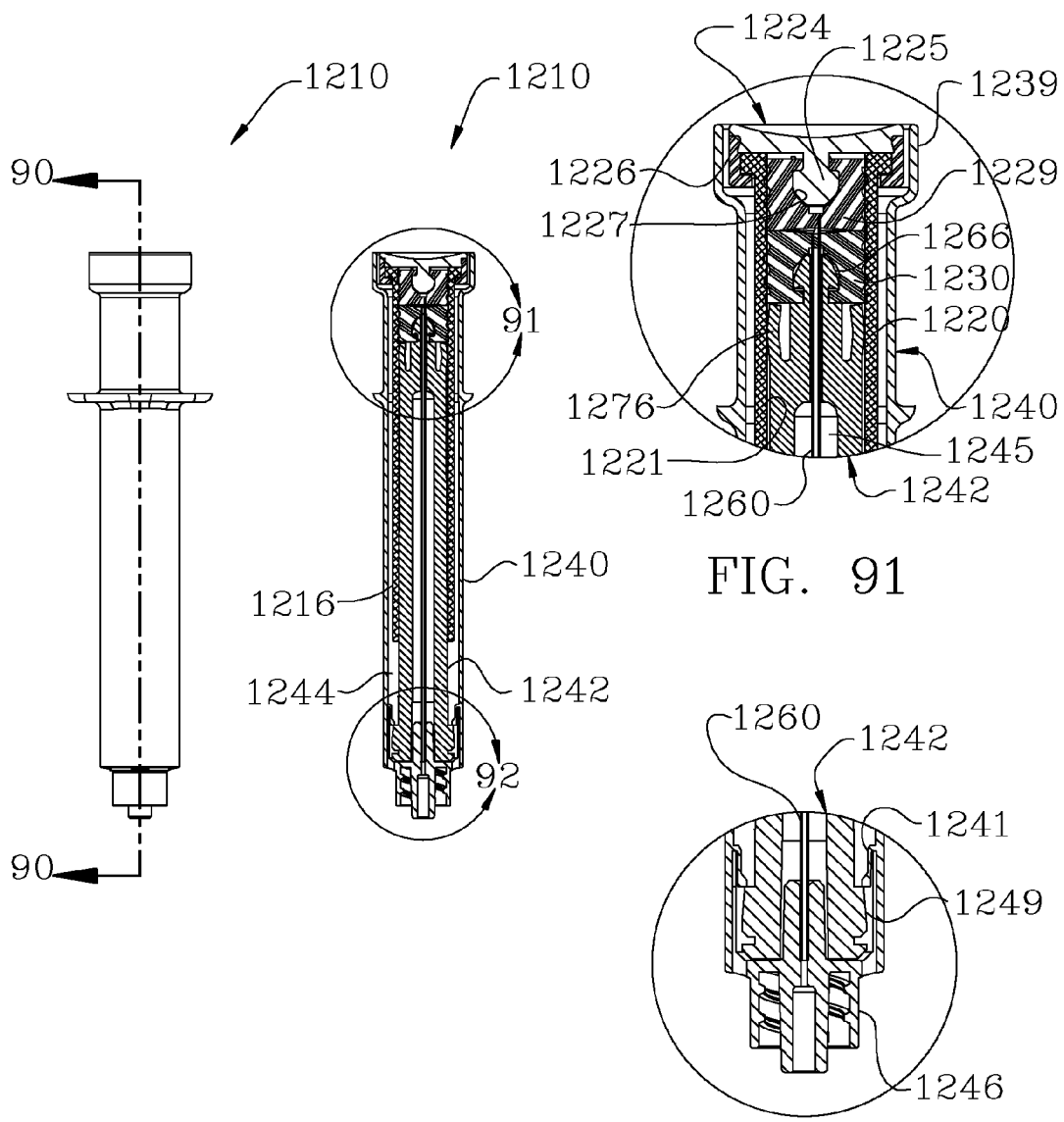
FIG. 89 is a front elevational view of the fluid delivery device of FIG. 84, with the cartridge and the syringe (not shown in FIG. 89) connected to one another, and with the syringe positioned axially within the cartridge to achieve fluid delivery.
FIG. 90 is a cross-sectional view taken along line 90-90 in FIG. 89.
FIG. 92 is an enlarged view of a second encircled portion of FIG. 90, depicting an inner core of the syringe in a locked position relative to the outer body of the syringe to prevent relative axial movement between the inner core and the outer body.

The syringe 1214 can include an outer body 1240 and an inner core 1242. The inner core 1242 can be positioned within, and surrounded by, the outer body 1240 of syringe 1214 as shown in FIGS. 85 and 90. The outer body 1240 and inner core 1242 of the syringe can be made separately from one another, and the inner core 1242 can be movable within the outer body 1240 to achieve a "staged" insertion of cartridge 1212 within syringe 1214. The outer body 1240 and inner core 1242 can cooperate to define a cavity 1244 that can receive at least a portion of the housing 1216, as shown in FIG. 90. The outer body 1240 can include a proximal collar 1239, which can be generally cylindrical. The syringe 1214 can also include a male luer connection 1246, which can be integrally formed with the outer body 1240 and can be positioned at a distal end of the outer body 1240 as shown in FIG. 88. The syringe 1214 can also include a proximal end cap 1250, which can be removably secured to the outer body 1240, for example to the proximal collar 1239 of the outer body 1240, as shown in FIGS. 84-86, and a distal end cap 1252, which can be removably secured to at least one of the outer body 1240 and the male luer connection 1246 as shown in FIGS. 84-86. Syringe 1214 can also include a tamper evident label 1254, which can be secured to the proximal end cap 1250 and the proximal collar 1239 of the outer body 1240, and a tamper evident label 1256, which can be secured to the distal end cap 1252 and the outer body 1240. The combination of the proximal end cap 1250, the distal end cap 1252, and the tamper evident labels 1254, 1256 can provide an indication to an end user that a fluid flow path through the syringe 1214 is sterile prior to initial use.

The syringe 1214 can also include a needle 1260 and a barb 1266, which can be integral with a proximal end 1243 (FIG. 85) of the inner core 1242. The inner body 1242 and barb 1266 can cooperate to define a cavity 1245, or lumen. As shown in FIG. 85, a substantial portion of needle 1260 can be positioned within cavity 1245. The needle 1260 can include a distal end 1264, which can be secured, or fixed, to the outer body 1240, as shown in FIG. 85, for example using adhesives. Suitable adhesives can include those described with respect to needle 1160 and outer body 1140. A lumen defined by the needle can be in fluid communication with a lumen defined by the male luer connection 1246. The syringe 1214 can also include a flange 1265 that can be integral with the outer body 1240 and can facilitate operation of the fluid delivery device 1210.

The syringe 1214 can also include a plurality of flexible guides 1276, or friction fingers (FIGS. 85 and 91), which can be formed at the proximal end 1243 of the inner core 1242 of syringe 1214. As shown in FIG. 91, the flexible guides 1276 can project radially outwardly such that they press against an inner surface 1221 of the generally cylindrical portion 1220 of the housing 1216 of cartridge 1212. The flexible guides 1276 can be generally "bow-shaped" as shown in FIG. 91, to facilitate sliding engagement with housing 1216 during insertion of cartridge 1212. The contacting engagement of the flexible guides 1276 with the inner surface 1221 of the generally cylindrical portion 1220 of housing 1216, can prevent the cartridge 1212 from falling out of, or disengaging, the syringe 1214, if the fluid delivery device 1210 is temporarily turned upside down and the barb 1266 has not yet been connected to the stopper 1230.

After removing the cap 1234 of cartridge 1212 and the proximal end cap 1250 of the syringe 1214, the cartridge 1212 can be connected to the syringe 1214 by initially inserting a portion of the cartridge 1212 into syringe 1214. The initial operation of the fluid delivery device 1210, prior to fluid delivery, can be a two-stage sequence, or process, similar to that described with respect to fluid delivery device 1110. For example, during an initial stage, the cartridge 1212 can be inserted, moved, or translated distally within syringe 1214 until the barb 1266 of syringe 1214 engages stopper 1230 of cartridge 1212, without a proximal tip 1261 of needle 1260 extending through the stopper 1230 into the fluid chamber 1218. During the second stage, the cartridge 1212 can be inserted farther axially, and the stopper 1230 of cartridge 1212 and the barb 1266 and inner core 1242 of the syringe 1214 can move, or translate, distally relative to the outer body 1240 and needle 1260 until the proximal tip 1261 of needle 1260 extends into the fluid chamber 1218 and the inner core 1242 bottoms out on, or engages, the outer body 1240, such that further movement of the inner core 1242 distally relative to the outer body 1240 is prevented. Tabs 1241 of outer body 1240 can engage a distal end 1249 of inner core 1242 to retain inner core 1242 in a locked-out position in engagement with the outer body 1240 to prevent the inner core 1242 from moving proximally relative to the outer body 1240. Aspiration can be achieved if desired by removing the distal end cap 1252 and pulling or moving the housing 1216 of cartridge 1212 in a proximal direction, relative to syringe 1214. The stopper 1230 can remain connected to the inner core 1242 during aspiration such that it does not move relative to the syringe 1214.

After removal of the distal end cap 1252 of syringe 1214, the cartridge 1212 can be inserted farther, to the end of the stroke of cartridge 1212, as shown in FIGS. 89-92, to deliver, expel, or discharge, fluid from the fluid delivery device 1210. Unlike the fluid delivery device 1110, the fluid delivery device 1210 does not include fingers or arms, such as the retaining fingers 1175, or arm, of the fluid delivery device 1110, to disable the fluid delivery device 1210 after delivery of fluid. Instead, the proximal collar 1239 of the outer body 1240 of syringe 1214 can perform this function. For example, as shown in FIGS. 90 and 91, at the end of the stroke of cartridge 1212, the cartridge 1212 can be completely inserted into the syringe 1214, with the proximal collar 1239 of the outer body 1240 of syringe 1214 surrounding the collar 1226 and proximal button 1224 of cartridge 1212 to prevent, or at least substantially prevent, access to the cartridge 1212. This lack of access can prevent a user from grasping the cartridge 1212 and moving the cartridge 1212 axially relative to the syringe 1214, such that the fluid delivery device 1210 is disabled. The expulsion of fluid from the fluid chamber 1218 and the disablement of the fluid delivery device 1210 can be considered to be a third stage of operation of the fluid delivery device 1210.

Figure 96:
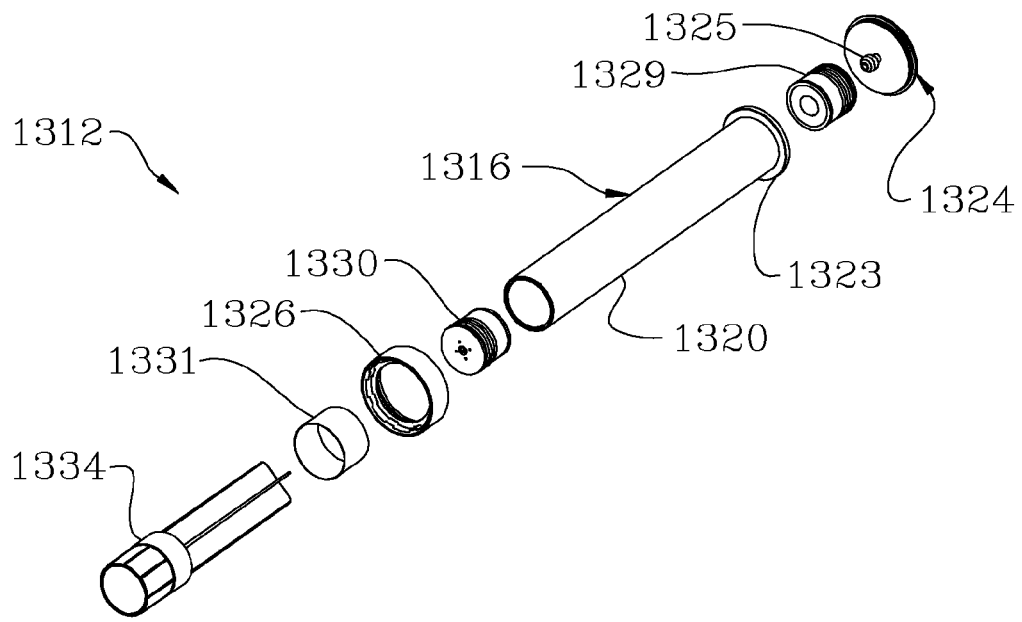
FIG. 96 is an exploded view of the cartridge of the fluid delivery device of FIG. 93.

FIGS. 93-112 illustrate a fluid delivery device 1310 according to another embodiment. The fluid delivery device 1310 can include a cartridge 1312 and a syringe 1314. In this embodiment, dimensional relationships among various components of the cartridge 1312 and syringe 1314 can cooperate to establish a "staged" insertion of the cartridge 1312 into the syringe 1314. The cartridge 1312 can be similar to the cartridges 1112 and 1212 of the fluid delivery devices 1110 and 1210, respectively. For example, cartridge 1312 can include a housing 1316 that can define a fluid chamber 1318 (FIG. 94). The housing 1316 of cartridge 1312 can include a generally cylindrical portion 1320 and a proximal flange 1323, which can be integral with a proximal end of the generally cylindrical portion 1320 as shown in FIG. 96. The cartridge 1312 can also include a proximal button 1324, a collar 1326 or crimp, a stopper 1329 and a stopper 1330. The stopper 1329 can be a fixed stopper and the stopper 1330 can be a movable stopper. The proximal button 1324 can include a distal protrusion 1325 that can engage a recess defined by the stopper 1329 to retain the stopper 1329 in position within the fluid chamber 1318. As shown in FIG. 94, the collar 1326 can secure the proximal button 1324 to the housing 1316 of cartridge 1314. Similar to cartridges 1112 and 1212, the cartridge 1312 can also include a cap 1334 that can be used to position the movable stopper 1330 within the fluid chamber 1318, prior to connection of the cartridge 1312 with the syringe 1314. The cartridge 1312 can also include a tamper evident label 1331, which can be secured to the cap 1334 and housing 1316. Certain ones of the components of the cartridge 1312, e.g., housing 1316, can be longer than corresponding components of the cartridges 1112 and 1212 to facilitate the staged insertion of cartridge 1312 into the syringe 1314.

Figures 98, 99, 102:
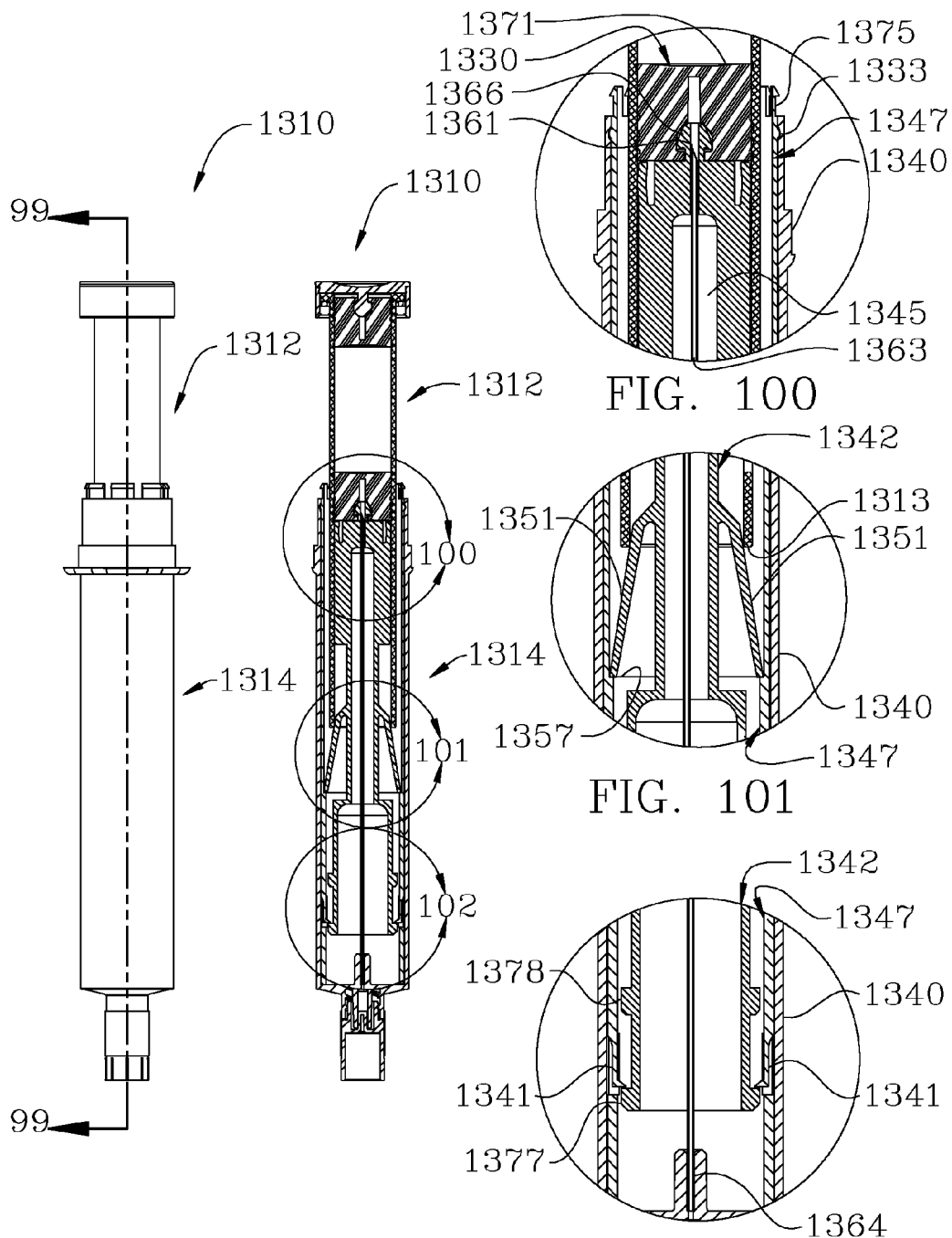
FIG. 98 is a side elevational view of the fluid delivery device of FIG. 93, depicting the fluid delivery device in a first configuration, with the cartridge and the syringe connected to one another.
FIG. 99 is a cross-sectional view taken along line 99-99 in FIG. 98.
FIG. 102 is an enlarged view of a third encircled portion of FIG. 99, depicting a pair of flexible tabs of the sleeve engaged with a first annular member of the inner core.

Similar to the syringes 1114 and 1214, the syringe 1314 can include an outer body 1340, an inner core 1342 and a male luer connection 1346, which can be integrally formed with the outer body 1340. The male luer connection 1346 can define a lumen 1348. The syringe 1314 can also include a needle 1360, having a proximal tip 1361 and a distal end 1364. The distal end 1364 can be secured to the outer body 1340 as shown in FIG. 102. The syringe 1314 can also include a proximal end cap 1350, a distal end cap 1352, and tamper evident labels 1354 and 1356. Unlike the syringes 1114 and 1214, the syringe 1314 can also include a sleeve 1347 that can be positioned radially between the outer body 1340 and the inner core 1342. The sleeve 1347 can include an annular member 1333 (FIG. 100) that can engage an annular groove, which can be a snap fit engagement in one embodiment, formed in the outer body 1340 to retain the relative axial positions of the sleeve 1347 and the outer body 1340. The sleeve 1347 can also include a plurality of circumferentially spaced flexible tabs 1341, and a plurality of circumferentially spaced retaining fingers 1375, or retaining members. The sleeve 1347 and the inner core 1342 can cooperate to define a cavity 1344 that can be configured to receive at least a portion of the housing 1316 of cartridge 1312. The inner core 1342 can include a plurality of flexible guides 1376, which can function in a manner similar to the flexible guides 1176 of the inner core 1142 of the fluid delivery device 1110.

Figure 97:
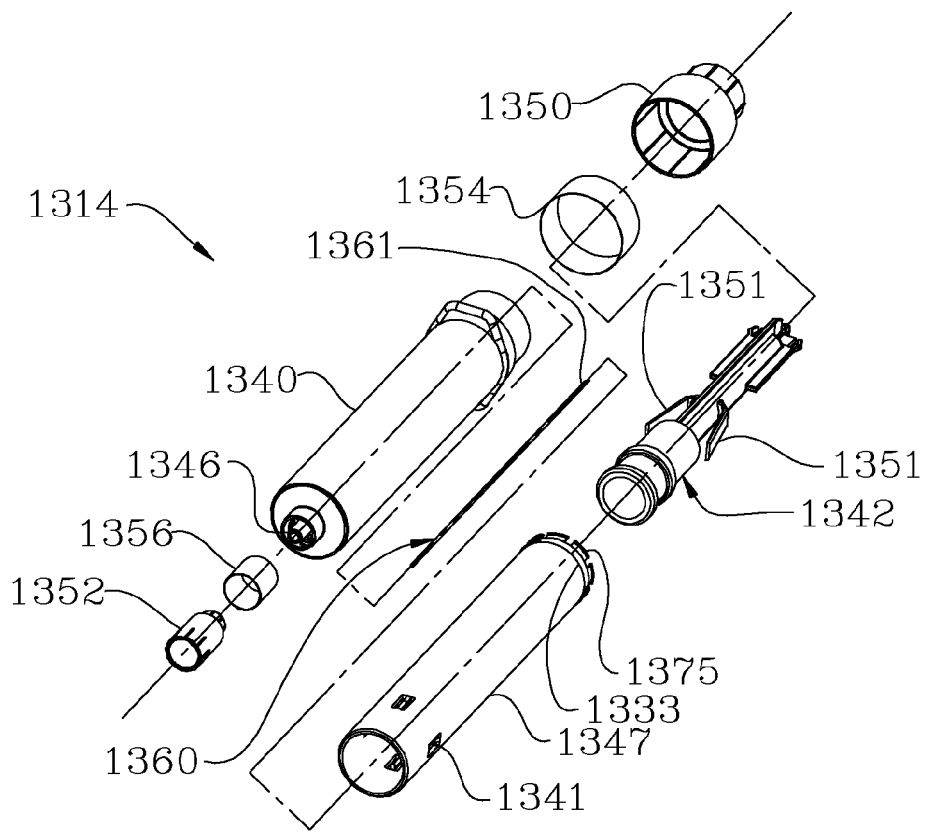
FIG. 97 is an exploded view of the syringe of the fluid delivery device of FIG. 93.

The inner core 1342 can include a plurality of flexible positioning members 1351, or wings. Each of the flexible positioning members 1351 extend generally outwardly and distally from a proximal end toward a distal end (FIGS. 94 and 97). The inner core 1342 can also include an annular member 1377, which can be formed at a distal end thereof, and an annular member 1378 which can be positioned proximal of the annular member 1377 (FIG. 102). The syringe 1314 can also include a barb 1366 that can be integral with a proximal end 1343 of the inner core 1342 as shown in FIG. 94.

After removal of the tamper evident label 1331 and cap 1334 from cartridge 1312, and removal of the tamper evident label 1354 and proximal end cap 1350 of syringe 1314, the cartridge 1312 can be inserted into the syringe 1314, for example as shown in FIG. 98. FIGS. 98-102 depict the fluid delivery device 1310 in a first configuration, in which the movable stopper 1330 can be engaged with the barb 1366, to connect the movable stopper 1330 with the inner core 1342. The inner core 1342 and barb 1366 can cooperate to define a lumen 1345, which can be configured to receive at least a substantial portion of the needle 1360. As shown in FIGS. 99-100, in this first configuration, the proximal tip 1361 of needle 1360 can be positioned within the lumen 1345 such that the proximal tip 1361 does not extend beyond the barb 1366 and is distal of a proximal surface 1371 of the movable stopper 1330, and such that a lumen 1363 defined by the needle 1360 is not in fluid communication with the fluid chamber 1318.

When the fluid delivery device 1310 is in the first configuration shown in FIGS. 98-102, a distal end of the flexible positioning member 1351 of the inner core 1342 can engage an annular ledge 1357 of sleeve 1347, and the flexible tabs 1341 of sleeve 1347 can engage the annular member 1377 of the inner core 1342, to temporarily retain the inner core 1342 in the position shown in FIGS. 99-102. As shown in FIG. 101, the housing 1316 of cartridge 1312 can be positioned axially such that a distal end 1313 of the housing 1316 contacts, but does not compress, or flex, the flexible positioning members 1351 of the inner core 1342.

The engagement of the flexible positioning members 1351 with the annular ledge 1357 can provide a resistive force that can facilitate the engagement of the barb 1366 with the movable stopper 1330. Forming the retaining fingers 1375, ledge 1357 and flexible tabs 1341 as part of the sleeve 1347 can facilitate the associated molding process, as compared to a molding process used to form an outer body of a syringe having these features. Forming the flexible tabs 1341 in the sleeve 1347, can result in process holes extending through an outer, generally cylindrical surface of the sleeve 1347. These process holes can be covered, or surrounded by, the outer body 1340, which surrounds the sleeve 1347, to maintain a sterile environment within syringe 1314.

FIGS. 103-107 depict the fluid delivery device 1310 in a second configuration, with the cartridge 1312 translated distally within the syringe 1314, relative to the position of cartridge 1312 shown in FIGS. 98-102. As shown in FIG. 105, in the second configuration of fluid delivery device 1310, the proximal tip 1361 of the needle 1360 can extend through the proximal surface 1371 of the movable stopper 1330 into the fluid chamber 1318, such that the lumen 1363 defined by the needle 1360 is in fluid communication with the fluid chamber 1318. As shown in FIG. 106, due to the distal translation of cartridge 1312, the distal end 1313 of the housing 1316 can compress, or flex, or deflect, the flexible positioning members 1351, resulting in the flexible positioning members 1351 being disengaged from the annular ledge 1357, which permits the inner core 1342, barb 1366 and stopper 1330 to move distally relative to the sleeve 1347, outer body 1340 and needle 1360. The thickness of the stopper 1330, in an axial or longitudinal direction along cartridge 1312, can be sized to permit some compression if required, as a result of possible manufacturing tolerances, to achieve the desired timing of the disengagement of the flexible positioning members 1351 from the annular ledge 1357. As shown in FIG. 107, the annular member 1377 of the inner core 1142 can abut the outer body 1340, and the flexible tabs 1341 of sleeve 1347 can engage the annular member 1378 of inner core 1342, such that axial movement of the inner core 1342 is prevented, which permits using the fluid delivery device 1310 for aspiration when desired, for example by pulling the housing 1316 of cartridge 1312 in a proximal direction relative to syringe 1314 to aspirate a fluid from a source (not shown) external of the fluid delivery device 1310 into the fluid chamber 1318, after removal of the distal end cap 1352. The stopper 1330 can remain connected to the inner core 1342 during aspiration such that it does not move relative to the syringe 1314.

Figures 108, 109, 110, 111, 112:
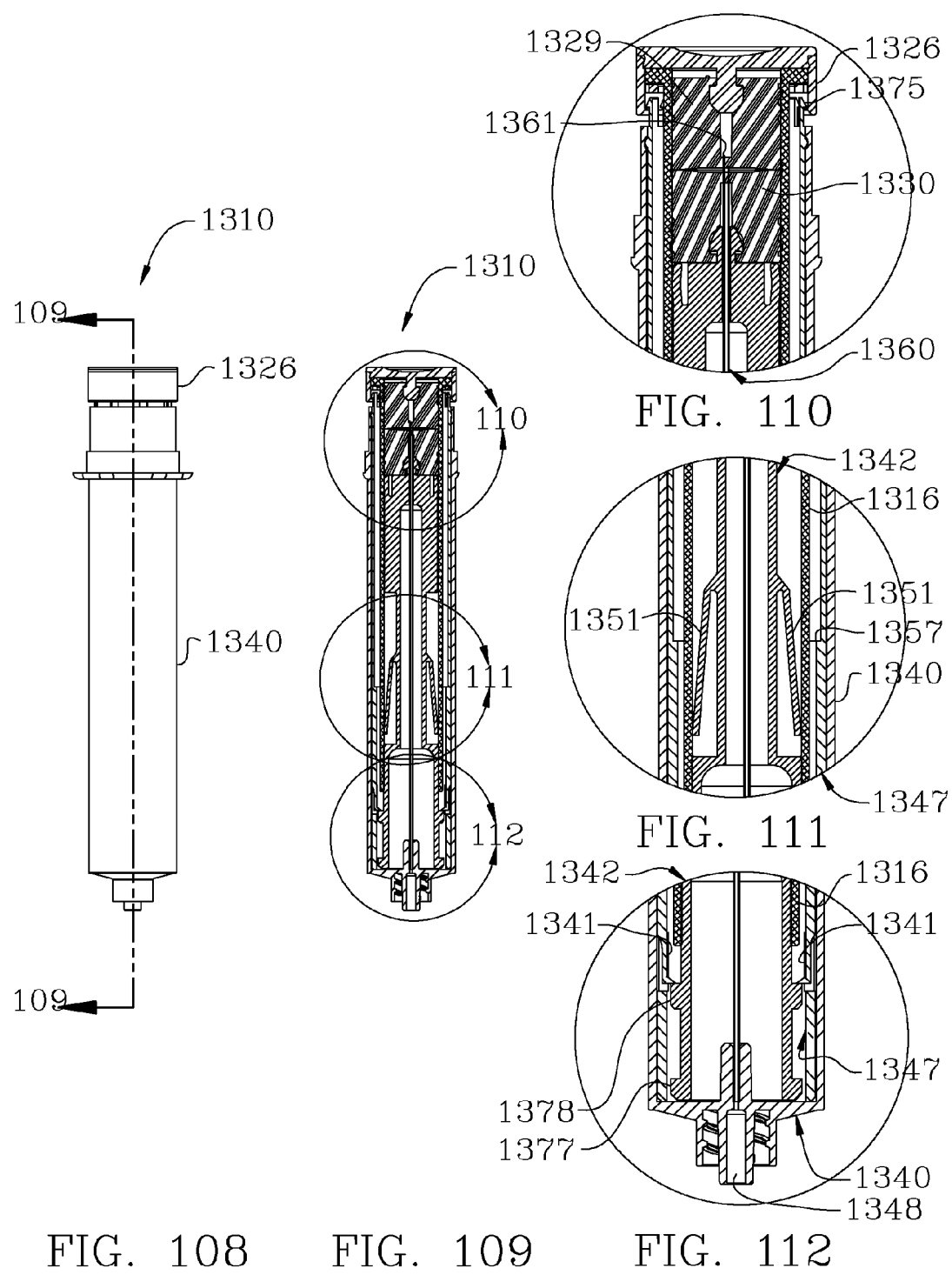
FIG. 108 is a side elevational view of the fluid delivery device of FIG. 93, depicting the fluid delivery device in a third configuration, with the cartridge translated distally within the syringe relative to the position of the cartridge shown in FIG. 103, to achieve fluid delivery.
FIG. 109 is a cross-sectional view taken along line 109-109 in FIG. 108.
FIG. 110 is an enlarged view of a first encircled portion of FIG. 109, depicting the movable stopper engaged with a fixed stopper and depicting the proximal tip of the needle extending into the fixed stopper.

FIGS. 108-112 depict the fluid delivery device 1310 in a third configuration, with the cartridge 1312 inserted farther distally into the syringe 1314, relative to the position of the cartridge shown in FIGS. 103-107, to achieve fluid delivery, or fluid discharge, out of the lumen 1348 defined by the male luer connection 1346. In this configuration of the fluid delivery device 1310, the proximal tip 1361 of the needle 1360 can extend into the fixed stopper 1329, as shown in FIG. 110. FIG. 111 depicts the flexible positioning members 1351 deflected farther inwardly, relative to the position of the flexible positioning members 1351 shown in FIG. 106, due to the axial position of the housing 1316 of cartridge 1312. FIG. 112 depicts the inner core 1342, sleeve 1347 and outer body 1340 in the same relative positions as shown in FIG. 107. As shown in FIG. 110, the retaining fingers 1375 can engage the collar 1326, which can be a snap fit engagement, to prevent relative axial movement between the cartridge 1312 and syringe 1314 to disable the fluid delivery device 1310.

FIGS. 113-132 illustrate a fluid delivery device 1410, according to another embodiment. The fluid delivery device 1410 can include a cartridge 1412 and a syringe 1414. The cartridge 1412 can be inserted into the syringe 1414 to achieve fluid delivery. The fluid delivery device 1410 can function in a similar manner as the fluid delivery device 1310, but can be considered to be a construction variant of the fluid delivery device 1310. For example, the syringe 1414 can include an outer body 1440 and an inner core 1442, but does not include an annular sleeve positioned radially between the outer body 1440 and inner core 1442, unlike syringe 1314 that includes annular sleeve 1347, which can be positioned radially between the outer body 1340 and the inner core 1342 as shown in FIG. 94. In this embodiment, the outer body 1440 can include retaining fingers 1475, or members, ledge 1457, and flexible tabs 1441. A distal end of the outer body 1440 can include manufacturing process holes 1488 (FIGS. 122, 127 and 132), which can facilitate the formation of the flexible tabs 1441. Similar to cartridge 1312 of fluid delivery device 1310, the cartridge 1412 of fluid delivery device 1410 can include a proximal button 1424 having a distal protrusion 1425, a housing 1416 that can include a generally cylindrical portion 1420 and a proximal flange 1423 integral with the generally cylindrical portion 1420. The outer body 1440 and the inner core 1442 can cooperate to define a cavity 1444 configured to receive at least a portion of the housing 1416. The cartridge 1412 can further include a fixed stopper 1429 and a movable stopper 1430, with each of the stoppers 1429 and 1430 positioned within a fluid chamber 1418 defined by the housing 1416. Cartridge 1412 can also include a collar 1426, a cap 1434 that can be used to initially position the movable stopper 1430 within the fluid chamber 1418, and a tamper evident label 1431 that can be secured to the cap 1434 and the housing 1416. In addition to the outer body 1440 and the inner core 1442, the syringe 1414 can include a male luer connection 1446, which can be integrally formed with the outer body 1440 and can define a lumen 1448. Syringe 1414 can also include a proximal end cap 1450, a distal end cap 1452, tamper evident labels 1454 and 1456, a needle 1460 having a proximal tip 1461 and a distal end 1464, and a barb 1466 which can be integral with a proximal end 1443 (FIG. 114) of the inner core 1442. The needle 1460 can define a lumen 1463 (FIG. 120). The distal end 1464 of needle 1460 can be secured to the outer body 1440, as shown in FIG. 114, and the lumen 1463 can be in fluid communication with the lumen 1448. The barb 1466 and inner core 1442 can cooperate to define a lumen 1445, which can receive at least a substantial portion of the needle 1460, as shown in FIG. 119.

After removal of the tamper evident label 1431 and cap 1434 from the cartridge 1412, and removal of the tamper evident label 1454 and the proximal end cap 1450 of syringe 1414, the cartridge 1412 can be inserted into the syringe 1414, for example as shown in FIG. 118. FIGS. 118-122 depict the fluid delivery device 1410 in a first configuration, in which the movable stopper 1430 is engaged with the barb 1466, to connect the movable stopper 1430 with the inner core 1442. The proximal tip 1461 of the needle 1460 can be distal of a proximal surface 1471 of the movable stopper 1430, as shown in FIG. 120, such that the lumen 1463 defined by the needle 1460 is not in fluid communication with the fluid chamber 1418. As shown in FIG. 120, the proximal tip 1461 of needle 1460 can be positioned within the lumen 1445 such that the proximal tip 1461 of needle 1460 does not extend beyond the barb 1466, when the fluid delivery device is in the first configuration shown in FIGS. 118-122.

A distal end of the flexible positioning members 1451 of the inner core 1442 can engage an annular ledge 1457 of the outer body 1440, and the flexible tabs 1441 of the outer body 1440 can be positioned distally from an annular member 1477 of the inner core 1442 as shown in FIG. 122. As shown in FIG. 121, the housing 1460 of cartridge 1412 can be positioned axially such that a distal end 1413 of the housing 1416 contacts but does not compress, or deflect, or flex, the flexible positioning members 1451 of the inner core 1442. The engagement of the flexible positioning member 1451 with the annular ledge 1457 can provide a resistive force that can facilitate the engagement of the barb 1466 with the movable stopper 1430. The outer body 1440 can include an outer wall 1402 and an inner guide 1403, or sleeve, which can be positioned radially inward of the outer wall 1402 and can extend proximally from a distal end of the outer body 1440 along a portion of the outer wall 1402. The outer wall 1402 and inner guide 1403 can cooperate to define a cavity 1404 that can be configured to receive a distal portion of the inner core 1442 as shown in FIGS. 119 and 122. The inner guide 1403 can include a ring (not shown) formed on an outer surface, and the inner core 1442 can include a ring (not shown) formed on an inner surface that can be positioned distally from the ring of the inner guide 1403, such that the ring of the inner core 1442 can cooperate with the ring of the inner guide 1403 to prevent the inner core 1442 from moving proximally relative to the outer body 1440.

FIGS. 123-127 depict the fluid delivery device 1410 in a second configuration, with the cartridge 1412 translated distally within the syringe 1414, relative to the position of the cartridge 1412 shown in FIGS. 118-122. As shown in FIG. 125, in the second configuration of fluid delivery device 1410, the proximal tip 1461 of the needle 1460 can extend through the proximal surface 1471 of the movable stopper 1430 into the fluid chamber 1418, such that the lumen 1463 defined by the needle 1460 is in fluid communication with the fluid chamber 1418. As shown in FIG. 126, the position of the cartridge 1412 can be such that the distal end 1413 of the housing 1416 contacts and compresses the flexible positioning members 1451 such that the flexible positioning members 1451 move radially inwardly and are disengaged from the annular ledge 1457, which permits the inner core 1442 and the movable stopper 1430 to move distally relative to the outer body 1440 and the needle 1460. As a result of this distal movement, the proximal tip 1461 of needle 1460 can extend through the proximal surface 1471 of the movable stopper 1430 and into the fluid chamber 1418, such that the lumen 1463 defined by needle 1460 is in fluid communication with the fluid chamber 1418. The presence of the inner guide 1403 can facilitate maintaining a desired orientation of the inner core 1442, for example, such that the inner core 1442 can be substantially coaxial with a longitudinal centerline axis (not shown) of the fluid delivery device 1410 as the inner core 1442 moves distally relative to the outer body 1440. As shown in FIG. 127, the annular member 1477 of the inner core 1442 can abut the outer body 1440, and the flexible tabs 1441 of the outer body 1440 can be engaged with a proximal surface of the annular member 1477, such that axial movement of the inner core 1442 is prevented, which permits using the fluid delivery device 1410 for aspiration when desired, after removal of the distal end cap 1452. When installed, for example when secured to the outer body 1440, the distal end cap 1452 can cover the process holes 1488 prior to insertion of cartridge 1412 into syringe 1414, and while the fluid delivery device 1410 is in the first and second configurations, as shown in FIGS. 114, 119, 122, 124 and 127, which can facilitate maintaining a sterile environment within syringe 1414.

FIGS. 128-132 depict the fluid delivery device 1410 in a third configuration, with the cartridge 1412 inserted farther distally into the syringe, relative to the position of the cartridge shown in FIGS. 123-127 to achieve fluid delivery. In this configuration of the fluid delivery device 1410, the movable stopper 1430 can be in contacting engagement with the fixed stopper 1429 as shown in FIG. 130, and the proximal tip 1461 of the needle 1460 can extend into the fixed stopper 1429. FIG. 131 depicts the flexible positioning members 1451 compressed, or deflected, farther inwardly, relative to the position of the flexible positioning members 1451 shown in FIG. 126, due to the axial position of the housing 1416 of cartridge 1412. FIG. 132 depicts the inner core 1442 and outer body 1440 in the same relative positions as shown in FIG. 127. As shown in FIG. 130, the retaining fingers 1475, or retaining members, can engage the collar 1426 of the cartridge 1412 to prevent relative axial movement between the cartridge 1412 and the syringe 1414, to disable the fluid delivery device 1410. For example, each of the retaining fingers 1475 can engage a respective one of a plurality of inwardly extending and circumferentially spaced tabs formed at a distal end of the collar 1426. Alternatively, an annular lip can be formed at the distal end of the collar 1426 in lieu of the inwardly extending and circumferentially spaced tabs such that each of the retaining fingers 1475 engage the annular lip.

FIGS. 133-149 illustrate a fluid delivery device 1510 according to another embodiment. The fluid delivery device 1510 can include a cartridge 1512 and a syringe 1514. The cartridge 1512 can be similar to the design of cartridge 1212.

In this regard, cartridge 1512 can include a proximal button 1524 that can include a distal protrusion 1525, and a housing 1516 that can include a generally cylindrical portion 1520 having an inner surface 1521 (FIG. 134). Housing 1516 can also include a proximal flange 1523 that can be integral with a proximal end of the generally cylindrical portion 1520. The housing 1516 can define a fluid chamber 1518 (FIG. 134). Cartridge 1512 can also include a fixed stopper 1529, which can be positioned within the fluid chamber 1518 and can be secured to the distal protrusion 1525 of proximal button 1524, and a movable stopper 1530, which can be positioned within fluid chamber 1518 and can be movable relative to housing 1516. Cartridge 1512 can also include a collar 1526, which can be used to secure the proximal button 1524 to housing 1516, and a cap 1534 that can include an annular distal portion 1536 and a proximal portion 1538 that can be formed as a plurality of circumferentially spaced fins. Cartridge 1512 can also include a tamper evident label 1531 that can be secured to the housing 1516 and cap 1534.

The syringe 1514 can include an outer body 1540 and an inner core 1542. The inner core 1542 can be positioned within, and surrounded by, the outer body 1540 of syringe 1514, as shown in FIGS. 134, 139, 143, and 147. The inner core 1542 can be movable within the outer body 1540, which can result in a "staged" insertion of cartridge 1512 with syringe 1514. Unlike previous embodiments of the fluid delivery device, a removable safety clip 1580 can be placed between the inner core 1542 and outer body 1540 to prevent relative axial movement between the inner core 1542 and outer body 1540 until such movement is desired and the end user removes the safety clip 1580.

The syringe 1514 can also include a male luer connection 1546, which can be integrally formed with the outer body 1540. The male luer connection 1546 can define a lumen 1548 (FIG. 141) extending therethrough in an axial, or longitudinal, direction. The male luer connection 1546 can permit the fluid delivery device 1510 to be connected with standard devices normally connected to a male luer connection, for example, intravenous sets or female luer attachment needles. The configuration of lumen 1548 in an axial or longitudinal direction can permit the male luer connection 1546 to be connected to a wide variety of commonly available female needle-free valves, or any other suitable valve. As shown in FIG. 137, the syringe 1514 can also include a proximal end cap 1550, which can be removably secured to a proximal end of the outer body 1540 as shown in FIG. 134, and a distal end cap 1552, which can be removably secured to the male luer connection 1546 adjacent a distal end of the outer body 1540 as shown in FIG. 134. Syringe 1514 can also include a tamper evident label 1554, which can be secured to both the proximal end cap 1550 and the outer body 1540, and a tamper evident label 1556, which can be secured to the distal end cap 1552 and the male luer connection 1546. The combination of the proximal end cap 1550, the distal end cap 1552, and the tamper evident labels 1554, 1556 can provide an indication to an end user of the fluid delivery device 1510 that a fluid flow path through the syringe 1514 is sterile prior to initial use.

The syringe 1514 can also include a needle 1560, which can include a proximal tip 1561 and a distal end 1564, and can define a lumen 1563 (FIG. 140). The distal end 1564 of needle 1560 can be secured to the outer body 1540 as shown in FIG. 134, for example using adhesives. The syringe 1514 can also include a flange 1565 (FIG. 137), which can be integrally formed within the outer body 1540. The flange 1565 can facilitate operation of the fluid delivery device 1510. For example, the flange 1565 can be sized and configured to receive one or more fingers of a health care provider using the fluid delivery device 1510.

The syringe 1514 can include a barb 1566, which can be integrally formed with the inner core 1542. The syringe 1514 can also include a plurality of flexible guides 1576 (FIG. 137), or friction fingers, which can be formed integrally with the inner core 1542 of syringe 1514. The flexible guides 1576 can project radially outwardly such that they can press against the inner surface 1521 (FIG. 134) of the generally cylindrical portion 1520 of the housing 1516 of cartridge 1512. The flexible guides 1576 can be generally "bow-shaped" to facilitate sliding engagement with housing 1516 during insertion of cartridge 1512. The contacting engagement of the flexible guides 1576 with the inner surface 1521 can prevent the cartridge 1512 from falling out of, or disengaging, the syringe 1514, if the fluid delivery device 1510 is temporarily turned upside down and the barb 1566 has not yet been connected to the stopper 1530. During the initial insertion of the cartridge 1512 within the syringe 1514, the distal end cap 1552 of syringe 1514 can remained installed as shown in FIG. 134, to prevent fluid from inadvertently spraying out of, or discharging from, the fluid delivery device 1510.

After removing the cap 1534 of cartridge 1512 and the proximal end cap 1550 of the syringe 1514, the cartridge 1512 can be inserted, at least partially, into the syringe 1514. The inner core 1542 can define a cavity 1544 that can be configured for receiving the cartridge 1512. FIGS. 138-141 depict the fluid delivery device 1510 in a first configuration, with the cartridge 1512 inserted into the syringe 1514 by an axial distance, i.e., a distance along a longitudinal axis (not shown) of the fluid delivery device 1510, which results in a barb 1566 of syringe 1514 engaging a recess 1568 defined by the stopper 1530 of cartridge 1512, such that at least a portion of the barb 1566 is positioned within the recess 1568. In one embodiment, the barb 1566 can be positioned substantially entirely within the recess 1568, as shown in FIG. 140. The barb 1566 and inner core 1542 can cooperate to define a lumen 1545, which can receive at least a substantial portion of needle 1560, as shown in FIG. 138. The barb 1566 and the recess 1568 can have mating portions with complementary shapes that can facilitate the connection of barb 1566 to stopper 1530, which can also secure the inner core 1542 of syringe 1514 to stopper 1530 of cartridge 1512. When the cartridge 1512 and syringe 1514 are positioned as shown in FIGS. 138-141, the proximal tip 1561 of the needle 1560 is shown not to extend beyond barb 1566, such that the lumen 1563 defined by the needle 1560 is not in fluid communication with the fluid chamber 1518.

A proximal end 1543 (FIG. 140) of the inner core 1542 can include a flange 1581 that can be similar to the flange 1565 integral with the outer body 1540. The proximal end 1543 of the inner core 1542 can also include a cylindrical housing 1589, which can define a set of distal notches 1583 and a set of proximal notches 1585 as shown in FIG. 138. The distal notches 1583 and proximal notches 1585 defined by the cylindrical housing 1589 of the inner core 1542 can be configured to receive a set of flexible tabs 1541 of the outer body 1540. The flexible tabs 1541 can be initially placed in the distal notches 1583, as shown in FIG. 140, to position the flange 1581 of the inner core 1542 a predetermined distance from the flange 1565. The safety clip 1580 can be placed between the flanges 1581 and 1565 to prevent the movement of the inner core 1542 distally into the outer body 1540, until removed by an end user. This prevents the needle 1560 from penetrating the stopper 1530 until the safety clip 1580 is removed and sufficient force is exerted on the inner core 1542 to disengage the flexible tabs 1541 from the notches 1583 and move the inner core 1542 and stopper 1530 distally relative to the outer body 1540 and needle 1560, such that the fluid delivery device 1510 has transitioned to a second configuration, for example the configuration shown in FIGS. 142-145. In this configuration, the flange 1581 of inner core 1542 can contact the flange 1565, a distal end of the inner core 1542 can contact the outer body 1540, and each of the flexible tabs 1541 of the outer body 1540 can engage a respective one of the notches 1585. As a result, the proximal tip 1561 of the needle 1560 can penetrate through a proximal surface 1571 of stopper 1530, such that the lumen 1563 defined by the needle 1560 is in fluid communication with the fluid chamber 1518, as shown in FIGS. 143 and 144.

The distal end cap 1552 can remain secured to the male luer connection 1546, during further insertion of the cartridge 1512 into the syringe 1514, for example from FIG. 138 to 142, which can prevent fluid from inadvertently spraying out of, or discharging from, the lumen 1548 defined by the male luer connection 1546. In this regard, the distal end cap 1552 can include a plug 1570 that can extend into the lumen 1548, as shown in FIGS. 141 and 145.

The previously described configurations of the fluid delivery device 1510, and the movements, or positioning, of cartridge 1512 relative to syringe 1514, and the movements of the inner core 1542 of syringe 1514 relative to the outer body 1540 of syringe 1514, prior to fluid delivery, can be considered to be a two-stage sequence, or operation. The initial stage can be considered to be the insertion of cartridge 1512 into syringe 1514, with safety clip 1580 installed, until the stopper 1530 of cartridge 1512 engages the barb 1566 of syringe 1514, without the needle 1560 extending through the stopper 1530. The second stage can be considered to be the further insertion of cartridge 1512 into syringe 1514, after removal of the safety clip 1580, with the stopper 1530 and inner core 1542 moving distally relative to the outer body 1540, male luer connection 1546 and needle 1560 such that the proximal tip 1561 of the needle 1560 extends through the proximal surface 1571 of the stopper 1530, with the lumen 1563 defined by needle 1560 being in fluid communication with the fluid chamber 1518.

FIGS. 146-149 depict the fluid delivery device 1510 in a third configuration, which can result in fluid delivery. After removal of the distal end cap 1552 of syringe 1514, the cartridge 1512 can be inserted farther distally into syringe 1514, relative to the position of the cartridge 1512 shown in FIGS. 142-144, to the end of stroke position of cartridge 1512 that is shown in FIGS. 146-149, to deliver, expel, or discharge, fluid from the fluid delivery device 1510. The cylindrical housing 1589, or proximal collar, of the inner core 1542 of syringe 1514 can be used to disable the fluid delivery device 1510, after fluid delivery, instead of the use of retaining fingers, such as retaining fingers 1175 of fluid delivery device 1110. For example, as shown in FIGS. 147-148, at the end of the stroke of cartridge 1512, the cartridge 1512 can be completely inserted into the syringe 1514, with the proximal collar 1589 of the inner core 1542 of syringe 1514 surrounding the collar 1526 and proximal button 1524 of cartridge 1512 to prevent, or at least substantially prevent, access to the cartridge 1512. The lack of access to the cartridge 1512 can prevent a user from grasping the cartridge 1512 and moving the cartridge 1512 axially relative to the syringe 1514, such that the fluid delivery device 1510 is disabled.

FIGS. 150-167 illustrate a fluid delivery device 1610, according to another embodiment. The fluid delivery device 1610 can include a cartridge 1612 and a syringe 1614. The cartridge 1612 can include a proximal button 1624 having a distal protrusion 1625 and a housing 1616 that can define a fluid chamber 1618 (FIG. 151). Housing 1616 can include a generally cylindrical portion 1620 and a proximal flange 1623 that can be integral with a proximal end of the generally cylindrical portion 1620 (FIG. 153). The cartridge 1612 can also include a fixed stopper 1629 secured to the distal protrusion 1625 of proximal button 1624 and a movable stopper 1630. Each of the stoppers 1629 and 1630 can be positioned within the fluid chamber 1618. The cartridge 1612 can also include a collar 1626, a tamper evident label 1631 and a cap 1634. The components of the cartridge 1612 can be configured, and can function, the same as or substantially the same as, the components of cartridge 1512.

The syringe 1614 can include an outer body 1640 and an inner core 1642. The syringe 1614 can also include a barb 1666 that can be integral with a proximal end of the inner core 1642. In one embodiment, the barb 1666 and the inner core 1642 can be integrally formed as a unitary structure. The outer body 1640 and inner core 1642 can cooperate to define a cavity 1644 that can be configured to receive the housing 1616 of cartridge 1612. The outer body can include a proximal collar 1639, and the inner core 1642 can include a plurality of flexible guides 1676, which can function in a manner similar to the flexible guides 1176 of the fluid delivery device 1110, described previously. The syringe 1614 can also include a needle 1660 having a proximal tip 1661 and a distal end 1664. Needle 1660 can define a lumen 1663. The barb 1666 and inner core 1642 can define a lumen 1645 that can receive the needle 1660. As shown in FIG. 151, at least a substantial portion of the needle 1660 can be positioned within lumen 1645. The syringe 1614 can also include a male luer connection 1646, which can be integral with the outer body 1640 and can define a lumen 1648. The distal end 1664 of the needle 1660 can be secured to the outer body 1640, such that the lumen 1663 can be in fluid communication with the lumen 1648 as shown in FIG. 158. The syringe 1614 can also include a proximal end cap 1650, which can be removably secured to the outer body 1640, and a tamper evident label 1654, which can be removably secured to the proximal end cap 1650 and the outer body 1640. The syringe 1614 can also include a distal end cap 1652, which can be removably secured to at least one of the male luer connection 1646 and the outer body 1640. The syringe 1614 can also include a tamper evident label 1656, which can be removably secured to the outer body 1640 and the distal end cap 1652.

FIGS. 155-158 depict the fluid delivery device 1610 in a first configuration, with the cartridge 1612 inserted into the syringe 1614 such that the movable stopper 1630 of the cartridge 1612 engages the barb 1666. As shown in FIG. 157, in this configuration, the needle 1660 can be positioned within the lumen 1645 such that the proximal tip 1661 of needle 1660 does not extend beyond the barb 1666, and is positioned distally from a proximal surface 1671 of the movable stopper 1630. As a result, in this configuration the lumen 1663 defined by needle 1660 is not in fluid communication with the fluid chamber 1618. The outer body 1640 can include a plurality of flexible tabs 1641. As shown in FIG. 158, each flexible tab 1641 can include a proximal end 1635 and a distal end 1637. The inner core 1642 can include a distal end 1649, which can define an annular notch or groove 1659 (FIG. 158). In the first configuration of fluid delivery device 1610 that is shown in FIGS. 155-158, the distal end 1637 of each flexible tab 1641 can engage the annular notch 1659 defined by the distal end 1649 of the inner core 1642 to prevent the inner core 1642 from moving axially relative to the outer body 1640, which can facilitate seating the movable stopper 1630 onto the barb 1666.

FIGS. 159-162 depict the fluid delivery device in a second configuration, with the cartridge 1612 inserted farther distally into the syringe 1614, as compared to the relative position of the cartridge 1612 shown in FIG. 156. An end user, such as a healthcare provider, can transition the fluid delivery device from the first configuration shown in FIGS. 154-158 to the second configuration shown in FIGS. 159-162, by removing the distal end cap 1652 and depressing the proximal end 1635 of the flexible tabs 1641, which can cause the flexible tabs 1641 to pivot, or rotate, such that the proximal end 1637 of each of the tabs 1641 moves outwardly and is disengaged from the annular notch 1659 defined by the proximal end 1649 of the inner core 1642. This allows the inner core 1642 and the stopper 1630, which is connected to the barb 1666, to move distally relative to the outer body 1640 and the needle 1660, such that the inner core 1642 can be positioned as shown in FIGS. 160-162. Since the flexible tabs 1641 can be disengaged from the annular notch 1659 without pushing on the cartridge 1612, the flexible tabs 1641 can be disengaged from the annular notch 1659 without generating any hydraulic pressure within the fluid chamber 1618, which can avoid undesirable spraying of fluid out of the lumen 1648 as a result of this action. The cartridge 1612 can then be pushed distally such that the inner core can be positioned as shown in FIG. 162, and the proximal tip 1661 of the needle 1660 can extend through the proximal surface 1671 of the stopper 1630 into the fluid chamber 1618, such that the lumen 1663 defined by the needle 1660 is in fluid communication with the fluid chamber 1618. The distal end 1649 of the inner 1642 can contact the outer body 1640, as shown in FIG. 162, and the distal end 1637 of each of the flexible tabs 1641 can engage, or rest on top of, a proximal surface 1658 of the distal end 1649 of the inner core 1642, which can prevent the inner core 1642 from moving either distally or proximally relative to the outer body 1640 and permits the fluid delivery device 1610 to be used for aspiration as desired.

FIGS. 163-167 depict the fluid delivery device 1610 in a third configuration, with the cartridge 1612 inserted, or translated, farther distally into the syringe 1614 to achieve fluid delivery with the fluid delivery device 1610, i.e., delivery or discharge of fluid contained within the fluid chamber 1618 out of the lumen 1648. In this third configuration, the fixed stopper 1629 and movable stopper 1630 can be engaged with one another, as shown in FIG. 166, and the proximal tip 1661 of the needle 1660 can extend into the fixed stopper 1629. The inner core 1642 can remain in the same position relative to the outer body 1640, as shown in FIG. 167. In this third configuration of the fluid delivery device 1610, the cartridge 1612 can be positioned entirely within the syringe 1614, and the proximal collar 1639 of the outer body 1640 can surround the collar 1626 and proximal button 1624 of cartridge 1612 as shown in FIG. 166 to prevent, or substantially prevent, access to the cartridge 1612, which can prevent an end user from grasping the cartridge 1612 and moving it axially relative to the syringe 1614, such that the fluid delivery device 1610 is disabled.

FIGS. 181-199 illustrate a fluid delivery device 1710 according to another embodiment. The fluid delivery device 1710 can include a cartridge 1712 and a syringe 1714. The cartridge 1712 can include a housing 1716, which can include a generally cylindrical portion 1720 and a proximal flange. The cartridge 1712 can also include a proximal button 1724 and a collar 1726, or crimp, which can secure the proximal button 1724 to the housing 1716, for example to the proximal flange of the housing 1716 of cartridge 1712. The cartridge 1712 can also include a plurality of stoppers. For example, cartridge 1712 can include a fixed proximal stopper 1729 that can be secured, or fixed, to the proximal button 1724 to prevent relative axial movement between housing 1716 and the fixed proximal stopper 1729. Cartridge 1712 can also include a middle, or intermediate, movable stopper 1730A, and a distal movable stopper 1730B, with each of the stoppers 1729, 1730A and 1730B being positioned within an interior space, or chamber, defined by the housing 1716, as shown in FIG. 182. The movable stoppers 1730A and 1730B can be movable axially relative to the housing 1716.

The cartridge 1712 can also include a cap 1734 which can be inserted into the interior chamber defined by the housing 1716 and can be used to establish the initial axial position of the distal movable stopper 1730B within the interior chamber defined by the housing 1716. The cartridge 1712 can also include a tamper evident label 1731 that can be secured to the cap 1734 and the housing 1716. The fixed stopper 1729, intermediate movable stopper 1730A and distal movable stopper 1730B can cooperate with the housing 1716 to define a proximal chamber 1718A and a distal chamber 1718B, as shown in FIG. 182. The chambers 1718A and 1718B can be configured to contain a variety of substances, for example a variety of medicinal substances. In some instances, it may be desirable to avoid mixing the substances contained within chambers 1718A and 1718B, until just prior to use. In one embodiment, each of the proximal chamber 1718A and the distal chamber 1718B can contain a fluid, and the fluid in the proximal chamber 1718A can be different than the fluid in the distal chamber 1718B. In another embodiment, one of the proximal chamber 1718A and the distal chamber 1718B can contain a fluid and the other one of the proximal chamber 1718A and the distal chamber 1718B can contain a powder. In one embodiment, the proximal chamber 1718A can contain a powder and the distal chamber 1718B can contain a fluid. The volume of each of the proximal chamber 1718A and the distal chamber 1718B can vary, depending upon the positions of the movable stoppers 1730A and 1730B with respect to each other, and with respect to the fixed stopper 1729. For example, when the fluid delivery device 1710 is configured as shown in FIGS. 188-191, such that the movable stoppers 1730A and 1730B contact one another, the volume of the distal chamber 1718B can be zero, or substantially zero. When the proximal movable stopper 1730A engages each of the fixed proximal stopper 1729 and the distal movable stopper 1730B, as shown in FIG. 199, the volume of each of the proximal chamber 1718A and 1718B can be zero, or substantially zero.

The cartridge 1712 can also include a plurality of protuberances 1793, or bulges, which can be integral with housing 1716 and can extend outwardly from housing 1716. The protuberances 1793 and housing 1716 can be integrally formed as a unitary structure. The protuberances 1793 can be circumferentially spaced around the housing 1716 as shown in FIGS. 181-183. Each of the protuberances 1793 can define a bypass channel 1798, as shown in FIG. 187A. In other embodiments, cartridges can be provided that include one or more protuberances, with each of the protuberances defining more than one bypass channel. Depending upon the positions of the movable intermediate stopper 1730A and the movable distal stopper 1730B, the bypass channels 1798 can be in fluid communication with the proximal chamber 1718A but not the distal chamber 1718B, as shown in FIGS. 181-185, or with each of the proximal chamber 1718A and the distal chamber 1718B, as shown in FIGS. 187 and 187A. In other configurations, for example, when the fluid delivery device 1710 is configured as shown in FIGS. 190 and 191, the stoppers 1730A and 1730B can be positioned within the interior chamber defined by the housing 1716 such that the bypass channels are not in fluid communication with either the proximal chamber 1718A or the distal chamber 1718B. In order to achieve the desired selective fluid communication of the bypass channels 1798 with the proximal chamber 1718A and the distal chamber 1718B, each of the bypass channels 1798 can be sized such that a length of the bypass channel 1798, along a longitudinal centerline axis (not shown) of cartridge 1712, is greater than a width of the intermediate movable stopper 1730A, along the longitudinal centerline axis of the cartridge 1712, but is less than the sum of the width of the intermediate movable stopper 1730A and a width of the distal movable stopper 1730B, along the longitudinal centerline axis of the cartridge 1712.

The bypass channels 1798 can be utilized to transfer a substance that is initially in the distal chamber 1718B, to the proximal chamber 1718A, when desired. The placement or position of the intermediate movable stopper 1730A and the distal movable stopper 1730B within the interior chamber defined by the housing 1716, as well as the position or location of the protuberances 1793 and bypass channels 1798 relative to housing 1716, can be adjusted as required depending upon the substances initially contained within the proximal chambers 1718A and the distal chamber 1718B.

The syringe 1714 can include an outer body 1740 and an inner core 1742. The inner core 1742 can be positioned within, and surrounded by, the outer body 1740 of syringe 1714, as shown in FIG. 182. The inner core 1742 can be movable within the outer body 1740 to achieve a "staged" insertion of cartridge 1712 within syringe 1714. The syringe 1714 can also include a male luer connection 1746, which can be integral with the outer body 1740 and can define a lumen 1748, as shown in FIG. 199. The syringe 1714 can also include a barb 1766, which can be integral with a proximal end of the inner core 1742. The syringe 1714 can also include a needle 1760, which can be secured at a distal end to the outer body 1740. The inner core 1742 and barb 1766 can cooperate to define a lumen that can be configured to receive the needle 1760.

The syringe 1714 can also include a proximal end cap 1750, which can be removably secured to the outer body 1740, and a tamper evident label 1754, which can be removably secured to the outer body 1740 and the proximal end cap 1750. The syringe 1714 can also include a distal end cap 1752, which can be removably secured to at least one of the male luer connection 1746 and the outer body 1740, and a tamper evident label 1756, which can be removably secured to the outer body 1740 and the distal end cap 1752. The inner core 1742 can include an annular member 1777, at a distal end thereof, and a plurality of flexible positioning members 1751, as shown in FIG. 182. The outer body 1740 can include a plurality of flexible tabs 1741 and a proximal collar 1739.

The flexible positioning members 1751 can initially engage a ledge 1757 (FIG. 185), or step feature, of the outer body 1740 to provide a resistive force that can facilitate seating the distal movable stopper 1730B onto the barb 1766, and that can also, during various stages of operation of the fluid delivery device 1710, facilitate movement of the distal movable stopper 1730B in a proximal direction, movement of the intermediate movable stopper 1730A in a proximal direction, and transfer of the substance initially in the distal chamber 1718B to the proximal chamber 1718A.

The tamper evident tape 1731, or label, and cap 1734 of cartridge 1712 can be removed, and the tamper evident tape 1754, or label, and proximal end cap 1750 of syringe 1714 can be removed, to permit insertion of the cartridge 1712 into syringe 1714. The cartridge 1712 can be initially inserted into the syringe 1714 so that the distal movable stopper 1730B is engaged with the barb 1766, as shown in FIG. 185. The cartridge 1712 can be advanced distally into the syringe 1714, which can cause the distal movable stopper 1730B, the substance in chamber 1718B, and the intermediate movable stopper 1730A to move in a proximal direction. These movements can continue until the intermediate movable stopper 1730A crosses the by-pass channels 1798, as shown in FIGS. 187 and 187A, which allows the substance in distal chamber 1718B to move into proximal chamber 1718A, for example by shaking the fluid delivery device 1710. In this configuration, hydrostatic force may not be applied to the intermediate movable stopper 1730A since the substance initially in the distal chamber 1718B can move through the bypass channels 1798.

As the cartridge 1712 is advanced farther in the distal direction, relative to the position of the cartridge 1712 shown in FIGS. 187 and 187A, the distal movable stopper 1730B can continue to move proximally until it reaches, or contacts, the intermediate movable stopper 1730A and all of the substance originally contained within the distal chamber 1718B has been transferred to the proximal chamber 1718A via the bypass channels 1798, as shown in FIG. 189. Further advancement of the cartridge 1712 in a distal direction can cause the distal movable stopper 1730B and the intermediate movable stopper 1730A to move proximally relative to housing 1716 of cartridge 1712 until the intermediate movable stopper 1730A seals the bypass channels 1798, as shown in FIG. 191, such that the substance initially in the distal chamber 1718B can be mixed with the substance initially in the proximal chamber 1718A, for example by shaking the fluid delivery device 1710. In this configuration of the fluid delivery device 1710, a distal end of the housing 1716 of cartridge 1712 can contact the flexible positioning members 1751 of syringe 1714, without compressing or inwardly deflecting, the flexible positioning members 1751, as shown in FIG. 191.

As the cartridge 1712 is advanced farther in the distal direction, the distal end of the cartridge housing 1716 can compress the flexible positioning members 1751 of the inner core 1740, such that the flexible positioning members 1751 can be deflected inwardly and can be disengaged with the ledge 1757 of outer body 1740, as shown in FIG. 193, to permit the inner core of the syringe 1714 to move distally. FIG. 195 depicts the inner core 1742 translated distally relative to the position of the inner core 1742 shown in FIG. 193, and FIG. 197 depicts the inner core 1742 translated distally relative to the position of the inner core 1742 shown in FIG. 195. FIG. 195 depicts the inner core 1742 translated distally relative to the position of the inner core 1742 shown in FIG. 193, and FIG. 197 depicts the inner core 1742 translated distally relative to the position of the inner core 1742 shown in FIG. 195. FIG. 195 depicts the annular member 1777 of the inner core 1742 spaced proximally from the distal end of the outer body 1740 and depicts a proximal tip 1761 of needle 1760 positioned within the intermediate stopper 1730A. FIG. 197 depicts the annular member 1777 of inner core 1742 "bottomed-out" against the distal end of the outer body 1740 such that the proximal tip 1761 of the needle 1760 can penetrate through the intermediate movable stopper 1730A as shown in FIG. 197 and a lumen (not shown) defined by the needle 1760 can be in fluid communication with the proximal chamber 1718A. Fluid or a mixture of fluid and powder, depending upon the substances originally in the proximal chamber 1718A and the distal chamber 1718B, can then be discharged through the device 1710, by removing the distal cap 1752 and inserting the cartridge farther into the syringe 1714. The cartridge 1712 can be inserted farther distally, such that it is inserted completely within the syringe 1714, as shown in FIG. 199, to complete the discharge of fluid, or the mixture of fluid and powder, from the proximal chamber 1730A through the lumen defined by the needle 1760, and through the lumen 1748 defined by the male luer connection 1746. When the cartridge 1712 has been inserted completely within the syringe 1714 as shown in FIG. 199, the proximal collar 1739 of the outer body 1740 can surround the proximal button 1724 and collar 1726 of the cartridge 1712 to prevent, or substantially prevent, access to the cartridge 1712, for example, by preventing an end user from grasping the cartridge 1712, which can disable the fluid delivery device 1710 by preventing an end user from moving the cartridge 1712 axially relative to syringe 1714.

FIGS. 200-220 illustrate a fluid delivery device 1810 according to another embodiment. The fluid delivery device 1810 can include a cartridge 1812 and a syringe 1814. As shown in FIG. 203, the cartridge 1812 can include a proximal button 1824 that can include a distal protrusion 1825. The cartridge 1812 can also include a housing 1816, which can include a generally cylindrical portion 1820 and a proximal flange 1823 that can be integral with a proximal end of the generally cylindrical portion 1820. The housing 1816 can define a fluid chamber 1818 (FIG. 206). The cartridge 1812 can also include a collar 1826, which can be used to secure the proximal button 1824 to the housing 1816, for example to the proximal flange 1823. Cartridge 1812 can also include a fixed stopper 1829 and a movable stopper 1830. The fixed stopper 1829 can be secured to the distal protrusion 1825 of the proximal button 1824. Each of the stoppers 1829 and 1830 can be positioned in the fluid chamber 1818, and the movable stopper 1830 can be movable axially relative to the housing 1816. Cartridge 1812 can also include a tamper evident label 1831, or tape, and a cap 1834. The cap 1834 can be inserted into the fluid chamber 1818 and can be used to position the movable stopper 1830 within the fluid chamber 1812 to achieve the desired volume for receiving medicinal fluid. For example, the fixed stopper 1829 and movable stopper 1830, which are initially spaced apart from one another, can cooperate with the housing 1816 to define a sealed portion of the fluid chamber 1818, which is suitable for receiving medicinal fluid. The tamper evident label 1831 can be secured to both the cap 1834 and the housing 1816, to facilitate maintaining a sterile environment within the cartridge 1812.

The syringe 1814 can include an outer body 1840 and an inner core 1842 that can be positioned within, and surrounded by, the outer body 1840 as shown in FIGS. 201 and 206, for example. The outer body 1840 and the inner core 1842 can cooperate to define a cavity that can be configured to receive at least a portion of the housing 1816 of cartridge 1812. The inner core 1842 can be movable relative to the outer body 1840 to achieve a "staged" insertion of the cartridge 1812 into the syringe 1814. The syringe 1814 can also include a male luer connection 1846, which can define a lumen 1848 (FIG. 220) and which can be integral with the outer body 1840. The syringe 1814 can also include a proximal end cap 1850, a distal end cap 1852 and tamper evident labels 1854 and 1856. The proximal end cap 1850 can be removably secured to the outer body 1840 and the tamper evident label 1854 can be secured to each of the proximal end cap 1850 and the outer body 1840. The distal end cap 1852 can be removably secured to at least one of the outer body 1840 and the male luer connection 1846, and the tamper evident label 1856 can be secured to each of the distal end cap 1852 and the outer body 1840. The syringe 1814 can also include a needle 1860, which can include a proximal tip 1861 and a distal end 1864, as shown in FIG. 204. Needle 1860 can define a lumen 1863. The distal end 1864 of needle 1860 can be secured to the outer body 1840 (FIG. 208) such that the lumen 1863 is in fluid communication with the lumen 1848 defined by the male luer connection 1846. Syringe 1814 can also include a barb 1866, which can be integral with a proximal end 1843 of the inner core 1842, as shown in FIG. 207. The outer body 1840 can include a plurality of flexible tabs 1841 (FIG. 208) and a ledge 1857 (FIG. 209), or step, and a proximal collar 1839. The syringe 1814 can also include a flange 1865 which can be integral with the outer body 1840 and can be used to facilitate operation of the fluid delivery device 1810. The inner core 1842 can include a plurality of flexible positioning members 1851, and can also include a plurality of flexible guides 1876 that can engage the housing 1816 in a friction fit.

After removing the tamper evident label 1831 and cap 1834 of cartridge 1812 and the tamper evident label 1854 and proximal end cap 1850 of the syringe 1814, the cartridge 1812 can be inserted into the syringe 1814 as shown in FIGS. 205-208. In this initial configuration, the movable stopper 1830 of the cartridge 1812 can be spaced apart from the barb 1866, such that the stopper 1830 is not connected to the barb 1866 or the inner core 1842. The needle 1860 is shown in FIGS. 206 and 207 to be contained within a lumen 1845 defined by the inner core 1842 and the barb 1866, such that the lumen 1863 defined by needle 1860 is not in fluid communication with the fluid chamber 1818. As shown in FIG. 207, the flexible positioning members 1851 of the inner core, can be engaged with the ledge 1857 of the outer body to prevent distal movement of the inner core 1842 relative to the outer body 1840. Further resistance of movement of the inner core 1842 distally with respect to the outer body 1840 can be provided by the flexible tabs 1841 of the outer body 1840, which can contact a distal surface 1808 of a distal end 1849 of the inner core 1842.

As shown in FIG. 208, the outer body 1840 can include an outer wall 1802 and an inner guide 1803, which can cooperate to define a cavity 1804 that can receive the distal end 1849 of the inner core 1842. The inner guide 1803 can include a relatively small diameter annular ring formed on a radially outer surface, which can be positioned adjacent a proximal end of the inner guide 1803, and the distal end 1849 of the inner core 1842 can include a similarly shaped, relatively small annular ring formed on a radially inner surface, which can be positioned distally adjacent to the ring of the inner guide 1803, such that the rings of the inner guide 1803 and the distal end 1849 of the inner core 1842 can prevent, or at least inhibit, proximal movement of the inner core 1842 relative to the outer body 1840. In the configuration shown in FIG. 207, a distal end 1813 of the housing 1816 of the cartridge 1812 can contact but does not compress or deflect, the flexible positioning members 1851 of the syringe 1814. The flexible positioning members 1851 can be positioned adjacent to the proximal end 1843 of the inner core 1842.

FIGS. 209-210 depict the cartridge inserted farther distally into the syringe 1814, relative to the position of the cartridge 1812 shown in FIGS. 205 and 206. In this configuration, the stopper 1830 can be connected to the barb 1866 as shown in FIG. 211, which can connect the movable stopper 1830 to the inner core 1842 of syringe 1814. The needle 1861 can remain positioned within the inner core 1842, such that the proximal tip 1861 of the needle 1860 does not extend into the fluid chamber 1818, as shown in FIG. 211. The distal end 1813 of the housing 1816 can contact and compress the flexible positioning members 1851 such that the flexible positioning members 1851 can be deflected inwardly, which can result in the flexible positioning members 1851 being disengaged with the ledge 1857 of the outer body 1840, as shown in FIG. 211. The flexible tabs 1841 of the outer body 1840 can remain in contacting engagement with the distal surface 1808 of the distal end 1849 of the inner core 1842, as shown in FIG. 212, which can maintain the same, or substantially the same, relative positions of the inner core 1842 and outer body 1840 shown in FIG. 208.

Sufficient force can subsequently be exerted on the cartridge 1812 such that the resistive force provided by engagement of the flexible tabs 1841 with the distal surface 1808 of the distal end 1849 of the inner core 1842 can be overcome, which can permit the cartridge to be inserted farther distally into the syringe 1814 as shown in FIGS. 213-214, relative to the position of the cartridge 1812 shown in FIGS. 209 and 210. The further insertion of the cartridge 1812 can result in the inner core 1842 moving distally with respect to the outer body 1840 and needle 1860 such that the distal surface 1808 of the distal end 1849 of the inner core 1842 can "bottom out" on, or be in contacting engagement with, the outer body 1840 as shown in FIG. 216, and the proximal tip 1861 of the needle 1860 can extend through a proximal surface 1871 of stopper 1830, such that the lumen 1863 defined by the needle 1860 can be in fluid communication with the fluid chamber 1818, as shown in FIG. 215. In this configuration, the flexible tabs 1841 of the outer body 1840 can be in contacting engagement with a proximal surface 1858 of the distal end 1849 of the inner core 1842, to prevent proximal movement of the inner core 1842 relative to the outer body 1840, which can permit aspiration if desired after removal of the distal end cap 1852.

FIGS. 217-220 depict the fluid delivery device 1810 with the distal end cap 1852 removed and the cartridge 1812 inserted farther distally into the syringe 1814, relative to the position of the cartridge 1812 shown in FIGS. 213 and 214, such that the cartridge 1812 can be positioned entirely within the syringe 1814 to achieve fluid delivery, i.e., delivery or discharge of fluid contained within the fluid chamber 1818 through the lumen 1863 defined by the needle 1860 and out of the lumen 1848 defined by the male luer connection 1846. In this configuration, the distal end 1849 of the inner core 1842 can remain engaged with the outer body 1840, as shown in FIG. 220. The fixed stopper 1829 and the movable stopper 1830 can be engaged with one another, as shown in FIG. 219. In this configuration of the fluid delivery device 1810, the proximal collar 1839 of the outer body 1840 can surround the collar 1826 and proximal button 1824 of cartridge 1812, as shown in FIG. 219, to prevent, or substantially prevent, access to the cartridge 1812. The lack of access to the cartridge 1812 can prevent a user from grasping the cartridge 1812 and moving the cartridge 1812 axially relative to the syringe 1814, such that the fluid delivery device 1810 is disabled.

FIGS. 168-171 illustrate an outer body 1940 of a syringe of a fluid delivery device according to another embodiment. The outer body 1940 can include a side wall 1979 and can include a Fresnel lens 1997, or magnification member, that can be integrally formed with the side wall 1979. The side wall 1979 and Fresnel lens 1997 can be formed from a clear resin such as polypropylene (PP), polycarbonate (PC), or any other suitable clear resin, using any suitable molding process. Magnification members, such as Fresnel lens, can be used with any of a variety of other outer bodies of a syringe of a fluid delivery device. As known in the art, Fresnel lens can include a plurality of concentric zones, as will be appreciated with reference to the enlarged view of Fresnel lens 1997 depicted in FIG. 170, and can be relatively thin, as will be appreciated with reference to the enlarged view of Fresnel lens 1997 depicted in FIG. 171, while having a relatively short focal length. Fresnel lens 1997 can include a center 1998 (FIG. 170).

The Fresnel lens 1997 can be provided to magnify the graduations on a cartridge (not shown) used with the outer body 1940, to facilitate determining the volume, or dosage, of medicinal fluid within the fluid chamber of the cartridge. This can be accomplished by aligning the center 1998 of the Fresnel lens 1997 with a proximal surface of a movable stopper positioned within the fluid chamber of the cartridge after inserting the cartridge into, and connecting the cartridge with, the syringe that includes outer body 1940. For example, for purposes of illustration, if the cartridge 1112 would be inserted into a syringe including the outer body 1940, the center 1998 of Fresnel lens 1997 could be aligned with the proximal surface 1171 (FIG. 74) of the stopper 1130 of the cartridge 1112 of the fluid delivery device 1110, to facilitate reading the graduations 1132 (FIG. 67) formed with, or applied to, the cartridge 1112. It will be appreciated that outer body 1940 and other components of the syringe, as well as components of the associated cartridge, could be sized to achieve the desired alignment of the center 1998 of the Fresnel lens 1997 with the proximal surface of the movable stopper of the cartridge, with the cartridge inserted into the syringe and connected with the syringe.

FIGS. 172-180 illustrate a cartridge 2012 according to another embodiment that can include a unitary, or one-piece, cap 2024 which can be used, in lieu of the separate proximal button and collar components of the cartridges of any of a variety of other embodiments of a fluid delivery device, for example, in lieu of the proximal buttons 1124, 1324 and 1424, and collars 1126, 1326 and 1426, of the fluid delivery devices 1110, 1310 and 1410, respectively, in conjunction with housings of cartridges that can function in a manner similar to a housing 2016 of cartridge 2012 with respect to restraining a proximal stopper from moving distally.

In addition to the unitary cap 2024 and housing 2016, the cartridge 2012 can include a stopper 2029. The housing 2016 can include a generally cylindrical portion 2020 and a proximal neck 2022 that can be integral with the generally cylindrical portion 2020. The cartridge 2012 can also include a stopper 2030, which can be movable relative to housing 2016, a cap 2034 and a tamper evident label 2031. The cap 2034 can be used to initially position the stopper 2030 within a chamber 2018 defined by the housing 2016. The tamper evident label 2031 can be secured to the cap 2034 and the housing 2016.

The unitary cap 2024 can be molded, using any suitable process, from any suitable plastic material including those described herein for various other components of a fluid delivery device. FIGS. 178-180 depict the unitary cap 2024 in an "as-molded" configuration. Due to manufacturing considerations, the unitary cap 2024 may not include a distal protrusion, for example a barb, to retain or fix a proximal stopper, such as stopper 2029 in position with the fluid chamber 2018. For example, the unitary cap 2024 can exclude a distal protrusion such as the distal protrusion 1125 of the proximal button 1124 of the fluid delivery device 1110. Instead, the neck 2022 of the housing 2016 and stopper 2029 can have complementary shapes, as shown in FIGS. 173 and 174, which can prevent the stopper 2029 from moving distally within the fluid chamber 2018. At least a substantial portion of the stopper 2029 can be contained within the proximal neck 2022, as shown in FIG. 173. A width of a proximal portion of the stopper can be greater than a width of a distally adjacent portion of the proximal neck 2022, such that the stopper 2029 is prevented from moving distally within the fluid chamber 2018. The housing 2016 can be made of glass, or any suitable plastic material, including those described herein for various components of a fluid delivery device, or any other suitable material which can, for example, exhibit a high moisture barrier property.

The unitary cap 2024 can include a first plurality of foldable tabs 2035 which can be circumferentially spaced, and can include a second plurality of foldable tabs 2037, which can be circumferentially spaced, as shown in FIGS. 175-180. The first plurality of foldable tabs 2035 and the second plurality of foldable tabs 2037 can be arranged in an alternating configuration around a circumference or periphery of the unitary cap 2024. The first plurality of foldable tabs 2035 can be relatively larger than the second plurality of foldable tabs 2037. The first plurality of foldable tabs 2035 can engage the neck 2022 of housing 2016, when the foldable tabs 2035 are in a folded configuration such as that shown in FIGS. 175-177. When the cartridge 2012 is positioned at an end-of-stroke, or full stroke, position that results in fluid delivery, the second plurality of foldable tabs 2037 can be folded and configured as shown in FIGS. 175-177 to engage a syringe (not shown), for example, an outer body of a syringe that is used with the cartridge 2012, to disable the fluid delivery device. Each of the first plurality of foldable tabs 2035 and each of the second plurality of foldable tabs 2037 can include a living hinge to facilitate folding.

Figure 221A:
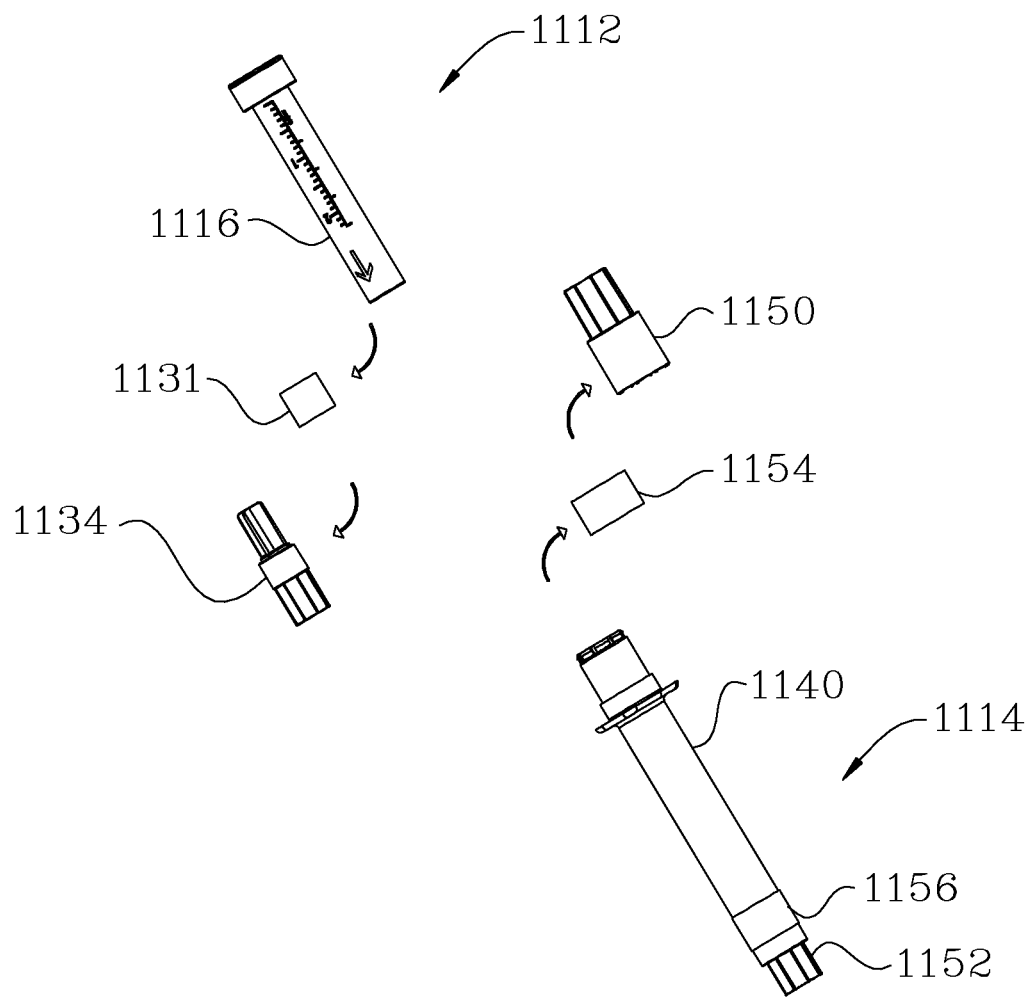

FIGS. 221A-221E illustrate a method, according to one embodiment, of using the fluid delivery device 1110 depicted in FIGS. 67-83. As shown in FIG. 221A, and as preparation for inserting the cartridge 1112 into the syringe 1114, the tamper evident label 1131 can be removed from the housing 1116 and cap 1134 of cartridge 1112. The cap 1134 can then be removed from the housing 1116. As further preparation, the tamper evident label 1154 of syringe 1114 can be removed from the outer body 1140 and proximal end cap 1150 of syringe 1114. The proximal end cap 1150 can then be removed, with the distal end cap 1152 and tamper evident label 1156 remaining installed as shown in FIG. 221A.

Figure 221B:
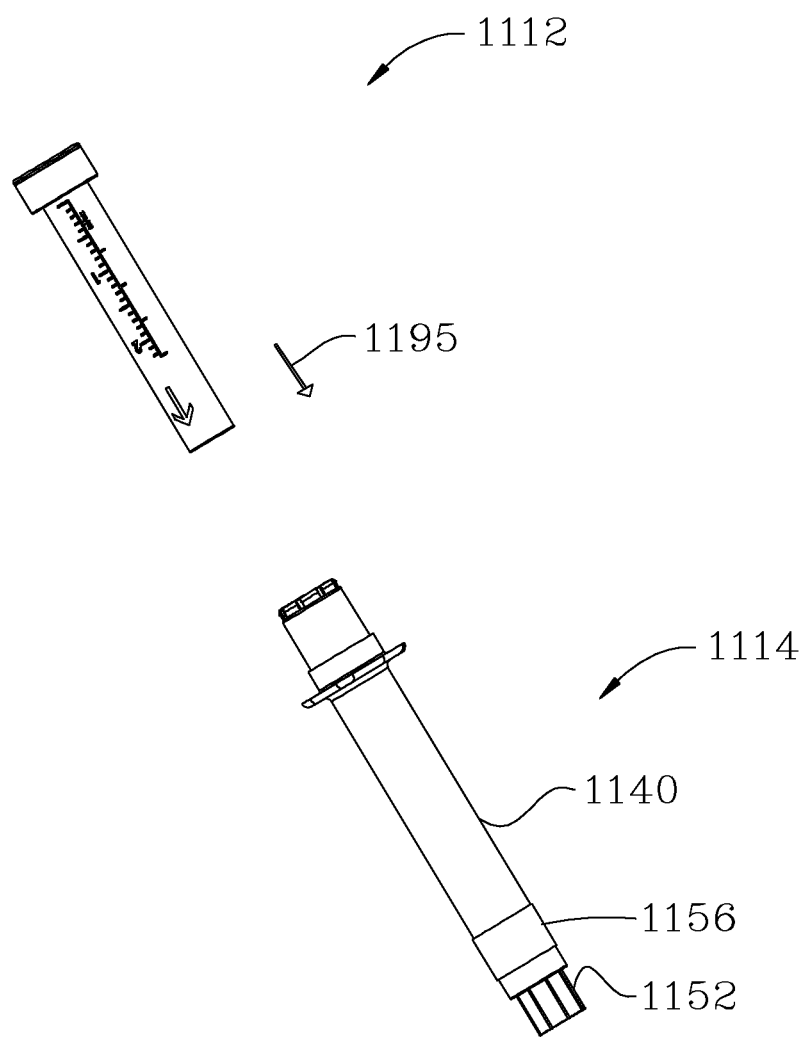
Figure 221C:
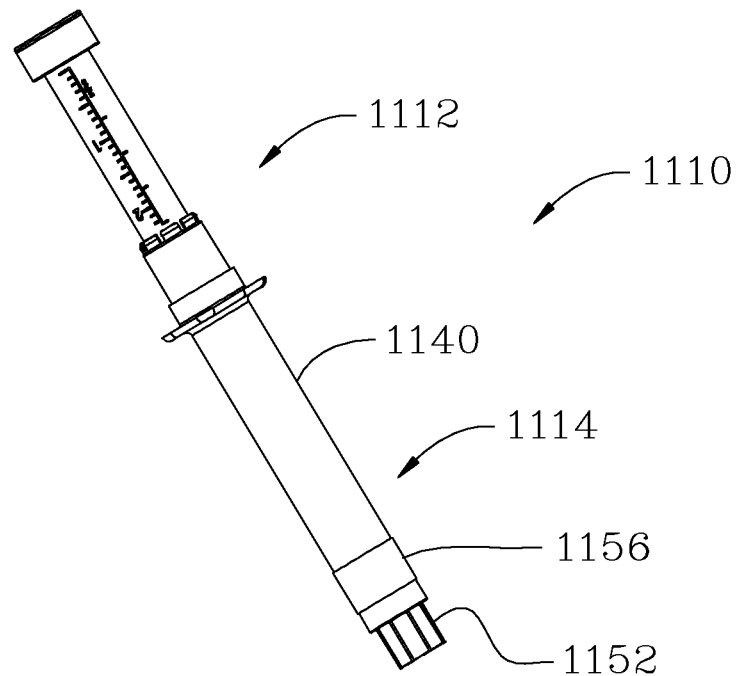

The cartridge 1112 can then be inserted into the syringe 1114 as indicated generally by the arrow 1195 in FIG. 221B. The distal end cap 1152 can remain installed during the initial insertion of the cartridge 1112 into the syringe 1114. FIG. 221C depicts the fluid delivery device in a first configuration, with the cartridge 1112 inserted into the syringe 1114, such that the stopper 1130 of the cartridge 1112 engages the barb 1166 of syringe 1114, which can be integrally formed with the inner core 1142 of syringe 1114 as a unitary structure. In this configuration, the proximal tip 1161 of the needle 1160 does not extend beyond barb 1166 and does not extend through the stopper 1130. The stopper 1130, inner core 1142, barb 1166 and needle 1160 are not shown in FIGS. 221A-221E, but are shown in FIGS. 73 and 74 that depict the fluid delivery device 1110 in this configuration.

Figure 221D:
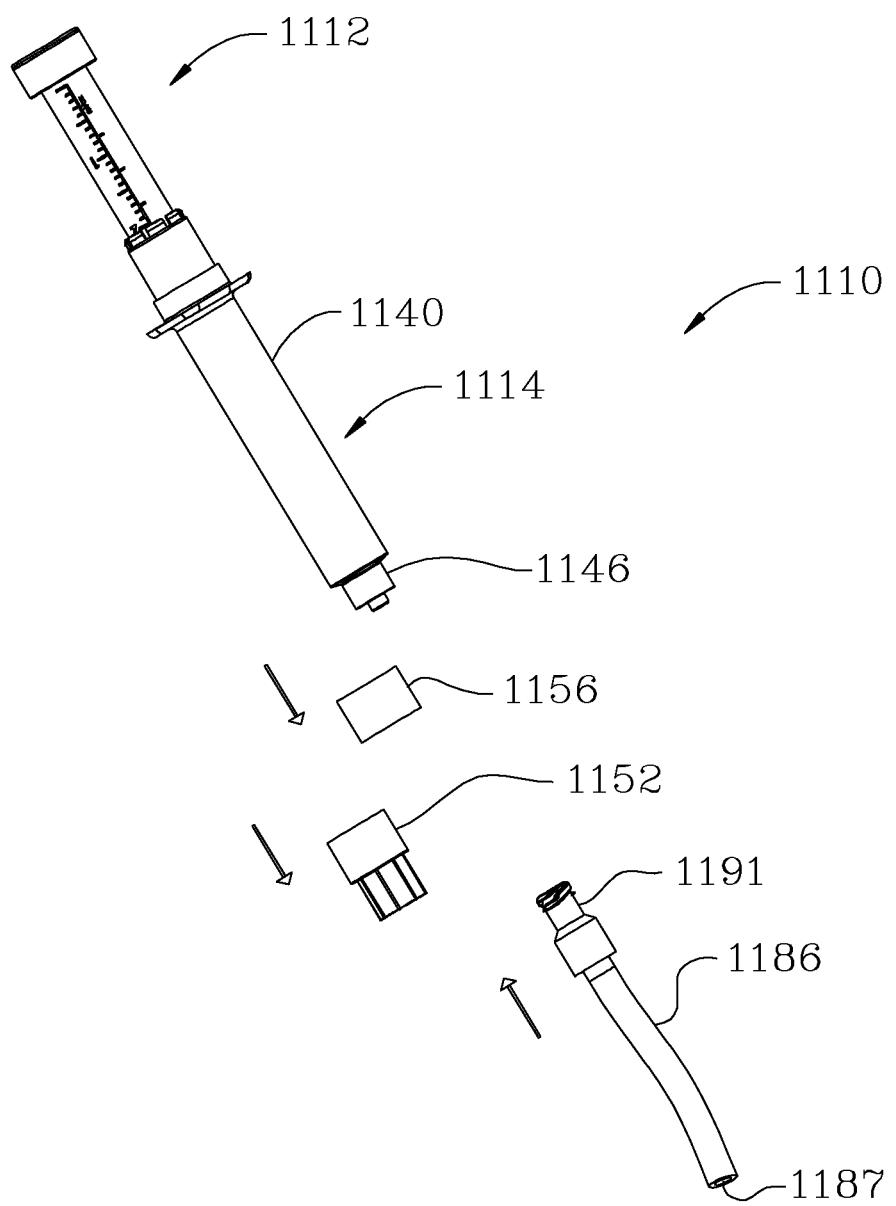

The cartridge 1112 can then be inserted slightly farther into the syringe 1114, as shown in FIG. 221D, relative to the position of the cartridge 1112 shown in FIG. 221C, such that the stopper 1130, barb 1166 and inner core 1142 (not shown in FIGS. 221A-221E) move distally with respect to the outer body 1140 and needle 1160 (not shown in FIGS. 221A-221E), such that the proximal tip 1161 of needle 1160 extends through the stopper 1130, with the lumen 1163 defined by the needle 1160 being in fluid communication with the fluid chamber 1118 (not shown in FIGS. 221A-221E), as shown in FIGS. 77 and 78. During this process, the distal end cap 1152 can remain installed to prevent fluid from unintentionally, or inadvertently, spraying out from the lumen 1148 (not shown FIGS. 221A-221E) of the male luer connection 1146, until such time that fluid delivery is desired. In this regard, the distal end cap 1152 can include a plug 1170 (not shown in FIGS. 221A-221E) that can be inserted into the lumen 1148, as shown in FIG. 79. The tamper evident label 1156 and distal end cap 1152 can then be removed from the syringe 1114, as indicated generally in FIG. 221D.

Figure 221E:
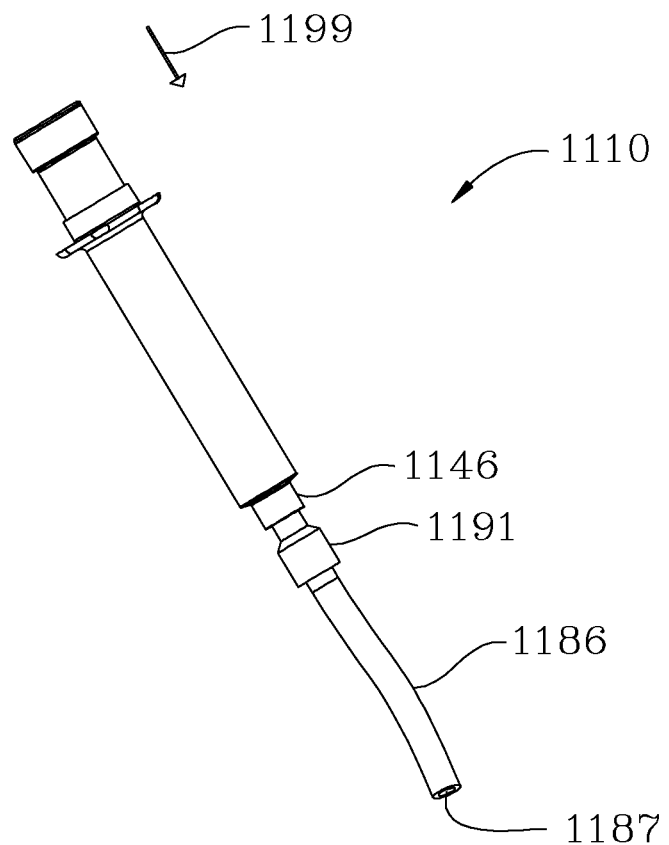

The fluid delivery device 1110 can then be connected to any of a variety of devices that can be utilized to administer the medicinal fluid within the fluid delivery device 1110 to a patient. For example, in one application, the male luer connection 1146 of the fluid delivery device 1110 can be connected to a female luer connection 1191 that can be secured to a tube 1186 of an intravenous set, as illustrated in FIGS. 221D and 221E. The medicinal fluid within the fluid chamber 1118 can be discharged, or delivered, through the lumen 1163 defined by the needle 1160 and through the lumen 1148 defined by the male luer connection 1146 into a lumen 1187 defined by the tube 1186, by inserting the cartridge 1112 farther into the syringe 1114 in a distal direction, relative to the position of the cartridge 1112 shown in FIG. 221D, as indicated generally by arrow 1199 in FIG. 221E. The medicinal fluid can then be selectively administered to a patient as desired. When the fluid delivery device 1110 is configured as shown in FIG. 221E, the fluid delivery device 1110 can be disabled. For example, the retaining fingers 1175 (not shown in FIGS. 221A-221B) of the outer body 1140 can engage the collar 1126 of cartridge 1112, as shown in FIG. 82, to prevent an end user from moving the cartridge 1112 axially relative to the syringe 1114.

The above method of using the fluid delivery device 1110 is provided by a way of illustration, not limitation. For example, the method can be completed in a different order, and may include other actions or sequences in certain applications, for example the use of aspiration. In this regard, the housing 1116 of cartridge 1112 can be moved proximally relative to the syringe 1114 to aspirate fluid from a source of fluid (not shown) into the lumen 1148 and through the lumen 1163 defined by the needle 1160 into the fluid chamber 1118, when the fluid delivery device 1110 is configured such that the inner core 1142 is prevented from moving proximally, for example by the engagement of tabs 1141 of the outer body 1140 with the distal end 1149 of the inner core 1142, the stopper 1130 of cartridge 1112 has been connected to the barb 1166 of syringe 1114, fluid communication has been established between the fluid chamber 1118 and lumen 1148, as shown in FIGS. 77-79, the distal end cap 1152 has been removed, and the fluid delivery device 1110 has not been disabled. Furthermore, the methods of using other embodiments of the fluid delivery device can be different than the method described above.

The materials of construction of the components of the fluid delivery devices 110, 210, 310, 410, 510, 610, 710, 810, 910, 1010, 1110, 1210, 1310, 1410, 1510, 1610, 1710 and 1810, as well as the syringe body shown in FIGS. 168-171 and the cartridge and included unitary cap shown in FIGS. 172-180, can be the same as the materials of construction of the corresponding components of fluid delivery device 10, or any other suitable materials. Although not shown for each embodiment illustrated herein, the syringe of each embodiment of the fluid delivery device can include proximal and distal end caps.

Each embodiment of the fluid delivery device can deliver or discharge a fluid, which can be a medicinal fluid, or medicament. In some embodiments the fluid can be a single liquid. In other embodiments, the fluid can be a mixture of at least two liquids. In still other embodiments, the fluid can be a mixture of one or more liquids and one or more solids, such as one or more powders.

Various embodiments of the fluid delivery device can include a cartridge having a housing and a plug, or a stopper, with the plug or the stopper positioned within a fluid chamber defined by the housing, and with the plug or the stopper fixed with respect to the housing. For example, the stopper 1129 of the cartridge 1112 of fluid delivery device 1110 can be fixed with respect to the housing 1116 of the cartridge 1112. However, the stopper 1129 can move with the housing 1116 of cartridge 1112 as the cartridge 1112 is inserted into the syringe 1114. Various embodiments of the fluid delivery device can include a cartridge having a housing and a stopper that is positioned within a fluid chamber defined by the housing, with the stopper being initially movable with the housing, for example, during initial insertion of the cartridge into the associated syringe, but is subsequently movable relative to the housing during further insertion of the cartridge into the syringe. For example, stopper 1130 of the cartridge 1112 of fluid delivery device 1110 can be movable with the housing 1116 of cartridge 1112 relative to syringe 1114 during initial insertion of cartridge 1112 into syringe 1114, for example until the stopper 1130 is connected to the barb 1166, and the proximal tip 1161 of needle 1160 does not extend through the proximal surface 1171 of stopper 1130, as shown in FIG. 74. After the proximal tip 1161 of needle 1160 has extended through the proximal surface 1171 of stopper 1130 due to movement of the inner core 1142 and stopper 1130 distally relative to the outer body 1140 and needle 1160, such that the lumen 1163 defined by needle 1160 is in fluid communication with the fluid chamber 1118 as shown in FIG. 78, the stopper 1130 can remain connected to barb 1166 such that it does not move relative to the inner core 1142. However, the stopper 1130 can be movable relative to the housing 1116 as the housing 1116 is inserted farther distally into the syringe 1114. The cartridge of each embodiment of the fluid delivery device can be insertable into a cartridge-receiving device, or a cartridge receptacle. For example, the cartridge 12 of the fluid delivery device 10 can be inserted into syringe 14 and the cartridge 1112 of the fluid delivery device 1110 can be inserted into the syringe 1114.

Certain embodiments of the fluid delivery device can provide various advantages, for example flexibility with regard to the use and/or manufacture of the fluid delivery device. For example, various embodiments of the fluid delivery device can be designed such that they are able to mate, connect, or otherwise couple with standard devices normally connected to a male luer connection, or any other suitable device, such as, but not limited to, intravenous sets or female luer attachment needles. The incorporation of a generic male luer distal connection, in certain embodiments, can allow the respective fluid delivery devices to be used with alternative configurations of devices that can accommodate various end user requirements and set-up configurations, which may reduce inventories (and associated costs) without requiring complex manipulations, or adaptations, by the end user, which may result in reduced assembly errors. Also in certain embodiments incorporating a generic male luer connection at a distal end of the fluid delivery device, or a generic male luer distal connection, the configuration of the lumen defined by the male luer distal connection, in an axial or longitudinal direction, can permit the male luer distal connection to be connected to a wide variety of commonly available female needle-free valves, or any other suitable valve. In other embodiments, the fluid delivery device can include alternative attachment structures or arrangements. For example, the distal end of the syringe can be designed to include a blunt cannula, a plurality of spikes, or conically tapered fittings for connection to non-luer connections that may be used on the ports of intravenous sets, or catheter funnels, or other connections.

Certain embodiments of the fluid delivery device can be configured such that the fluid delivery device can be disabled, by preventing relative axial movement between the cartridge and the syringe, once fluid has been expelled from the fluid chamber defined by the cartridge. Disablement of the fluid delivery device can be coincident with the positioning of the cartridge at an end-of-stroke position within the syringe, for example when the cartridge 1112 of the fluid delivery device 1110 is positioned relative to the syringe 1114 as shown in FIGS. 80-83. The end-of-stroke position may be otherwise denoted, for example as a full stroke, complete stroke, end-of-travel, full travel, or complete travel, position. In each of these embodiments, one or more components of the fluid delivery device can be omitted or modified such that the fluid delivery device does not include a disablement feature. For example, the retaining fingers 1175 of the outer body 1140 of syringe 1114 of fluid delivery device 1110 can be omitted, such that the cartridge 1112 can be withdrawn proximally relative to syringe 1114 after the cartridge 1112 has been inserted to the end-of-stroke position shown in FIGS. 80-83. Similarly, the retaining fingers of other embodiments, such as the retaining fingers 1375 of the fluid delivery device 1310, can be omitted to permit the respective cartridge to be withdrawn proximally relative to the respective syringe after the cartridge has been inserted to an end-of-stroke position. As another example, the proximal collar 1239 of the outer body 1240 of syringe 1214 can be omitted such that a user can grasp the cartridge 1212 and withdraw the cartridge 1212 proximally relative to syringe 1214, after the cartridge 1212 has been inserted to an end-of-stroke position as shown in FIGS. 89-92.

Certain embodiments of the fluid delivery device can include components that can interact to produce various audible indications during use, such as audible "clicks", which can signify certain events to the end user and can facilitate use of the fluid delivery device. For example, with respect to the fluid delivery device 1110, prior to connection of cartridge 1112 and syringe 1114 (FIGS. 67-69) and during an initial stage of insertion of cartridge 1112 into syringe 1114, when the fluid delivery device 1110 can be configured as shown in FIGS. 72-75, the flexible tabs 1141 of the outer body 1140 of syringe 1114 can engage the annular notch 1159 of syringe 1114 to temporarily retain the inner core 1142 in the axial position shown in FIGS. 68 and 73-75. The flexible tabs 1141 can engage the annular notch 1159 in a snap fit. The outer body 1140 and the inner core 1142 of syringe 1114 can be molded from clear or opaque resins such as polypropylene (PP), polycarbonate (PC), or the like.

As shown in FIGS. 73 and 74, the stopper 1130 of cartridge 1112 can be connected to the barb 1166 of syringe 1114, which connects the cartridge 1112 and the syringe 1114. As also depicted in FIGS. 73 and 74, in this configuration of fluid delivery device 1110, the proximal tip 1161 of needle 1160 does not extend through the stopper 1130 into the fluid chamber 1118, i.e., the proximal tip 1161 is distal of the proximal surface 1171 of stopper 1130, such that the lumen 1163 defined by needle 1160 is not in fluid communication with the fluid chamber 1118.

As a user pushes on cartridge 1112 to insert cartridge 1112 farther into syringe 1114, the flexible tabs 1141 disengage from the annular notch 1159, permitting the inner core 1142, barb 1166 and stopper 1130 to move distally, relative to the needle 1160 and outer body 1140, such that the fluid delivery device 1110 can be configured as depicted in FIGS. 76-79, wherein the proximal tip 1161 of needle 1160 can be positioned within the fluid chamber 1118 such that the lumen 1163 defined by the needle 1160 is in fluid communication with the fluid chamber 1118. When the flexible tabs 1141 disengage from the annular notch 1159, the flexible tabs 1141 can be initially compressed by the distal end 1149 of inner core 1142 as the inner core 1142 moves distally, such that they can be deflected outwardly, until the distal end 1149 of the inner core 1142 is positioned distally from the flexible tabs 1141. When this occurs, the flexible tabs 1141 can be released, such that they deflect, or spring, inwardly and engage, or rest on top of, the proximal surface 1158 of the distal end 1149 of the inner core 1142, as shown in FIG. 79. Releasing the flexible tabs 1141 can result in an audible indication, which can be an audible "click", which provides an indication to the end user that the cartridge 1112 is engaged with, or connected to, the syringe 1114, and that the fluid delivery device 1110 is configured for fluid delivery, or fluid expulsion, from fluid chamber 1118 through the lumen 1148 defined by the male luer connection 1146, after removal of the distal end cap 1152.

When the cartridge 1112 is inserted farther distally within syringe 1114, such that fluid delivery is complete, the fluid delivery 1110 can be configured as shown in FIGS. 80-83. In this configuration, the retaining fingers 1175 of outer body 1140 of syringe 1114 can engage the collar 1126 of cartridge 1112 as shown in FIG. 82 to disable the fluid delivery device 1110, i.e., to prevent the cartridge 1112 from being removed from syringe 1114. The engagement of the retaining fingers 1175 with the collar 1126, which can be a snap fit engagement, can produce a second audible indication, which can be a second audible "click", which provides an indication to the end user that fluid delivery is complete and the fluid delivery device 1110 is disabled.

The cartridge or container of the fluid delivery device can be configured to permit the correct delivery of a specific fluid volume. The cartridges or containers can have a variety of configurations and sizes, which can accommodate a range of medicinal fluids within the respective fluid chambers. Cartridges may be provided with or without volume markers, or indicia, to permit either user-defined dosages, or pre-filled unit dosages. The cartridge can be pre-filled with medicinal fluid. In certain embodiments, the cartridge can be configured to permit "vial filling". In other embodiments, the cartridge can be configured to permit use of another type of filling process, e.g., a process that may be commonly referred to as "cartridge filling". In certain embodiments, e.g., where a stopper of the cartridge is fixed to the inner core of the syringe to permit bi-directional fluid flow, aspiration can be used with the delivery of certain fluids or when there is a need to mix fluids. In embodiments where the fluid delivery device is capable of bi-directional fluid flow, the cartridge of the fluid delivery device can be pre-filled with medicinal fluid, i.e., prior to connection with the syringe of the device, or alternatively, the cartridge can be filled with fluid after connection to the syringe using aspiration.

Caps or closures can be applied to the distal and proximal ends of the syringe of the fluid delivery device, and/or to the proximal end of the cartridge. These caps or closures can be sealed to permit removal, and can act as a sterile barrier. In certain embodiments, caps or closures can be vented with, for example, a torturous path to permit terminal sterilization with ethylene oxide gas (ETO). The combination of caps and tamper evident labels can eliminate the need for a second layer of packaging to act as a sterile barrier. Caps can incorporate a feature that can seal against one of several sealing surfaces of a male luer on the syringe outer body or inner core, including exterior tapered surfaces or face seals, or an inner surface of the tapered male luer. In certain embodiments, the distal and proximal end caps of the syringe can be eliminated by packaging the syringe in a film blister that can serve as a primary sterile barrier.

A variety of manufacturing processes can be used to manufacture the fluid delivery device. For example, in some embodiments, adhesive can be employed to bond or join components, such as for needle attachment or to connect multiple syringe body components. Adhesives that can be used include, but are not limited to: cynoacrylate, 2-part epoxy, heat activated resin, UV cured adhesive, and hot melt. Joining can also be achieved through, but not limited to, the use of solvent bonding, ultrasonics, or heat-staking. Additionally, in some embodiments, single tool molding, ultrasonic welding, or mechanical retention can be utilized to join components of a fluid delivery device. Furthermore, where dissimilar materials may be advantageously used, a two-shot or insert molding technique can be utilized.

One or more components of the fluid delivery device can be injection molded. This can be achieved such that these components are molded with simple open/closed tooling to reduce tool cost and cycle times. Components of the fluid delivery device can be molded from clear or opaque resins such as polypropylene (PP), polycarbonate (PC), or the like. The cartridge of the fluid delivery device can be made of plastic or glass, or other suitable materials that can, for example, exhibit a high moisture barrier property.

The outer body and inner core of the syringe of the fluid delivery device can be integrally molded as a unitary structure, or can be molded separately and subsequently joined using any suitable process, including any of the processes described previously. A male luer connection can be integrally molded with either the outer body or the inner core of the syringe. In one embodiment, when the male luer connection is integrally molded with the inner core, and the inner core and outer body of the syringe are separately formed, the inner core and outer body can include mating anti-rotation features to prevent rotation of the inner core relative to the outer body during connection of the male luer connection to a female luer connection. In certain embodiments, a metal needle of the syringe can be overmolded with the inner core of the syringe. In other embodiments, a metal needle can be fixed to the inner core using an adhesive. In yet another embodiment, a plastic distal tip of a needle can be molded integrally with the inner core and can be in fluid communication with a lumen, or flow passage, defined by the inner core. The cartridge and the syringe can be packaged separately or together, for example, in a kit format.

The fluid delivery device can be configured to at least minimize any residual medicinal fluid within the fluid chamber defined by the cartridge, after completion of the full stroke of the cartridge within the syringe to deliver the medicinal fluid. As will be appreciated, this can result in a significant cost reduction to the end user, particularly in the case of high volume usage of fluid delivery devices.

The foregoing description of embodiments and examples has been presented for purposes of illustration and description, and is not intended to restrict or in any way limit the scope. Numerous modifications are possible in light of the above teachings. Some of those modifications have been discussed, and others will be understood by those skilled in the art.

What is claimed is:

1. A fluid delivery device comprising:
   a cartridge comprising a housing and a stopper, the housing defining a fluid chamber, the stopper being positioned within the fluid chamber and comprising a proximal surface; and
   a syringe comprising an outer body, an inner core, and a needle, the outer body and the inner core cooperating to define a cavity configured to receive at least a portion of the housing of the cartridge, the needle defining a lumen and comprising a proximal tip; wherein
   when the fluid delivery device is in a first configuration, at least a portion of the cartridge is positioned within the syringe, the stopper of the cartridge is connected to the inner core, and the proximal tip of the needle is positioned distal of the proximal surface of the stopper;
   when the fluid delivery device is in a second configuration, the proximal tip of the needle extends through the proximal surface of the stopper such that the lumen defined by the needle is in fluid communication with the fluid chamber, wherein the inner core and the stopper are movable distally relative to the outer body and the needle as the fluid delivery device is transitioned from the first configuration to the second configuration; and
   when the fluid delivery device is in a third configuration, the cartridge and the syringe cooperate to prevent relative axial movement between the cartridge and the syringe such that the fluid delivery device is disabled.

2. The fluid delivery device of claim 1, wherein:
   the inner core of the syringe comprises a distal end, the distal end of the inner core defining an annular notch and comprising a proximal surface;
   the outer body of the syringe comprises at least one flexible tab;
   when the fluid delivery device is in the first configuration, the at least one flexible tab engages the annular notch; and
   when the fluid delivery device is in each of the second and third configurations, the at least one flexible tab is disengaged from the annular notch and is engaged with the proximal surface of the distal end of the inner core.

3. The fluid delivery device of claim 1, wherein:
   the housing of the cartridge comprises a generally cylindrical portion having an inner surface;
   the syringe further comprises a plurality of circumferentially spaced flexible guides formed at the proximal end of the inner core; and
   the flexible guides are slidably engaged with the inner surface of the housing.

4. The fluid delivery device of claim 1, wherein:
   the outer body of the syringe comprises an annular ledge;
   the inner core of the syringe comprises a plurality of flexible positioning members;
   when the fluid delivery device is in the first configuration, the flexible positioning members of the inner core engage the annular ledge of the outer body; and
   the housing of the cartridge comprises a distal end which compresses the flexible positioning members as the fluid delivery device is transitioned from the first configuration to the second configuration, such that the flexible positioning members are disengaged from the annular ledge thereby permitting the inner core and the stopper to move distally relative to the outer body and the needle.

5. The fluid delivery device of claim 1, wherein:
   the fluid delivery device provides a first audible indication as the fluid delivery device is configured in the second configuration; and
   the fluid delivery device provides a second audible indication as the fluid delivery device is configured in the third configuration, the second audible indication providing an indication to a user of the fluid delivery device that fluid delivery is complete and the fluid delivery device is disabled.

6. The fluid delivery device of claim 1, wherein:
the cartridge further comprises a proximal button and a collar, the collar securing the proximal button to the housing;
the outer body comprises a proximal collar; and
when the fluid delivery device is in the third configuration, the cartridge is inserted completely within the syringe and the proximal collar of the outer body of the syringe surrounds the collar and the proximal button of the cartridge to disable the fluid delivery device.

7. The fluid delivery device of claim 1, wherein:
the outer body of the syringe comprises a plurality of circumferentially spaced retaining fingers; and
when fluid delivery device is in the third configuration, at least some of the retaining fingers engage the cartridge to disable the fluid delivery device.

8. The fluid delivery device of claim 7, wherein:
the cartridge further comprises a proximal button and a collar, the collar comprising a plurality of circumferentially spaced tabs;
the collar secures the proximal button to the housing; and
at least some of the retaining fingers of the outer body of the syringe engage respective ones of the tabs of the collar of the cartridge when the fluid delivery device is in the third configuration.

9. The fluid delivery device of claim 1, wherein:
the syringe further comprises a barb, the barb being integrally formed with the inner core as a unitary structure, the barb and the inner core cooperating to define a lumen;
the barb is connected to the stopper when the fluid delivery device is in each of the first, second and third configurations; and
when the fluid delivery device is in the first configuration, the proximal tip of the needle is positioned within the lumen defined by the barb and the inner core.

10. The fluid delivery device of claim 9, wherein:
the stopper defines a recess; and
the barb is positioned at least partially within the recess when the fluid delivery device is in each of the first, second and third configurations.

11. The fluid delivery device of claim 1, wherein:
the syringe further comprises a male luer connection, the male luer connection being integral with the outer body and defining a lumen; and
the lumen defined by the needle is in fluid communication with the lumen defined by the male luer connection when the fluid delivery device is in each of the first, second and third configurations.

12. The fluid delivery device of claim 11, wherein:
the stopper comprises a first stopper;
the cartridge further comprises a second stopper, the second stopper being fixed in position within the fluid chamber;
the second stopper is spaced proximally from the first stopper when the fluid delivery device is in each of the first and second configurations; and
the second stopper is in contacting engagement with the first stopper when the fluid delivery device is in the third configuration.

13. The fluid delivery device of claim 12, wherein:
the housing is movable distally within the cavity defined by the outer body and the inner core, and the second stopper is movable distally with the housing, relative to each of the outer body, the inner core, the needle and the first stopper, as the fluid delivery device is transitioned from the second configuration to the third configuration, such that fluid is expelled from the fluid cavity through the lumen defined by the needle and the lumen defined by the male luer connection.

14. A fluid delivery device comprising:
a cartridge comprising a housing and a stopper, the housing defining a fluid chamber, the stopper being positioned within the fluid chamber and comprising a proximal surface; and
a syringe comprising an outer body, an inner core, a barb, and a needle, the outer body and the inner core cooperating to define a cavity configured to receive at least a portion of the housing of the cartridge, the inner core being integrally formed with the barb as a unitary structure, the inner core and the barb cooperating to define a first lumen, the needle defining a second lumen and comprising a proximal tip; wherein
when the fluid delivery device is in a first configuration, at least a portion of the cartridge is positioned within the syringe, the barb of the syringe is connected to the stopper of the cartridge, and the proximal tip of the needle is positioned within the first lumen defined by the inner core and the barb;
when the fluid delivery device is in a second configuration, the proximal tip of the needle extends beyond the barb and through the proximal surface of the stopper such that the second lumen defined by the needle is in fluid communication with the fluid chamber, wherein the inner core, the barb, and the stopper are movable distally relative to the outer body and the needle as the fluid delivery device is transitioned from the first configuration to the second configuration;
when the fluid delivery device is in a third configuration, the cartridge and the syringe cooperate to prevent relative axial movement between the cartridge and the syringe such that the fluid delivery device is disabled.

15. The fluid delivery device of claim 14, wherein:
the outer body of the syringe comprises a plurality of circumferentially spaced retaining fingers; and
when fluid delivery device is in the third configuration, at least some of the retaining fingers engage the cartridge to disable the fluid delivery device.

16. The fluid delivery device of claim 14, wherein:
the cartridge further comprises a proximal button and a collar, the collar securing the proximal button to the housing;
the outer body comprises a proximal collar; and
when the fluid delivery device is in the third configuration, the cartridge is inserted completely within the syringe and the proximal collar of the outer body of the syringe surrounds the collar and the proximal button of the cartridge to disable the fluid delivery device.

17. The fluid delivery device of claim 14, wherein:
the syringe further comprises a male luer connection, the male luer connection being integral with the outer body and defining a third lumen; and
the first lumen defined by the needle is in fluid communication with the third lumen defined by the male luer connection when the fluid delivery device is in each of the first, second and third configurations.

18. The fluid delivery device of claim 14, wherein:
the fluid delivery device provides a first audible indication as the fluid delivery device is configured in the second configuration; and
the fluid delivery device provides a second audible indication as the fluid delivery device is configured in the third configuration, the second audible indication providing an indication to a user of the fluid delivery device that fluid delivery is complete and the fluid delivery device is disabled.

19. A fluid delivery device comprising:

a cartridge comprising a housing and a stopper, the housing defining a fluid chamber, the stopper being positioned within the fluid chamber and comprising a proximal surface; and a syringe comprising an outer body, an inner core, a barb, a needle, and a male luer connection, the outer body and the inner core cooperating to define a cavity configured to receive at least a portion of the housing of the cartridge, the inner core being integrally formed with the barb as a unitary structure, the inner core and the barb cooperating to define a first lumen, the needle defining a second lumen and comprising a proximal tip, the male luer connection being integral with the outer body and defining a third lumen; wherein the outer body of the syringe comprises a plurality of circumferentially spaced retaining fingers and at least one flexible tab;

the inner core of the syringe comprises a distal end, the distal end of the inner core defining an annular notch and comprising a proximal surface;

when the fluid delivery device is in a first configuration, at least a portion of the cartridge is positioned within the syringe, the barb of the syringe is connected to the stopper of the cartridge, the at least one flexible tab of the outer body engages the annular notch defined by the inner core, and the proximal tip of the needle is positioned within the first lumen defined by the inner core and the barb and is distal of the proximal surface of the stopper;

when the fluid delivery device is in a second configuration, the proximal tip of the needle extends beyond the barb and through the proximal surface of the stopper such that the second lumen defined by the needle is in fluid communication with the fluid chamber, wherein the inner core, the barb, and the stopper are movable distally relative to the outer body and the needle as the fluid delivery device is transitioned from the first configuration to the second configuration;

when the fluid delivery device is in a third configuration, at least some of the retaining fingers of the outer body of the syringe engage the cartridge to prevent relative axial movement between the cartridge and the syringe such that the fluid delivery device is disabled;

the at least one flexible tab of the outer body is disengaged from the annular notch defined by the inner core when the fluid delivery device is in each of the second and third configurations; and the second lumen defined by the needle is in fluid communication with the third lumen defined by the male luer connection when the fluid delivery device is in each of the first, second and third configurations.

20. The fluid delivery device of claim 19, wherein:

the fluid delivery device provides a first audible indication as the fluid delivery device is configured in the second configuration; and the fluid delivery device provides a second audible indication as the fluid delivery device is configured in the third configuration, the second audible indication providing an indication to a user of the fluid delivery device that fluid delivery is complete and the fluid delivery device is disabled.

* * * * *